(12) United States Patent
Katzenellenbogen et al.

(10) Patent No.: US 10,703,698 B2
(45) Date of Patent: Jul. 7, 2020

(54) COMPOUNDS WHICH ACTIVATE ESTROGEN RECEPTORS AND COMPOSITIONS AND METHODS OF USING THE SAME

(71) Applicants: The Board of Trustees of the University of Illinois, Urbana, IL (US); Board of Regents of the University of Texas System, Austin, TX (US)

(72) Inventors: John A. Katzenellenbogen, Urbana, IL (US); Benita Katzenellenbogen, Urbana, IL (US); Sung Hoon Kim, Champaign, IL (US); Zeynep Madak-Erdogan, Champaign, IL (US); Philip Shaul, Richardson, TX (US)

(73) Assignees: The Board of Trustees of the University of Illinois, Urbana, IL (US); Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 16/067,676

(22) PCT Filed: Jan. 6, 2017

(86) PCT No.: PCT/US2017/012586
§ 371 (c)(1),
(2) Date: Jul. 2, 2018

(87) PCT Pub. No.: WO2017/120507
PCT Pub. Date: Jul. 13, 2017

(65) Prior Publication Data
US 2019/0002380 A1    Jan. 3, 2019

Related U.S. Application Data

(60) Provisional application No. 62/275,416, filed on Jan. 6, 2016.

(51) Int. Cl.
| | | |
|---|---|---|
| *A61K 31/047* | (2006.01) |
| *A61K 31/055* | (2006.01) |
| *A61K 31/05* | (2006.01) |
| *A61K 31/025* | (2006.01) |
| *C07C 39/17* | (2006.01) |
| *C07C 39/06* | (2006.01) |
| *C07C 39/42* | (2006.01) |
| *C07C 235/34* | (2006.01) |
| *C07C 255/47* | (2006.01) |
| *A61P 25/00* | (2006.01) |
| *A61P 35/00* | (2006.01) |
| *C07C 49/755* | (2006.01) |
| *C07C 43/196* | (2006.01) |
| *C07C 49/733* | (2006.01) |
| *C07C 39/12* | (2006.01) |
| *C07C 39/14* | (2006.01) |
| *C07C 57/38* | (2006.01) |
| *C07C 39/367* | (2006.01) |
| *C07C 39/23* | (2006.01) |

(52) U.S. Cl.
CPC .............. *C07C 39/17* (2013.01); *A61P 25/00* (2018.01); *A61P 35/00* (2018.01); *C07C 39/06* (2013.01); *C07C 39/12* (2013.01); *C07C 39/14* (2013.01); *C07C 39/23* (2013.01); *C07C 39/367* (2013.01); *C07C 39/42* (2013.01); *C07C 43/196* (2013.01); *C07C 49/733* (2013.01); *C07C 49/755* (2013.01); *C07C 57/38* (2013.01); *C07C 235/34* (2013.01); *C07C 255/47* (2013.01); *C07C 2601/14* (2017.05); *C07C 2602/08* (2017.05); *C07C 2602/10* (2017.05); *C07C 2603/74* (2017.05)

(58) Field of Classification Search
CPC ......... C07C 39/17; C07C 39/06; C07C 39/42; C07C 235/34; C07C 255/47; A61K 31/047; A61K 31/055; A61K 31/05; A61K 31/025; A61P 25/00; A61P 35/00
USPC .......................... 514/765, 764; 568/734, 737
See application file for complete search history.

(56) References Cited

U.S. PATENT DOCUMENTS

2007/0066628 A1    3/2007   Zhang et al.
2009/0214698 A1    8/2009   Topsoe et al.

FOREIGN PATENT DOCUMENTS

WO          2003/051805 A2      6/2003
WO      WO-2007096647 A2 *      8/2007   .............. C07C 37/62

OTHER PUBLICATIONS

Wang, Z., Y. Li, C. Ai and Y. Wang, "In Silico prediction of estrogen receptor subtype binding affinity and selectivity using statistical methods and molecular docking with 2-Arylnapthalenes and 2-Arylquinolines" Int. J. Mol. Sci. (2010), 11: pp. 3434-3458. (Year: 2010).*

(Continued)

*Primary Examiner* — Matthew P Coughlin
*Assistant Examiner* — Sagar Patel
(74) *Attorney, Agent, or Firm* — Michael Best & Friedrich LLP

(57) ABSTRACT

Provided are compounds of formulae provided herein. The compounds may include pathway-preferential estrogens (PaPEs) derivatives with tissue-selective activities. Also provided are pharmaceutical compositions comprising the compounds, as well as methods of treating a disease or condition including administering the compounds. The disease or condition may include postmenopausal symptoms, cardiovascular disease, stroke, vascular disease, bone disease, metabolic disease, arthritis, osteoporosis, obesity, vasomotor/hot flush, cognitive decline, cancer including breast cancer.

21 Claims, 47 Drawing Sheets

(56) References Cited

OTHER PUBLICATIONS

Allegretti, P., M. Mercedes Schiavoni, E. Castro and J. Furlong, "Tautomeric Equilibria Studies by Mass Spectrometry" World Journ. Chem. (2007), 2 (2), pp. 25-62. (Year: 2007).*
STN CAS Registry RN 1270832-99-9 (Entered STN: Mar. 28, 2011). (Year: 2011).*
Abot et al., "The uterine and vascular actions of estetrol delineate a distinctive profile of estrogen receptor α modulation, uncoupling nuclear and membrane activation," EMBO Mol Med, 2014, 6(10):1328-46.
Adlanmerini et al., "Mutation of the palmitoylation site of estrogen receptor α in vivo reveals tissue-specific roles for membrane versus nuclear actions," Proc Natl Acad Sci USA, 2014, 111(2):E283-90.
Albert et al., "mTOR signaling in cellular and organismal energetics," Curr Opin Cell Biol, 2015, 33, 55-66.
Almeida et al., "Classical genotropic versus kinase-initiated regulation of gene transcription by the estrogen receptor alpha," Endocrinology, 2006, 147(4):1986-96.
Anstead et al., "The estradiol pharmacophore: ligand structure-estrogen receptor binding affinity relationships and a model for the receptor binding site," Steroids, 1997, 62, 268-303.
Appachi et al., "Non-nuclear estrogen receptor activation is protective in cardiac ischemia-reperfusion injury in mice," Journal of Molecular and Cellular Cardiology, 2012, 53, Abstract 086, p. S25.
Ayroldi et al., "Mechanisms of the anti-inflammatory effects of glucocorticoids: genomic and nongenomic interference with MAPK signaling pathways," FASEB journal: official publication of the Federation of American Societies for Experimental Biology, 2012, 26, 4805-4820.
Bai et al., "Breast Cancer, Estrogen Receptor and Ligands," Arch. Pharm. Chem. Life Sci., 2009, 342, 133-149.
Banerjee et al., "Recent insights into non-nuclear actions of estrogen receptor alpha," Steroids, 2014, 81, 64-69.
Bartell et al., "Non-Nuclear—Initiated Actions of the Estrogen Receptor Protect Cortical Bone Mass," Mol Endocrinol, 2013, 27(4):649-56.
Beaven et al., "Reciprocal regulation of hepatic and adipose lipogenesis by liver X receptors in obesity and insulin resistance," Cell Metab, 2013, 18, 106-117.
Berge et al., "Pharmaceutical salts," J. Pharm. Sci., 1977, 66:1-19.
Boonyaratanakornkit et al., "The role of extranuclear signaling actions of progesterone receptor in mediating progesterone regulation of gene expression and the cell cycle," Molecular endocrinology (Baltimore, Md.), 2007, 21, 359-375.
Braga-Sobrinho et al., "Action of ANP on the nongenomic dose-dependent biphasic effect of aldosterone on NHE1 in proximal S3 segment," The Journal of steroid biochemistry and molecular biology, 2012, 128, 89-97.
Bravo et al., "The classic receptor for 1α,25-dihydroxy vitamin D3 is required for non-genomic actions of 1α,25-dihydroxy vitamin D3 in osteosarcoma cells," Journal of cellular biochemistry, 2006, 99, 995-1000.
Buitrago et al., "Role of VDR in 1α,25-dihydroxyvitamin D3-dependent non-genomic activation of MAPKs, Src and Akt in skeletal muscle cells," The Journal of steroid biochemistry and molecular biology, 2013, 136, 125-130.
Carlson et al., "Altered ligand binding properties and enhanced stability of a constitutively active estrogen receptor: evidence that an open pocket conformation is required for ligand interaction," Biochemistry, 1997, 36, 14897-14905.
Centrella et al., "Estren (4-Estren-3α,17β-diol) is a prohormone that regulates both androgenic and estrogenic transcriptional effects through the androgen receptor," Mol Endocrinol, 2004, 18(5):1120-30.
Chambliss et al., "Non-nuclear estrogen receptor alpha signaling promotes cardiovascular protection but not uterine or breast cancer growth in mice," J Clin Invest, 2010, 120(7):2319-30.
Chang et al., "Estrogen Receptors alpha and beta as determinants of gene expression: influence of ligand, dose, and chromatin binding," Molecular Endocrinology, 2008, 22, 1032-1043.
Chang et al., "Impact of Estrogen Receptor β on Gene Networks Regulated by Estrogen Receptor α in Breast Cancer Cells," Endocrinology, 2006, 147, 4831-4842.
Chiang et al., "The anti-cancer actions of vitamin D," Anti-cancer agents in medicinal chemistry, 2013, 13, 126-139.
Clark et al., "Estrogen receptor-mediated transcription involves the activation of multiple kinase pathways in neuroblastoma cells," J Steroid Biochem Mol Biol, 2014, 139, 45-53.
Deng et al., "Rapid Glucocorticoid Feedback Inhibition of ACTH Secretion Involves Ligand-Dependent Membrane Association of Glucocorticoid Receptors," Endocrinology, 2015, 156, 3215-3227.
Dennis et al., "DAVID: Database for Annotation, Visualization, and Integrated Discovery," Genome biology, 2003, 4:R60.1-R60.11.
Deroo et al., "Estrogen receptors and human disease," Journal of Clinical Investigation, 2006, 116, 561-570.
Dupont et al., "Effect of single and compound knockouts of estrogen receptors α (ERα) and ß (ERß) on mouse reproductive phenotypes," Development, 2000, 127, 4277-4291.
Finan et al., "Targeted estrogen delivery reverses the metabolic syndrome," Nat Med, 2012, 18(12):1847-56.
Fox et al., "ERß in breast cancer—Onlooker, passive player, or active protector?," Steroids, 2008, 73, 1039-1051.
Gee et al., "Coactivator peptides have a differential stabilizing effect on the binding of estrogens and antiestrogens with the estrogen receptor," Molecular endocrinology, 1999, 13, 1912-1923.
Gonzalez Deniselle et al., "Experimental and clinical evidence for the protective role of progesterone in motoneuron degeneration and neuroinflammation," Hormone molecular biology and clinical investigation, 2011, 7(3):403-411.
Gonzalez-Montelongo et al., "Androgens differentially potentiate mouse intestinal smooth muscle by nongenomic activation of polyamine synthesis and Rho kinase activation," Endocrinology, 2006, 147, 5715-5729.
Gossye et al., "Differential mechanism of NF-kappaB inhibition by two glucocorticoid receptor modulators in rheumatoid arthritis synovial fibroblasts," Arthritis and rheumatism, 2009, 60, 3241-3250.
Groeneweg et al., "Mineralocorticoid and glucocorticoid receptors at the neuronal membrane, regulators of nongenomic corticosteroid signalling," Molecular and cellular endocrinology, 2012, 350, 299-309.
Hammes et al., "Minireview: Recent advances in extranuclear steroid receptor actions," Endocrinology, 2011, 152, 4489-4495.
Hara et al., "Estrogen Effects on Cognitive and Synaptic Health Over the Lifecourse," Physiological reviews, 2015, 95. 785-807.
Harrington et al., "Estrogen dendrimer conjugates that preferentially activate extranuclear, nongenomic versus genomic pathways of estrogen action," Mol Endocrinol, 2006, 20(3):491-502.
Hatanaka et al., "Rapid increase of spines by dihydrotestosterone and testosterone in hippocampal neurons: Dependence on synaptic androgen receptor and kinase networks," Brain research, 2015, 1621, 121-132.
Haussler et al., "Vitamin D receptor (VDR)-mediated actions of 1α,25(OH)$_2$vitamin D$_3$: genomic and non-genomic mechanisms," Best practice & research. Clinical endocrinology & metabolism, 2011, 25, 543-559.
Haynes et al., "Occurrence of pharmaceutically acceptable anions and cations in the Cambridge Structural Database," J. Pharm. Sci., 2005, 94:2111-2120.
Hewitt et al., "Biological and biochemical consequences of global deletion of exon 3 from the ERα gene," FASEB J., 2010, 24, 4660-4667.
Hewitt et al., "Estren behaves as a weak estrogen rather than a nongenomic selective activator in the mouse uterus," Endocrinology, 2006, 147(5):2203-14.
Higuchi et al., "Liver X receptor in cooperation with SREBP-1c is a major lipid synthesis regulator in nonalcoholic fatty liver disease," Hepatol Res, 2008, 38, 1122-1129.
Hsu et al., "Extra-nuclear activation of progesterone receptor in regulating arterial smooth muscle cell migration," Atherosclerosis, 2011, 217, 83-89.

(56) References Cited

OTHER PUBLICATIONS

Ishikawa et al., "LXRbeta/estrogen receptor-alpha signaling in lipid rafts preserves endothelial integrity," J Clin Invest 123, 2013, 3488-3497.
Islander et al., "Estren promotes androgen phenotypes in primary lymphoid organs and submandibular glands," BMC Immunol, 2005, 6:16, 12 pages.
Jeyakumar et al., "A dual-acceptor time-resolved Foster resonance energy transfer assay for simultaneous determination of thyroid hormone regulation of corepressor and coactivator binding to the thyroid hormone receptor: Mimicking the cellular context of thyroid hormone action," Analytical biochemistry, 2009, 386, 73-78.
Jeyakumar et al., "Exploration of dimensions of estrogen potency: parsing ligand binding and coactivator binding affinities," The Journal of biological chemistry, 2011, 286, 12971-12982.
Jia et al., "Overnutrition, mTOR signaling, and cardiovascular diseases," Am J Physiol Regul Integr Comp Physiol, 2014, 307, R1198-1206.
Joëls et al., "Unraveling the time domains of corticosteroid hormone influences on brain activity: rapid, slow, and chronic modes," Pharmacological reviews, 2012, 64, 901-938.
Karlsson et al., "Vitamin D and prostate cancer: the role of membrane initiated signaling pathways in prostate cancer progression," The Journal of steroid biochemistry and molecular biology, 2010, 121, 413-416.
Karolchik et al., "The UCSC Genome Browser Database," Nucleic Acids Res, 2003, 31, 51-54.
Kato et al., "Activation of the estrogen receptor through phosphorylation by mitogen-activated protein kinase," Science, 1995, 270, 1491-1494.
Kousteni et al., "Induction of Osteoblast Differentiation by Selective Activation of Kinase-Mediated Actions of the Estrogen Receptor," Mol Cell Biol, 2007, 27(4):1516-30.
Kousteni et al., "Kinase-mediated regulation of common transcription factors accounts for the bone-protective effects of sex steroids," J Clin Invest, 2003, 111(11):1651-64.
Kousteni et al., "Nongenotropic, sex-nonspecific signaling through the estrogen or androgen receptors: dissociation from transcriptional activity," Cell, 2001, 104(5):719-30.
Kousteni et al., "Reversal of bone loss in mice by nongenotropic signaling of sex steroids," Science, 2002, 298(5594):843-6.
Krishnan et al., "The nongenotropic synthetic ligand 4-estren-3α17ß-diol is a high-affinity genotropic androgen receptor agonist," Mol Pharmacol, 2005, 67(3):744-8.
Lee et al., "Non-genomic effect of glucocorticoids on cardiovascular system," Pflugers Archiv: European journal of physiology, 2012, 464, 549-559.
Lesuisse et al., "Biphenyls as surrogates of the steroidal backbone. Part 1: synthesis and estrogen receptor affinity of an original series of polysubstituted biphenyls," Bioorganic & medicinal chemistry letters, 2001, 11, 1709-1712.
Liu et al., "Cistrome: an integrative platform for transcriptional regulation studies," Genome biology, 2011, 12, R83, 10 pages.
Liu et al., "Androgens and cardiovascular disease," Endocrine reviews, 2003, 24, 313-340.
Luong et al., "The role of vitamin D in asthma," Pulmonary pharmacology & therapeutics, 2012, 25, 137-143.
Madak-Erdogan et al., "Design of pathway preferential estrogens that provide beneficial metabolic and vascular effects without stimulating reproductive tissues," Science Signaling, 2016, 9(429):ra53, 17 pages.
Madak-Erdogan et al., "Genomic collaboration of estrogen receptor alpha and extracellular signal-regulated kinase 2 in regulating gene and proliferation programs," Mol Cell Biol, 2011, 31, 226-236.
Madak-Erdogan et al., "Integrative genomics of gene and metabolic regulation by estrogen receptors alpha and beta, and their coregulators," Mol Syst Biol, 2013, 9, 676, 19 pages.
Madak-Erdogan et al., "Novel roles for ERK5 and cofilin as critical mediators linking ERα-driven transcription, actin reorganization, and invasiveness in breast cancer," Mol Cancer Res, 2014, 12, 714-727.
Madak-Erdogan et al., "Nuclear and extranuclear pathway inputs in the regulation of global gene expression by estrogen receptors," Mol Endocrinol, 2008, 22(9):2116-27.
Mani et al., "Progesterone signaling mechanisms in brain and behavior," Frontiers in endocrinology, 2012, 3, 7, 8 pages.
Mani et al., "Neural progestin receptors and female sexual behavior," Neuroendocrinology, 2012, 96, 152-161.
McDonnell et al., "The molecular mechanisms underlying the pharmacological actions of ER modulators: implications for new drug discovery in breast cancer," Current opinion in pharmacology, 2010, 10, 620-628.
McLean et al., "GREAT improves functional interpretation of cis-regulatory regions," Nature biotechnology, 2010, 28, 495-501.
Moore et al., "Multiple functional therapeutic effects of the estrogen receptor beta agonist indazole-Cl in a mouse model of multiple sclerosis," Proceedings of the National Academy of Sciences of the United States of America, 2014, 111, 18061-18066.
Osipo et al., "The consequences of exhaustive antiestrogen therapy in breast cancer: Estrogen-induced tumor cell death," Experimental Biology and Medicine, 2004, 229, 722-731.
Otto et al., "Exploiting nongenomic estrogen receptor-mediated signaling for the Development of pathway-selective Estrogen receptor ligands," Ernst Schering Found Symp Proc, 2006, (1):163-181.
Otto et al., "In vivo characterization of estrogen receptor modulators with reduced genomic versus nongenomic activity in vitro," J Steroid Biochem Mol Biol, 2008, 111(1-2):95-100.
Pang et al., "Progesterone increases nitric oxide synthesis in human vascular endothelial cells through activation of membrane progesterone receptor-α," American journal of physiology. Endocrinology and metabolism, 2015, 308, E899-911.
Paris et al., "Phenylphenols, biphenols, bisphenol-A and 4-tert-octylphenol exhibit α and ß estrogen activities and antiandrogen activity in reporter cell lines," Molecular and cellular endocrinology, 2002, 193, 43-49.
Pasricha et al., "Rapid effects of corticosterone in the mouse dentate gyrus via a nongenomic pathway," Journal of neuroendocrinology, 2011, 23, 143-147.
Paterni et al., "Estrogen Receptors Alpha (ERα) and Beta (ERβ): Subtype-Selective Ligands and Clinical Potential," Steroids, 2014, 90, 13-29.
Pedram et al., "Developmental phenotype of a membrane only estrogen receptor α (MOER) mouse," J Biol Chem, 2009, 284(6):3488-95.
Pedram et al., "Estrogen reduces lipid content in the liver exclusively from membrane receptor signaling," Sci Signal, 2013, 6(276):ra36, 12 pages.
Pedram et al., "Membrane and nuclear estrogen receptor α collaborate to suppress adipogenesis but not triglyceride content," FASEB J, 2016, 30(1):230-40.
Pedram et al., "Membrane-localized estrogen receptor alpha is required for normal organ development and function," Dev Cell, 2014, 29, 482-490.
Pruitt et al., "NCBI reference sequences (RefSeq): a curated non-redundant sequence database of genomes, transcripts and proteins," Nucleic Acids Res, 2007, 35, D61-65.
PubChem Substance Record for SID 230773243. <https://pubchem.ncbi.nlm.nih.gov/substance/230773243> Feb. 12, 2015.
PubChem Substance Record for SID 89960275. <https://pubchem.ncbi.nlm.nih.gov/compound/89960275 > Mar. 22, 2010.
PubChem Substance Record for SID 223685320. <https://pubchem.ncbi.nlm.nih.gov/substance/223685320> Jan. 6, 2015.
PubChem Substance Record for SID 131321332. <https://pubchem.ncbi.nlm.nih.gov/compound/131321332> Dec. 12, 2011.
PubChem Substance Record for SID 143533528. <https://pubchem.ncbi.nlm.nih.gov/substance/143533528> Aug. 29, 2012.
PubChem Substance Record for SID 227716744. <https://pubchem.ncbi.nlm.nih.gov/substance/227716744> Feb. 12, 2015.
Rubio-Patiño et al., "Glycogen synthase kinase-3ß is involved in ligand-dependent activation of transcription and cellular localiza-

(56) References Cited

OTHER PUBLICATIONS tion of the glucocorticoid receptor," Molecular endocrinology (Baltimore, Md.), 2012, 26, 1508-1520.
Rai et al., "Distinctive actions of membrane-targeted versus nuclear localized estrogen receptors in breast cancer cells," Molecular endocrinology, 2005, 19, 1606-1617.
Rich et al., "Kinetic analysis of estrogen receptor/ligand interactions," Proceedings of the National Academy of Sciences of the United States of America, 2002, 99, 8562-8567.
Sarabdjitsingh et al., "Ultradian corticosterone pulses balance glutamatergic transmission and synaptic plasticity," Proceedings of the National Academy of Sciences of the United States of America, 2014, 111, 14265-14270.
Schoneveld et al., "Nongenomic glucocorticoid signaling: new targets for immunosuppressive therapy?," Arthritis and rheumatism, 2011, 63, 3665-3667.
Schweiger et al, "Synthesis of a C,D-ring analog of 17-α-hydroxyprogesterone," Tetrahedron letters, 1997, 38(35):6127-6130.
Seetharam et al., "High-density lipoprotein promotes endothelial cell migration and reendothelialization via scavenger receptor-B type I," Circulation research, 2006, 98, 63-72.
Sen et al., "Paxillin regulates androgen- and epidermal growth factor-induced MAPK signaling and cell proliferation in prostate cancer cells," The Journal of biological chemistry, 2010, 285, 28787-28795.
Swedenborg et al., "Regulation of estrogen receptor beta activity and implications in health and disease," Cellular and Molecular Life Sciences, 2009, 66, 3873-3894.
Tamrazi et al., "Molecular sensors of estrogen receptor conformations and dynamics," Mol Endocrinol, 2003, 17, 2593-2602.
Tchkonia et al., "Mechanisms and metabolic implications of regional differences among fat depots," Cell Metab, 2013, 17, 644-656.
Trapnell et al., "TopHat: discovering splice junctions with RNA-Seq," Bioinformatics, 2009, 25, 1105-1111.
Trochoutsou et al., "Vitamin-D in the Immune System: Genomic and Non-Genomic Actions," Mini reviews in medicinal chemistry, 2015, 15, 39 pages.
Tsai et al., "Increased expression of mineralocorticoid receptor in human atrial fibrillation and a cellular model of atrial fibrillation," Journal of the American College of Cardiology, 2010, 55, 758-770.
Valéra et al., "Protective Hematopoietic Effect of Estrogens in a Mouse Model of Thrombosis: Respective Roles of Nuclear Versus Membrane Estrogen Receptor α," Endocrinology, 2015, 156(11):4293-4301.
Vasudevan et al., "Early membrane estrogenic effects required for full expression of slower genomic actions in a nerve cell line," Proceedings of the National Academy of Sciences of the United States of America, 2001, 98, 12267-12271.
Waters et al., "Ultrastructural localization of extranuclear progestin receptors in the rat hippocampal formation," The Journal of comparative neurology, 2008, 511, 34-46.
Wendler et al., "Translational research on rapid steroid actions," Steroids, 2010, 75, 619-623.
Wessler et al., "Identification of estrogen receptor ligands leading to activation of non-genomic signaling pathways while exhibiting only weak transcriptional activity," J Steroid Biochem Mol Biol, 2006, 98(1):25-35.
Windahl et al., "Bone protection by estrens occurs through non-tissue-selective activation of the androgen receptor," J Clin Invest, 2006, 116(9):2500-9.
Wright et al., "A-CD estrogens. I. Substituent effects, hormone potency, and receptor subtype selectivity in a new family of flexible estrogenic compounds," J Med Chem, 2011, 54, 433-448.
Yecies et al., "Akt stimulates hepatic SREBP1c and lipogenesis through parallel mTORC1-dependent and independent pathways," Cell Metab, 2011, 14, 21-32.
Yecies et al., "Transcriptional control of cellular metabolism by mTOR signaling," Cancer Res, 2011, 71, 2815-2820.
Yoshiya et al., "Corticosterone rapidly increases thorns of CA3 neurons via synaptic/extranuclear glucocorticoid receptor in rat hippocampus," Frontiers in neural circuits, 2013, 7, 191, 9 pages.
Zarif et al., "Androgen receptor non-nuclear regulation of prostate cancer cell invasion mediated by Src and matriptase," Oncotarget, 2015, 6, 6862-6876.
Zhang et al., "Glucocorticoid acts on a putative G protein-coupled receptor to rapidly regulate the activity of NMDA receptors in hippocampal neurons," American journal of physiology. Endocrinology and metabolism, 2012, 302, E747-758.
Zhao et al., "Dual suppression of estrogenic and inflammatory activities for targeting of endometriosis," Sci Transl Med, 2015, 7, 271ra9, 30 pages.
Zhao et al., "Membrane localization, Caveolin-3 association and rapid actions of vitamin D receptor in cardiac myocytes," Steroids, 2010, 75, 555-559.
Zhao et al., "The Coregulator, Repressor of Estrogen Receptor Activity (REA), Is a Crucial Regulator of the Timing and Magnitude of Uterine Decidualization," Endocrinology, 2013, 154, 1349-1360.
Zoller et al., "Estrogen induces thymic atrophy by eliminating early thymic progenitors and inhibiting proliferation of beta-selected thymocytes," J Immunol, 2006, 176, 7371-7378.
International Search Report and Written Opinion for Application No. PCT/US2017/012586 dated Apr. 19, 2017 (17 pages).
European Patent Office Partial Supplementary Search Report for Application No. 17736458.5 dated Jun. 17, 2019 (21 pages).
Wetzel et al., "Introduction of an Electron Withdrawing Group on the Hydroxyphenylnaphthol Scaffold Improves the Potency of 17β-Hydroxysteroid Dehydrogenase Type 2 (17β-HSD2) Inhibitors," Journal of Medicinal Chemistry, 2011, 54(21):7547-7557.
Allan et al., "Novel inhibitors of 17β-hydroxysteroid dehydrogenase type 1: Templates for design," Bioorganic & Medicinal Chemistry, 2008, 16(8):4438-4456.
Chordia et al., "6-Aryl-8H-indeno[1,2-d]thiazol-2-ylamines: A1 Adenosine Receptor Agonist Allosteric Enhancers Having Improved Potency," Journal of Medicinal Chemistry, 2005, 48(16):5131-5139.
European Patent Office Extended Search Report for Application No. 17736458.5 dated Sep. 27, 2019 (15 pages).

* cited by examiner

| Property | E2 | PaPE-1 | PaPE-2 | PaPE-3 | PaPE-4 |
|---|---|---|---|---|---|
| Molecular Formula | $C_{18}H_{24}O_2$ | $C_{17}H_{18}O_2$ | $C_{16}H_{18}O_2$ | $C_{18}H_{20}O_2$ | $C_{21}H_{26}N_2O_4$ |
| MW | 272.4 | 254.3 | 242.1 | 268.4 | 370.5 |
| cLogP | 3.78 | 3.64 | 3.53 | 4.20 | 1.54 |
| Volume | 269 $Å^3$ | 244 $Å^3$ | 238 $Å^3$ | 261 $Å^3$ | 351 $Å^3$ |
| Polar Surface Area | 40.5 $Å^2$ | 40.5 $Å^2$ | 40.5 $Å^2$ | 40.5 $Å^2$ | 98.7 $Å^2$ |
| ERα $K_i$ [RBA] | 0.2 nM [100] | 10 µM [0.002] | 10 µM [0.002] | 10 µM [0.002] | 20 µM [0.001] |
| ERβ $K_i$ [RBA] | 0.5 nM [100] | 25 µM [0.002] | 13 µM [0.004] | 17 µM [0.003] | 17 µM [0.003] |

Compound 2 (PaPE-1) and selective estrogen receptor modulators (SERMs) hydroxytamoxifen (HO-TAM) and raloxifene (RAL)

COMPOUNDS WHICH ACTIVATE ESTROGEN RECEPTORS AND COMPOSITIONS AND METHODS OF USING THE SAME

CROSS-REFERENCE TO RELATED APPLICATIONS

This patent application is the U.S. national stage entry, under 35 U.S.C. § 371, of international application number PCT/US2017/012586, filed Jan. 6, 2017, which claims priority to U.S. Provisional Application No. 62/275,416, filed Jan. 6, 2016, the entire contents of which are hereby incorporated by reference.

STATEMENT REGARDING FEDERALLY SPONSORED RESEARCH OR DEVELOPMENT

This invention was made with government support under AT006288, DK015556, and HL087564 awarded by National Institutes of Health, and ILLU-698-909 awarded by the U.S. Department of Agriculture. The government has certain rights in the invention.

BACKGROUND

Estrogens regulate many essential physiological processes and are needed for the functional maintenance of many adult target tissues within and outside of the reproductive system. They can, however, have deleterious actions in promoting breast and uterine cancers. This balance of desirable versus undesirable activities in diverse target tissues offers an intriguing opportunity for the development of tissue-selective estrogens that provide a net benefit with minimal risk for menopausal hormone replacement, such as ones affording bone health, relief from vasomotor symptoms, and metabolic and vascular protection without stimulation of the breast or uterus.

It is now recognized that estrogens act through estrogen receptors (ERs) by utilizing two distinct signaling pathways, the direct nuclear-initiated ("genomic") pathway, wherein ER functions as a chromatin-binding ligand-regulated transcription factor, and the extranuclear-initiated ("non-genomic") pathway, which involves kinase cascades initiated by ER action from outside the nucleus. The activation of specific kinases by the action of estrogens through extranuclear ER action is generally rapid and often transient, and its initiation likely requires only the input of a triggering signal by the ER-hormone complex to initiate a kinase cascade and cellular activities through the extranuclear-initiated ER signaling pathway. By contrast, the activation of genes through the direct nuclear ER signaling pathway appears to require a more sustained action of ER-hormone complexes, sufficient to effect dissociation of heat shock proteins, recruit coregulator proteins, stimulate ER binding to chromatin, alter chromatin architecture and modify histones, and activate RNA pol II to initiate gene transcription. ER ligands with potent nuclear ER activity form more kinetically stable receptor-cofactor complexes, and coactivator binding can slow ligand dissociation rates by orders of magnitude (Gee, Mol Endocrinol 13, 1912-1923, 1999). Thus, it seemed possible that ER ligands preferential for extranuclear over nuclear ER signaling might be obtained by redesigning the structures of certain estrogens in ways that would preserve their essential chemical features, a phenol and often a secondary alcohol, as well as their overall composition and geometry, but would reduce considerably their high affinity ER binding.

There is great medical need for estrogens having favorable pharmacological profiles, supporting desirable activities for menopausal women such as bone health, relief from vasomotor symptoms, and metabolic and vascular protection but lacking stimulatory activities on the breast and uterus.

SUMMARY

In an aspect, the present disclosure provides a compound of formula (i):

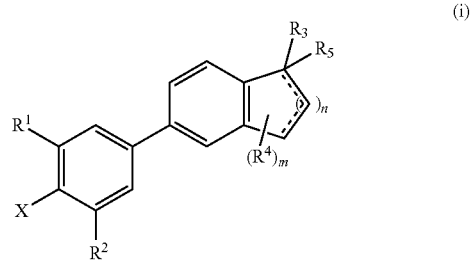

(i)

and stereoisomers and pharmaceutically acceptable salts thereof;
wherein
  n is an integer from 0 to 4;
  m is an integer from 0 to 4;
  X is H, hydroxy, or $C_{1-4}$ alkoxy;
  $R_1$ and $R_2$ are independently H, hydroxy, $C_{1-4}$ alkyl, $C_{1-4}$ alkoxy, amino, —S—$C_{1-4}$ alkyl, or halo;
  $R_3$ is H, hydroxy, oxo, cyano, halo, $C_{1-4}$ alkyl, or $C_{1-4}$ alkoxy;
  each $R_4$ is independently hydrogen, hydroxy, oxo, halo, $C_{1-4}$ alkyl, or $C_{1-4}$ alkoxy;
  $R_5$ is H, $C_{1-4}$ alkynyl, or is absent if a double bond is present; and
  --- is an optional double bond.

In another aspect, the present disclosure provides a compound according to formula (iii):

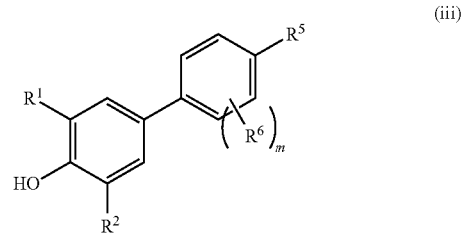

(iii)

and stereoisomers and salts thereof;
wherein
  m is an integer from 0 to 3;
  $R_1$ and $R_2$ are independently H, hydroxy, $C_{1-4}$ alkyl, $C_{1-4}$ alkoxy, amino, —S—$C_{1-4}$ alkyl, or halo;
  $R_5$ is H, hydroxy, or $C_{1-4}$ alkyl; and
  each $R_6$ is independently H, hydroxy, halo, or $C_{1-4}$ alkyl.

In another aspect the present disclosure provides a compound having the formula (iv):

(iv)

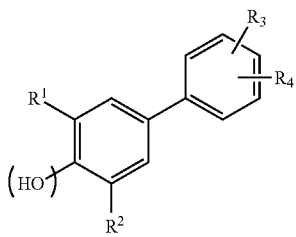

wherein $R_1$ and $R_2$ is selected from H, $C_{1-4}$ alkyl group, haloalkyl, hydroxyalkyl, alkyloxyalkyl, cycloalkyloxyalkyl, alkylthio, alkylthioalkyl, cycloalkylthioalkyl, R'R"N-alkyl where R' and R" are independently alkyl, alkylcarbonyl, or cyclic alkyl, and the parenthesis represents the presence or absence of hydroxyl; and $R_3$ and $R_4$ are independently selected from H, hydroxy, $C_{1-4}$ alkyl, hydoxy-$C_{1-4}$alkyl, cyano, cyanoalkyl, nitro, nitroalkyl, —C(O)-aryl, —C(O)H, alkyl aldehyde, carboxyl, and carboxyalkyl; or $R_3$ and $R_4$ form a ring of from 4 to 8 member atoms, wherein the ring is substituted with cyano or hydroxy.

In another aspect, the present disclosure provides a compound according to formula (vi):

(vi)

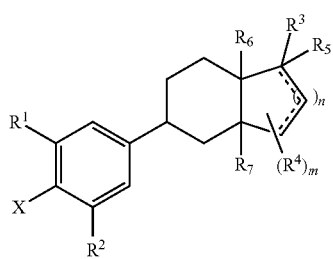

and stereoisomers and pharmaceutically acceptable salts thereof;
wherein
n is an integer from 0 to 4;
m is an integer from 0 to 4;
X is H, hydroxy, or $C_{1-4}$ alkoxy;
$R_1$ and $R_2$ are independently H, hydroxy, $C_{1-4}$ alkyl, $C_{1-4}$ alkoxy, amino, —S—$C_{1-4}$ alkyl, or halo;
$R_3$ is H, hydroxy, oxo, cyano, halo, $C_{1-4}$ alkyl, or $C_{1-4}$ alkoxy;
each $R_4$ is independently hydrogen, hydroxy, oxo, halo, $C_{1-4}$ alkyl, or $C_{1-4}$ alkoxy;
$R_5$ is H, alkynyl, or is absent if a double bond is present;
$R_6$ and $R_7$ are independently selected from $C_{1-4}$ alkyl and H; and
--- is an optional double bond.

In another aspect, the present disclosure provides a compound according to formula (vii):

(vii)

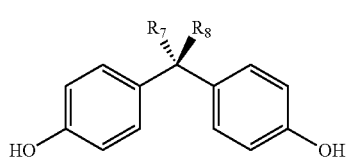

and stereoisomers and salts thereof;

wherein
$R_7$ and $R_8$ are independently H, $C_{1-5}$ alkyl, amino, hydroxyl, cyano, amido, cyclic $C_{3-8}$ alkyl, or heterocyclyl.

In another aspect, the present disclosure provides a pharmaceutical composition comprising a compound described herein and a pharmaceutically acceptable excipient.

In another aspect, the present disclosure provides methods of using the compounds and compositions described herein.

BRIEF DESCRIPTION OF THE DRAWINGS

The features, objects and advantages other than those set forth above will become more readily apparent when consideration is given to the detailed description below. Such detailed description makes reference to the following drawings, wherein.

Figure 1:
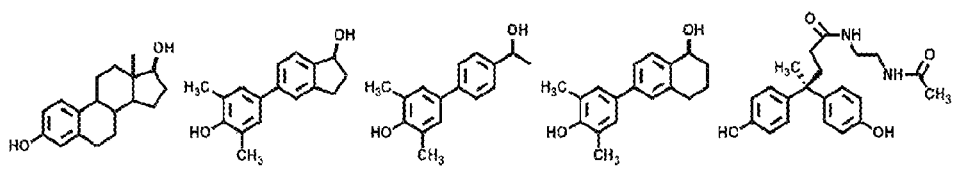
FIG. 1. Structures and molecular and binding properties of E2 and four PaPEs. MW is molecular weight, c Log P is $Log_{10}$ of the calculated octanol-water partition coefficient, Volume is molecular volume, Polar Surface Area is a measure of compound polarity, all obtained using ChemBioDraw Ultra (ver. 13.0.0.3015). Relative binding affinity (RBA) values were determined by competitive radiometric binding assays (Carlson et. al. Biochemistry 36, 14897-14905, 1997). E2 is set at 100 on both ERs. $K_i$ values calculated as $K_i=K_d$ (for E2)×(100/RBA), where $K_d$ of E2 is 0.2 nM (ERα) and 0.5 nM (ERβ). Values are average of 3-4 determinations with coefficients of variation <0.3.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

The patent or application file contains at least one drawing executed in color. Copies of this patent or patent application publication with color drawing(s) will be provided by the Office upon request and payment of the necessary fee.

DETAILED DESCRIPTION

The compositions now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the compositions described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Overview

The present disclosure includes compounds of the claimed formulae. The compounds may be capable of having interaction with ER that may be sufficient to activate the extranuclear-initiated signaling pathway preferentially over the direct nuclear-initiated pathway. In embodiments, the compound has an affinity for ER that is about 50,000-fold less than that of the standard estrogen estradiol, or about 25,000-fold less, or about 10,000-fold less, or about 5,000-fold less, or about 1,000-fold less. The compounds may comprise Pathway Preferential Estrogens (PaPEs) that have higher activity or potency on the extranuclear-initiated pathway of estrogen receptor action over the direct nuclear-initiated pathway. The preference of the compounds for activating the extranuclear-initiated pathway may result in a favorable pattern of cellular and in vivo biological effects that can be beneficial to human health. The compounds may elicit a pattern of gene regulation and cellular and biological processes that may result in minimal or no stimulation of reproductive tissues, mammary tissues, or breast cancer cells. Without wishing to be bound by theory, the stimulation of these tissues is usually considered to be due largely to the nuclear-initiated actions of estrogens; hence the compounds have only limited activity compared to the stimulation effected by the standard estrogen estradiol. In embodiments, the compounds may result in less than about 20% stimulation of reproductive tissues, mammary tissues, or breast cancer cells, compared to the stimulation effected by the standard estrogen estradiol, or less than about 15%, or less than about 10%, or less than about 5%, or less than about 2%, or less than about 1%, or less than about 0.5%, or less than about 0.1%, compared to the stimulation effected by the standard estrogen estradiol. By contrast, the compounds may have a favorable pattern of activity on metabolic tissues (adipose, liver) and the vasculature, reducing body weight gain and fat accumulation after ovariectomy and accelerating repair of endothelial damage. The stimulation of these tissues is considered to be due to a large extent to the extranuclear-initiated actions of estrogens. Hence, in the responses in these tissues, the compound may have beneficial health effects that are the same as that of the standard estrogen estradiol, or even greater, or they may be about 50% that of estradiol. This designed ligand structure alteration process represents a novel approach to govern the balance in utilization of extranuclear-initiated versus nuclear-initiated pathways of ER action to obtain tissue-selective/non-nuclear pathway-preferential estrogens that may prove to be beneficial for postmenopausal hormone replacement.

The compounds described herein may represent novel tissue-selective estrogens. In embodiments, the compounds may provide favorable actions in metabolic and vascular tissues by selective activation of signaling pathways critical for ERα action in these tissues, yet they fail to activate these pathways in reproductive tissues that would increase growth of the uterus or stimulate proliferation of mammary tissue. Without wishing to be bound by theory, it is thought that the tissue-selective actions of the compounds results from the greater retention of their activity through the non-genomic pathway than through the genomic pathway.

While the affinity of PaPE-1 and the other PaPEs for ER is approximately 50,000-fold less than that of E2, non-genomic effects were stimulated using only a ca. 100-fold excess of PaPE over E2, an observation suggesting that the non-genomic signaling pathway might have a lesser dependence on the affinity of ligand for the receptor than the genomic pathway. Also, whereas PaPE-1, -2, and -3, which were patterned after E2, all have physical characteristics (lipophilicity, polar surface area, volume, etc.) similar to that of E2, PaPE-4 is considerably larger and more polar than E2 and the other PaPEs, yet PaPE-4 has biological activities very similar to those of the other three PaPEs, suggesting that the class of PaPE-like compounds can cover a rather broad range of physical and structural characteristics.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond and from 1 to 10 carbon atoms.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "alkenylenyl," as used herein, refers to a divalent group derived from a straight or branched chain hydrocarbon of 1 to 10 carbon atoms, wherein at least one carbon-carbon bond is a double bond.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl," as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxa-adamantane (2-oxatricyclo[3.3.1.1 3,7]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate and acyl.

The term "≡" designates a single bond (—) or a double bond (═).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

In accordance with a convention used in the art, the group:

is used in structural formulas herein to depict the bond that is the point of attachment of the moiety or substituent to the core or backbone structure.

The term "acceptable" or "pharmaceutically acceptable" with respect to a compound, formulation, composition, ingredient, salt, or the like, as used herein, means having no persistent detrimental effect on the general health of the subject being treated.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. As used herein, "prevent," "preventing" and the like compared to an appropriate control subject.

As such, "preventing" means an application that involves a slowing, stopping or reversing of progression of a disease or disorder, or the application or administration of a pharmaceutical composition comprising at least one of any of the compounds described herein, where the subject has a disease or a symptom of a disease, where the purpose is to cure, heal, alleviate, relieve, alter, remedy, ameliorate, improve or affect the disease or symptoms of the disease. Although there can be overlap between "treating" and "preventing," it is intended that the latter is a more drastic (i.e., less subtle) reduction in the disease or disorder than would be observed during the former. Likewise, it is intended that "treating" can occur in an individual having a disease or disorder, whereas "preventing" can occur in an individual merely susceptible to or not yet exhibiting overt signs and symptoms of a disease or disorder.

Compounds

One aspect of the present disclosure provides compounds of the following formula:

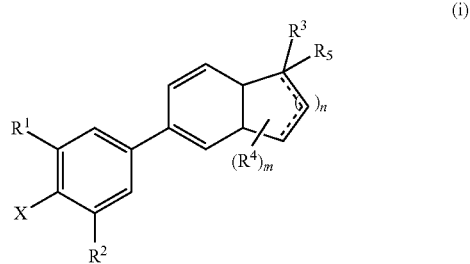

(i)

and stereoisomers and pharmaceutically acceptable salts thereof;

wherein n is an integer from 0 to 4;

m is an integer from 0 to 4;

X is H, hydroxy, or $C_{1-4}$ alkoxy;

$R_1$ and $R_2$ are independently H, hydroxy, $C_{1-4}$ alkyl, $C_{1-4}$ alkoxy, amino, —S—$C_{1-4}$ alkyl, or halo;

$R_3$ is H, hydroxy, oxo, cyano, halo, $C_{1-4}$ alkyl, or $C_{1-4}$ alkoxy;

each $R_4$ is independently hydrogen, hydroxy, oxo, halo, $C_{1-4}$ alkyl, or $C_{1-4}$ alkoxy;

$R_5$ is H, $C_{1-4}$ alkynyl, or is absent if a double bond is present; and

--- is an optional double bond.

In embodiments, $R_3$ is H, OH, oxo, chloro, cyano, or methoxy. Suitably, $R_3$ is hydroxyl.

In embodiments, at least one of $R_1$ and $R_2$ is $C_{1-4}$ alkyl. In embodiments, both $R_1$ and $R_2$ are $C_{1-4}$ alkyl. In embodiments, at least one of $R_1$ and $R_2$ is methyl. In embodiments, both $R_1$ and $R_2$ are methyl. In embodiments, $R_1$ and $R_2$ are independently selected from H, methyl, ethyl, chloro, —$CH_2OH$, and —$CH_2OMe$.

In embodiments, a $C_{1-4}$ alkyl or $C_{1-4}$ alkoxy is optionally substituted with one or more of halo, cyano, amino, hydroxy, and $C_{1-4}$ alkoxy. Suitably, the substituent is hydroxy.

In embodiments, $R_4$ is selected from fluoro, chloro, bromo, methoxy, hydroxy, or oxo.

In embodiments, $R_5$ is H. In embodiments, $R_5$ is —CCH.

In embodiments, m is 0. In embodiments, n is 1. In embodiments, n is 2.

Combinations and permutations of the preferred substituents identified in the preceding six paragraphs are explicitly contemplated.

In an aspect the present disclosure provides a compound selected from the group consisting of:

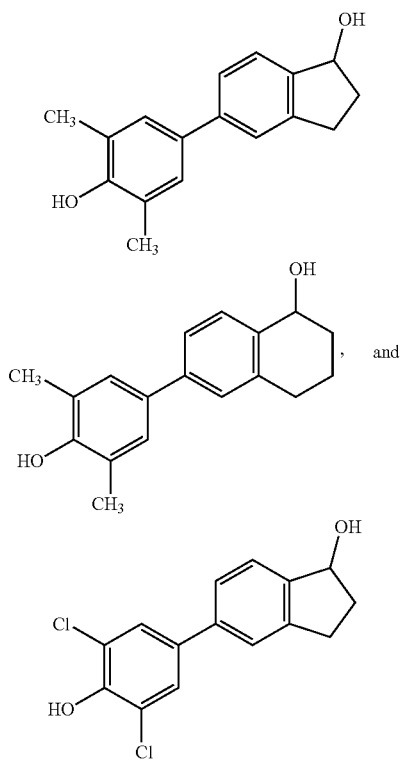

In another aspect, the present disclosure provides compounds of the following formula:

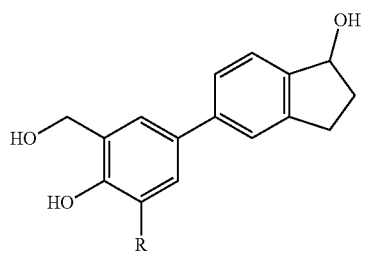

and stereoisomers and pharmaceutically acceptable salts thereof;
wherein R is H or methyl.

In another aspect, the present disclosure provides compounds of the following formula:

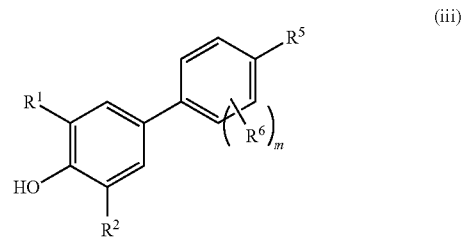

and stereoisomers and pharmaceutically acceptable salts thereof;
wherein
m is an integer from 0 to 3;
$R_1$ and $R_2$ are independently H, hydroxy, $C_{1-4}$ alkyl, $C_{1-4}$ alkoxy, amino, —S—$C_{1-4}$ alkyl, or halo;
$R_5$ is H, hydroxy, or $C_{1-4}$ alkyl; and
each $R_6$ is independently H, hydroxy, halo, or $C_{1-4}$ alkyl.

In embodiments, the $C_{1-4}$ alkyl or $C_{1-4}$ alkoxy is substituted with one or more of halo, cyano, amino, hydroxy, and $C_{1-4}$ alkoxy. Suitably, the substituent is hydroxy.

In embodiments, at least one of $R_1$ and $R_2$ is $C_{1-4}$ alkyl. In embodiments, both $R_1$ and $R_2$ are $C_{1-4}$ alkyl. In embodiments, at least one of $R_1$ and $R_2$ is methyl. In embodiments, both $R_1$ and $R_2$ are methyl. In embodiments, at least one of $R_1$ and $R_2$ is halogen, and preferably, chlorine.

In embodiments, $R_5$ is hydroxy. In embodiments, $R_5$ is $C_{1-4}$ alkyl. Suitably, $R_5$ is substituted $C_{1-4}$ alkyl. In embodiments, $R_5$ is —CH(OH)($CH_3$).

In embodiments, $R_6$ is $C_{1-4}$ alkyl. Suitably, $R_6$ is substituted $C_{1-4}$ alkyl. In embodiments, $R_6$ is —$CH_2OH$.

In embodiments, m is 1.

Combinations and permutations of the preferred substituents identified in the preceding five paragraphs are explicitly contemplated.

In an aspect the present disclosure provides a compound selected from the group consisting of:

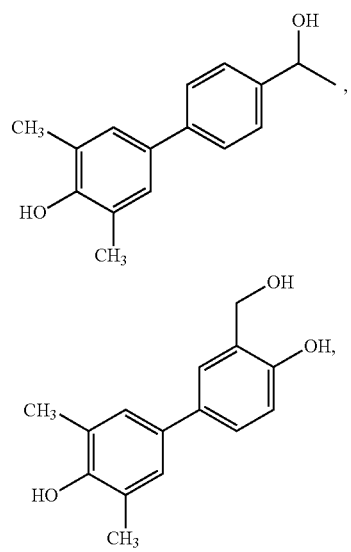

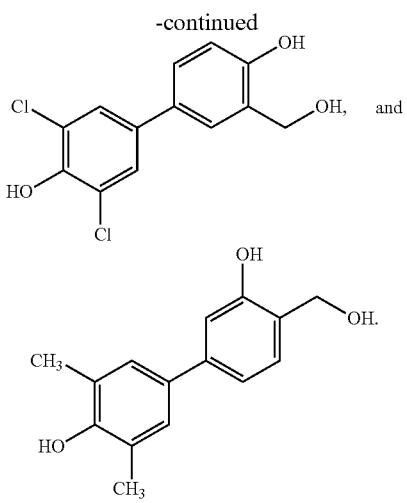

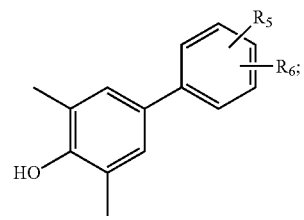

wherein $R_5$ and $R_6$ are independently selected from hydroxyl, cyano, hydroxylalkyl, cyanoalkyl, halogenated hydroxylalkyl, and halogenated cyanoalkyl.

In another aspect the present disclosure provides compounds of the following formula:

In another aspect, the present disclosure provides a compound having the formula:

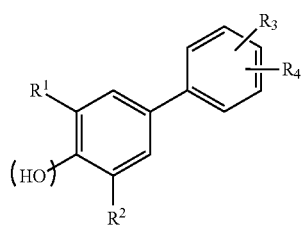

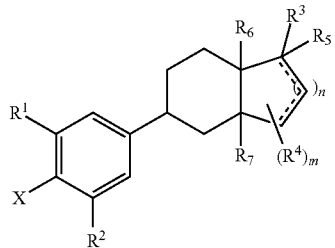

and stereoisomers and pharmaceutically acceptable salts thereof;
wherein
n is an integer from 0 to 4;
m is an integer from 0 to 4;
X is H, hydroxy, or $C_{1-4}$ alkoxy;
$R_1$ and $R_2$ are independently H, hydroxy, $C_{1-4}$ alkyl, $C_{1-4}$ alkoxy, amino, —S—$C_{1-4}$ alkyl, or halo;
$R_3$ is H, hydroxy, oxo, cyano, halo, $C_{1-4}$ alkyl, or $C_{1-4}$ alkoxy;
each $R_4$ is independently hydrogen, hydroxy, oxo, halo, $C_{1-4}$ alkyl, or $C_{1-4}$ alkoxy;
$R_5$ is H, alkynyl, or is absent if a double bond is present;
$R_6$ and $R_7$ are independently selected from $C_{1-4}$ alkyl and H; and
--- is an optional double bond.

wherein $R_1$ and $R_2$ is selected from H, $C_{1-4}$ alkyl group, haloalkyl, hydroxyalkyl, alkyloxyalkyl, cycloalkyloxyalkyl, alkylthio, alkylthioalkyl, cycloalkylthioalkyl, R'R''N-alkyl where R' and R'' are independently alkyl, alkylcarbonyl, or cyclic alkyl, and the parenthesis represents the presence or absence of hydroxyl, and wherein $R_3$ and $R_4$ are independently selected from H, hydroxy, $C_{1-4}$ alkyl, hydoxy-$C_{1-4}$alkyl, cyano, cyanoalkyl, nitro, nitroalkyl, —C(O)-aryl, —C(O)H, alkyl aldehyde, carboxyl, and carboxyalkyl, or wherein $R_3$ and $R_4$ form a ring of from 4 to 8 member atoms, wherein the ring is substituted with cyano or hydroxy.

In embodiments, the $C_{1-4}$ alkyl or $C_{1-4}$ alkoxy is substituted with one or more of halo, cyano, amino, hydroxy, and $C_{1-4}$ alkoxy. Suitably, the substituent is hydroxy.

In embodiments, at least one of $R_1$ and $R_2$ is $C_{1-4}$ alkyl. In embodiments, both $R_1$ and $R_2$ are $C_{1-4}$ alkyl. In embodiments, at least one of $R_1$ and $R_2$ is methyl. In embodiments, both $R_1$ and $R_2$ are methyl. In embodiments, at least one of $R_1$ and $R_2$ is halogen, and preferably, chlorine.

In embodiments, $R_3$ is hydroxy. In embodiments, $R_3$ is $C_{1-4}$ alkyl. Suitably, $R_3$ is substituted $C_{1-4}$ alkyl. In embodiments, $R_3$ is —CH(OH)(CH$_3$).

In embodiments, $R_4$ is $C_{1-4}$ alkyl. Suitably, $R_4$ is substituted $C_{1-4}$ alkyl. In embodiments, $R_4$ is —CH$_2$OH.

In embodiments, $R_3$ and $R_4$ form a 5 or 6 membered ring.

Combinations and permutations of the preferred substituents identified in the preceding five paragraphs are explicitly contemplated.

In an aspect the present disclosure provides a compound having the formula:

In embodiments, $R_3$ is H, OH, oxo, chloro, cyano, or methoxy. Suitably, $R_3$ is hydroxyl.

In embodiments, at least one of $R_1$ and $R_2$ is $C_{1-4}$ alkyl. In embodiments, both $R_1$ and $R_2$ are $C_{1-4}$ alkyl. In embodiments, at least one of $R_1$ and $R_2$ is methyl. In embodiments, both $R_1$ and $R_2$ are methyl. In embodiments, $R_1$ and $R_2$ are independently selected from H, methyl, ethyl, chloro, —CH$_2$OH, and —CH$_2$OMe.

In embodiments, a $C_{1-4}$ alkyl or $C_{1-4}$ alkoxy is optionally substituted with one or more of halo, cyano, amino, hydroxy, and $C_{1-4}$ alkoxy. Suitably, the substituent is hydroxy.

In embodiments, $R_4$ is selected from fluoro, chloro, bromo, methoxy, hydroxy, or oxo.

In embodiments, $R_5$ is H. In embodiments, $R_5$ is —CCH.
In embodiments, $R_6$ is methyl. In embodiments, $R_7$ is H.
In embodiments, m is 0. In embodiments, n is 1. In embodiments, n is 2.

Combinations and permutations of the preferred substituents identified in the preceding seven paragraphs are explicitly contemplated.

In another aspect, the present disclosure provides compound of the following formula:

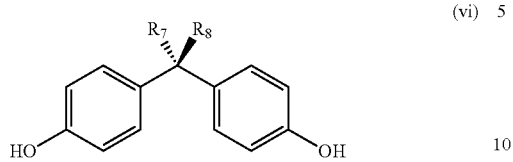

(vi)

and stereoisomers and pharmaceutically acceptable salts thereof;
wherein
$R_7$ and $R_8$ are independently H, $C_{1-5}$ alkyl, amino, hydroxyl, cyano, amido, cyclic $C_{3-8}$ alkyl, and heteocyclyl.

In embodiments, $R_7$ and $R_8$ are selected from $C_{1-4}$ alkylaminocarboxy-$C_{1-4}$ alkyl, $C_{1-4}$ alkylamino-$C_{1-4}$ alkyl, $C_{1-4}$ alkylamino-$C_{1-4}$ alkyl-amino-carboxy-$C_{1-4}$ alkyl, $C_{1-4}$ alkyloxy-$C_{1-4}$ alkylamino-carboxy-$C_{1-4}$ alkyl, $C_{1-4}$ alkylthio-$C_{1-4}$ alkylamino-carboxy-$C_{1-4}$ alkyl, or $C_{1-4}$ alkylthio-$C_{1-4}$ alkyl.

In embodiments, $R_7$ is methyl.

In embodiments, $R_8$ is substituted $C_{1-5}$ alkyl. Suitably, $R_8$ is substituted with —C(O)—R, —C(O)NR$_{N1}$RN$_2$, —C(O)OR, —NR$_{N1}$C(O)R, or —OC(O)R, wherein R$_{N1}$, R$_{N2}$ and R are independently selected from H or $C_{1-4}$ alkyl. In embodiments, at least one of R$_{N1}$, R$_{N2}$, or R is —(CH$_2$)$_n$—R$_{10}$, wherein n is an integer of from 2 to 5, and wherein R$_{10}$ is —C(O)—R, —C(O)NR$_{N1}$R$_{N2}$, —C(O)OR, —NR$_{N1}$C(O)R, or —OC(O)R, wherein R$_{N1}$, R$_{N2}$ and R are independently selected from H, aryl, cycloalkyl, or $C_{1-4}$ alkyl optionally substituted with OH or amino.

Combinations and permutations of the preferred substituents identified in the three paragraphs are explicitly contemplated.

In an aspect the present disclosure provides a compound having the formula:

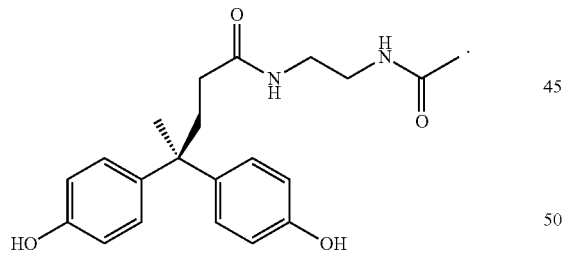

In another aspect, the present disclosure provides a compound selected from the group consisting of:

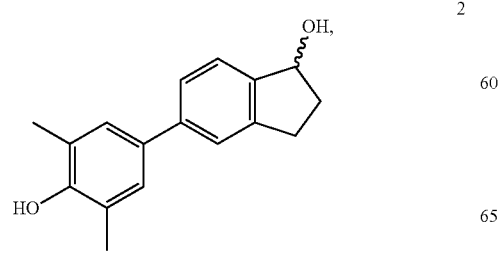

2

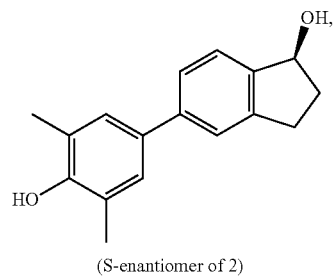

3

(S-enantiomer of 2)

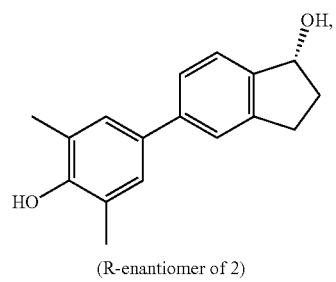

4

(R-enantiomer of 2)

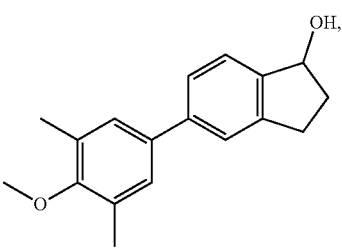

5

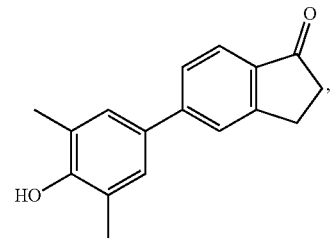

6

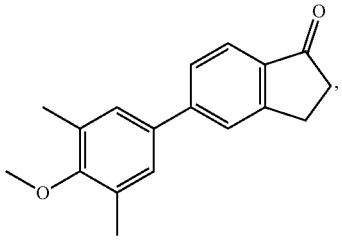

7

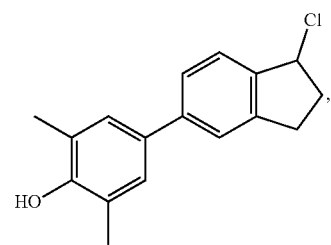

8

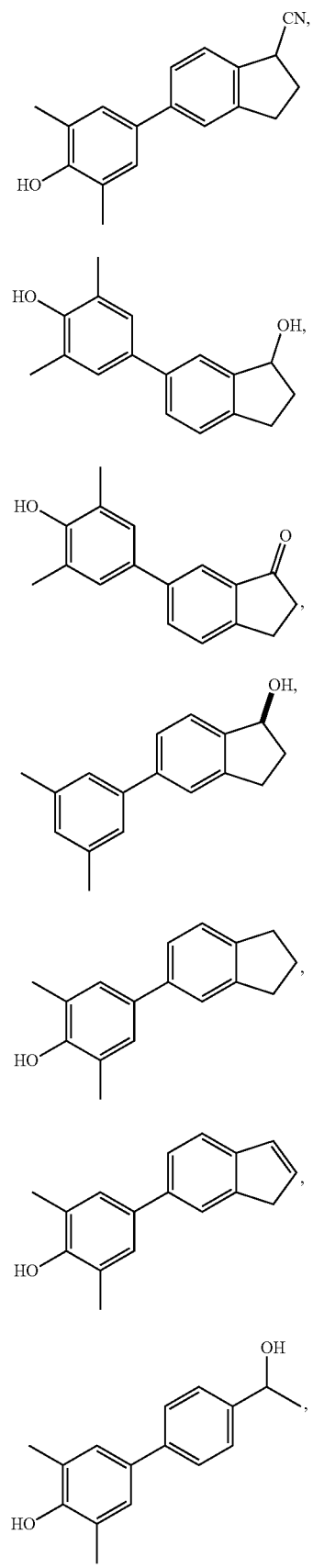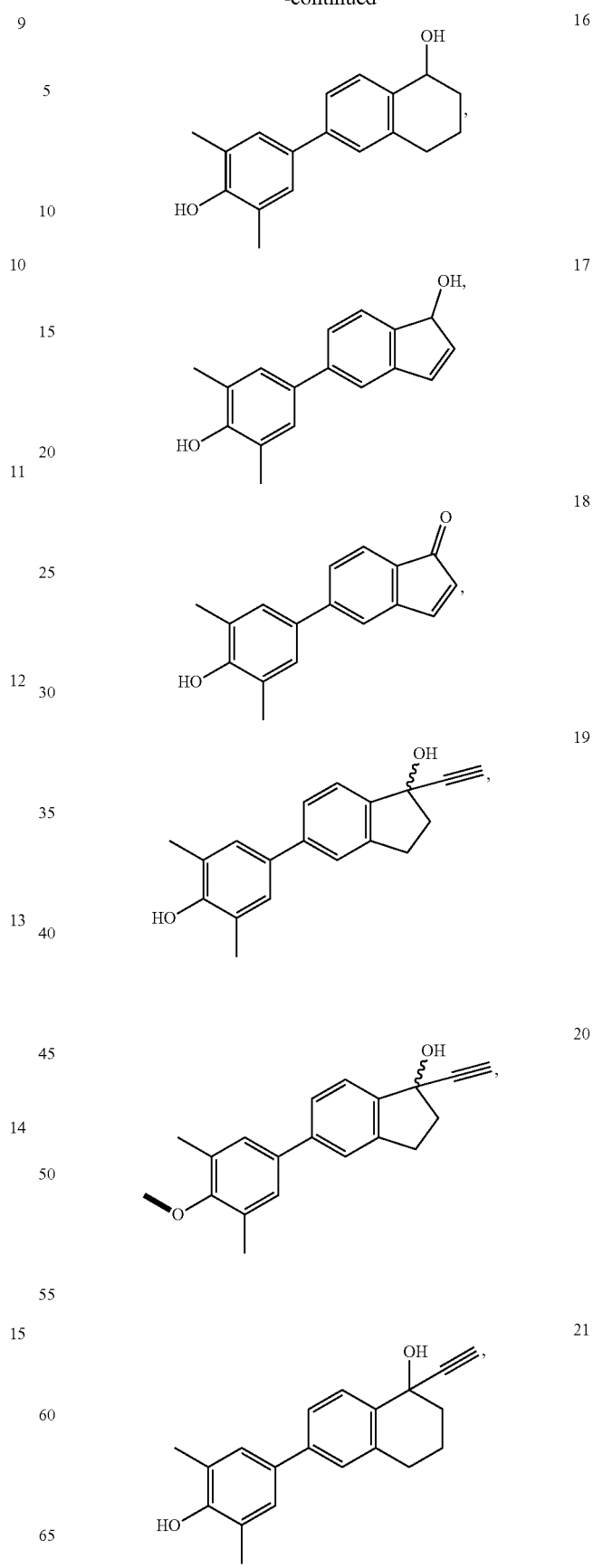

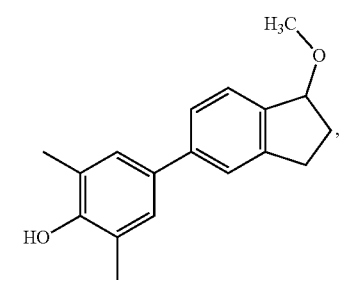
22
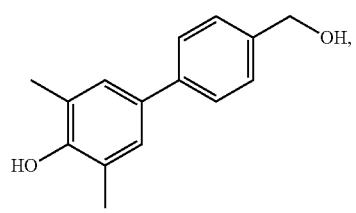
23
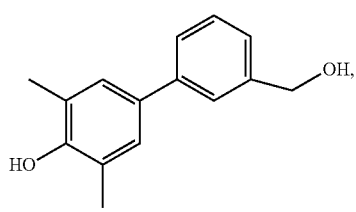
24
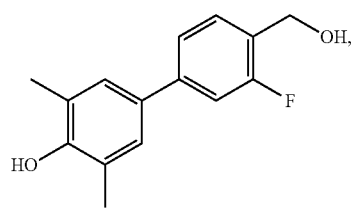
25
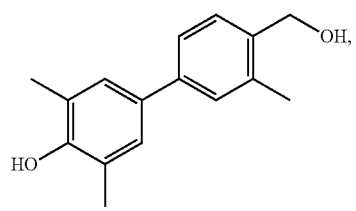
26
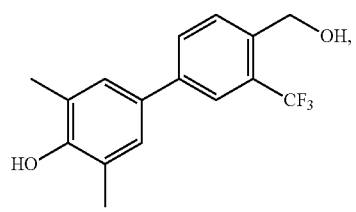
27
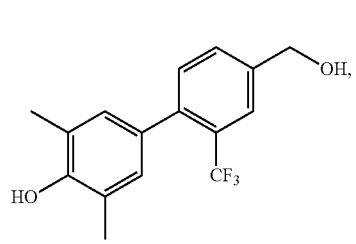
28
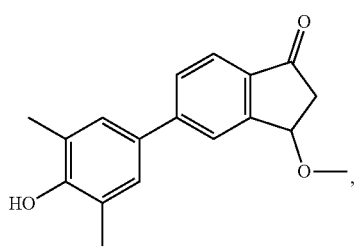
29
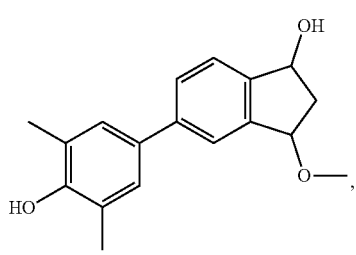
30
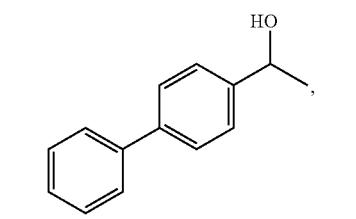
31
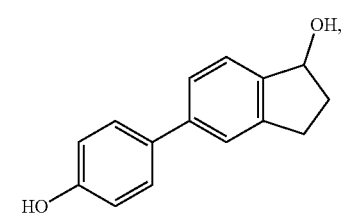
32
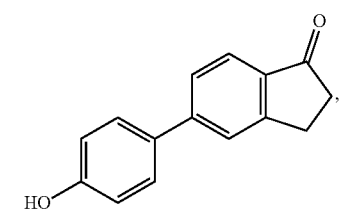
33
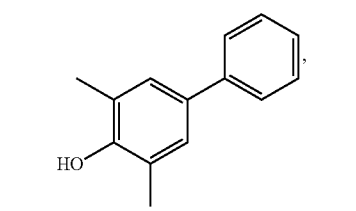
34
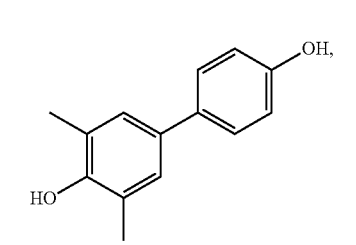
35

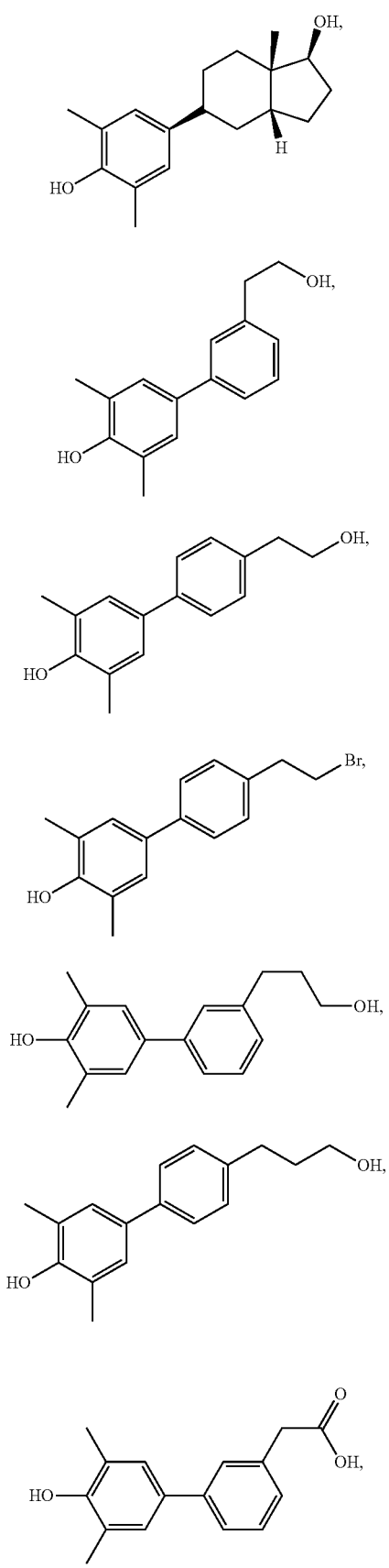
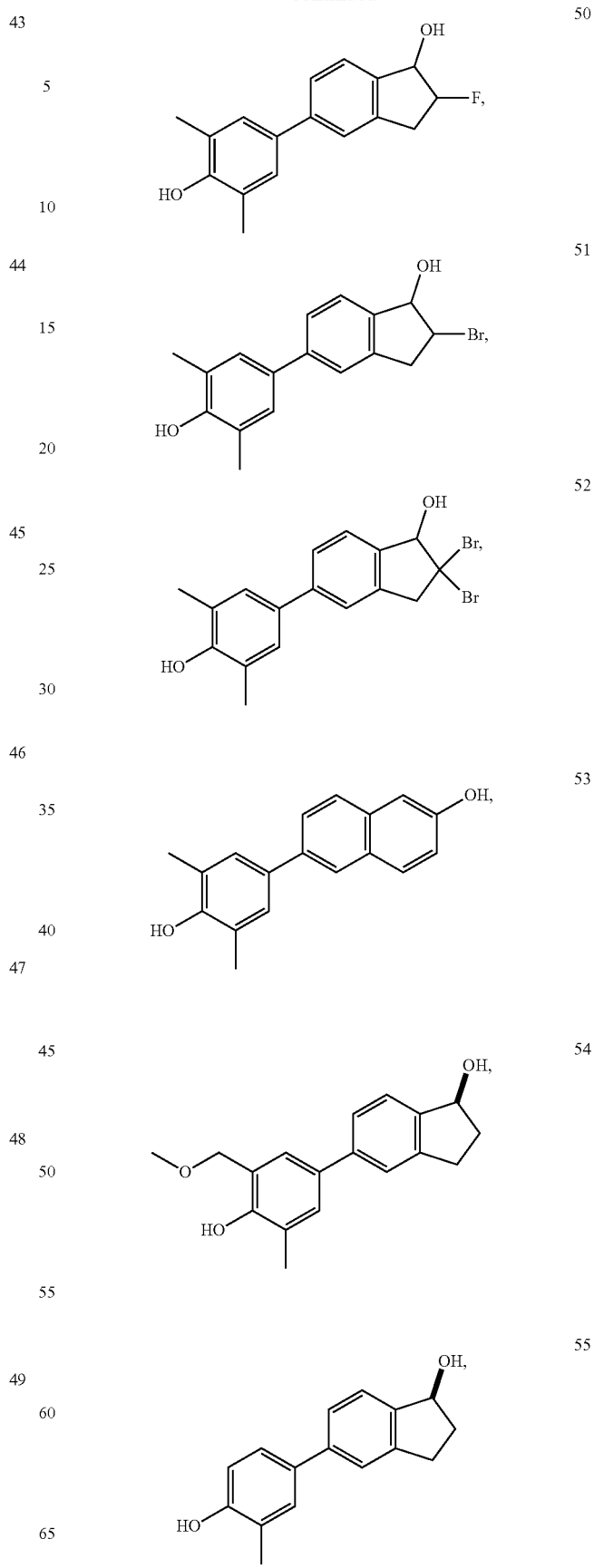

56 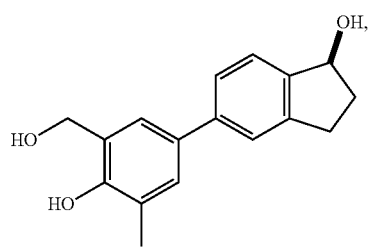
57 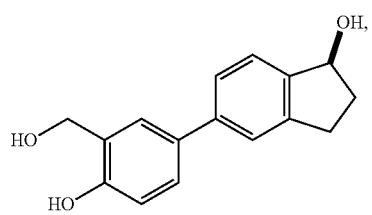
58 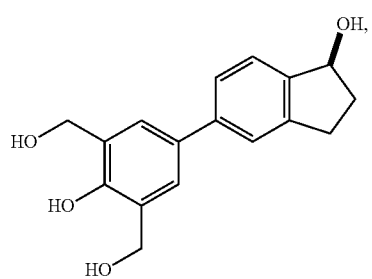
59 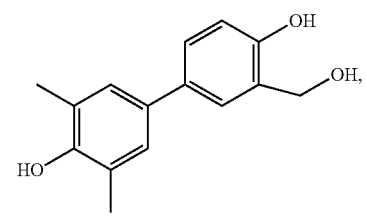
60 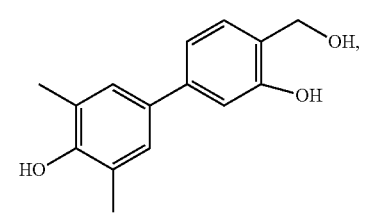
61 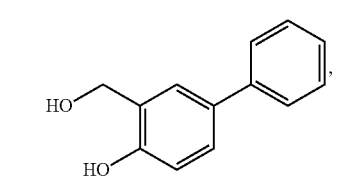
62 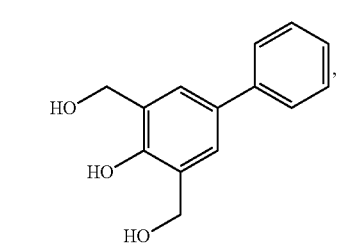
63 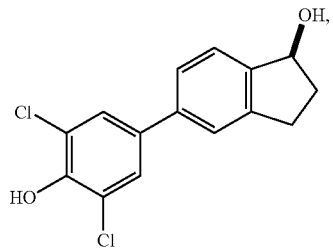
64 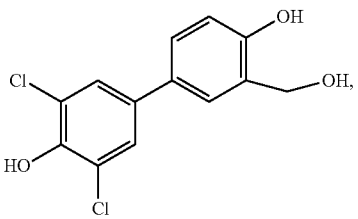
65 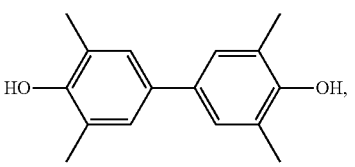
66 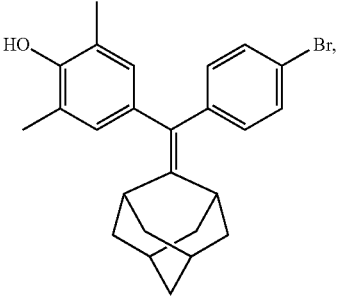
67 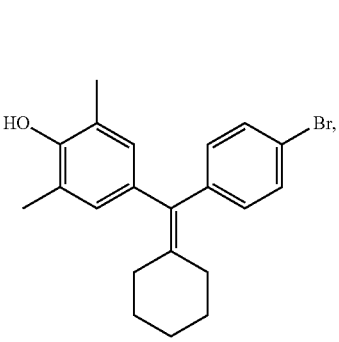
68 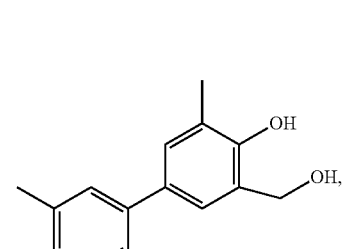

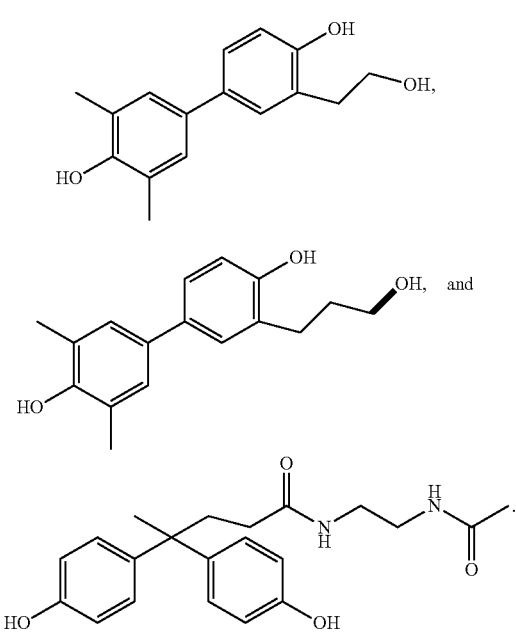

The compounds presented herein may possess one or more stereocenters and each center may exist in the R or S configuration. The compounds presented herein include all diastereomeric, enantiomeric, and epimeric forms as well as the appropriate mixtures thereof. Individual stereoisomers may be obtained, if desired, by methods known in the art as, for example, the separation of stereoisomers by chiral chromatographic columns.

In the formulas for the compounds of the present disclosure, variable or undefined substitution positions and stereochemistry are indicated using common chemical structure drawing conventions such as "line through a ring system", "squiggly bonds", or a "straight line bond" in place of a "bold wedge bond" or "dashed wedge bond", which by convention indicate a substituent coming out from the indicate plane ("bold wedge bond") or going away from the indicated plane ("dashed wedge bond").

For compounds according to the present disclosure, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Compounds according to the present disclosure include compounds that differ only in the presence of one or more isotopically enriched atoms. For example, compounds may have the present structures except for the replacement of hydrogen by deuterium or tritium, or the replacement of a carbon by a $^{13}C$- or $^{14}C$-enriched carbon.

Compounds according to the present disclosure can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this invention include acid addition salts which may, for example, be formed by mixing a solution of the compound according to the invention with a solution of a pharmaceutically accept-able acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quatemary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

Various pharmaceutically acceptable salts are well known in the art and may be used with instant compound such as those disclosed in Berge S, et al., "Pharmaceutical salts," J. Pharm. Sci. 66:1-19 (1977) and Haynes D, et al., "Occurrence of pharmaceutically acceptable anions and cations in the Cambridge Structural Database," J. Pharm. Sci. 94:2111-2120 (2005), each of which is incorporated herein by reference as if set forth in its entirety. For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate and triethiodide.

In addition to salt forms, the present invention may also provide compounds according to the present disclosure that are in a prodrug form. Prodrugs of the compounds are those compounds that readily undergo chemical changes under physiological conditions to provide the compounds. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Compounds according to the present disclosure can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

A preparation of a compound according to the present disclosure may be enriched for an isomer of the compound having a selected stereochemistry, e.g., R or S, corresponding to a selected stereocenter. For example, the compound may have a purity corresponding to a compound having a selected stereochemistry of a selected stereocenter of at least about 60%, 65%, 70%, 75%, 80%, 85%, 90%, 95%, 96%, 97%, 98%, or 99%. A compound can, for example, include a preparation of a compound disclosed herein that is enriched for a structure or structures having a selected stereochemistry, e.g., R or S, at a selected stereocenter.

In some embodiments, a preparation of a compound according to the present disclosure may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound according to the present disclosure can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivalates or fatty acid substituents, conversion to carbamates, hydroxylation of aromatic rings, and heteroatom substitution in aromatic rings.

Synthesis of Compounds

A general route for the synthesis of many of these compounds is shown below:

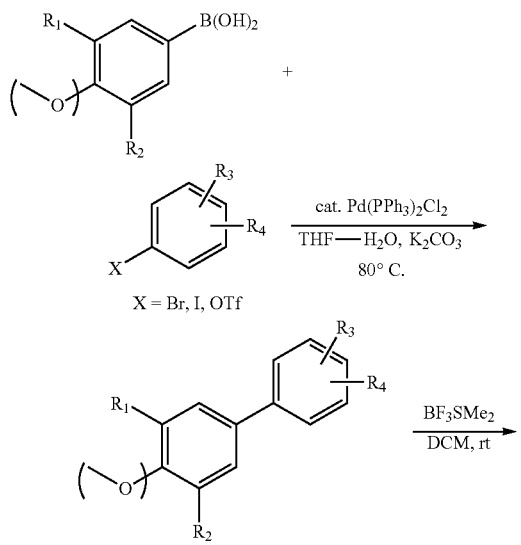

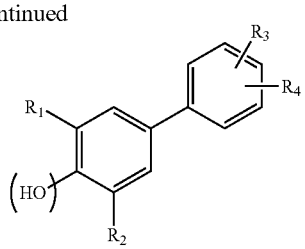

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluation of Compounds

Compounds may be analyzed using a number of methods and assays, including receptor ligand binding kinetic and equilibrium assay, coregulator binding assays, subcellular distribution immunohistochemical and proximity ligation assays of receptors and other proteins that relate to the selective action of estrogens through nuclear-initiated versus extranuclear-initiated pathways; cell activity studies including regulation of specific genes and whole transcriptome (RNA-sequencing, RNA-seq) analyses, receptor, kinase, and RNA polymerase chromatin binding studies using chromatin immunoprecipitation (ChIP) and ChIP-sequencing methods, and cell proliferation assays and signal transduction pathway analyses that further define the pathways by which ligands for the estrogen receptor work in target cells; in vivo assays, including uterine weight assessments and mammary tissue development assays that can be predictive of compounds that will or will not be stimulatory to reproductive tissues and might or might not initiate or promote human breast and uterine cancers; animal body weight and organ weight studies, and blood and tissue lipid and metabolomics analyses on animals on different diets that might be related to the prevention or development of metabolic disorders or metabolic syndrome in humans; assays in animals of endothelial cell function involving estrogen-responsive genes regulated by nuclear and non-nuclear estrogen receptor action, assays of vascular health including endothelial repair assays and suppression of atheroma and neointima development in wild type and mutant animals on normal and high fat diets that are predictive of activity on vascular and metabolic diseases in humans. Effects of the compounds can be assayed on metabolic health and glucose utilization in wild type and mutant animals under various diets that are associated with diabetes in humans. Compounds can be assayed for their suppression of injury to the heart ex vivo or brain in vivo under conditions of enforced ischemia that are models of human diseases of stroke, or cardiac insufficiency or heart attack. Compounds can be assayed for their protection of bone mineral density, strength, and architecture due to low estrogen conditions in mouse or rat models that are predictive of effects on osteoporosis or osteopenia in humans. Certain of these methods are described in the examples.

Methods of Use

In another aspect, a method of treating a disease or condition in a subject is provided, the method comprising administering a pharmaceutically effective amount of at least one compound of any of the claims herein.

In another aspect, a method of ameliorating a disease or condition in a subject is provided, the method comprising administering a pharmaceutically effective amount of at least one compound of any of the claims herein.

In another aspect, a method of preventing or slowing the progress of a disease or condition in a subject is provided, the method comprising administering a pharmaceutically effective amount of at least one compound of any of the claims herein.

In embodiments, the disease or condition is affected by the extranuclear-initiated pathway of the estrogen receptor.

The disease or condition is selected from, for example, postmenopausal symptoms, cardiovascular disease, stroke, vascular disease, bone disease, metabolic disease, diabetes, arthritis, osteoporosis, obesity, cognitive decline, vasomotor/hot flush, and cancer.

In embodiments, the disease is stroke. In embodiments, the disease is metabolic disease. In embodiments, the disease is diabetes. In embodiments, the disease is cancer, such as breast cancer. In embodiments, the breast cancer is estrogen-responsive breast cancer or obesity-related breast cancer. In embodiments, the disease is vascular disease. In embodiments, the disease is osteoporosis.

Compositions and Routes of Administration

The present disclosure also provides pharmaceutical compositions comprising compounds according to the present disclosure and a pharmaceutically acceptable excipient.

The pharmaceutical compositions of this disclosure can be administered by a variety of routes including by way of non-limiting example, oral, transdermal, subcutaneous, intravenous, intramuscular and intranasal. Depending upon the intended route of delivery, the pharmaceutical composition preferably is formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. As used herein, "unit dosage forms" means physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the combination therapy is usually a minor component (from about 0.1% to about 50% by weight or preferably from about 1% to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions typically are based upon injectable sterile saline or phosphate-buffered saline or other injectable carriers known in the art. As before, the active compound in such compositions is typically a minor component, often being from about 0.05% to 10% by weight with the remainder being the injectable carrier and the like.

Transdermal compositions are typically formulated as a topical ointment or cream containing the active ingredient(s), generally in an amount ranging from about 0.01% to about 20% by weight, preferably from about 0.1% to about 20% by weight, preferably from about 0.1 to about 10% by weight, and more preferably from about 0.5% to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well known in the art and generally include additional ingredients to enhance the dermal penetration or stability of the active ingredients or the formulation. All such known transdermal formulations and ingredients are included within the scope of this invention.

The pharmaceutical composition also can be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th ed., 1985, Mack Publishing Company, Easton, Pa.

The pharmaceutical compositions also can be administered in sustained release forms or from sustained release drug delivery systems. A description of representative sustained release materials can be found in Remington's Pharmaceutical Sciences, supra.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations disclosed compounds and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be co-administered, either in concomitant therapy or in a fixed combination.

The following formulation examples illustrate representative pharmaceutical compositions that may be prepared in accordance with this invention. The present invention, however, is not limited to the following pharmaceutical compositions.

Formulation 1—Tablets: A pharmaceutical composition may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules: A pharmaceutical composition may be admixed as a dry powder with a starch diluent in an approximate 1:1 weight ratio. The mixture is filled into 250 mg capsules (125 mg of active compound per capsule).

Formulation 3—Liquid: A pharmaceutical composition (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets: A pharmaceutical composition may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection: A pharmaceutical composition may be dissolved or suspended in a buffered sterile saline injectable aqueous medium to a concentration of approximately 5 mg/mL.

Formulation 6—Topical: Stearyl alcohol (250 g) and a white petrolatum (250 g) may be melted at about 75° C. and then a mixture of a pharmaceutical composition (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

The following non-limiting examples are intended to be purely illustrative of some aspects and embodiments, and show specific experiments that were carried out in accordance with the disclosure.

EXAMPLES

Materials and Methods
Cell Culture and siRNA Treatments

MCF-7 cells were obtained from and grown as recommended by the American Type Culture Collection. Receptor expression was verified by qPCR and Western blotting, and gene expression and proliferative response to estradiol (E2) was monitored regularly. For experiments with E2 and PaPE treatment, cells were maintained in phenol red-free tissue culture medium for at least 5 days prior to use. ERα knockdown experiments utilized the SMART pool of 4 siRNAs from Dharmacon and were performed as described (see Madak-Erdogan et. al., Mol Endocrinol 22, 2116-2127, 2008) with 30 nM siCtrl or siERα or siGPR30 for 72 h. This resulted in knockdown of the corresponding mRNA and protein by greater than 80%. Primary bovine aortic endothelial cells were harvested, maintained and employed as previously described in Chambliss, J Clin Invest 120, 2319-2330, 2010).

Animals and Ligand Treatments

Studies used wild type and ERα knockout mice in C57BL/6 background. All experiments involving animals were conducted in accordance with National Institutes of Health standards for the use and care of animals, with protocols approved by the University of Illinois at Urbana-Champaign and the University of Texas Southwestern Medical Center. Wild-type C57BL/6 mice were purchased from Jackson Laboratories/National Cancer Institute. ERα knockout mice with complete excision of ERα and wild type littermates were obtained from Taconic and were used as described previously in Dupont et al., Development, 127, 4277-4291, 200, and Hewitt et al. FASEB J., 24, 4660-4667, 2010.

In studies of metabolic parameters and gene expression in vivo, ligands were administered to ovariectomized recipient mice by subcutaneous implantation of pellets containing compound mixed with cholesterol to a total weight of 20 mg. Animals were single-housed during the study. For 3-week studies, estradiol (E2, Sigma-Aldrich) dosage (0.125 mg/pellet) was chosen based on previous findings. In carotid artery reendothelialization experiments, compounds were delivered at a dose of 6 µg/day by a 4-week (Model 2006) Alzet minipump, as described (Chambliss, J Clin Invest 120, 2319-2330, 2010). Total body weight and food intake were monitored every week after ovariectomy. Body fat and lean mass composition were monitored at the end of 3 weeks using EchoMRI-700 Body Composition Analyzer (Echo Medical Systems, Houston, Tex.), which enables one to quantify longitudinal body composition in the live animal.

Western Blotting, and ChIP Assays

Western blot analysis used specific antibodies for ERα (HC-20, Santa Cruz); ERK2 (D-2, Santa Cruz); and $pS^6$, pS6K, pmTOR, pRAPTOR, pRICTOR, pMAPK (Cell Signaling). Coimmunoprecipitation assays used antibodies for SRC3 (Santa Cruz, C-20) and ERα (Santa Cruz, F10).

ChIP assays were carried out as described (Madak-Erdogan et al. Mol Syst Biol 9, 676 2013 and Madak-Erdogan et al., Mol Cell Biol 31, 226-236, 2011). Antibodies used were for ERα (HC20), ERK2 (Santa Cruz, D2 and C14), and pSer5 RNA Pol II (Santa Cruz, sc-47701). ChIP DNA was isolated using QIAGEN PCR purification kit and used for ChIP-seq analysis and quantitative real-time PCR (qPCR). qPCR was used to calculate recruitment to the regions studied, as described.

ChIP-seq Analysis and Clustering

For genome-wide ChIP-seq, the ChIP DNA was prepared into libraries according to Illumina Solexa ChIP-seq sample processing methods, and single read sequencing was performed using the Illumina HiSeq 2000. Sequences generated were mapped uniquely onto the human genome (hg18) by Bowtie2. MACS (Model-based Analysis of ChIP-Seq) algorithm was used to identify enriched peak regions (default settings) with a p-value cutoff of 6.0e-7 and FDR of 0.01, as was described in Madak-Erdogan, Mol Syst Biol 9, 676, 2013.

The seqMINER density array method with a 500-bp window in both directions was used for the generation of clusters, i.e., groups of loci having similar compositional features. BED files for each cluster were used for further analysis with Galaxy Cistrome integrative analysis tools (Venn diagram, conservation, CEAS).

RNA-Seq Transcriptional Profiling

For gene expression analysis, total RNA was extracted from 3 biological replicates for each ligand treatment using Trizol reagent and further cleaned using the RNAeasy kit (QIAGEN). For time course studies, MCF-7 cells were treated with Veh (0.1% EtOH), 10 nM E2 or 1 jiM PaPE for 4 h and 24 h. For inhibitor studies, MCF-7 cells were pretreated with Ctrl (0.1% DMSO), 1 μM PP242 or 1 μM AZD6244 for 30 min and then treated with Veh, 10 nM E2 or 1 μM PaPE-1 in the presence or absence of inhibitors for 4 h. Once the sample quality and replicate reproducibility were verified, 2 samples from each group were subjected to sequencing. RNA at a concentration of 100 ng/μL in nuclease-free water was used for library construction. cDNA libraries were prepared with the mRNA-TruSeq Kit (Illumina, Inc.). Briefly, the poly-A containing mRNA was purified from total RNA, RNA was fragmented, double-stranded cDNA was generated from fragmented RNA, and adapters were ligated to the ends.

The paired-end read data from the HiSeq 2000 were processed and analyzed through a series of steps. Base calling and de-multiplexing of samples within each lane were done with Casava 1.8.2. FASTQ files were trimmed using FASTQ Trimmer (version 1.0.0). TopHat2 (version 0.5) was employed to map paired RNA-Seq reads to version hg19 of the *Homo sapiens* reference genome in the UCSC genome browser in conjunction with the RefSeq genome reference annotation. Gene expression values (raw read counts) from BAM files were calculated using StrandNGS (version 2.1) Quantification tool. Partial reads were considered and option of detecting novel genes and exons was selected. Default parameters for finding novel exons and genes were specified. DESeq normalization algorithm using default values was selected. Differentially expressed genes were then determined by fold-change and p-value with Benjamini and Hochberg multiple test correction for each gene for each treatment relative to the vehicle control. Genes with fold-change >2 and p-value <0.05 were considered as statistically significant, differentially expressed. All RNA-Seq datasets have been deposited with the NCBI under GEO accession number GSE73663.

Motif and GO Category Analysis

Overrepresented GO biological processes were determined by the web-based DAVID Bioinformatics Resources database, ClueGO and web-based GREAT software. Motifs enrichment analysis was done using Seqpos.

Immunohistochemistry (IHC)

Hematoxylin and eosin (H&E) staining, and whole mount staining were performed on paraffin-embedded tissue sections. Images were quantified by monitoring average cell size from 3 randomly chosen fields in Fiji software (http://fiji.sc/wiki/index.php/Fiji).

Immunofluorescence Microscopy, Proximity Ligation Assays in Cells and Data Analysis Cells treated with vehicle (0.1% EtOH), 10 nM E2 or 1 μM PaPE-1 for 15 min were washed in PBS, fixed on glass coverslips and incubated with antibodies against ERα (F10, Santa Cruz), pSer5 RNA Pol II (Santa Cruz, 47701), or RAPTOR (Cell Signaling). Next day, the proximity ligation assay (PLA) was performed using the Duolink In Situ kit (Olink Bioscience) according to the manufacturer's instructions, as described in Zhao et. al., Endocrinology, 154, 1349-1360, 2013. Briefly, overnight incubation with primary antibodies was followed by hybridization with two PLA probes at 37° C. for 1 h, and then by ligation for 15 min and amplification for 90 min at 37° C. A coverslip was mounted on each slide and image acquisition and analysis conducted. Samples were imaged using a 63×/1.4 Oil DIC M27 objective in a Zeiss LSM 700 or 710 laser scanning confocal microscope. Images were obtained in a sequential manner using a 488 Ar (10 mW) laser line for PLA signal. The individual channels for DAPI and PLA signal were obtained using a sequential scanning mode to prevent bleed-through of the excitation signal. Laser power, gain and offset were kept constant across the samples and scanned in a high resolution format of 512×512 or 1024×1024 pixels with 2/4 frames averaging. Further quantification of the images used Fiji software (http://fiji.sc/wiki/index.php/Fiji). Briefly, images were converted to 8 bit for segmentation for each channel, and images were background subtracted using a rolling-ball method, with a pixel size of 100 and segmented using the DAPI channel.

Cell Proliferation Assays

Cells were seeded at 1000 cells/well in 96-well plates. On the second day, the cells were treated with Veh, E2 or PaPE at the concentrations indicated and proliferation was assessed using WST-1 reagent (Roche) as described in Madak-Erdogan, Mol Syst Biol 9, 676, 2013.

eNOS Activation eNOS activation was assessed in intact primary endothelial cells by measuring $^{14}$C-L-arginine conversion to $^{14}$C-L-citrulline over 15 min using previously reported methods (Chambliss et. al., J Clin Invest 120, 2319-2330, 2010). Cells were treated with vehicle (yielding basal activity), E2, or PaPE alone or with the antiestrogen ICI 182,780 at the concentrations indicated.

Carotid Artery Reendothelialization

Carotid artery reendothelialization was studied following perivascular electric injury in mice by assessing Evans blue dye uptake 72 h after injury. Endothelial denudation and recovery after injury in this model have been confirmed by immunohistochemistry for von Willebrand Factor. At the time of ovariectomy at 8-9 weeks of age, female mice received intraperitoneal osmotic minipumps prepared to deliver 6 µg/d E2 or PaPE-1. Carotid artery denudation was performed 21d later. In select studies additional treatments included subcutaneous injections of vehicle or ICI 182,780 (360 µg/mouse) administered 3d prior to carotid injury and on the day of injury. At the end of the study, uteri were also harvested and weighed.

Pharmacokinetic Analyses

For short-term studies, ovariectomized C57BL/6 mice were injected SC with 100 µg of PaPE-1 in 100 µl DMSO. Three mice were sacrificed at each time point, and 400 µl of blood was obtained from the abdominal aorta. Samples were centrifuged at 2000 g for 10 min, and serum was collected. A 50 µl portion of each sample was submitted to the Metabolomics Center at the University of Illinois for analysis. For longer-term studies, ovariectomized C57BL/6 mice were implanted SC with a pellet fabricated with 8 mg PaPE-1 and 12 mg cholesterol. Blood samples (30 µl) were collected by tail snipping every week until the third week of treatment. Samples were centrifuged at 2000 g for 10 min and serum was collected. Serum (10 µl) was mixed with 40 µl of PBS and submitted to the Metabolomics Center for analysis. For analysis, a mass standard of PaPE-1 (labeled with three deuterium atoms) was added to each sample before analysis by liquid chromatography-mass spectrometry using the 5500 QTrap with Agilent 1200 HPLC.

Ligand Dissociation Assays

The fluorescence polarization or anisotropy characteristics of fluorescein attached to C530 in ERα is sensitive to the nature of the bound ligand. These differences can be exploited to detect the dissociation of one ligand and the association of a second ligand, with the rate of ligand exchange being limited by the rate of dissociation of the initially bound ligand. PaPE-1 gives an anisotropy value about 20% lower than that of E2 when bound to ER, and OH-Tam gives an 80% lower anisotropy value than E2 when bound to the ER. Therefore, each ligand pair (PaPE-1/E2 or E2/OH-Tam) gives a distinct change in anisotropy that can be used to monitor the rate of dissociation of the initially bound ligand.

ERα-ligand binding domain (LBD), mutated to have one active cysteine at C530, was site-specifically labeled with 5-iodoacetamidofluorescein and then diluted into t/g buffer (50 mM Tris, 10% glycerol, pH 8) with 0.01 M mercaptoethanol and 0.03 mg/ml ovalbumin added as a carrier protein to give 2 nM ER. To minimize homoFRET, a 5-fold excess (10 nM) of unlabeled ERα-LBD (10 nM) was added, and the fluorescein-labeled and unlabeled ER dimers were allowed to exchange at room temperature in the dark, for 1 h, thereby producing dimers in which essentially only one monomer is fluorescein labeled. The ER was then bound with 100 nM E2, or 100 nM/RBA of PaPE-1; the RBA of PaPE-1 is 0.002%; therefore, 100 nM/RBA=50 µM of PaPE was used. These samples were allowed to complete ligand binding at room temperature in the dark for 2.5 h.

The anisotropy was measured on a Spex fluorolog II cuvette-based fluorimeter under constant wavelength conditions. The excitation was set at 488 nm and emission at 520 nm, under magic angle conditions, and three to five time points were taken for a zero time. To initiate the dissociation of PaPE-1, 300 nM of E2 was added to the PaPE-1 sample, and the time course of dissociation was subsequently followed by changes in anisotropy. Due to glycerol viscosity changes, there is a change in the protein anisotropy between room temperature and 5° C.; therefore, care was taken to prechill the protein as well as the cuvette chamber to 5° C.

To measure the dissociation of E2, 300 nM E2 was added to the pre-exchanged sample of fluorescein-labeled and unlabeled apo-ER dimer and allowed to bind for 2.5 h, as above. The cuvette and chamber were chilled to 5° C., and after taking the zero time points, E2 dissociation was initiated by adding 5 µM OH-Tam, and change in anisotropy was followed with time. The data for both dissociation experiments were fitted to an exponential decay function by linear regression using Prism 4.

Computational Modeling of the Complex of ERα with PaPE-1 or E2.

Figure 2:
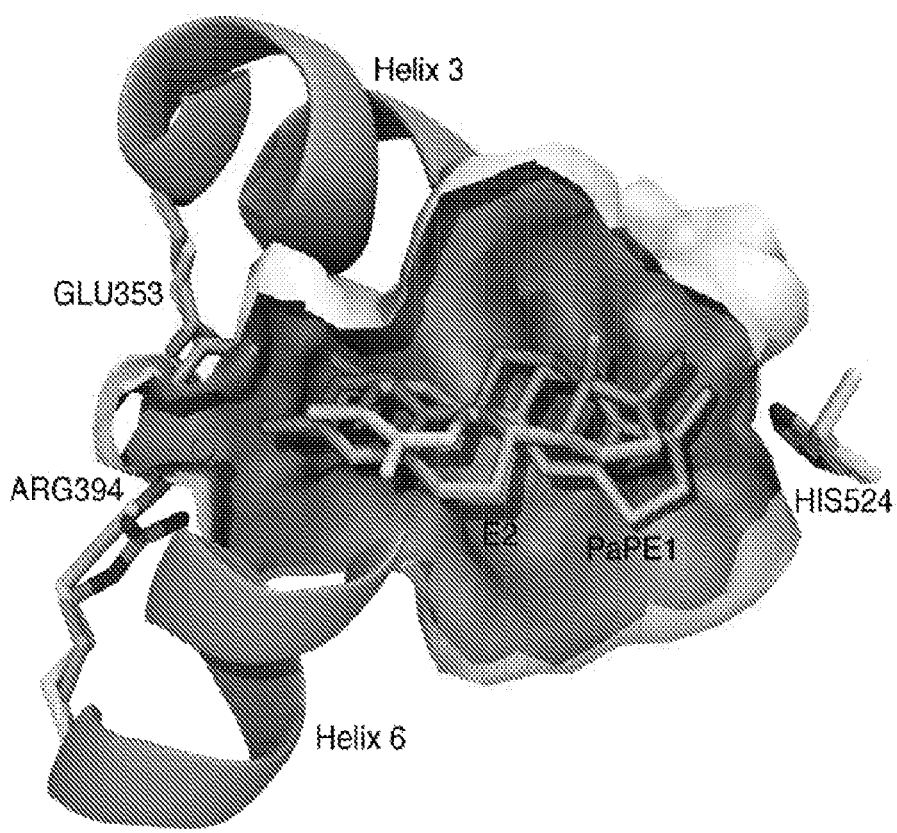
FIG. 2. Computational model comparing PaPE-1 and E2 in the ligand-binding pocket of ERα. The model of ERα+E2, based on a crystal structure (1GWR), has E2 and helical elements shown in silver/grey and the pocket volume contour in slate blue. The model for PaPE-1 was generated from the ERα+E2 structure by progressive transformation of the ligand structure from E2 to PaPE-1, partnered with progressive minimization of the ligand and the ligand-binding domain. The resulting positions of the PaPE-1 ligand and hydrogen bonding residues are shown in orange. For details, see Methods below.

Starting from the ERu+E2 crystal structure (PDB code: 1GWR), the structure preparation routine in MOE (MOE: Molecular Operating Environment, Chemical Computing Group) was used to fill missing loops, side chains, add explicit hydrogen atoms. A custom volume visualization code was used to create the binding volume for the ERu+E2 structure, shown in slate blue in FIG. 2B; the red dot is a structural water. The model of the binding of PaPE-1 was built by progressive generation of the PaPE-1 ligand structure from that of E2, coupled with progressive minimization of the ligand-binding domain: Atoms were first deleted from E2 to open the B-ring and convert the C ring into an aromatic ring, but the two ortho-methyl groups on the A-ring were not yet added. At this stage, the positions of the ligand oxygen atoms and all protein atoms were fixed, and energy minimization was performed using the MMFF94x force field with a termination gradient cutoff of 0.1 kcal/(mol·Å) to obtain a low energy conformation of the PaPE-1 ligand core. All atoms were then unfixed, and energy minimization was further performed while constraining protein backbones to optimize interactions with hydrogen bonding side chains. After the two A-ring ortho-methyl groups were added, another energy minimization was performed with constrained backbone atoms, and then a final unconstrained energy minimization was performed, all to the same gradient cutoff. The resulting positions of the ligand and hydrogen bonding residues are shown in yellow in FIG. 2B.

Statistical Analyses

Data from in vivo animal metabolism studies were analyzed using either one-way ANOVA to compare different ligand effects or two-way-ANOVA to compare time dependent changes followed by Bonferroni post hoc test using GraphPad Prism 6. Data from gene expression studies were analyzed using t-test.

General Synthetic Procedures

NMR measurement: $^1$H NMR spectra were recorded on a Varian vxr500 MHz, u500, or u400 MHz spectrometer and chemical shifts are given in δ-values [ppm] referenced to the residual solvent peak chloroform ($CDC_3$) at 7.26 and methanol ($CD_3OD$) at 3.31 ppm. Coupling constants, J, are reported in Hertz. Materials and solvents were of highest grade available from commercial sources and were used without further purification. Molecular weight was determined by using the Waters Quattro ultima ESI or Waters 70-VSE EI/CI/FD/FI mass spectrometers.

Example 1. Synthesis of 5-(4-hydroxy-3,5-dimethylphenyl)-2,3-dihydro-1H-inden-1-ol (2)

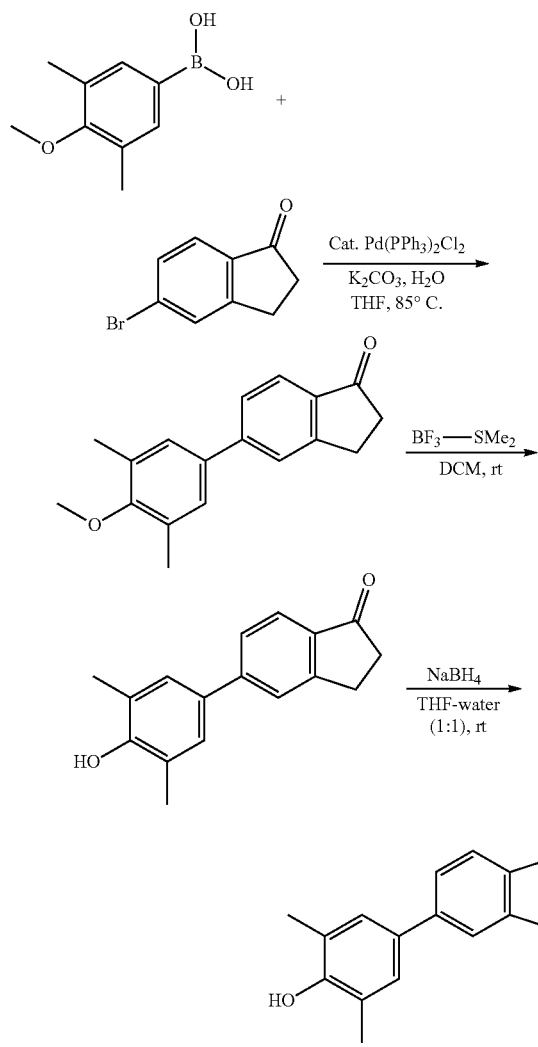

The mixture of 3,5-dimethyl-4-methoxyphenylboronic acid (200 mg, 1.11 mmol), 5-bromo-1-indanone (211 mg, 1.00 mmol), bis(triphenylphosphine)palladium(II) dichloride (35 mg, 0.05 mmol), potassium carbonate (307 mg, 2.22 mmol), and deionized (DI) water (39 mg, 2.22 mmol) in THF (10 mL) was stirred under the argon atmosphere at 85° C. for 4 hr to 8 hr. After starting materials disappeared on TLC analysis, ethyl acetate (20 mL) was added into reaction mixture. When DI water (20 mL) was added to reaction mixture, an insoluble solid precipitated. The suspended solid was collected by filtration and more solid was collected after evaporating the ethyl acetate filtrate. Recrystallization of the combined solids from ethyl acetate afforded the 5-(4-methoxy-3,5-dimethylphenyl)-2,3-dihydro-1H-inden-1-one (223 mg, 84%). $^1$H NMR (500 MHz, CDCl$_3$) δ 2.82 (s, 6H), 2.75 (t, 2H, J=6.0 Hz), 3.20 (t, 2H, J=6.0 Hz), 3.79 (s, 3H), 7.31 (s, 2H), 7.58 (d, 1H, J=8.0 Hz), 7.65 (s, 1H), 7.80 (d, 1H, J=8.0 Hz); $^{13}$C NMR (126 MHz, CDCl$_3$) δ 16.55, 26.12, 36.78, 60.07, 122.06, 124.21, 125.06, 126.81, 128.21, 131.74, 135.88, 147.72, 156.10, 157.70, 206.92.

Boron trifluoride methyl sulfide complex (1.04 g, 0.08 mmol) was added to the 5-(4-methoxy-3,5-dimethylphenyl)-2,3-dihydro-1H-inden-1-one (266 mg, 1.00 mmol) solution in DCM (10 mL) and stirred for 6 hr at rt, followed by evaporation of solvent, addition of water, and filtration to afford 5-(4-hydroxy-3,5-dimethylphenyl)-2,3-dihydro-1H-inden-1-one as a slightly dark white solid (240 mg, 95%). Upon the demethylation, the product appears as a blue fluorescent spot on TLC when exposed to 254 nm UV light. $^1$H NMR (500 MHz, CDCl$_3$) δ 2.31 (s, 6H), 2.72 (t, 2H, J=5.5 Hz), 3.17 (t, 2H, J=5.5 Hz), 7.26 (s, 2H), 7.55 (d, 1H, J=8.0 Hz), 7.62 (s, 1H), 7.76 (d, 1H, J=8.0 Hz); $^{13}$C NMR (126 MHz, CDCl$_3$) δ 16.49, 26.11, 36.77, 122.09, 124.22, 124.56, 126.52, 127.91, 128.87, 135.27, 148.19, 153.50, 156.39.

To the solution of 5-(4-hydroxy-3,5-dimethylphenyl)-2,3-dihydro-1H-inden-1-one in THF-water mixture (200 mg, 0.79 mmol) was added portionwise NaBH$_4$ (50 mg, 1.31 mmol) at rt and the mixture was stirred until starting material disappeared on silica gel TLC analysis. Upon reduction by NaBH$_4$, the blue fluorescence disappeared on silica gel TLC at 254 nm. Compound 2 (189 mg) was obtained in 94% yield after passing through short silica gel pad by using 35% ethyl acetate in n-hexane. $^1$H NMR (500 MHz, CDCl$_3$+methanol-d$_4$) δ 1.95-2.05 (m, 1H), 2.31 (s, 6H), 2.48-2.58 (m, 1H), 2.84-2.92 (m, 1H), 3.02-3.16 (m, 1H), 4.66 (s, 1H, phenolic OH), 5.29 (t, 1H, J=5.5 Hz), 7.20 (s, 2H), 7.39-7.46 (m, 3H); $^{13}$C NMR (126 MHz, CDCl$_3$) δ 16.30, 30.06, 36.40, 76.48, 123.47, 123.50, 124.57, 125.83, 127.69, 133.61, 141.83, 143.50, 144.17, 152.07; ESI (m/z) 255.3 (M++1, 25%), 237.2 (M++1-H$_2$O, 85%)

Example 2. Synthesis of S-5-(4-hydroxy-3,5-dimethylphenyl)-2,3-dihydro-1H-inden-1-ol (3: S-2)

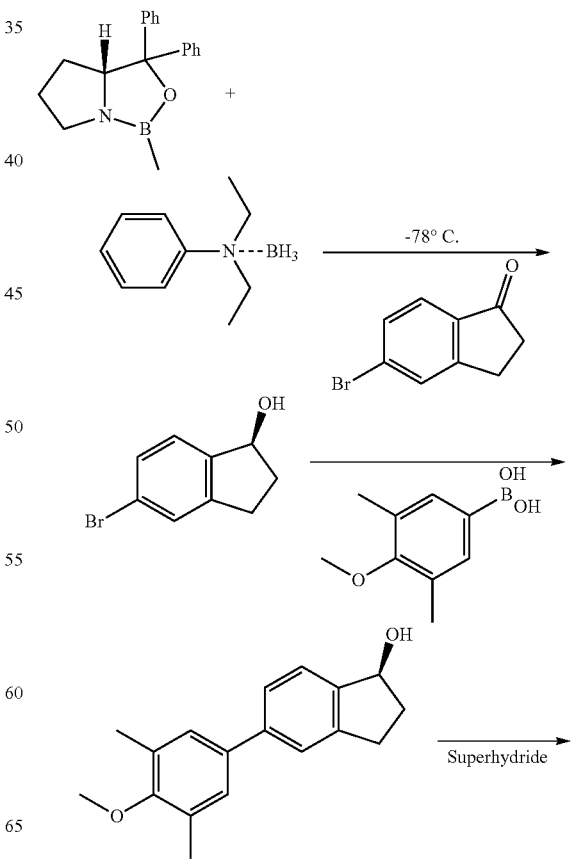

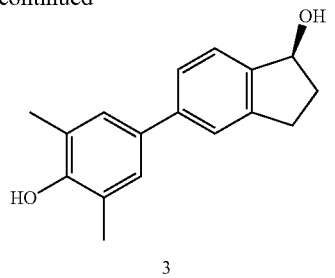

S-5-(4-methoxy-3,5-dimethylphenyl)-2,3-dihydro-1H-inden-1-ol

The mixture of 98% ee (S)-5-Bromo-2,3-dihydro-1H-inden-1-ol (100 mg, 0.47 mmol), which was obtained from the asymmetric reduction of 5-bromo-1-indanone using cat. (R)-(+)-2-methyl-CBS-oxazaborolidine and 2 eq. diethylaniline borane, according to the literature (S H Lee et al, *J. Org. Chem.* 2011, 76, 10011-10019) and 3,5-dimethyl-4-methoxyphenylboronic acid (101 mg, 0.56 mmol), bis(triphenylphosphine)palladium(II) dichloride (18 mg, 0.028 mmol), potassium carbonate (155 mg, 1.12 mmol), and DI water (40 mg, 2.22 mmol) in THF (10 mL) was stirred under the argon atmosphere at 80° C. for 4 hr to 8 hr until the starting alcohol spot disappeared on silica gel TLC analysis. After cooling down the temperature of reaction mixture, water (20 mL) was added followed by extraction with ethyl acetate (10 mL×3), drying over $Na_2SO_4$, concentrating the solvent before loading on silica gel for column chromatography. Elution with 20% ethyl acetate in n-hexane provided the title compound as an off-white solid (110 mg, 0.41 mmol, 87%). Spectroscopic data was identical to that of compound 5 described at example 4.

S-5-(4-hydroxy-3,5-dimethylphenyl)-2,3-dihydro-1H-inden-1-ol (S-2)

To a solution of S-5-(4-methoxy-3,5-dimethylphenyl)-2,3-dihydro-1H-inden-1-ol (134 mg, 0.5 mmol) in THF (10 mL) was added 1M super-hydride solution in THF (4 ml, 4.0 mmol) at rt. This solution was refluxed for 24 hr and after cooling down the temperature, water (10 mL) was added dropwise with cooling in an ice-bath. This solution was extracted with ethyl acetate (10 mL×3), dried over $Na_2SO_4$, concentrated by rotary evaporator to load onto silica gel for column chromatography. Elution with 35% ethyl acetate in n-hexane afforded S-5-(4-hydroxy-3,5-dimethylphenyl)-2,3-dihydro-1H-inden-1-ol as an off-white solid (81 mg, 0.32 mmol, 64%). Enantiomeric excess was confirmed by supercritical phase chromatography (SFC) as 98% ee. Spectroscopic data was identical to that of compound 2. (Supercritical Fluid Chromatography (SFC) column condition: 15% $MeOH/CO_2$, 1 mL/min, Daicel Chiralpak AD column (25 cm×4.6 mm), retention time: 10.94 min)

Example 3. Synthesis of R-5-(4-hydroxy-3,5-dimethylphenyl)-2,3-dihydro-1H-inden-1-ol (4-R-2)

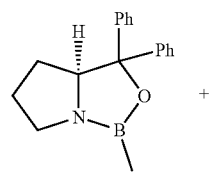

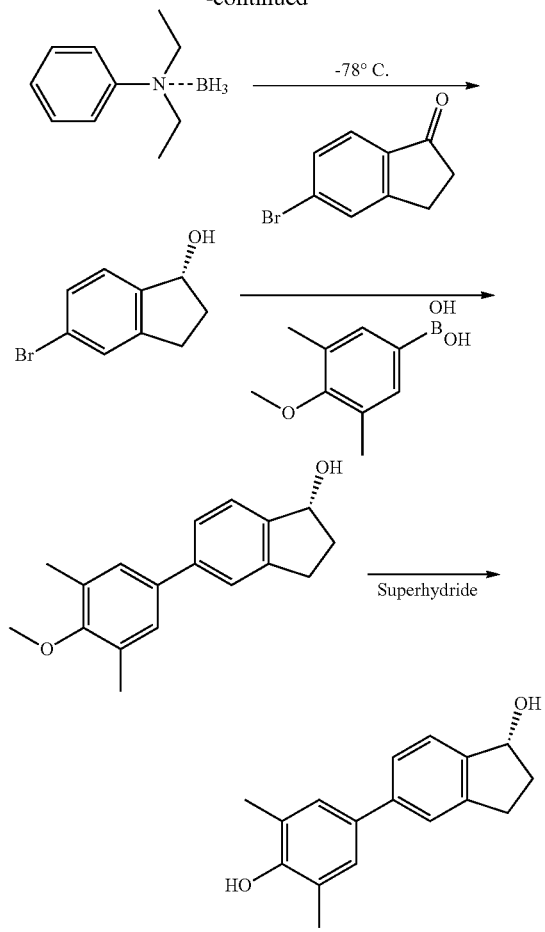

A similar procedure was followed except for the use of (S)-(+)-2-methyl-CBS-oxazaborolidine as a catalyst to obtain 98% ee (R)-5-Bromo-2,3-dihydro-1H-inden-1-ol precursor. (Supercritical Fluid Chromatography (SFC) column condition: 15% $MeOH/CO_2$, 1 mL/min, Daicel Chiralpak AD column (25 cm×4.6 mm), retention time: 15.18 min)

Example 4. 5-(4-methoxy-3,5-dimethylphenyl)-2,3-dihydro-1H-inden-1-ol (5)

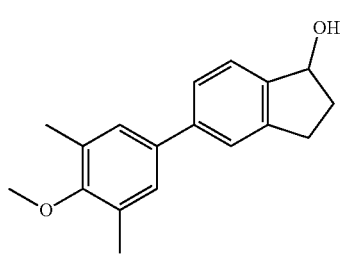

Compound 7 (55 mg, 0.21 mmol) in example 1 was treated with $NaBH_4$ (15 mg, 0.39 mmol) in the mixed solvent (MeOH-THF=1:1, v/v, 5 mL). Once starting material disappeared on $SiO_2$ TLC, solvent was concentrated by evaporation and passed through a silica gel pad with EtOAc:n-Hexane (1:1, v/v) to collect compound 5 (48 mg) as an off-white solid. $^1$H NMR (500 MHz, CDCl$_3$+methanol-d$_4$) δ 1.97-2.04 (m, 1H), 2.35 (s, 6H), 2.51-2.57 (m, 1H), 2.84-2.90 (m, 1H), 3.08-3.14 (m, 1H), 3.77 (s, 3H), 5.85 (t, 1H, J=5.5 Hz), 5.30 (s, 1H, phenolic OH), 7.23 (s, 2H), 7.12 (d, 1H, J=8.5 Hz), 7.43 (s, 1H), 7.45 (d, 1H, J=8.5 Hz); 13C NMR (126 MHz, CDCl$_3$) δ 16.50, 30.07, 36.42, 60.03, 76.46, 123.73, 124.59, 126.07, 127.91, 131.33, 137.10, 141.69, 143.91, 144.17, 156.76.

Example 5. 6-(4-hydroxy-3,5-dimethylphenyl)-1,2,3,4-tetrahydronaphthalen-1-ol (16)

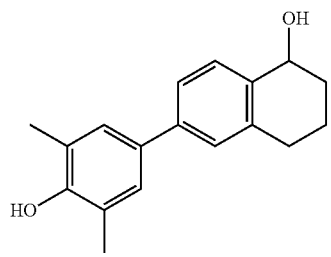

Compound 16 was synthesized according to the method described in example 1 with 3,5-dimethyl-4-methoxyphenylboronic acid (200 mg, 1.11 mmol) and 6-bromo-1-tetralone (225 mg, 1.00 mmol). The yield was comparable to that of compound 2. $^1$H NMR (500 MHz, CDCl$_3$) δ 1.78-1.85 (m, 1H), 1.91-1.97 (m, 1H), 1.98-2.05 (m, 1H), 2.31 (s, 6H), 2.75-2.82 (m, 1H), 2.85-2.92 (m, 1H), 3.02-3.16 (m, 1H), 4.83 (t, 1H, J=5.5 Hz), 7.20 (s, 2H), 7.27 (d, 1H, J=1.5 Hz), 7.38 (dd, 1H, J, J=1.5, 8.5 Hz), 7.47 (d, 1H, J=8.5 Hz); $^{13}$C NMR (126 MHz, CDCl$_3$) δ 16.30, 19.09, 29.68, 32.63, 68.24, 123.50, 124.95, 126.58, 127.53, 129.25, 133.24, 137.31, 137.60, 140.66, 152.09.

Example 6. 4'-(1-hydroxyethyl)-3,5-dimethyl-[1,1'-biphenyl]-4-ol (15)

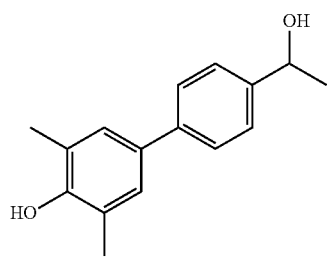

Compound 15 was synthesized according to the method described at example 1 with 3,5-dimethyl-4-methoxyphenylboronic acid (200 mg, 1.11 mmol) and 4-bromo-acetophenone (199 mg, 1.00 mmol). The yield was comparable to that of compound 2. $^1$H NMR (500 MHz, CDCl$_3$) δ 1.53 (d, 3H, J=5.0 Hz), 2.31 (s, 3H), 4.94 (q, 1H, J=5.0 Hz), 4.83 (t, 1H, J=5.5 Hz), 7.22 (s, 2H), 7.24 (d, 2H, J=8.5 Hz), 7.41 (d, 2H, J=8.5 Hz); $^{13}$C NMR (126 MHz, CDCl$_3$) δ 16.31, 25.34, 70.49, 123.54, 125.98, 126.49, 127.06, 127.37, 127.54, 133.19, 140.61, 152.09, 144.19, 152.09.

Example 7. Diphenolic acid-NHEtNHAc (71)

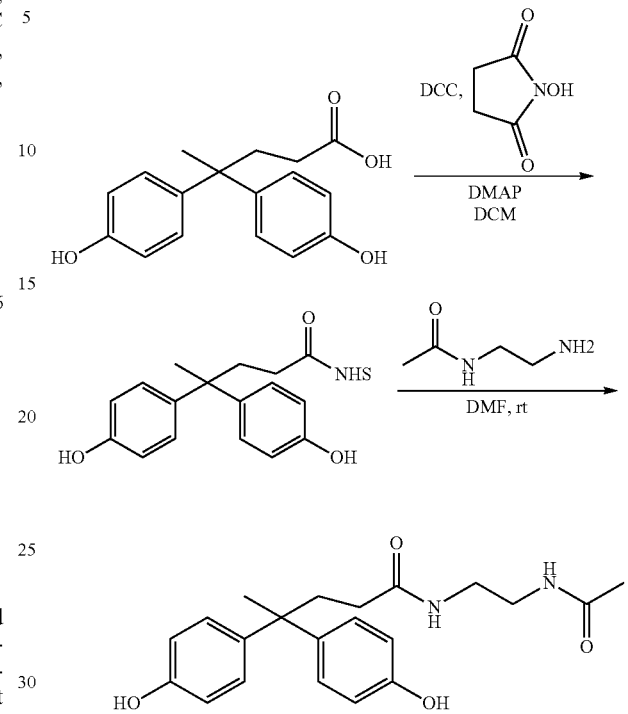

Diphenolic Acid NHS Ester.

To the solution of diphenolic acid (285 mg, 1.00 mmol) in DMF (1 mL) was added N-hydroxysuccinic acid (121 mg, 1.05 mmol), cat. amount of DMAP, and DCC (217 mg, 1.05 mmol). After stirring for 1 hr, EtOAc (10 mL) was added to precipitate the urea which was removed by filtration. The filtrate was washed with water (2 mL×4), sat. NaHCO$_3$, and dried over Na$_2$SO$_4$, and evaporation provided the NHS ester which is used without further purification. $^1$H NMR (400 MHz, CDCl$_3$+methanol-d$_4$) δ 1.49 (s, 3H), 2.26-34 (m, 2H), 2.34-2.43 (m, 2H), 2.75 (s, 4H), 6.66 (d, 4H, J=8.0 Hz), 6.94 (d, 4H, J=8.0 Hz); $^{13}$C NMR (126 MHz, CDCl$_3$+methanol-d$_4$) δ 25.72, 27.39, 30.19, 36.49. 44.53, 115.14, 128.32, 139.81, 154.86, 169.27, 169.57. ESI (m/z) 384.3 (M++1)

Diphenolic Acid-NHEtNHAc (71).

The reaction of NHS ester (38 mg, 0.1 mmol) with mono acetylated ethylene diamine (35 mg, 0.35 mmol) in DMF (500 μl) at rt. After sonicating (Branson sonicator Model 2210) the reaction mixture for 30 min at rt, added DI water (10 mL), and extracted with EtOAc (5 mL×3), washed with water (5 mL×3) again, dried over Na$_2$SO$_4$, concentrated to load 1 mm SiO$_2$ preparative thin layer chromatography. Rf 0.25 band developed with 5% MeOH in DCM was scraped out from Prep. TLC, followed by placing the SiO$_2$ chunk into sintered glass filter to extract out title compound with 20% MeOH in DCM to provide 28 mg of title compound. $^1$H NMR (500 MHz, CDCl$_3$+methanol-d$_4$) δ1.48 (s, 3H), 1.85-1.94 (m, 5H), 2.28 (q, 2H, J=5 Hz), 3.12-3.22 (m, 4H), 6.66 (d, 4H, J=8.0 Hz), 6.96 (d, 4H, J=8.0 Hz); $^{13}$C NMR (126 MHz, CDCl$_3$+methanol-d$_4$) δ 18.11, 26.61, 31.86, 36.35, 41.57, 43.42, 48.58, 118.81, 132.36, 144.36, 158.61. 176.42, 179.65; ESI (m/z) 371.2 (M++1)

Example 8. 1-ethynyl-5-(4-hydroxy-3,5-dimethyl-phenyl)-2,3-dihydro-1H-inden-1-ol (19)

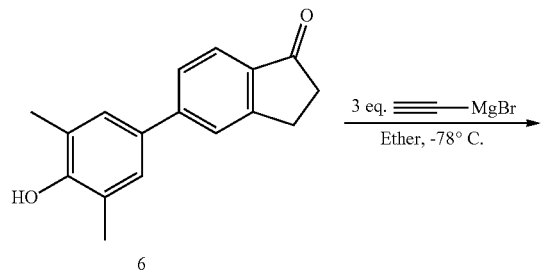

6

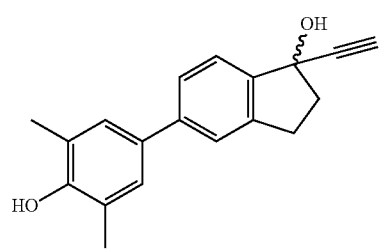

19

Compound 19 was synthesized by the reaction of compound 6 (80 mg, 0.32 mmol) with ethynylmagnesium bromide (1.2 mL×2, 0.5 M THF) in THF (10 mL) at −78° C. for 2 hr. After the reaction temperature rose to rt, water was carefully added dropwise to the reaction mixture, and 0.1 N HCl solution was added to acidify the reaction solution. The reaction mixture was extracted with EtOAc (5 mL×3), dried over $Na_2SO_4$, and concentrated to be loaded on a 1 mm $SiO_2$ prep TLC. Prep. TLC was developed with 20% EtOAc in n-hexane and the band at Rf 0.3 was scraped out to extract compound 19 (26 mg). $^1$H NMR (500 MHz, $CDCl_3$) δ 2.32 (s, 6H), 2.48-2.52 (m, 1H), 2.60-2.64 (m, 1H), 2.66 (s, 1H, OH), 2.92-3.01 (m, 1H), 3.17-3.22 (m, 1H), 4.74 (s, 1H, phenolic OH), 7.20 (s, 2H), 7.25 (s, 1H), 7.42 (d, 1H, J=8.5 Hz), 7.57 (d, 1H, J=8.5 Hz); $^{13}$C NMR (126 MHz, $CDCl_3$) δ 16.30, 29.80, 43.53, 73.20, 76.19, 86.13, 123.46, 123.56, 126.32, 127.75, 128.00, 133.43, 142.71, 143.75, 143.88, 152.22.

Example 9. 4-(1-chloro-2,3-dihydro-1H-inden-5-yl)-2,6-dimethylphenol (8)

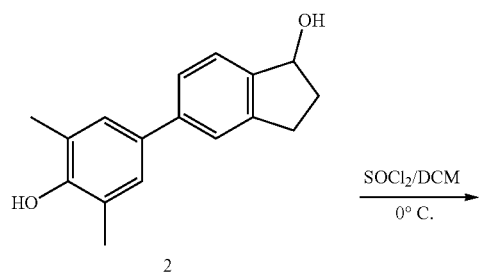

2

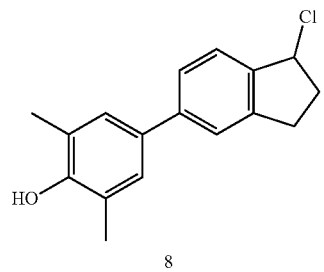

8

Compound 8 was synthesized by treating compound 2 (25 mg, 0.1 mmol) with $SOCl_2$ (40 mg, 0.34 mmol) in DCM (1 mL) at 0° C. for 2 hr. Washing with 5% $NaHCO_3$ and evaporation of the solvent afforded compound 8 (24 mg). $^1$H NMR (400 MHz, $CDCl_3$) δ 2.09-2.13 (m, 1H), 2.29 (s, 6H), 2.42-2.56 (m, 1H), 2.86-2.94 (m, 1H), 3.09-3.18 (m, 1H), 4.62 (s, 1H, phenolic OH), 6.20 (dd, 1H, J, J=3.0 Hz, 3.0 Hz), 7.18 (s, 2H), 7.37 (d, 1H, J=8.4 Hz), 7.41 (s, 1H), 7.42 (d, 1H, J=8.4 Hz); $^{13}$C NMR (100 MHz, $CDCl_3$) δ 16.29, 30.05, 32.72, 78.39, 123.26, 123.48, 125.83, 127.66, 127.77, 133.47, 139.54, 142.43, 145.32, 152.14.

Example 10. 5-(4-hydroxy-3,5-dimethylphenyl)-2,3-dihydro-1H-indene-1-carbonitrile (9)

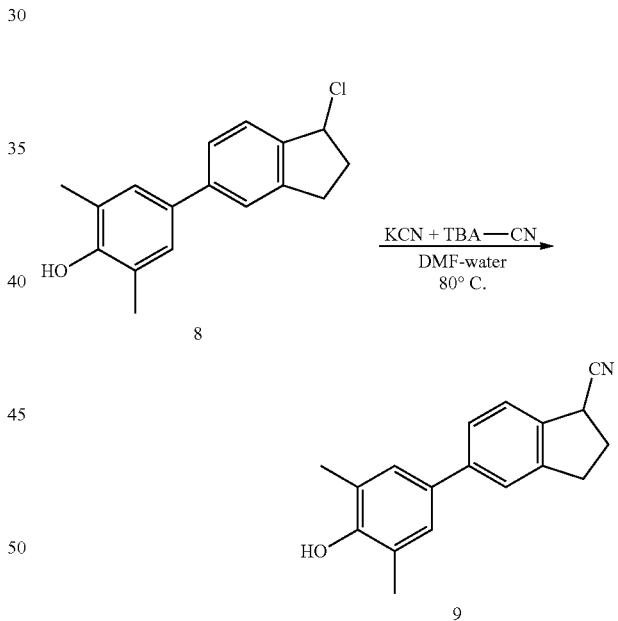

Compound 8 (14 mg, 0.51 mmol) was treated with potassium cyanide (50 mg, 1.56 mmol) and TBA-CN (100 mg) at DMF (1 mL) at 55° C. for 4 hr. The reaction mixture was poured into water (10 mL) and extracted with EtOAc (5 mL×3), dried over $Na_2SO_4$, concentrated under vacuum to load on a 0.2 mm $SiO_2$ TLC plate (20 cm×20 cm). TLC plate was developed by 15% EtOAc in n-hexane solvent, the Rf 0.5 band was scraped off and extracted to afford compound 9 (5 mg). $^1$H NMR (500 MHz, $CDCl_3$) δ 2.32 (s, 6H), 2.42-2.47 (m, 1H), 2.60-2.65 (m, 1H), 3.00-3.04 (m, 1H), 3.12-3.17 (m, 1H), 4.14 (t, 1H, J=8.0 Hz), 4.66 (s, 1H, phenolic OH), 7.20 (s, 2H), 7.43-7.47 (m, 3H).

Example 11. 4-(hydroxymethyl)-3',5'-dimethyl-[1,1'-biphenyl]-3,4'-diol (60)

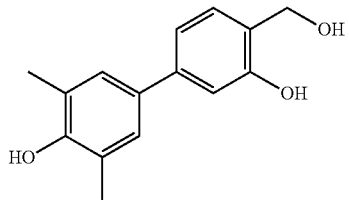

60

Compound 60 was synthesized according to the methods used in example 1 to synthesize compound 2, using 3,5-dimethyl-4-methoxyphenylboronic acid (200 mg, 1.11 mmol) and 4-bromo-2-methoxybenzaldehyde (215 mg, 1.00 mmol). The yield was comparable to that of compound 2. $^1$H NMR (500 MHz, CDCl$_3$) δ 2.31 (s, 6H), 4.70 (s, 1H, phenolic OH), 4.91 (s, 2H), 7.04 (dd, 1H, J, J=1.5 Hz, 8.5 Hz), 7.07 (d, 1H, J=8.5 Hz), 7.09 (d, 1H, J=1.5 Hz), 7.22 (s, 2H), 7.27 (s, 1H); $^{13}$C NMR (126 MHz, CDCl$_3$) δ 16.28, 64.88, 115.03, 118.65, 123.00, 123.52, 127.48, 132.81, 142.93, 152.26, 156.56.

Example 12. 3'-(hydroxymethyl)-3,5-dimethyl-[1,1'-biphenyl]-4,4'-diol (59)

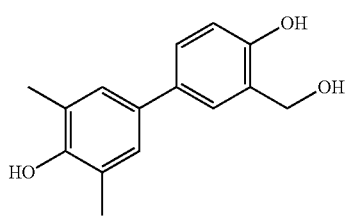

59

Compound 59 was synthesized according to the methods used in example 1 to synthesize compound 2, using 3,5-dimethyl-4-methoxyphenylboronic acid (200 mg, 1.11 mmol) and 5-bromo-2-methoxybenzaldehyde (215 mg, 1.00 mmol). The yield was comparable to that of compound 2. $^1$H NMR (500 MHz, CDCl$_3$) δ 2.31 (s, 6H), 4.70 (s, 1H, phenolic OH), 4.93 (s, 2H), 6.94 (d, 1H, J=8.5 Hz), 7.15 (s, 2H), 7.21 (d, 1H, J=1.5 Hz), 7.39 (dd, 1H, J, J=1.5 Hz, 8.5 Hz); $^{13}$C NMR (126 MHz, CDCl$_3$) δ 16.29, 65.16, 117.08, 123.51, 124.91, 126.33, 127.17, 127.96, 133.09, 133.55, 151.66, 155.31.

Example 13. 5-(3,5-dichloro-4-hydroxyphenyl)-2,3-dihydro-1H-inden-1-ol (63)

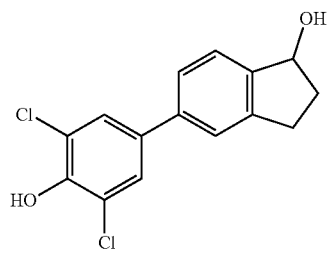

63

Compound 63 was synthesized according to the methods used in example 1 to synthesize compound 2, using 3,5-dichloro-4-methoxyphenylboronic acid (200 mg, 1.11 mmol) and 5-bromo-1-indanone (211 mg, 1.00 mmol). The yield was comparable to that of compound 2. $^1$H NMR (500 MHz, CDCl$_3$) δ 2.01-2.05 (m, 1H), 2.52-2.59 (m, 1H), 2.85-2.91 (m, 1H), 3.09-3.15 (m, 1H), 5.30 (t, 1H, J=5.5 Hz), 5.94 (s, 1H, phenolic OH), 7.37 (d, 1H, J=8.5 Hz), 7.38 (s, 1H), 7.47 (d, 1H, J=8.5 Hz), 7.48 (s, 2H); $^{13}$C NMR (126 MHz, CDCl$_3$) δ 30.04, 36.38, 76.35, 121.65, 123.46, 124.96, 125.76, 127.11, 135.29, 139.04, 144.59, 144.89, 147.31.

Example 14. 3,5-Dichloro-3'-(hydroxymethyl)-[1,1'-biphenyl]-4,4'-diol (64)

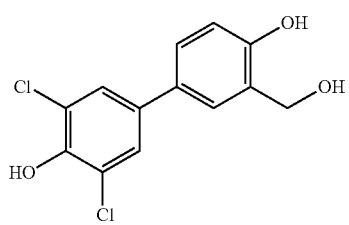

64

Compound 64 was synthesized according to the methods used in example 1 to synthesize compound 2, with 3,5-dichloro-4-methoxyphenylboronic acid (200 mg, 1.11 mmol), 5-bromo-2-methoxybenzaldehyde (215 mg, 1.00 mmol). The yield was comparable to that of compound 2. $^1$H NMR (500 MHz, CDCl$_3$+methanol-d$_4$) δ 4.75 (s, 2H), 7.04 (dd, 1H, J, J=1.5 Hz, 8.5 Hz), 6.83 (d, 1H, J=8.5 Hz), 7.19 (d, 1H, J=2.0 Hz), 7.24 (dd, 1H, J, J=2.0, 8.5 Hz), 7.35 (s, 2H); $^{13}$C NMR (126 MHz, CDCl$_3$+methanol-d$_4$) δ 63.16, 116.48, 122.02, 126.48, 126.56, 127.18, 130.36, 134.47, 139.95, 147.33, 155.80.

Example 15. 3'-fluoro-4'-(hydroxymethyl)-3,5-dimethyl-[1,1'-biphenyl]-4-ol (25)

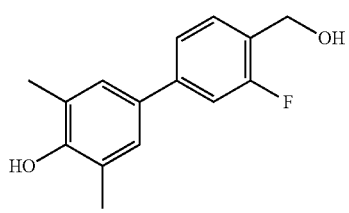

25

Compound 25 was synthesized according to the methods used in example 1 to synthesize compound 2, using 3,5-dimethyl-4-methoxyphenylboronic acid (200 mg, 1.11 mmol) and 4-bromo-2-fluorobenzaldehyde (203 mg, 1.00 mmol). The yield was comparable to that of compound 2. $^1$H NMR (500 MHz, CDCl$_3$+methanol-d$_4$) δ 2.32 (s, 6H), 4.79 (s, 2H), 4.81 (s, 1H, phenolic OH), 7.21 (s, 2H), 7.24 (d, 1H, J=11.5 Hz), 7.33 (d, 1H, J=8.0 Hz), 7.43 (t, 1H, J=8.0 Hz); $^{13}$C NMR (126 MHz, CDCl$_3$+methanol-d$_4$) δ 16.29, 59.60 (d, $J_{CF}$=3.9 Hz), 113.61 (d, $J_{CF}$=22.4 Hz), 122.56 (d, $J_{CF}$=2.8 Hz), 123.76, 125.80 (d, $J_{CF}$=14.5 Hz), 127.46, 129.85 (d, $J_{CF}$=4.9 Hz), 131.90, 143.16 (d, $J_{CF}$=7.8 Hz), 152.60, 161.82 (d, $J_{CF}$=245.9 Hz).

Example 16. 3'-(3-hydroxypropyl)-3,5-dimethyl-[1,1'-biphenyl]-4-ol (47)

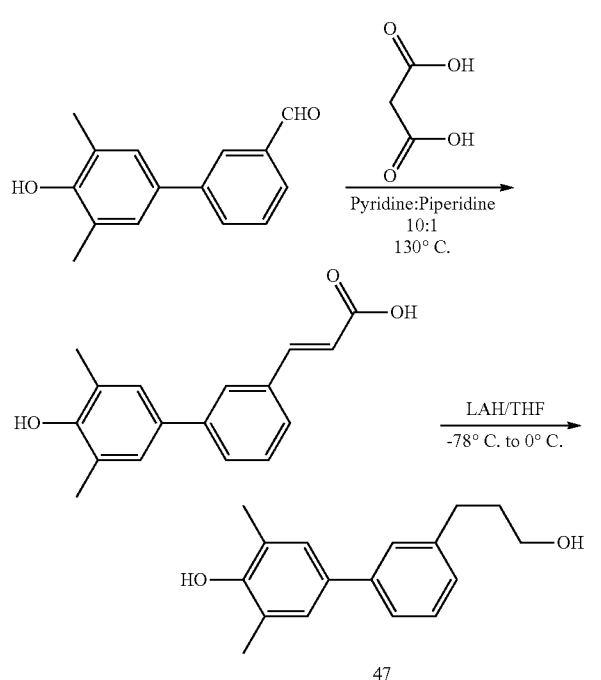

The mixture of 4'-hydroxy-3',5'-dimethyl-[1,1'-biphenyl]-3-carbaldehyde (40 mg, 0.18 mmol), and malonic acid (19 mg, 0.18 mmol), 11 µL of the mixture of pyridine and piperidine (10:1, v/v) was heated up at 130° C. for 3 hr. The reaction mixture was diluted with 1 mL EtOAc and loaded onto a 1 mm SiO₂ Preparative TLC place (20 cm×20 cm) and developed with 40% EtOAc in n-hexane solvent. Rf 0.45 band was scraped off to afford (E)-3-(4'-hydroxy-3',5'-dimethyl-[1,1'-biphenyl]-3-yl)acrylic acid (35 mg) after extraction using a sintered glass filter and 20% MeOH in DCM. Subsequently, reduction of the acid (20 mg, 0.07 mmol) with LAH (8.5 mg, 0.22 mmol) in THF (1 mL) at the temperature of −78° C. for addition and then 0° C. for a reaction, and a typical workup with Rochelle salt, and separation with 45% EtOAc in n-hexane afforded compound 47 (18 mg).

(E)-3-(4'-hydroxy-3',5'-dimethyl-[1,1'-biphenyl]-3-yl)acrylic Acid

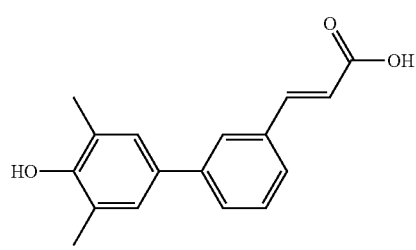 [SMILES: Cc1cc(-c2cccc(/C=C/C(=O)O)c2)cc(C)c1O]

¹H NMR (400 MHz, CDCl₃+methanol-d₄) δ 2.28 (s, 6H), 6.45 (d, 1H, J=16.0 Hz), 7.17 (s, 2H), 7.37 (t, 1H, J=7.5 Hz), 7.41 (d, 1H, J=7.5), 7.51 (d, 1H, J=7.5 Hz); ¹³C NMR (100 MHz, CDCl₃+methanol-d₄) δ 16.41, 118.14, 124.12, 126.39, 126.71, 127.47, 129.01, 129.37, 132.39, 134.79, 142.06, 146.26, 152.62, 169.96.

¹H NMR (500 MHz, CDCl₃) δ 1.94 (quintet, 2H, J=6.5 Hz), 2.31 (s, 6H), 2.76 (t, 2H, J=6.5 Hz), 3.70 (t, 2H, J=6.5 Hz), 7.12 (d, 1H, J=8.0 Hz), 7.21 (s, 2H), 7.31 (t, 1H, J=8.0 Hz), 7.36 (d, 1H, J=8.0); ¹³C NMR (126 MHz, CDCl₃) δ 16.33, 32.41, 34.51, 62.55, 123.62, 124.59, 126.85, 127.15, 127.59, 128.92, 133.55, 141.47, 142.35, 152.13.

Example 17. 4'-(3-hydroxypropyl)-3,5-dimethyl-[1,1'-biphenyl]-4-ol (48)

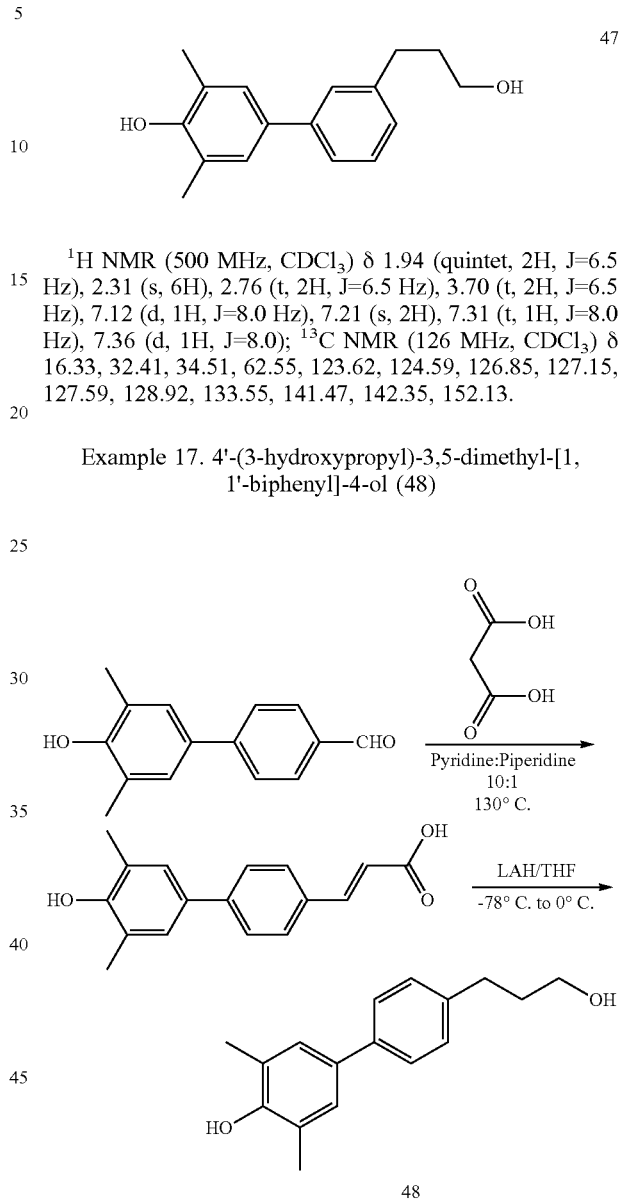

Using the same method to make compound 47, compound 48 (13 mg) was prepared from 4'-hydroxy-3',5'-dimethyl-[1,1'-biphenyl]-4-carbaldehyde (40 mg, 0.18 mmol) and malonic acid (21 mg, 0.2 mmol) in the mixture of pyridine and piperidine (10:1, v/v) and subsequent reduction using LAH in THF (1 ml).

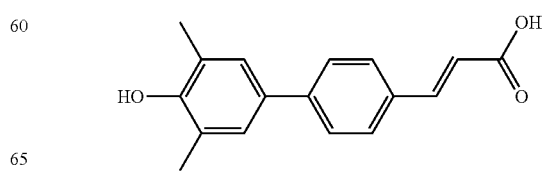

$^1$H NMR (400 MHz, CDCl$_3$+methanol-d$_4$) δ 2.23 (s, 6H), 6.36 (d, 1H, J=16.0 Hz), 7.23 (s, 2H), 7.50 (s, 4H), 7.64 (d, 1H, J 16.0 Hz).

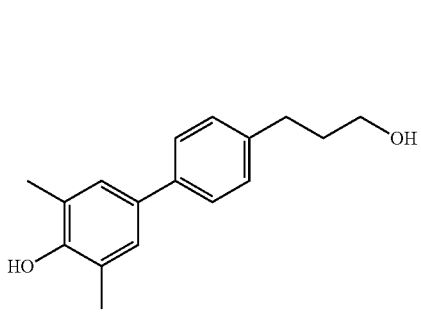

48

$^1$H NMR (500 MHz, CDCl$_3$) δ 1.94 (quintet, 2H, J=6.5 Hz), 2.30 (s, 6H), 2.75 (t, 2H, J=6.5 Hz), 3.72 (t, 2H, J=6.5 Hz), 7.22 (s, 2H), 7.25 (d, 2H, J=8.0 Hz), 7.47 (d, 2H, J=8.0); $^{13}$C NMR (126 MHz, CDCl$_3$) δ 16.28, 31.90, 34.46, 62.57, 123.49, 126.73, 126.80, 126.97, 127.46, 128.95, 139.01, 140.29, 151.92.

Example 18. 4-(2,3-dihydro-1H-inden-5-yl)-2 6-dimethylphenol (13)

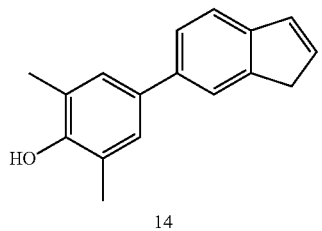

14

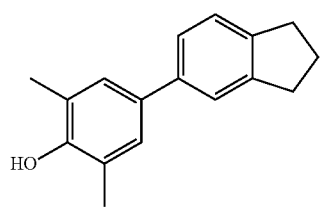

13

Compound 14 (24 mg, 0.1 mmol) was dissolved into MeOH (2 mL) containing cat. amount of 10% Pd/C and shaken under 30 PSI H$_2$ in a Parr shaker at rt for 1 hr. Filtration through a sintered glass filter and evaporation provided compound 13 (21 mg). $^1$H NMR (500 MHz, CDCl$_3$) δ 2.109 (q, 2H, J=7.5 Hz), 2.31 (s, 6H), 2.92 (d, 2H, J=7.5 Hz), 2.96 (d, 2H, J=7.5 Hz), 4.62 (s, 1H, Phenolic OH), 7.20 (s, 2H), 7.25 (d, 1H, J=8.5 Hz), 7.31 (d, 1H, J=8.5 Hz), 7.40 (s, 1H); $^{13}$C NMR (126 MHz, CDCl$_3$) δ 16.29, 25.79, 32.76, 33.13, 123.05, 123.25, 123.36, 127.61, 142.83, 144.98, 151.74, 154.50.

Example 19. 5-(3,5-dimethylphenyl)-2,3-dihydro-1H-inden-1-ol (12)

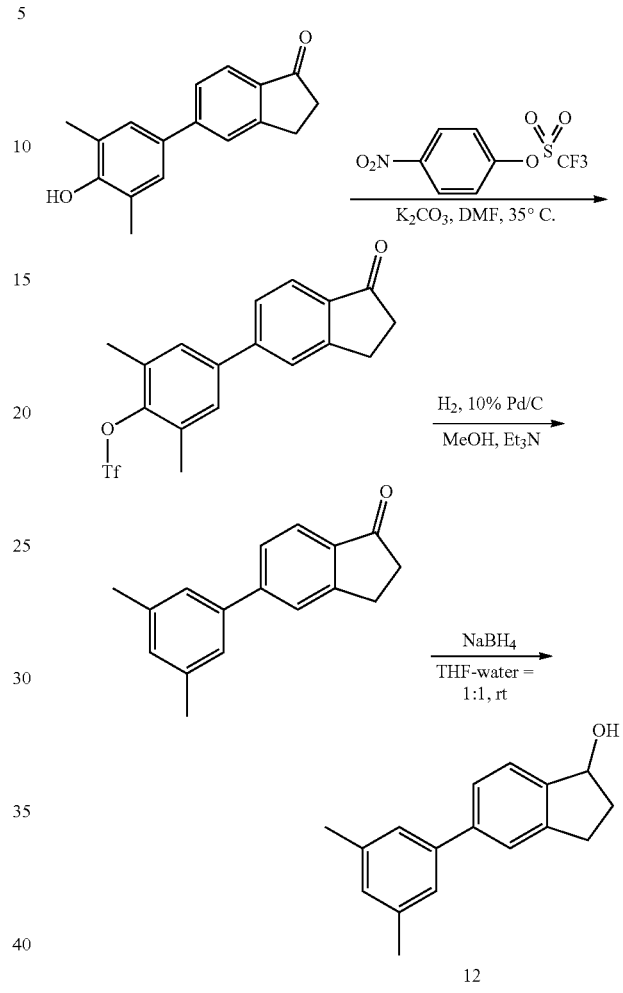

5-(4-Trifluoromethansulfonloxy-3,5-dimethylphenyl)-2,3-dihydro-1H-inden-1-one

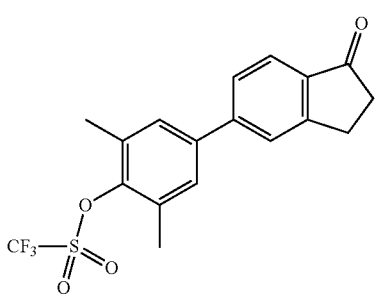 [SMILES: Cc1cc(-c2ccc3c(c2)CCC3=O)cc(C)c1OS(=O)(=O)C(F)(F)F]

Compound 6 (50 mg, 1.98 mmol) was reacted with p-nitrophenyl trifluoromethansulfonate (58 mg, 2.14 mmol) over K$_2$CO$_3$ (27.6 mg, 0.2 mmol) in DMF (1 mL) at 55° C. for 2 hr. The reaction solution was poured into water (10 mL), extracted with EtOAc (10 mL×3), washed with sat. NaHCO$_3$ aqueous solution, concentrated to load onto silica gel for column chromatography. Elution with 30% EtOAc in n-hexane solvent afforded 5-(4-Trifluoromethansulfonyloxy-3,5-dimethylphenyl)-2,3-dihydro-1H-inden-1-one (40 mg) as a colorless solid. (Rf=0.4) $^1$H NMR (500 MHz, CDCl$_3$) δ 2.46 (s, 6H), 2.78 (t, 2H, J=5.5 Hz), 3.22 (t, 2H, J=5.5 Hz), 7.36 (s, 2H), 7.56 (d, 1H, J=8.5 Hz), 7.65 (s, 1H), 7.83 (d, 1H, J=8.5 Hz); $^{13}$C NMR (126 MHz, CDCl$_3$) δ 17.56, 26.19, 36.83, 118.85 (q, J$_{CF}$=320.6), 124.56, 125.56, 127.13, 132.42, 136.33, 141.27, 146.65, 147.20, 156.59, 208.24; $^{19}$F NMR (470 MHz, CDCl$_3$) δ −73.78.

5-(3,5-dimethylphenyl)-2,3-dihydro-1H-inden-1-one

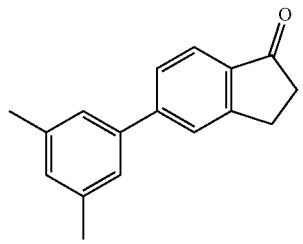 [SMILES: Cc1cc(C)cc(-c2ccc3c(c2)CCC3=O)c1]

The triflated compound (25 mg, 0.07 mmol) was dissolved into MeOH. Et$_3$N (20 μL) and catalytic amount of 10% Pd/C were added, and hydrogen (30 PSI) was applied. After shaking for 1 hr using a Parr Reactor, the reaction mixture was passed through a sintered glass filter to remove Pd/C and evaporated under vacuum to provide 5-(3,5-dimethylphenyl)-2,3-dihydro-1H-inden-1-one (15 mg). This residue used without further purification. $^1$H NMR (500 MHz, CDCl$_3$) δ 2.40 (s, 6H), 2.74 (t, 2H, J=5.5 Hz), 3.19 (t, 2H, J=5.5 Hz), 7.06 (s, 1H), 7.25 (s, 2H), 7.59 (d, 1H, J=8.0 Hz), 7.66 (s, 1H), 7.81 (d, 1H, J=8.0 Hz); $^{13}$C NMR (126 MHz, CDCl$_3$) δ 21.64, 26.11, 36.77, 124.19, 125.34, 125.63, 127.04, 130.21, 136.08, 138.76, 140.43, 148.23, 156.05, 206.91.

5-(3,5-dimethylphenyl)-2,3-dihydro-1H-inden-1-ol (12)

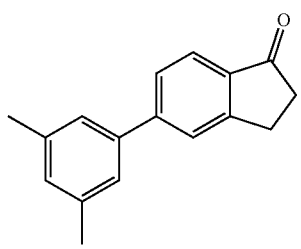

12

Subsequently, treatment of 5-(3,5-dimethylphenyl)-2,3-dihydro-1H-inden-1-one (15 mg, 0.06 mmol) with NaBH$_4$ (5 mg, 0.13 mmol) in THF-water (1:1, v/v, 1 mL), followed by extraction with EtOAc (5 mL×3), drying over Na$_2$SO$_4$, and passing through silica gel pad afforded 12 mg 12 as colorless solid, after solvent evaporation. $^1$H NMR (500 MHz, CDCl$_3$) δ 1.97-2.05 (m, 1H), 2.39 (s, 6H), 2.51-2.58 (m, 1H), 2.85-2.91 (m, 1H), 3.09-3.15 (m, 1H), 5.30 (t, 1H, J=5.5 Hz), 7.01 (s, 1H), 7.21 (s, 2H), 7.47 (s, 3H); 13C NMR (126 MHz, CDCl$_3$) δ 21.66, 30.07, 36.43, 76.49, 123.95, 124.60, 125.44, 126.29, 129.13, 138.48, 141.57, 142.18, 144.17, 144.16.

Example 20. 2-fluoro-5-(4-hydroxy-3,5-dimethylphenyl)-2,3-dihydro-1H-inden-1-ol (50)

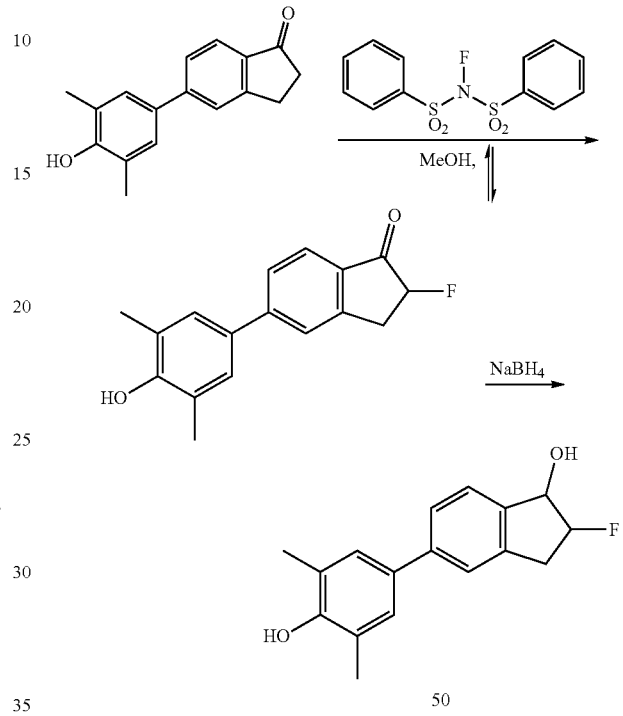

50

Compound 6 (40 mg, 0.16 mmol) was treated with Accufluor (55 mg., 1.74 mmol) in MeOH at reflux temperature for 4 hr. Once starting material disappeared on SiO$_2$ TLC analysis (10% EtOAc in n-Hexane), the temperature of the reaction solution was cooled down to rt and NaBH$_4$ (10 mg, 0.26 mmol) was added to the reaction mixture. The mixture was evaporated to load onto silica gel for column chromatography. Elution with 20% EtOAc in n-Hexane afforded 50 as a colorless solid (28 mg). $^1$H NMR (500 MHz, CDCl$_3$+methanol-d$_4$) δ 2.23 (s, 6H), 3.02-3.22 (m, 2H), 5.07 (dd, 1H, J$_H$-H, J$_H$-F=4.2, 17.9 Hz), 5.24 (ABXF, 1H, J, J, J=2.0, 4.4, 53.9 Hz), 7.12 (s, 2H), 7.35 (s, 1H), 7.40 (s, 2H); $^{13}$C NMR (126 MHz, CDCl$_3$) δ 16.44, 36.77 (d, J=22.2 Hz), 75.86, 95.06 (d, J=182.5 Hz), 123.56, 124.39, 124.79, 126.27, 127.43, 132.91, 139.11, 139.70, 152.56.

Example 21. 4'-(2-hydroxyethyl)-3,5-dimethyl-[1,1'-biphenyl]-4-ol (45)

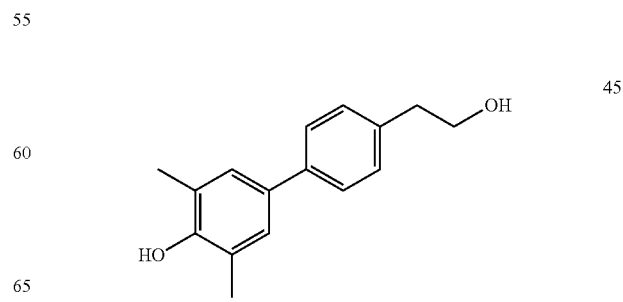

45

Compound 45 was synthesized according to the method described in example 1, using 3,5-dimethyl-4-methoxyphenylboronic acid (200 mg, 1.11 mmol) and 3-bromo-phenethylalcohol (201 mg, 1.00 mmol). The yield was comparable to that of compound 2. $^1$H NMR (500 MHz, CDCl$_3$) δ 2.31 (s, 6H), 2.90 (t, 2H, J=6.5 Hz), 3.90 (t, 2H, J=6.5 Hz), 7.21 (s, 2H), 7.27 (d, 2H, J=8.0 Hz), 7.49 (d, 2H, J=8.0); $^{13}$C NMR (126 MHz, CDCl$_3$) δ 16.33, 39.01, 63.94, 123.57, 127.16, 127.48, 129.57, 133.26, 136.87, 139.63, 152.04.

Example 22. 3'-(2-hydroxyethyl)-3,5-dimethyl-[1,1'-biphenyl]-4-ol (44)

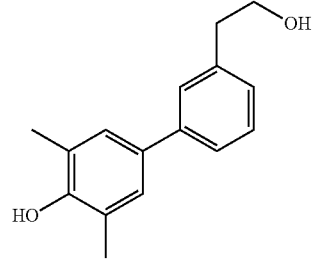

Compound 44 was synthesized according to the methods described at example 1, using 3,5-dimethyl-4-methoxyphenylboronic acid (200 mg, 1.11 mmol) and 4-bromo-phenethylalcohol (201 mg, 1.00 mmol). The yield was comparable to that of compound 2. $^1$H NMR (500 MHz, CDCl$_3$) δ 2.32 (s, 6H), 2.93 (t, 2H, J=6.5 Hz), 3.91 (t, 2H, J=6.5 Hz), 4.82 (s, 1H, Phenolic OH), 7.16 (d, 1H, J=8.0 Hz), 7.22 (s, 2H), 7.35 (d, 2H, J=8.0 Hz), 7.41 (d, 2H, J=8.0); $^{13}$C NMR (126 MHz, CDCl$_3$) δ 16.33, 39.53, 63.99, 123.61, 125.22, 127.43, 127.62, 127.74, 129.15, 133.38, 138.99, 141.70, 152.18.

Example 23. 4-(1-methoxy-2,3-dihydro-1H-inden-5-yl)-2,6-dimethylphenol (22), 5-(4-hydroxy-3-methyl-5-methoxymethylphenyl)-2,3-dihydro-1H-inden-1-ol (64), and 4-(1H-inden-6-yl)-2,6-dimethylphenol (14)

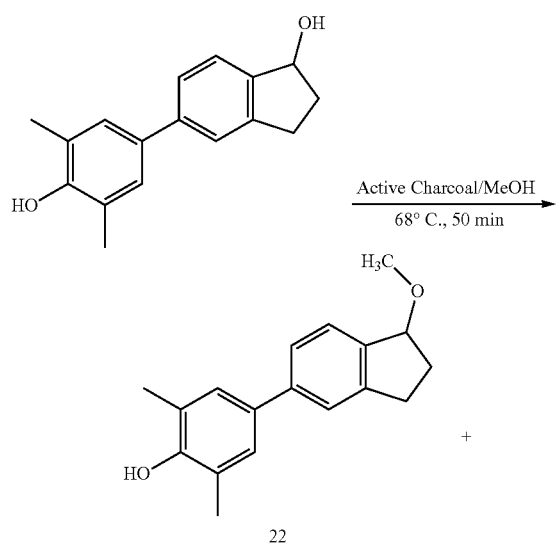

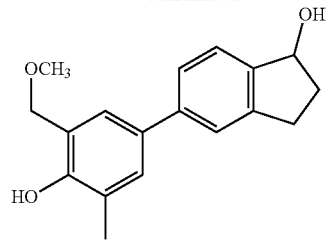

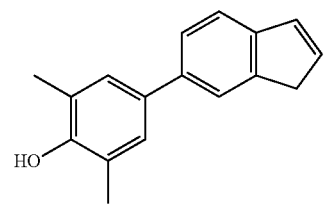

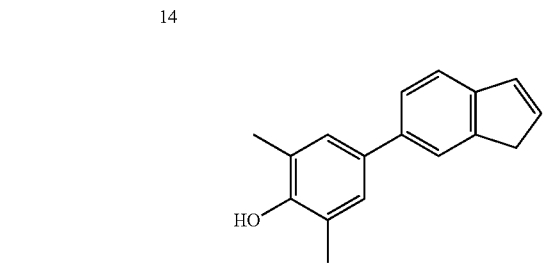

Compound 2 (400 mg) was treated with Activated charcoal (Norit, 4 g) in MeOH for 50 min by frequently heating at boiling temperature, followed by filtration, evaporation of filtrate to afforded the mixture of 2, 22, 64, and 14.

4-(1-methoxy-2,3-dihydro-1H-inden-5-yl)-2,6-dimethylphenol (22)

Compound 22 (80 mg) was obtained from the mixture by SiO$_2$ column chromatography with the eluent of 25% EtOAc in n-Hexane (rf=0.8). $^1$H NMR (500 MHz, CDCl$_3$) δ 2.17-2.23 (m, 1H), 2.34 (s, 6H), 2.38-2.47 (m, 1H), 2.88-2.94 (m, 1H), 3.15-3.21 (m, 1H), 3.49 (s, 3H), 4.91 (ABq, 1H, J=4.0, 6.5 Hz), 5.03 (s, 1H, phenolic OH), 7.25 (s, 2H), 7.43 (d, 1H, J=7.5 Hz), 7.47 (s, 1H), 7.48 (d, 1H, J=7.5 Hz); 13C NMR (126 MHz, CDCl$_3$) δ 16.37, 30.48, 32.32, 56.23, 84.64, 123.49, 123.76, 125.39, 125.49, 127.67, 133.68, 140.95, 141.93, 144.94, 152.14.

5-(5-Methoxymethyl-4-hydroxy-3-methylphenyl)-2,3-dihydro-1H-inden-1-ol (64)

Compound 64 (10 mg) was collected from the reaction by using HPLC column chromatography (Supelco semi prep Silica column, 10 μm particle size, L×I.D. 25 cm×10 mm, 5% IPA in n-Hexane, 4 ml/min, retention time: 11.79 min). $^1$H NMR (500 MHz, CDCl$_3$) δ 1.97-2.03 (m, 1H), 2.36 (s, 3H), 2.52-2.60 (m, 1H), 2.84-2.91 (m, 1H), 3.05-3.14 (mm, 1H), 3.46 (s, 3H), 4.73 (s, 2H, benzylic CH$_2$), 5.29 (q, 1H, J=5.5 Hz), 7.09 (s, 1H), 7.33 (s, 1H), 7.41 (d, 1H, J=8.5 Hz), 7.42 (s, 1H), 7.45 (d, 1H, J=8.5 Hz), 7.66 (s, 1H, Phenolic OH). 4-(1H-inden-6-yl)-2,6-dimethylphenol (14)

14

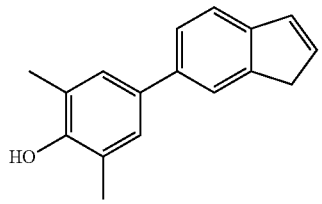

Compound 14 (15 mg) was isolated from the mixture obtained from the treatment of Activated charcoal, by chromatography using the mixed solvent (25% EtOAc in Hexane, Rf=0.9). The mixture of Compound 2 (35 mg, 0.14 mmol), cat. amount of p-toluene sulfonic acid monohydrate in benzene was refluxed under a system equipped with a Dean-Stark trap for 4 hr. After washing with sat. NaHCO₃ aqueous solution, evaporation of the solvent afford the compound 14 (28 mg). $^1$H NMR (500 MHz, CDCl₃) δ 2.33 (s, 6H), 3.47 (s, 2H), 7.06 (s, 1H), 7.25 (s, 2H), 6.57 (dt, 1H, J, J=1.9, 5.5 Hz), 6.92 (d, 1H, J=5.5 Hz), 7.26 (s, 2H), 7.43 (d, 1H, J=8.0 Hz), 7.47 (d, 1H, J=8.0 Hz), 7.67 (s, 1H); $^{13}$C NMR (126 MHz, CDCl₃) δ 16.34, 39.38, 121.19, 122.52, 123.51, 125.30, 127.66, 132.04, 134.17, 134.40, 137.99, 143.64, 144.57, 151.80.

Example 24. Synthesis of (1S,3aR,5S,7aS)-5-(4-hydroxy-3,5-dimethylphenyl)-7a-methyloctahydro-1H-inden-1-ol (43)

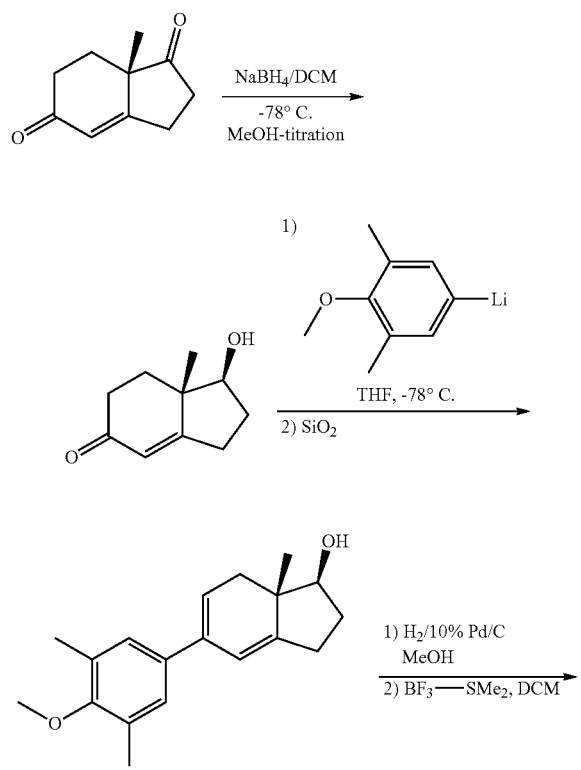

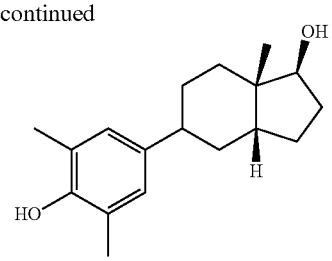

43

(1S,7aS)-1-hydroxy-7a-methyl-1,2,3,6,7,7a-hexahydro-5H-inden-5-one

This compound was prepared by the reaction of (S)-7a-methyl-2,3,7,7a-tetrahydro-1H-indene-1,5(6H)-dione (0.4 g, 2.43 mmol) with NaBH₄ (23.0 mg, 0.62 mmol) by titrating MeOH at =78° C., according to the literature (E. J. Schweiger et al, Tetrahedron letters, Vol. 38,No. 35,pp. 6127-6130, 1997).

(1S,7aS)-5-(4-methoxy-35-dimethylphenyl)-7a-methyl-2,3,7,7a-tetrahydro-1H-inden-1-ol To the solution of 2,6-dimethyl-4-bromo-anisole (777 mg, 3.6 mmol) was added dropwise n-BuLi (1.6 M in n-hexane, 2.25 mL) at −78° C. This mixture was stirred for 1 hr before adding dropwise a (1S,7aS)-1-hydroxy-7a-methyl-1,2,3,6,7,7a-hexahydro-5H-inden-5-one (150 mg, 0.90 mmol) solution in THF (5 mL) through a cannula needle at −78° C. The reaction mixture was stirred for 4 more hr at rt, followed by addition of water (20 mL), extraction with ethyl acetate (10 mL×3), drying over Na₂SO₄, and concentration under vacuum to load onto SiO₂ for column chromatography. Elution with 20% ethyl acetate in n-hexane afforded (1S,7aS)-5-(4-methoxy-3,5-dimethylphenyl)-7a-methyl-2,3,7,7a-tetrahydro-1H-inden-1-ol (130 mg). $^1$H NMR (500 MHz, CDCl₃) δ 1.02 (s, 3H), 1.48-1.55 (m, 1H), 2.02-2.08 (m, 1H), 2.31 (s, 6H), 2.41-2.48 (m, 1H), 2.58-2.68 (m, 2H), 3.74 (s, 3H), 4.08 (t, 1H, J=7.5 Hz), 5.42 (s, 1H), 6.54 (d, 1H, J=1.5 Hz), 7.16 (s, 2H); $^{13}$C NMR (126 MHz, CDCl₃) δ 15.05, 16.50, 25.85, 34.27, 38.50, 44.92, 59.97, 82.21, 119.41, 119.59, 126.00, 130.81, 136.90, 137.81, 146.80, 156.72.

(1 S,3aR,5S,7aS)-5-(4-hydroxy-3,5-dimethylphenyl)-7a-methyloctahydro-1H-inden-1-ol Hydrogen (30 PSI) in a Parr shaker was applied to a methanol solution of (1 S,7aS)-5-(4-methoxy-3,5-dimethylphenyl)-7a-methyl-2,3,7,7a-tetrahydro-1H-inden-1-ol (110 mg, 0.39 mmol) containing a cat. amount of 10% Pd/C for 2 hr at rt. The system was purged with nitrogen before passage through a celite pad to remove Pd/C to afford title compound (102 mg). $^1$H NMR (500 MHz, CDCl₃) δ 0.92 (s, 3H), 1.07-1.03 (m, 1H), 1.05-1.75 (m, 7H), 1.83-1.85 (m, 1H), 2.09-2.15 (m, 1H), 2.28 (s, 6H), 2.36-2.44 (m, 2H), 3.72 (s, 3H), 3.78 (t, 1H, J=7.5 Hz), 6.87 (s, 2H); $^{13}$C NMR (126 MHz, CDCl₃) δ 10.69, 16.41, 25.70, 30.12, 30.71, 33.73, 37.18, 42.76, 44.52, 45.62, 59.92, 82.05, 127.42, 130.67, 142.79, 155.21.

After evaporating and drying the MeOH solvent, the residue was re-dissolved into DCM (10 mL) to which was added a boron trifluoride methyl sulfide (350 mg, 2.7 mmol)

at rt, and the reaction was continuously stirred for 6 hr before adding MeOH dropwise at 0° C., followed by extraction with ethyl acetate (10 mL×3), drying over Na$_2$SO$_4$, and evaporation of solvent under vacuum to afford the title compound (81 mg). $^1$H NMR (500 MHz, CDCl$_3$) δ 0.87 (s, 3H), 0.91-0.94 (m, 1H), 1.00-1.05 (m, 1H), 1.38-1.78 (m, 8H), 1.95-1.97 (m, 1H), 2.03-2.09 (m, 1H), 2.23 (s, 6H), 2.35-2.42 (m, 1H), 3.74 (t, 1H, J=8.0 Hz), 6.85 (s, 2H); $^{13}$C NMR (126 MHz, CDCl$_3$) δ 10.69, 16.25, 25.72, 30.32, 30.74, 33.90, 37.23, 42.77, 44.38, 45.69, 82.09, 123.04, 127.23, 139.27, 150.53.

Example 25. 2-Bromo-5-(4-hydroxy-3,5-dimethylphenyl)-2,3-dihydro-1H-inden-1-one (51) and 2,2-dibromo-5-(4-hydroxy-3,5-dimethylphenyl)-2,3-dihydro-1H-inden-1-one (52)

Hz), 4.70 (ABq, 1H, J, J=7.5, 3.5 HZ), 7.29 (s, 2H), 7.59 (s, 1H), 7.62 (d, 1H, J=8.5 Hz), 7.87 (d, 1H, J=8.5 Hz); $^{13}$C NMR (126 MHz, CDCl$_3$) δ 16.32, 38.30, 44.79, 124.01, 124.20, 125.62, 127.41, 128.03, 131.82, 131.88, 149.34, 152.10, 153.45.

2,2-dibromo-5-(4-hydroxy-3,5-dimethylphenyl)-2,3-dihydro-1H-inden-1-ol (52)

$^1$H NMR (500 MHz, CDCl$_3$) δ 2.32 (s, 6H), 3.95 (d, 1H, J=16.5 Hz), 4.10 (d, 1H, J=16.5 Hz), 4.70 (s, 1H, phenolic OH), 5.20 (d, 1H, J=9.0 Hz), 7.21 (s, 2H), 7.40 (s, 1H), 7.46 (d, 1H, J=7.6 Hz), 7.50 (d, 1H, J=7.50 Hz).

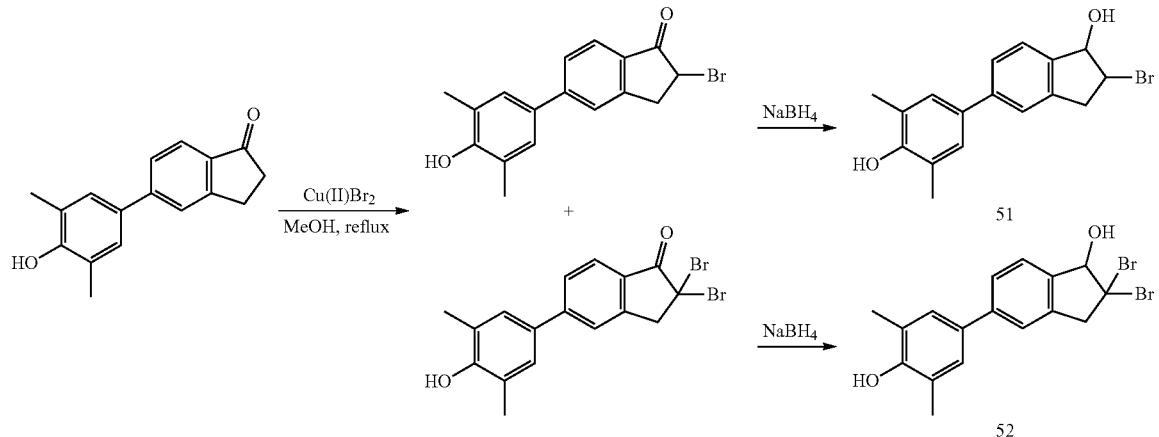

The mixture of copper(II) bromide (110 mg, 0.49 mmol) and 5-(4-hydroxy-3,5-dimethylphenyl)-2,3-dihydro-1H-inden-1-one (40 mg, 0.16 mmol) in MeOH was refluxed until starting material disappeared on SiO$_2$ TLC analysis (20% EtOAc in n-Hexane). The reaction mixture was concentrated under vacuum and re-dissolved into EtOAc to load onto a Silica gel column. First and second fraction with 25% EtOAc in n-Hexane provided 2-bromo-5-(4-hydroxy-3,5-dimethylphenyl)-2,3-dihydro-1H-inden-1-one (45 mg) and 2,2-dibromo-5-(4-hydroxy-3,5-dimethylphenyl)-2,3-dihydro-1H-inden-1-one (62 mg), respectively, and subsequently treatment with NaBH$_4$ in THF-water (1:1) afforded 51 (39 mg) (Rf=0.45) and 52 (56 mg) (Rf=0.38), respectively, as well.

2,2-dibromo-5-(4-hydroxy-3,5-dimethylphenyl)-2,3-dihydro-1H-inden-1-one $^1$H NMR (500 MHz, CDCl$_3$) δ 2.33 (s, 6H), 4.11 (s, 2H), 4.93 (s, 1H, phenolic OH), 7.28 (s, 2H), 7.52 (s, 1H), 7.66 (d, 1H, J=8.0 Hz), 7.94 (d, 1H, J=8.0 Hz); $^{13}$C NMR (126 MHz, CDCl$_3$) δ 16.32, 52.70, 57.62, 123.62, 124.06, 127.10, 127.15, 128.01, 128.07, 131.52, 148.05, 150.32, 153.65, 192.57.

2-bromo-5-(4-hydroxy-3,5-dimethylphenyl)-2,3-dihydro-1H-inden-1-one $^1$H NMR (500 MHz, CDCl$_3$) δ 2.34 (s, 6H), 3.45 (ABq, 1H, J, J=18.0 Hz, 3.0 Hz), 3.87 (ABq, 1H, J=18.0 Hz, 7.5

2-bromo-5-(4-hydroxy-3,5-dimethylphenyl)-2,3-dihydro-1H-inden-1-ol (51)

$^1$H NMR (500 MHz, CDCl$_3$) δ 2.35 (s, 6H), 3.39-3.52 (m, 2H), 4.69 (s, 1H, phenolic OH), 4.94-4.96 (m, 1H), 5.01-5.04 (m, 1H), 7.23 (s, 2H), 7.22 (s, 1H), 7.48 (s, 2H).

Example 26. 5-(4-hydroxy-3-(hydroxymethyl)phenyl)-2,3-dihydro-1H-inden-1-ol (57 and 5-(4-hydroxy-3 5-(dihydroxymethyl)phenyl)-2,3-dihydro-1H-inden-1-ol (58)

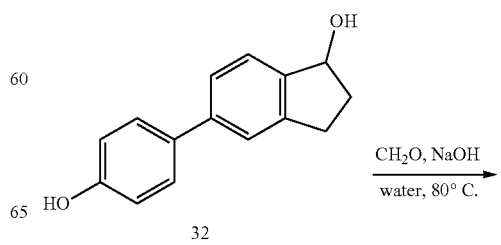

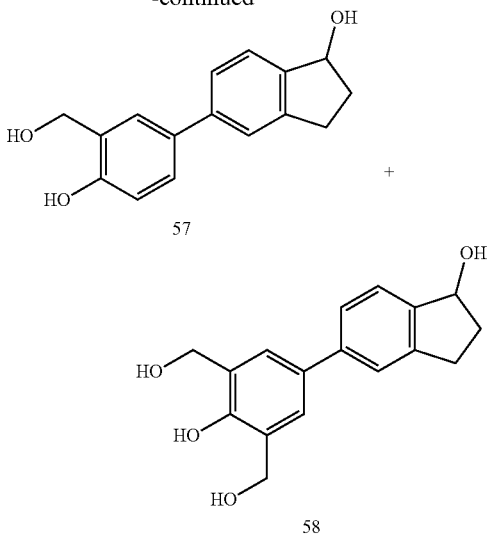

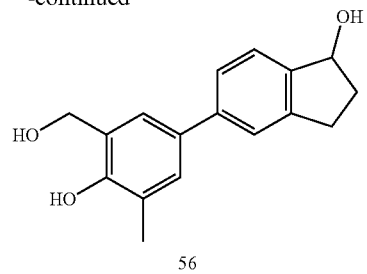

Compound 32 (30 mg, 0.13 mmol) was suspended in DI water (1 mL). PTP-83,C3 Formaldehyde solution 35 wt. % (105 µl) and NaOH (20 mg, 0.5 mmol) were added to the suspension. This solution was continuously stirred for 8 hr at 85° C. 1 N HCl was titrated to adjust pH at ~5.5. Solution was extracted with EtOAc (5 mL×3). The organic layer was dried over $Na_2SO_4$, concentrated under vacuum, and loaded onto a $SiO_2$ prep. TLC (0.1 mm) plate. Scraping off the Rf 0.55 and 0.45 bands and extraction of each of these bands provided compound 57 (12 mg) and 58 (18 mg), respectively.

5-(4-hydroxy-3-(hydroxymethyl)phenyl)-2,3-dihydro-1H-inden-1-ol (57)

$^1$H NMR (500 MHz, $CDCl_3$-$CD_3OD$) δ 1.93-2.01 (m, 1H), 2.42-2.50 (m, 1H), 2.78-2.84 (m, 1H), 3.02-3.08 (m, 1H), 4.79 (s, 2H, benzylic $CH_2$), 5.22 (t, 1H, J=5.5 Hz), 6.87 (d, 1H, J=8.0 Hz), 7.26 (s, 1H), 7.27-7.40 (m, 4H).

5-(4-hydroxy-3,5-(dihydroxymethyl)phenyl)-2,3-dihydro-1H-inden-1-ol (58)

$^1$H NMR (500 MHz, $CDCl_3$-$CD_3OD$) δ 1.84-1.95 (m, 1H), 2.36-2.2.42 (m, 1H), 2.72-2.79 (m, 1H), 2.98-3.02 (m, 1H), 4.72 (s, 4H, benzylic $CH_2$), 5.17 (t, 1H, J=5.5 Hz), 7.22 (s, 2H), 7.30 (d, 1H, J=8.0 Hz), 7.31 (s, 1H), 7.33 (d, 1H, J=8.0 Hz).

Example 27. 5-(4-hydroxy-3-methylphenyl)-2,3-dihydro-1H-inden-1-ol (55) and 5-(4-hydroxy-3-(hydroxymethyl)-5-methylphenyl)-2,3-dihydro-1H-inden-1-ol (56)

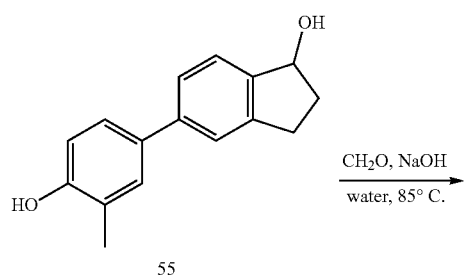

As described for the synthesis of compounds 57 and 58, compound 56 (18 mg) was prepared by the reaction of compound 55 (24 mg, 0.1 mmol), formaldehyde wt. % solution (80 µl), and NaOH (30 mg) in DI water at 85° C.

Compound 55 was synthesized according to the method described in example 1, using 3-methyl-4-methoxyphenylboronic acid (199 mg, 1.20 mmol) and 5-bromo-2,3-dihydro-1H-inden-1-one (211 mg, 1.00 mmol). The yield was comparable to that of compound 2.

5-(4-hydroxy-3-methylphenyl)-2,3-dihydro-1H-inden-1-ol (55)

$^1$H NMR (500 MHz, $CDCl_3$) δ 1.96-2.04 (m, 1H), 2.12 (s, 3H), 2.52-2.59 (m, 1H), 2.83-2.92 (m, 1H), 3.04-3.08 (m, 1H), 4.92 (s, 1H, phenolic OH), 5.24 (t, 1H, J=5.5 Hz), 6.82 (d, 1H, J=8.5 Hz), 7.32 (d, 1H, J=8.5 Hz), 7.35 (s, 1H), 7.41 (s, 2H), 7.43 (d, 1H, J=8.5 Hz).

5-(4-hydroxy-3-(hydroxymethyl)-5-methylphenyl)-2,3-dihydro-1H-inden-1-ol (56)

$^1$H NMR (500 MHz, $CDCl_3$-$CD_3OD$) δ 1.91-1.97 (m, 1H), 2.68 (s, 3H), 2.43-2.49 (m, 1H), 2.75-2.84 (m, 1H), 3.02-3.08 (m, 1H), 4.82 (s, 2H, benzylic $CH_2$), 5.21 (t, 1H, J=5.5 Hz), 7.05 (s, 1H), 7.25 (s, 1H), 7.34 (d, 1H, J=8.5 Hz), 7.36 (s, 1H), 7.38 (d, 1H, J=8.5 Hz); $^{13}$C NMR (126 MHz, $CDCl_3$) δ 15.99, 30.00, 64.44, 76.00, 123.21, 124.14, 124.59, 124.87, 125.57, 125.84, 129.29, 132.81, 141.48, 143.51, 144.15, 154.21.

Example 28. 3-(hydroxymethyl)-3',5,5'-trimethyl-[1,1'-biphenyl]-4,4'-diol; 3-(hydroxymethyl)-3',5,5'-trimethyl-[1,1'-biphenyl]-4,4'-diol

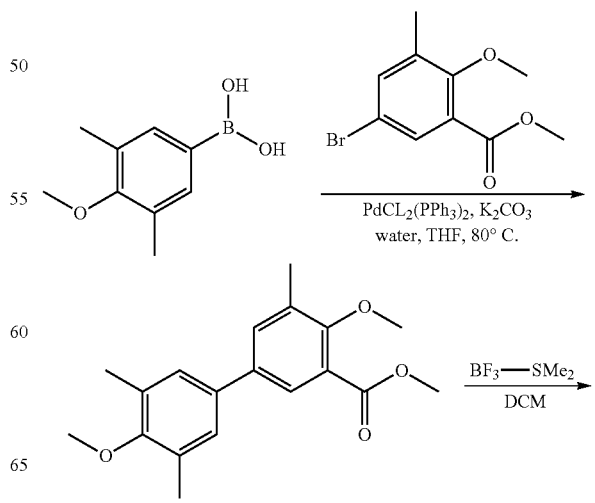

73

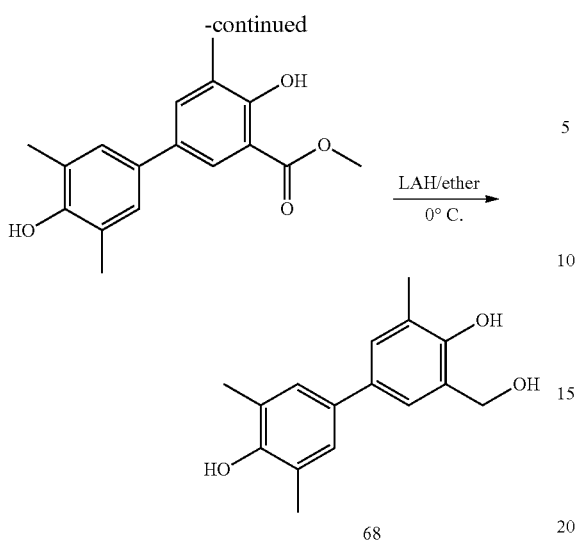

3-(Hydroxymethyl)-3',5,5'-trimethyl-[1,1'-biphenyl]-4,4'-diol (68)

Compound 68 was obtained from the reaction of methyl 4,4'-dihydroxy-3',5,5'-trimethyl-[1,1'-biphenyl]-3-carboxylate (60 mg, 0.21 mmol) with LAH (16 mg, 0.42 mmol) in dried diethyl ether (5 mL) at 0° C. and then rt for 2 hr, followed by quenching with 10% NaOH aqueous solution, adjusting pH to 5.5, extracting with EtOAc (5 mL×3) drying over $Na_2SO_4$, and evaporating to afford compound 68 (12 mg). 68: $^1$H NMR (500 MHz, $CDCl_3$) δ 2.32 (s, 6H), 2.34 (s, 3H), 4.93 (s, 2H), 7.06 (s, 1H), 7.16 (s, 2H), 7.29 (s, 1H).

Methyl 4,4'-dimethoxy-3',5,5'-trimethyl-[1,1'-biphenyl]-3-carboxylate

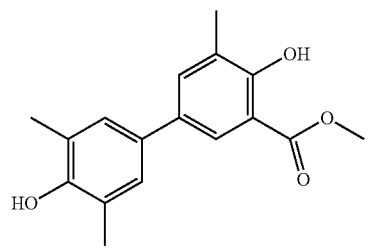 [SMILES: COC(=O)c1cc(-c2cc(C)c(O)c(C)c2)cc(C)c1O]

Methyl 4,4'-dimethoxy-3',5,5'-trimethyl-[1,1'-biphenyl]-3-carboxylate (295 mg) was obtained from the reaction as described method at example 1 with 3,5-dimethyl-4-methoxyphenylboronic acid (200 mg, 1.11 mmol) and 4-bromo-phenethylalcohol (259 mg, 1.00 mmol). $^1$H NMR (500 MHz, $CDCl_3$) δ 2.38 (s, 6H), 2.40 (s, 3H), 3.79 (s, 3H), 3.89 (s, 3H), 3.97 (s, 3H), 7.24 (s, 2H), 7.54 (d, 1H, J=1.5 Hz), 7.84 (d, 1H, J=1.5 Hz); $^{13}$C NMR (126 MHz, $CDCl_3$) δ 16.49, 52.49, 60.05, 61.84, 124.84, 127.64, 127.74, 131.45, 133.19, 133.76, 135.62, 136.62, 156.89, 157.70, 167.23.

74

Methyl 4,4'-dihydroxy-3',5,5'-trimethyl-[1,1'-biphenyl]-3-carboxylate

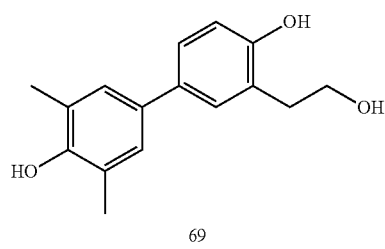

Methyl 4,4'-dihydroxy-3',5,5'-trimethyl-[1,1'-biphenyl]-3-carboxylate (125 mg) was obtained from the reaction of methyl 4,4'-dimethoxy-3',5,5'-trimethyl-[1,1'-biphenyl]-3-carboxylate (157 mg, 0.05 mmol) with $BF_3$—$SMe_2$ (600 mg, 4.6 mmol) at rt in DCM, as described in Example 1. $^1$H NMR (500 MHz, $CDCl_3$) δ 2.36 (s, 6H), 2.38 (s, 3H), 3.99 (s, 3H), 4.65 (brs, 1H), 7.18 (s, 2H), 7.53 (d, 1H, J=1.5 Hz), 7.83 (d, 1H, J=1.5 Hz); [$^{13}$C NMR (126 MHz, $CDCl_3$) δ 16.13, 16.30, 52.56, 111.93, 123.56, 125.29, 127.12, 129.99, 132.59, 135.32, 151.79, 159.21, 171.34.]

Example 29. 3'-(2-hydroxyethyl)-3,5-dimethyl-[1,1'-biphenyl]-4,4'-diol (69)

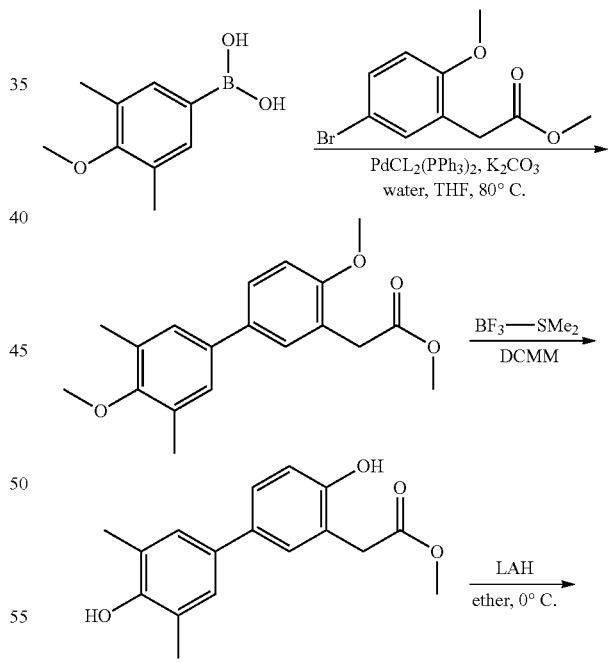

As described for the synthesis of compound 68, compound 69 prepared from the Suzuki coupling reaction with 3,5-dimethyl-4-methoxyphenylboronic acid (200 mg, 1.11 mmol) and methyl 2-(5-bromo-2-methoxyphenyl)acetate (259 mg, 1.00 mmol), deprotection of the methyl groups on the phenols with $BF_3$—$SMe_2$, and subsequent reduction of the methyl carboxylate (65 mg, 0.23 mmol) to the alcohol with LAH to afford compound 69 (43 mg). $^1$H NMR (500 MHz, $CDCl_3$-$CD_3OD$) δ 2.30 (s, 6H), 2.96 (t, 2H, J=6.5 Hz), 4.03 (t, 2H, J=6.5 Hz), 6.95 (d, 1H, J=10.5 Hz), 7.16 (s, 2H), 7.24 (d, 1H, J=2.5 Hz), 7.32 (dd, 1H, J, J=10.5 Hz, 2.5 Hz).

Example 30. 4-(((1r3r)-adamantan-2-ylidene)(4-bromophenyl)methyl)-2-dimethylphenol

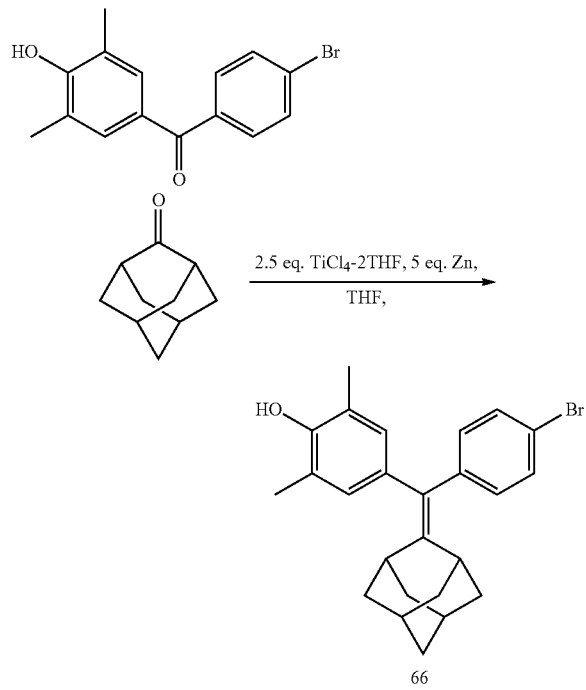

The mixture of titanium(IV) chloride THF complex (1.0 g, 3.0 mmol) and zinc powder (290 mg, 6.15 mmol) in THF (50 ml) was refluxed for 1.5 hr and cooled down to rt. To the mixture was added the mixed solution of (4-bromophenyl)(4-hydroxy-3,5-dimethylphenyl)methanone (308 mg, 1.01 mmol) and 2-adamantanone (150 mg, 1.00 mmol) at rt. This mixture was refluxed under a hot oil bath for 4 hr before pouring into the mixture of EtOAc (100 ml) and 10% $K_2CO_3$ aqueous solution (200 ml) and stirred until the color of aqueous solution turned to white. The organic layer was separated and washed aqueous solution with EtOAc (50 mL×2) and combined into previously collected organic solution, followed by dried over $Na_2SO_4$, concentration under vacuum, and chromatography with the Combiflash (Teledyne Co., LTD.). Gradient elution with n-Hexane and EtOAc (n-Hexane: EtOAc, 100:0 to 90:10 over 30 min) afforded the title compound (280 mg) as an off-white solid. $^1$H NMR (500 MHz, $CDCl_3$) δ 61.87 (brs, 10H), 2.00 (s, 2H), 2.20, (s, 6H), 2.71 (S, 1H), 2.81 (s, 1H), 4.65 (brs, 1H, phenolic OH), 6.72 (s, 2H), 7.01 (d, 2H, J=8.0 Hz), 7.38 (d, 2H, J=8.0 Hz); $^{13}$C NMR (126 MHz, $CDCl_3$) 16.27, 28.39, 34.68, 37.36, 39.80, 119.94, 122.74, 129.49, 129.92, 131.25, 131.46, 134.68, 142.56, 146.91. 150.93.

Example 31. 4-((4-Bromophenyl)(cyclohexylidene)methyl)-2,6-dimethylphenol

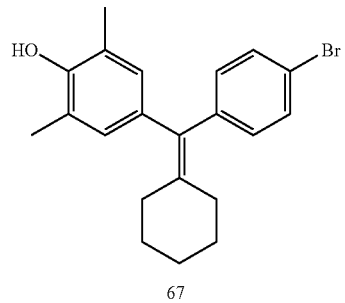 [SMILES: Cc1cc(C(=C2CCCCC2)c2ccc(Br)cc2)cc(C)c1O]

Title compound (235 mg) was obtained from the reaction of (4-bromophenyl)(4-hydroxy-3,5-dimethylphenyl)methanone (308 mg, 1.01 mmol), cyclohexanone (98 mg, 1.00 mmol), Titanium(IV) chloride THF complex (1.0 g, 3.0 mmol), and zinc powder (290 mg, 6.15 mmol) in THF (50 mL) as described above. $^1$H NMR (500 MHz, $CDCl_3$) δ 61.60 (brs, 6H), 2.20, (s, 6H), 2.24 (t, 4H, J=6.5 Hz), 4.59 (brs, 1H, phenolic OH), 6.70 (s, 2H), 6.99 (d, 2H, J=8.0 Hz), 7.39 (d, 2H, J=8.0 Hz); $^{13}$C NMR (126 MHz, $CDCl_3$) 16.20, 27.01, 28.86, 32.64, 32.75, 120.02, 122.63, 130.20, 131.18, 131.71, 133.32, 134.78, 139.42, 142.68, 150.91.

Figure 10:
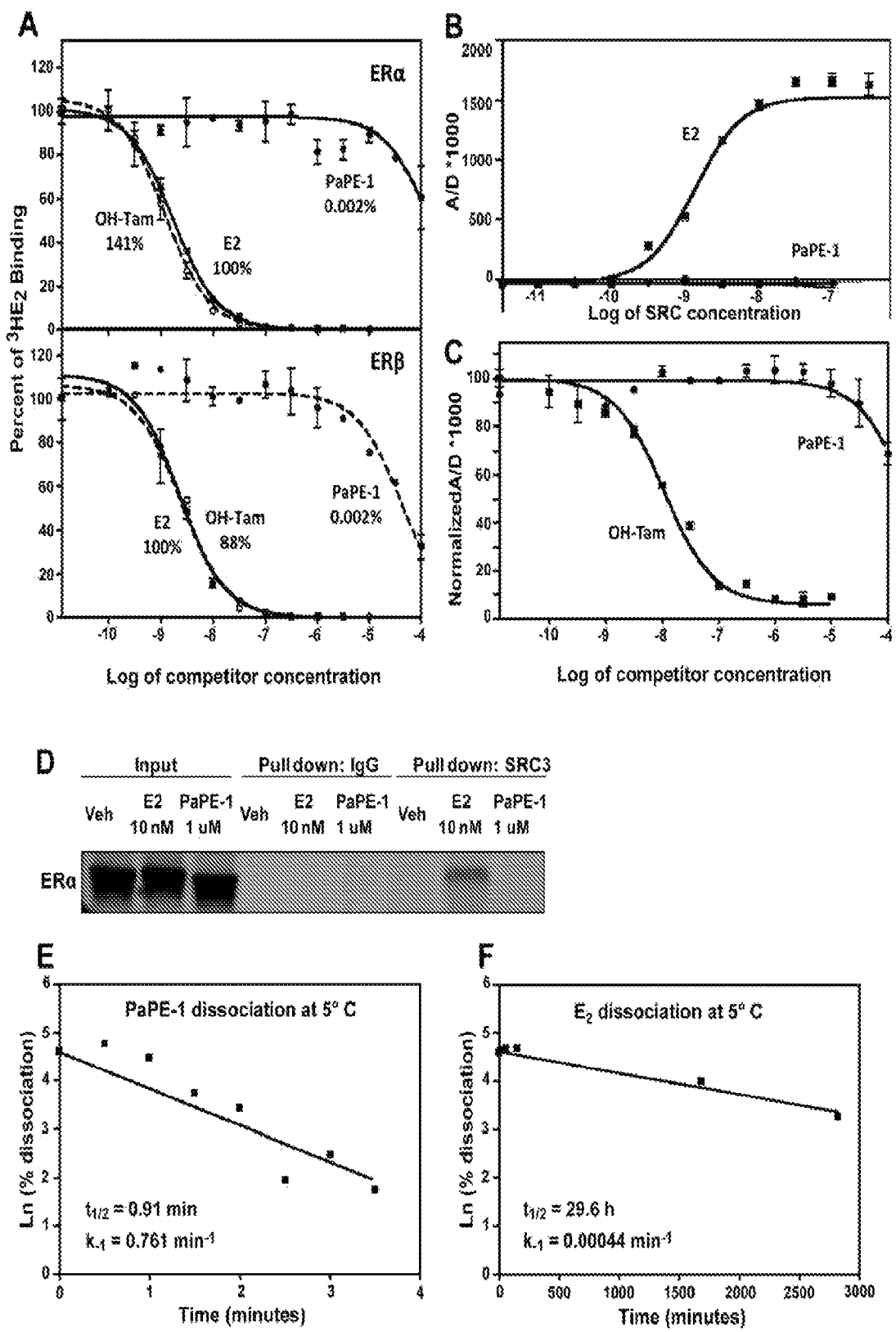
FIG. 10. Estrogen receptor and coactivator binding and interaction assays with ligands and ligand dissociation rates. (A) Comparison of binding affinities of PaPE-1, trans-hydroxytamoxifen (OH-Tam), and E2 for ERα (top) and ERβ (bottom) determined by $^3$H-E2 competition binding assays. (B) Binding of the coregulator SRC3 to the E2-ERα or PaPE-1-ERα complex. (C) Displacement of SRC3 from the 10 nM E2-ERα complex by OH-Tam or PaPE-1. (D) Co-immunoprecipitation assays to examine the interaction of ERα and SRC3 in MCF-7 cells after treatment of cells with control vehicle, 10 nM E2 or 1 µM PaPE-1 for 1 h. After ligand treatment, cell lysates were immunoprecipitated with antibody to SRC3 or control IgG, and immunoprecipitates were separated on SDS PAGE gels and blotted for ERα using anti-ERα antibody. (E) Time course of dissociation of PaPE-1 and E2 (F) from the ERα ligand-binding domain. ERα LBD (2 nM) was equilibrated with 100 nM E2 or 5 µM PaPE-1 for 1 h on ice. Samples held at 5° C. were assayed by fluorescence polarization for the zero-time point, and then excess E2 was added to the PaPE-1 or excess OH-Tam to the E2 sample, and the dissociation was followed with time as a change in anisotropy. For details, see methods below.

Example 32: Pathway Preferential Estrogen, PaPE-1, has Impeded Estrogen Receptor Binding and Coactivator Interactions The relative binding affinity (RBA) values of E2 and PaPE-1 (FIG. 1) were obtained by a competitive radiometric binding assay using purified full-length human ERα and ERβ (Carlson et. al., Biochemistry 36, 14897-14905, 1997). The RBAs for E2 are defined as 100, and relative to E2, PaPE-1 binds 50,000-fold less well to ERα and ERβ. The equivalent $K_D$ values are 10 and 25 μM for PaPE-1 on ERα and ERβ, respectively, compared to the sub-nanomolar $K_D$ values for E2 (FIG. 10A). Thus, the ER binding affinities of PaPE-1 for both ERs was lowered while preserving as much as possible the physical and functional group attributes of E2.

Using a time-resolved Forster resonance energy transfer (tr-FRET) assay, the binding of the steroid receptor coactivator 3 (SRC3) to ERu was monitored. (Jeyakumar et. al. J Biol Chem, 286, 12971-12982, 2011, Jeyakumar et. al., Anal Biochem 386, 73-78, 2009). In coactivator titration assays (FIG. 10B), SRC3 bound with high affinity to ERα complexes with E2, but showed no binding to ERα complexes with PaPE-1. Notably, however, the antagonist trans-hydroxytamoxifen (OH-Tam) reversed the ER-SRC3 interaction promoted by E2; PaPE-1 also reversed the ER-SRC3 interaction, but only at much higher concentrations, commensurate with its lower ERα binding affinity (FIG. 10C). The E2-elicited interaction of ERα with SRC3 was also observed by coimmunoprecipitation of the complexes from MCF-7 cells, whereas no coimmunoprecipitated complexes were observed for ERα and SRC3 after exposure to PaPE-1 (FIG. 10D).

Figure 3:
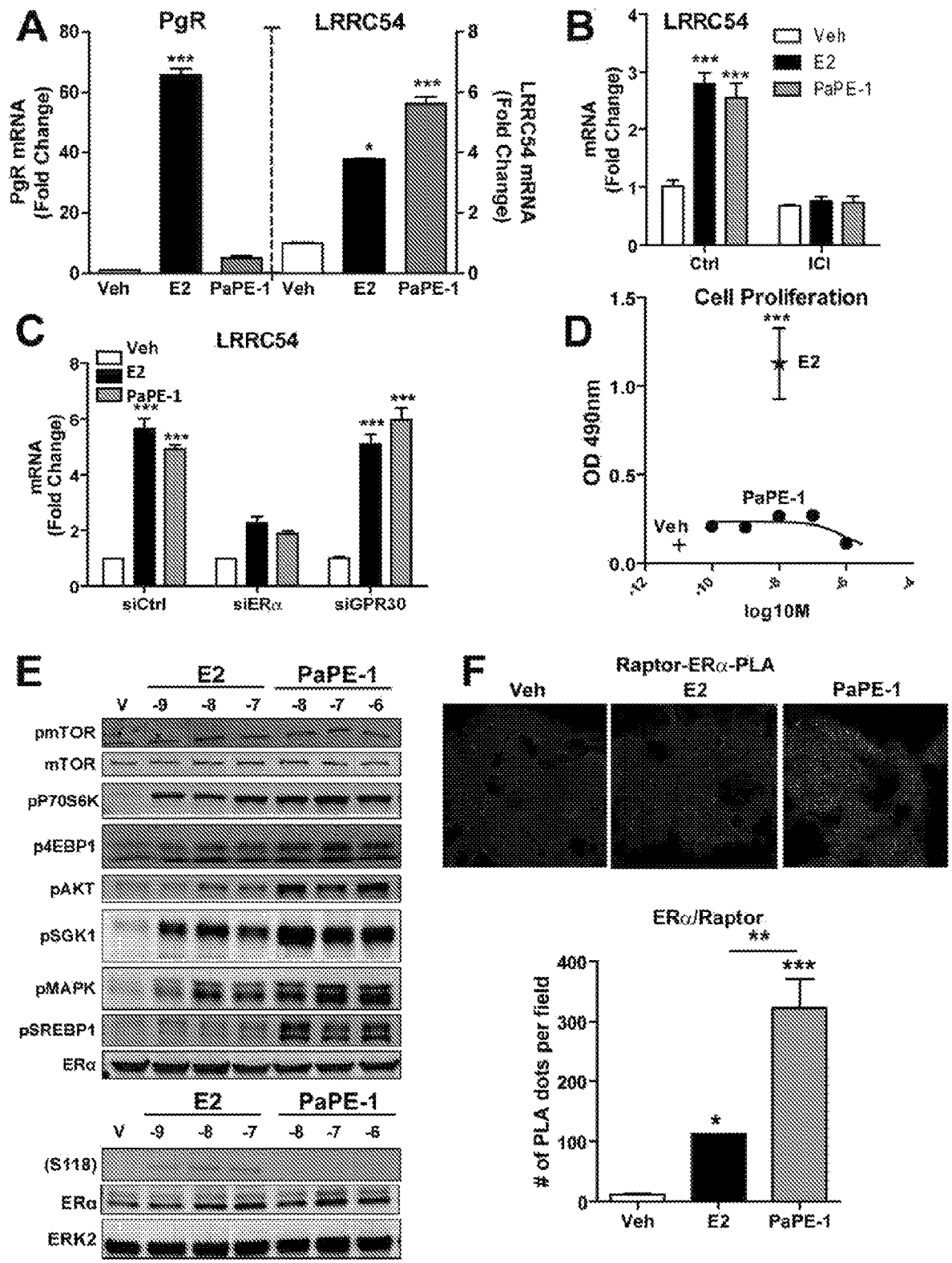
FIG. 3. Comparison of gene expression, cell proliferation, and pathway signaling regulation by PaPE-1 and E2. (A) PaPE-1 preferentially activates extranuclear-initiated (non-genomic) genes (LRRC54) over direct nuclear (genomic) genes (PgR) compared to E2 in MCF-7 cells. Cells were treated with control vehicle (0.1% ethanol), 10 nM E2 or 1 μM PaPE-1 for 4 h and gene expression was monitored by qPCR. (B) MCF-7 cells were pretreated with 1 μM ICI182, 780 (ICI) for 1 h and then treated with Veh (0.1% EtOH), 10 nM E2 or 1 μM PaPE-1 in the presence or absence of ICI for 4 h. RNA was isolated and subjected to qPCR analysis for the indicated genes. (C) MCF-7 cells were seeded and after 24 h the cells were transfected with siCtrl, siERα or siGPR30 (30 nM) for 72 h. Cells were then treated with Veh (0.1% EtOH), 10 nM E2 or 1 μM PaPE-1 for 4 h. RNA was isolated and subjected to qPCR analysis. (D) MCF-7 cells were treated with Veh, 10 nM E2 or the indicated concentrations of PaPE-1 for 6 days and proliferation was monitored by WST assay. (E) PaPE-1 selectively activated mTOR and MAPK signaling in MCF-7 cells. Cells were treated with control vehicle (V), or the indicated concentrations of E2 or PaPE-1 for 15 min (upper panel) and 45 min (lower panel) and Western blots were done to assess activated signaling proteins and S118 phosphorylation of ERα. Total ERα was monitored, and total ERK2 was used as a loading control. (F) PaPE-1 induces interaction between ERα and Raptor. MCF-7 cells were treated with 10 nM E2 or 1 μM PaPE-1 for 15 min. Cells were crosslinked and incubated with ERα and Raptor antibodies overnight and PLA was performed. Quantitation of signal intensities is shown in panel at the right. Two-way ANOVA, Bonferroni posttest, * p<0.05,  p<0.01, * p<0.001.

Example 33: PaPE-1 Regulates a Subset of Estrogen-Modulated Genes and Activates Kinases, but does not Stimulate Breast Cancer Cell Proliferation PaPE-1 was selective in activating non-genomic genes, as shown by LRRC54 stimulation, but was essentially without activity on the direct ER gene target PgR (FIG. 3A). Activation of LRRC54 gene expression by PaPE-1 was blocked by treatment with the antiestrogen (Fulvestrant) ICI 182,780 (FIG. 3B) and by knockdown of ERα (FIG. 3C). By contrast, knockdown of GPR30 did not have any effect on the gene stimulation (FIG. 3C). PaPE-1 also did not stimulate proliferation of MCF-7 cells, whereas E2 potently stimulated proliferation (FIG. 3D).

When activation of major signaling pathways in MCF-7 cells was monitored, it was observed that PaPE-1 was very efficient in activating mTOR and MAPK signaling (FIG. 3E), as seen by increased pP70S6K and p4EBP1 associated with mTORC1 activation, increased pSGK1 associated with mTORC2 activation, and increased pMAPK. Elevations of pAKT and pSREBP1 were also more notable with PaPE-1 compared with E2. However, PaPE-1 did not induce any detectable Ser118 phosphorylation of ERα, which was observed with E2 (FIG. 3E) and is associated with mitogenic activity of ERα.

Figure 11:
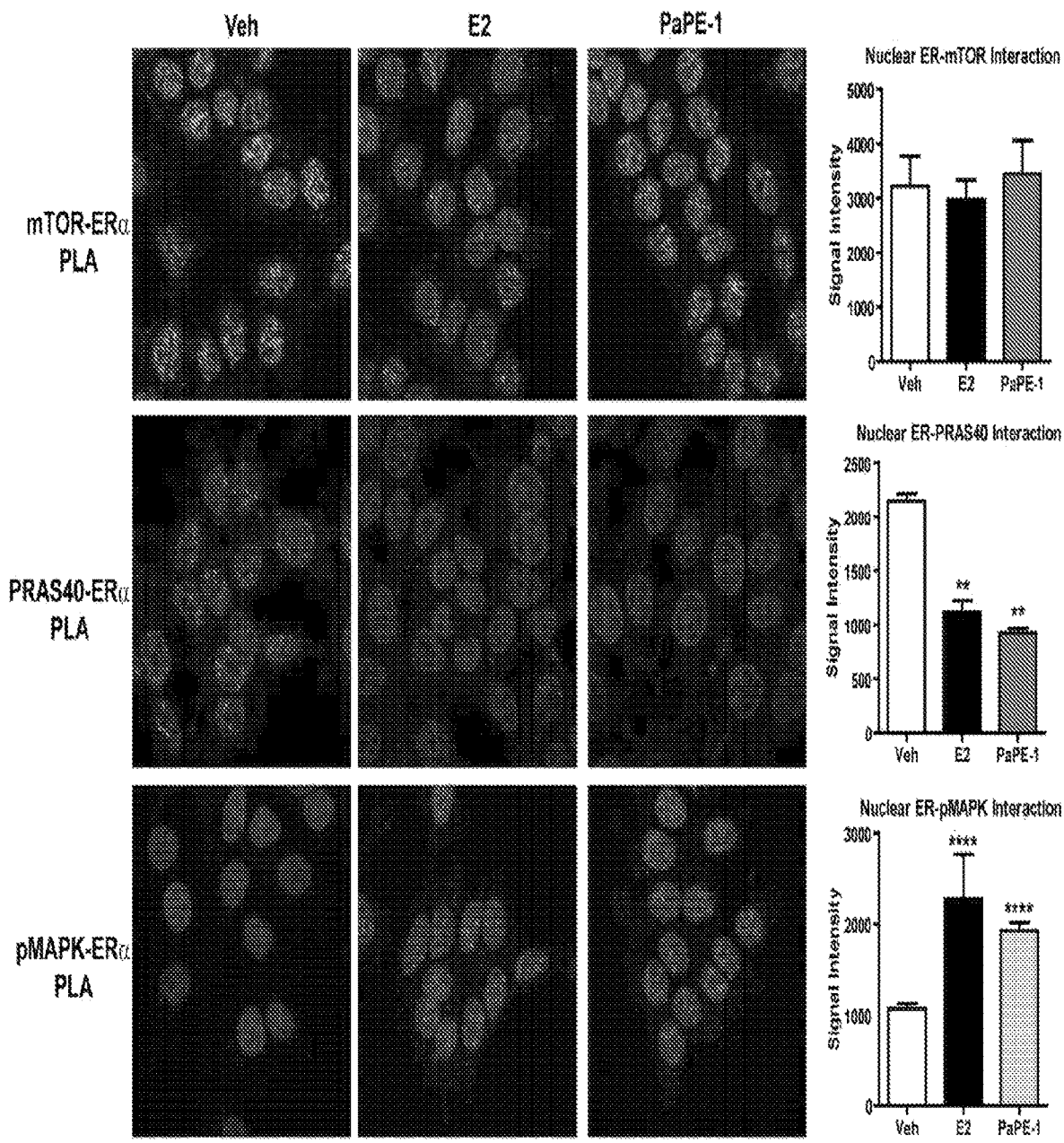
FIG. 11. Proximity ligation assays (PLAs) with E2 and PaPE-1. PLA was used compare the effects of control vehicle, 10 nM E2 or 1 µM PaPE-1 on the interaction of: ERα with mTOR; or ERα with PRAS40; or ERα with pMAPK. MCF-7 cells were treated with ligands for 15 min and PLA was then conducted. Quantitation of signal intensity of the PLAs is shown in panels at the right. One-way ANOVA, Bonferroni posttest, * $p<0.05$,  $p<0.01$, * $p<0.001$, **** $p<0.0001$.

The mTOR pathway is the major signaling system that senses the nutrient state of the environment and modulates metabolic functions in the cell. mTOR kinase is present in two distinct complexes, mTORC1 and mTORC2, which are distinguished by the presence of RAPTOR and RICTOR scaffolding proteins, respectively. It is thought that mTORC1 primarily modulates cell metabolism, whereas mTORC2 is principally involved in regulating the cytoskeleton and cell proliferation. To further characterize the mTOR activation by PaPE-1, proximity ligation assays (PLA) in MCF-7 cells were performed and it was found that ERα interacted with RAPTOR to a greater extent in the presence of PaPE-1 than E2 (FIG. 3F). No interaction was detected between ERα and mTOR, or ERα and proline-rich Akt substrate of 40 kDa (PRAS40), which is important in Akt and mTOR signaling, suggesting that ERα modulated the mTOR pathway through direct interactions with Raptor (FIG. 11).

Figure 4:
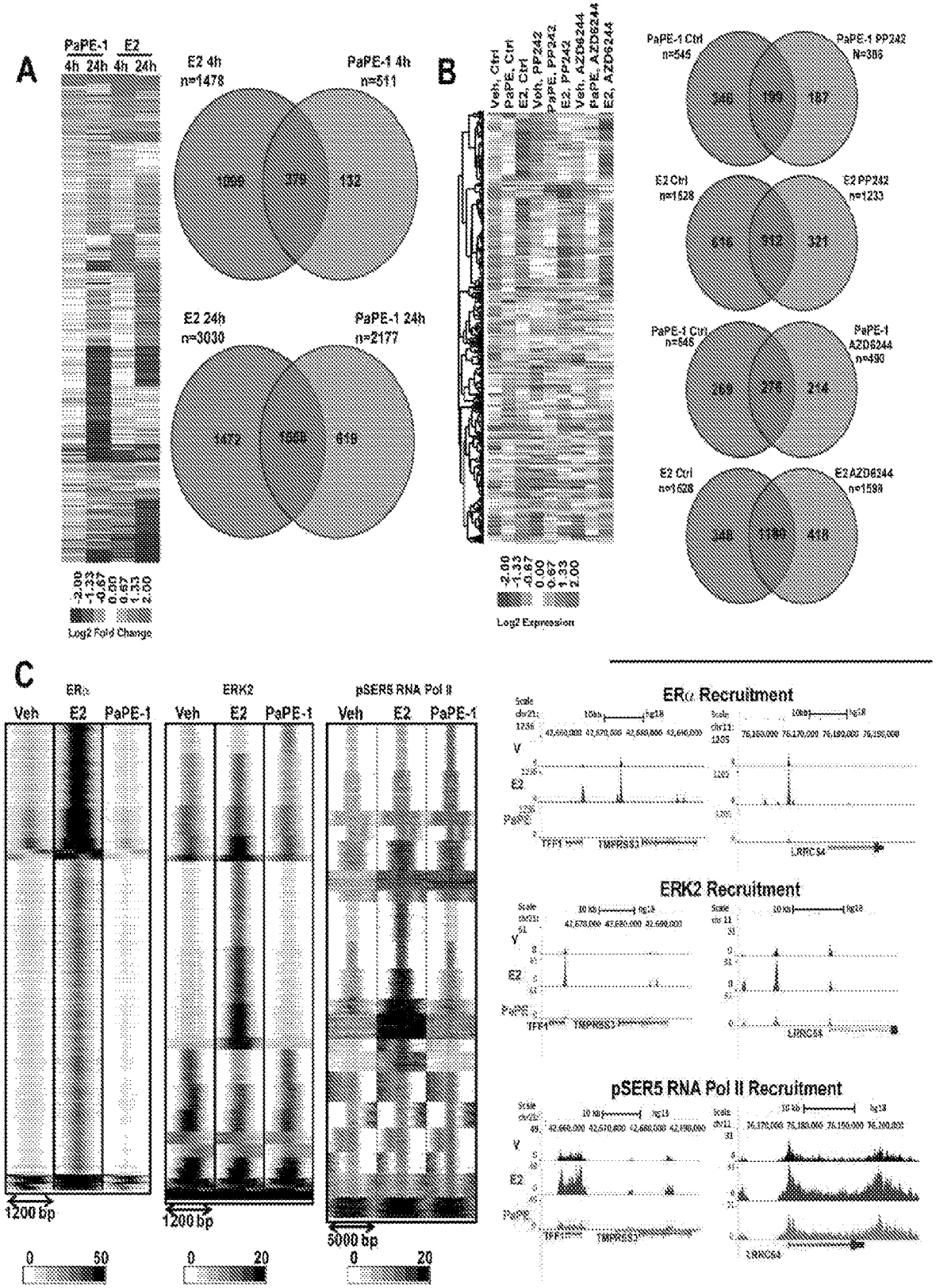
FIG. 4. PaPE-1 and E2 regulate common as well as distinct groups of genes in MCF-7 cells. (A) Cells were treated with 10 nM E2 or 1 μM PaPE-1 for 4 h and 24 h. RNA was isolated and RNA-Seq was performed. Regulated genes are considered to be those with P<0.05 and expression fold change >2. (B) PaPE-1 mediated gene expression changes are sensitive to mTOR and MAPK pathway inhibitors. Effect of mTOR and MAPK inhibitors on gene regulation by E2 and PaPE-1 in MCF-7 cells. Cells were pretreated with 1 μM PP242 or 1 μM AZD6244 for 1 h and then treated with 10 nM E2 or 1 μM PaPE-1 for 4 h in the presence or absence of inhibitors. RNA was isolated and RNA-Seq performed. (P<0.05, fold change >2). (C) PaPE-1 does not induce recruitment of ERα or ERK2 to chromatin but stimulates recruitment of RNA Pol II. MCF-7 cells were treated with 10 nM E2 or 1 μM PaPE-1 for 45 min. ChIP-Seq was performed for the indicated proteins. UCSC genome tracks of cistromes in the presence of E2 or PaPE-1 are shown (right panel).

Example 34: PaPE-1 Regulates Metabolism-Related Genes in an mTOR and MAPK Activity-Dependent Manner, but does not Cause Recruitment of ERα to Chromatin RNA-Seq analysis was performed to compare genes that were changed in their expression level by PaPE-1 and/or E2. MCF-7 cells were treated with 10 nM E2 or 1 μM PaPE-1 for 4 h and 24 h, and compared genes regulated by each compound at these two time points (FIG. 4A). At both times, E2 regulated more genes than did PaPE, and the magnitude of gene regulation by E2 was generally higher than that by PaPE. At 4 h, E2 regulated nearly 1500 genes, whereas PaPE-1 modulated expression of only 500 genes (FIG. 4A upper Venn diagram). At 24 h, about 3000 genes were regulated by E2, whereas PaPE-1 regulated 2200 genes (FIG. 4A lower Venn diagram). At both 4 h and 24 h, three quarters of the genes regulated by PaPE-1 were also targets of E2. Notably, only E2 upregulated mitosis genes and downregulated apoptosis genes at 24 h, consistent with the observation that PaPE-1 did not stimulate MCF-7 cell proliferation.

Pathway-selective inhibitors were used to assess the effect of mTOR pathway or MAPK pathway activation on PaPE- and E2-mediated gene regulation. The mTOR pathway inhibitor PP242 blocked the regulation of 60% of PaPE-regulated genes, whereas only 40% of E2 regulated genes were affected by this inhibitor. Similarly, the MAPK inhibitor AZD6244 blocked almost 50% of PaPE-1 regulated genes, whereas only 23% of E2 regulated genes were blocked by the same inhibitor (FIG. 4B). Examination of enriched gene ontology (GO) functions revealed that these inhibitors blocked E2 regulation of cell migration, immune, cell cycle and angiogenesis related genes, whereas they blocked PaPE-1 regulation of genes involved in nucleotide metabolism, inflammatory response, ncRNA processing, amino acid transport, and glycoprotein metabolism.

To investigate the roles of ERα, ERK2 and active RNA Pol II recruitment in PaPE-1-mediated transcriptional events, ChIP-Seq analysis was performed. ChIP-Seq (FIG. 4C, revealed that ERα was recruited to chromatin upon E2 treatment of cells, whereas ERα was not recruited to chromatin in the presence of PaPE-1. PaPE-1 induced recruitment of ERK2 to proximal promoter regions of genes, whereas E2 caused recruitment of ERK2 to enhancer regions together with ERα. Distinct RNA Pol II recruitment sites were observed with PaPE-1, further suggesting that PaPE-1 induces transcriptional events through recruitment of RNA Pol II without affecting ERα or ERK2 recruitment to enhancer regions of target genes. These distinct patterns of ERα, ERK2, and pSer5 RNA polymerase II binding after cell treatment with Veh, E2, and PaPE-1 are shown for the TFF1/pS2 gene and LRRC54/TSKU gene in FIG. 4C, right.

Figure 12:
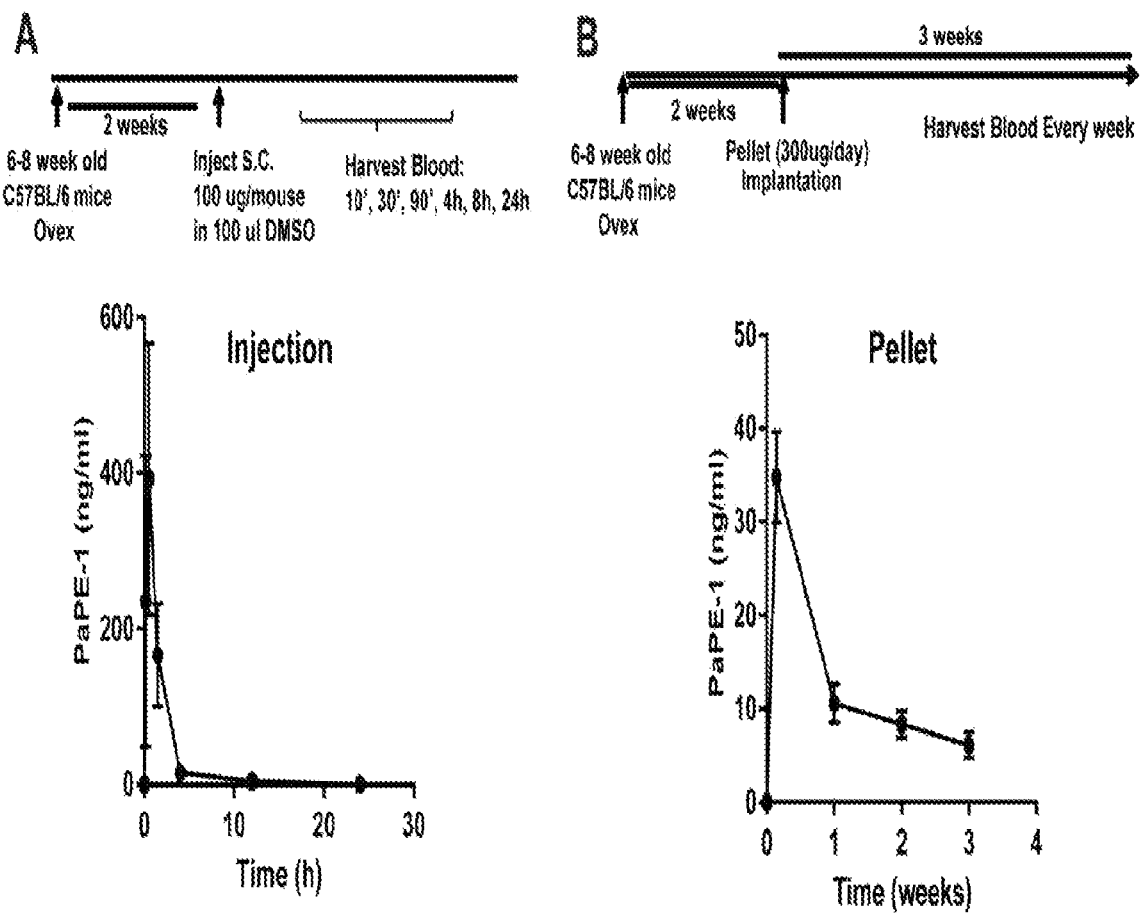
FIG. 12. Pharmacokinetic (PK) studies for analysis of blood levels of PaPE-1 after injection or pellet implantation. (A) Measurement of PaPE-1 level in the blood of ovex mice after SC injection of 100 µg PaPE-1 was done at the times indicated, up to 24 h. (B) Measurement of PaPE-1 levels in the blood of ovex mice over 3 weeks after implantation of a pellet containing 300 µg/day PaPE-1.

The in vivo biological activities of PaPE-1 were characterized in ovariectomized female mice. As is known with E2, PaPE-1 was cleared rapidly after subcutaneous injection ($t_{1/2}$ ca. 1 h, FIG. 12A); so, to provide more prolonged exposure for in vivo studies, administration by ALZET minipump or by a pellet containing PaPE-1 was used, both implanted subcutaneously (FIG. 12B).

Figure 5:
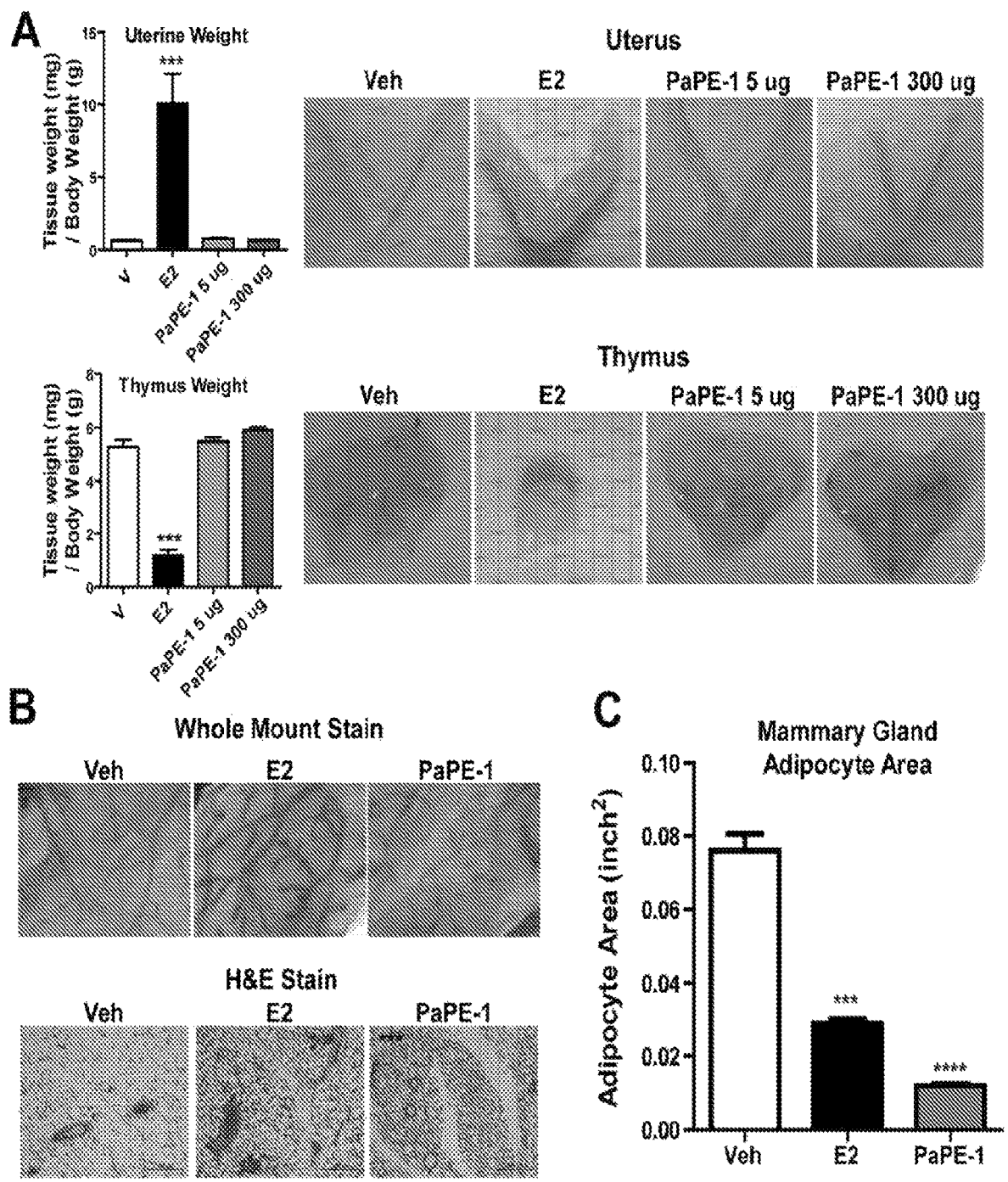
FIG. 5. PaPE-1, unlike E2, does not change uterus or thymus weight and does not induce mammary gland ductal branching but, like E2, PaPE-1 reduces mammary gland adipocyte area. (A) PaPE-1 does not affect uterus or thymus weight. C57BL/6 mice were ovariectomized and then were given daily subcutaneous injections of E2 (5 μg/day) or vehicle (V, Veh), or were implanted with PaPE-1 pellets (5 μg/day and 300 μg/day) for 4 days. Weights of uterus and thymus were monitored. (B) PaPE-1 stimulates only very minimal mammary ductal elongation but it greatly reduces adiposity (adipocyte size) in mammary gland. C57BL/6 mice were ovariectomized and then pellets of E2 (5 μg/day) or PaPE-1 (5 μg/day and 300 μg/day) were implanted for 3 weeks. Whole mount stain and H and E stain of mammary gland are shown. (C) Mammary gland adipocyte area was calculated from the H and E images. Two-way ANOVA, Bonferroni posttest, * p<0.05,  p<0.01, * p<0.001, **** p<0.0001.

PaPE-1 is a tissue-specific modulator of ER and mTOR signaling, with preferential estrogen-like activity in non-reproductive (metabolic and vascular) tissues. E2-like effects of PaPE-1 were seen on body weight, liver, adipose tissues, and vasculature vs absence of E2-like effects of PaPE-1 on uterus, thymus and mammary gland growth. Mice at 8 weeks of age were ovariectomized, and after 2 weeks, they were treated with control Veh, E2 or PaPE-1 for 3 weeks. While E2 was very effective in increasing growth of the uterus, PaPE-1 did not exhibit any stimulatory effects on uterine weight (FIG. 5A). As is well known, it was observed that E2 induced marked involution of the thymus, but PaPE-1, even at a high dose, had no effect on thymus size (FIG. 5A). Likewise, PaPE-1 did not change mammary gland ductal morphology from that of vehicle control mice, whereas E2 elicited marked ductal growth (elongation and branching) (FIG. 5B). Of interest, however, both E2 and PaPE-1 reduced mammary gland adiposity that develops in mice after ovariectomy. This was associated with reduced adipocyte area after E2 or PaPE-1 treatment (FIG. 5C).

Figure 6:
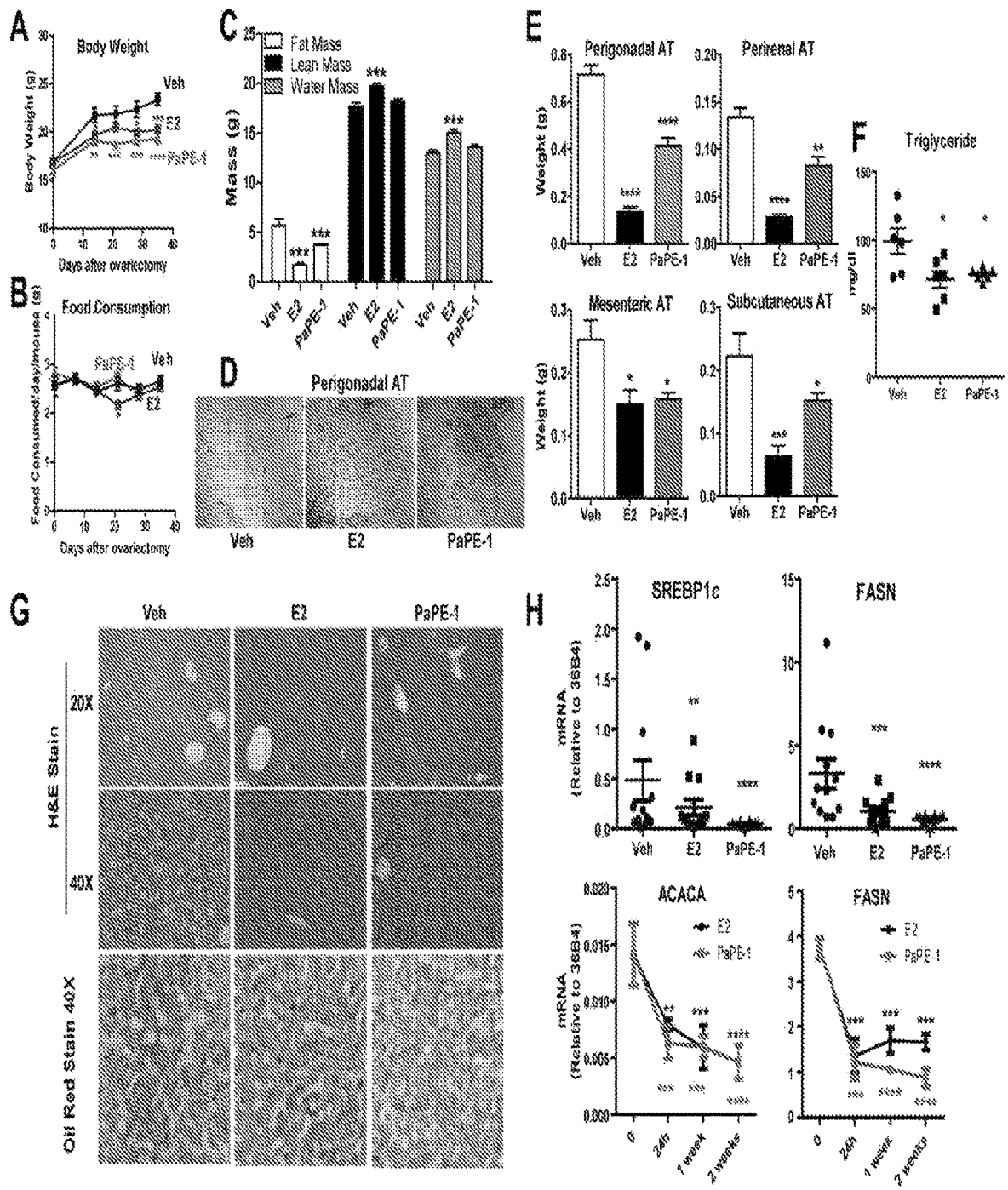
FIG. 6. PaPE-1, like E2, reduces the increase in body weight after ovariectomy and reduces adipose stores and the blood triglyceride level. (A) PaPE-1 is effective in normalizing body weight after ovariectomy. C57BL/6 mice were ovariectomized and, after 3 weeks, pellets containing E2 (5 μg/day) or PaPE-1 (300 μg/day) or Veh control were implanted for 3 weeks (n=8/group). Animals were on normal chow diet. Two-way ANOVA, Bonferroni posttest, * p<0.05,  p<0.01, * p<0.001, **** p<0.0001, comparing treatments to vehicle (Veh.) (B) Food consumption for each mouse from A was monitored weekly. (C) Body composition for each mouse from A was monitored using EchoMRI at the end of 3 weeks. One-way ANOVA, Newman-Keuls post-test, * p<0.05,  p<0.01, * p<0.001, **** p<0.0001. (D) H and E staining of perigonadal Adipose Tissue (AT). (E) Weights of various fat depots monitored after 3 weeks of control vehicle or ligand exposure. (F) Triglycerides were measured in the blood of animals (n=6/group) at the end of 3 weeks of Veh, E2 or PaPE-1 treatment. (G) H and E staining (upper 2 panels) and Oil Red O staining (lower panel) of the liver at 3 weeks of treatment. (H) Gene expression analysis of SREBP1c and FASN in liver at 3 weeks (upper panel) (n=12/group), and time course of FASN and ACACA expression in livers of E2 and PaPE-1 treated mice over 2 weeks. Two-way ANOVA, Bonferroni posttest, * p<0.05,  p<0.01, * p<0.001, **** p<0.0001.

Effects of PaPE-1 and E2 were seen on body weight and metabolic effects in liver and adipose tissues. Body weights of the mice increased after ovariectomy, as is well-known, and this increase in weight was suppressed by PaPE-1 and by E2 over the 3-week period monitored (FIG. 6A). Body weights were statistically lower in E2- and PaPE-1-treated mice vs. Veh control treated animals (two-way ANOVA with Bonferroni post-test, E2 $p<0.05$; PaPE-1 $p<0.01$), and the PaPE-1 and E2 groups were not statistically different from one another. The reduction in body weight gain that was observed with PaPE-1 was not due to a change in food consumption (FIG. 6B). Because of the known anorexigenic effect of E2, there was an early drop in food intake in E2-treated animals; however, this was not observed in PaPE-1-treated animals, suggesting that this was not a determinant of differing body weights and changes in the fat depots (FIG. 6B).

A major impact of PaPE-1 was on fat depots of the animals, as observed in EchoMRI measurements. Both E2 and PaPE-1 greatly reduced fat mass, but total lean mass and water mass were increased only by E2 and were not affected by PaPE-1, further indicating that PaPE-1 worked by changing overall adiposity rather than lean mass of the animals (FIG. 6C). H&E and Oil Red O staining of perigonadal adipose tissue (FIG. 6D) highlighted the similar and marked estrogenic effects of both PaPE-1 and E2 on this tissue. PaPE-1 and E2 decreased the weight of all of the fat depots examined (FIG. 6E). Perigonadal, perirenal, and subcutaneous adipose tissues were reduced by both ligands, but to a larger extent by E2 at the dosages tested. Mesenteric adipose tissue was similarly reduced by both ligands, and both ligands also decreased triglyceride levels in blood (FIG. 6F).

A very dramatic liver phenotype was observed when histological changes in the liver were monitored. Removal of estrogens by OVX increased lipid droplet accumulation, and E2 or PaPE-1 decreased hepatocyte lipid content, as observed in Oil Red O staining of liver sections (FIG. 6G). Changes in fatty acid synthesis pathways were verified by monitoring two biomarkers of hepatic steatosis, FASN and SREBP-1c, and found that the level of expression of these genes was reduced following 3 weeks of E2 or PaPE-1 treatment (FIG. 6H). Expression of SREBP-1 transcriptional targets, FASN and the gene encoding the enzyme acetyl-CoA carboxylase alpha (ACACA), which catalyzes the carboxylation of acetyl-CoA to malonyl-CoA, the rate-limiting step in fatty acid synthesis, was decreased by 24 h of PaPE-1 or E2 treatment, and remained low over the 2 weeks monitored (FIG. 6H).

Gene expression and signaling pathway activations by PaPE-1 vs. E2 were studied in multiple tissues in vivo. PaPE-1 was found to induce tissue-specific molecular changes in gene expression and signaling pathway activation patterns. To characterize these changes in the various tissues harvested from animals in long-term studies, an analysis of the expression of genes reported in the literature to be altered in liver, skeletal muscle, perigonadal fat, pancreas, and uterus was performed. PaPE-1 and E2 generated quite similar profiles in metabolic tissues, namely in liver and skeletal muscle; in stark contrast, only E2 induced gene expression changes in uterus (FIG. 7A), consistent with the selective stimulatory actions of PaPE-1 in non-reproductive tissues.

Figure 7:
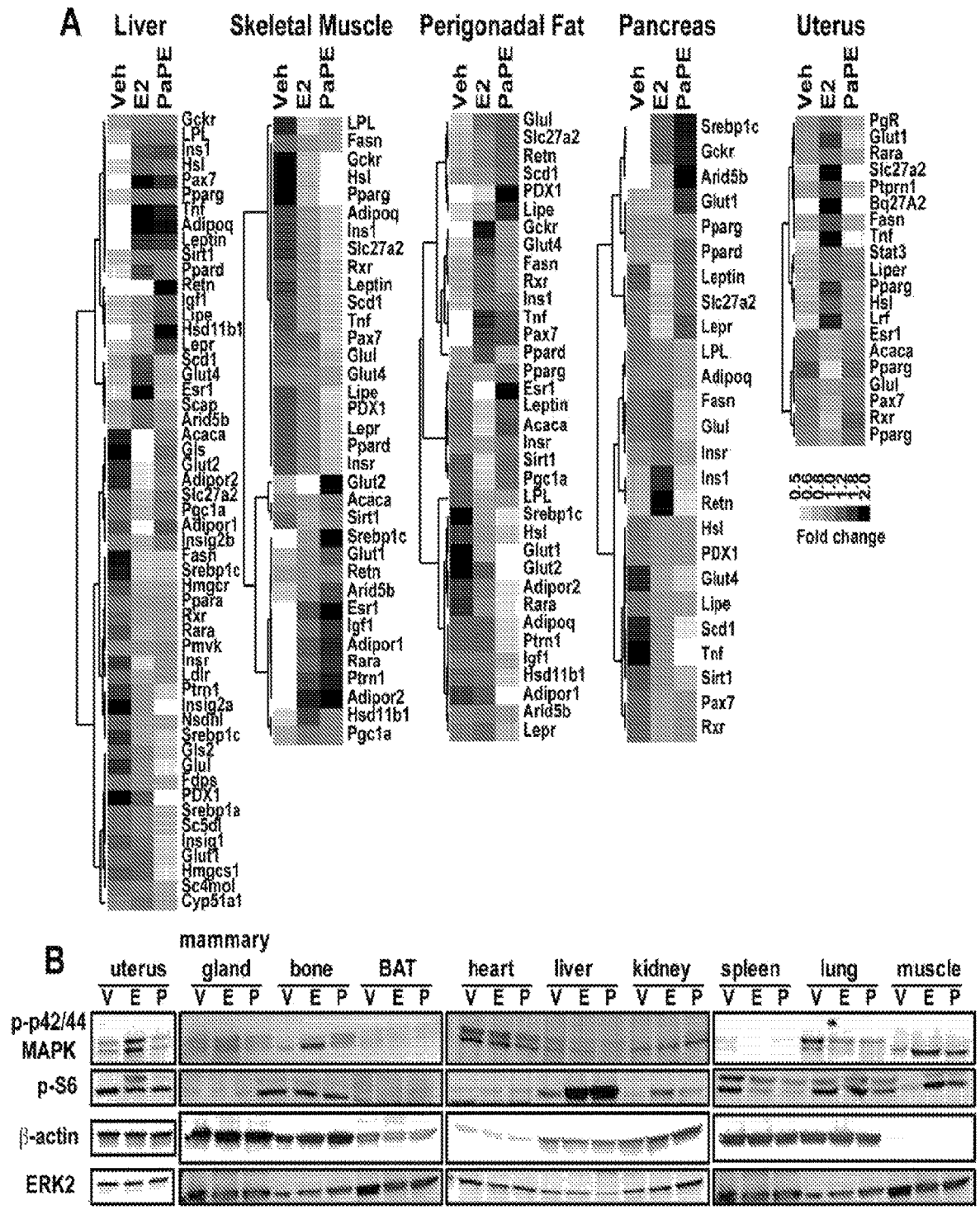
FIG. 7. Gene regulation and signaling pathway activations by PaPE-1 and E2 in tissues in vivo. (A) C57BL/6 mice were ovariectomized and after 3 weeks, cholesterol pellets containing E2 (5 μg/day), PaPE-1 (300 μg/day), or vehicle (Veh, cholesterol alone) were implanted for 3 weeks. Liver, skeletal muscle, perigonadal fat, pancreas, and uterus were harvested. RNA was isolated and qPCR performed for the indicated genes. (B) PaPE-1 activates mTOR signaling (monitored by increase in p-S6) in liver and skeletal muscle. Ovariectomized C57BL/6 mice were injected with 5 μg of E2 or 300 μg of PaPE-1 for 2 h. Indicated tissues were collected and subjected to Western blot analysis for p-S6 and p-p42/44 MAPK. β-actin and total ERK2 were used as loading controls.

To gain more mechanistic insight, the signaling pathways activated by E2 and PaPE-1 were profiled in different tissues (FIG. 7B). E2 and PaPE-1 had similar pathway effects in non-reproductive tissues, whereas E2 and PaPE-1 had contrasting effects in reproductive tissues (uterus and mammary gland), with only E2 being stimulatory. Furthermore, in metabolic tissues like liver and skeletal muscle, both E2 and PaPE-1 were highly effective in inducing mTOR signaling, as observed by S6 phosphorylation.

Figure 13:
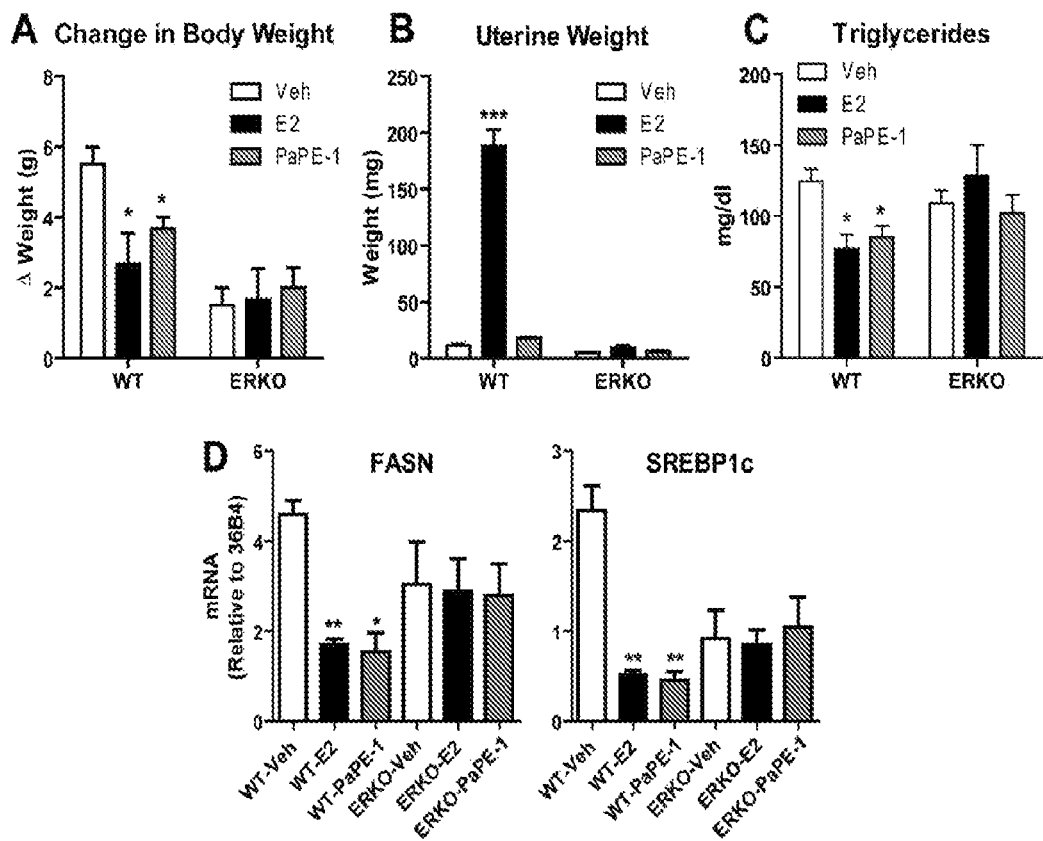
FIG. 13. Effects of PaPE-1 require ERα. (A) Wild type (WT) or ERα knock-out (ERKO) C57BL/6 mice were ovariectomized, and after 3 weeks, pellets containing E2 (5 µg/day) or PaPE-1 (300 µg/day) were implanted for 3 weeks. Animals were on normal chow diet. Change in body weight was monitored. (B) Uterus weights of animals from (A) at the end of 3 weeks of vehicle (Veh) or ligand treatment. (C) Triglyceride levels in the blood of animals from (A) after 3 weeks of ligand exposure. (D) Gene expression analysis of FASN and SREBP1c in livers of WT or ERKO mice treated with Veh, E2 and PaPE-1 for 3 weeks. t-test, * $p<0.05$,  $p<0.01$, * $p<0.001$.
Figure 14:
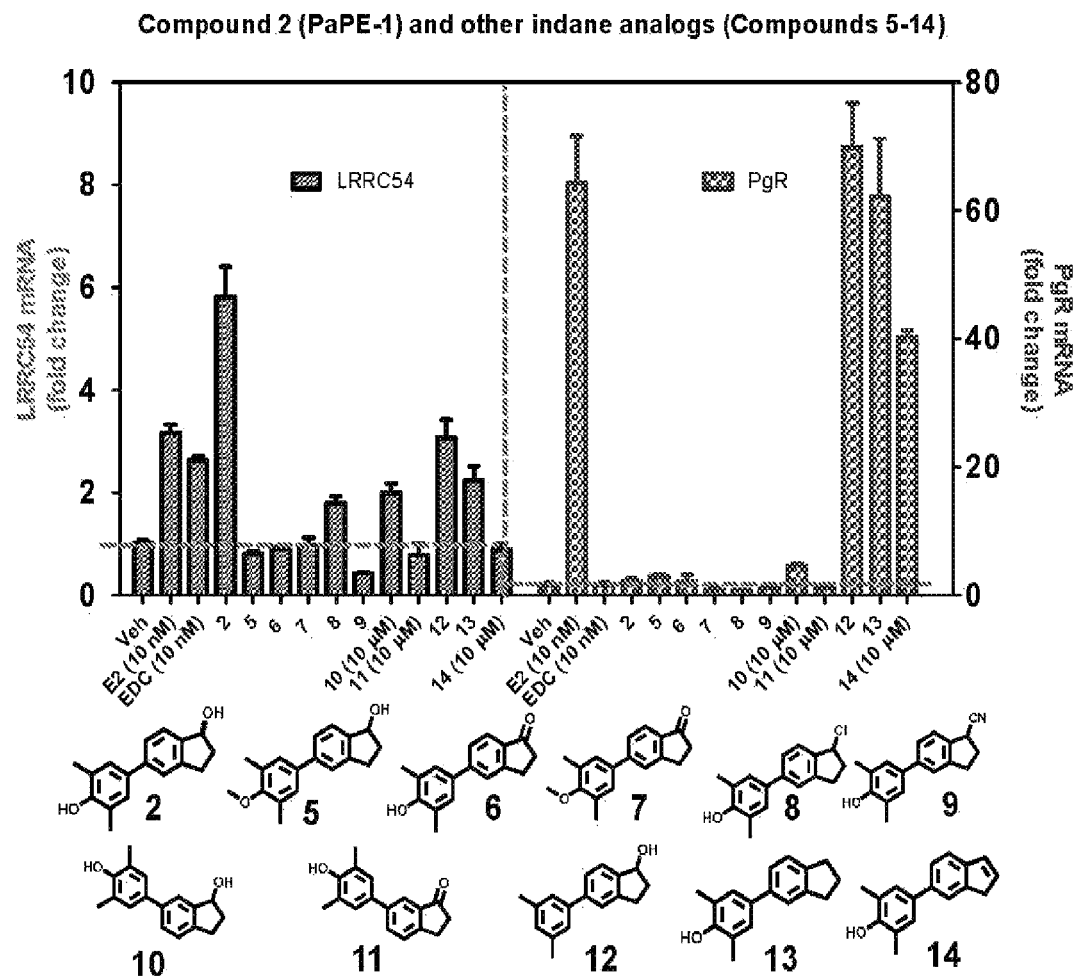
FIG. 14. Compound 2, which is the same as PaPE-1, activated the non-genomic gene, LRRC54, to a 1.9 fold higher level than E2. In contrast to LRRC54 mRNA expression, the level of induction of the PgR mRNA by compound 2 is almost unchanged from the vehicle (veh.) level. Hence, it has good preferential activity on the non-genomic signaling pathway. When the phenolic OH is blocked with a methyl group, as in compound 5, there is a marked loss of this non-genomic activity. When the aliphatic alcohol is oxidized to a ketone (compound 6), the non-genomic activity is lost as well. With a chlorine in place of the aliphatic alcohol (compound 8), there is stimulation of the nongenomic gene (LRRC54), but to a lesser degree than compound 2 (and only 50% compared to E2), and the cyano analog (compound 9) shows no non-genomic activity. The positional isomer (compound 10) has quite good selective non-genomic activity, but the ketone analog (compound 11) is inactive. Compounds 12, 13, and 14 have hydroxyl groups deleted, and while the first two have some non-genomic activity, all three of them strongly stimulate the genomic gene PgR.
Figure 15:
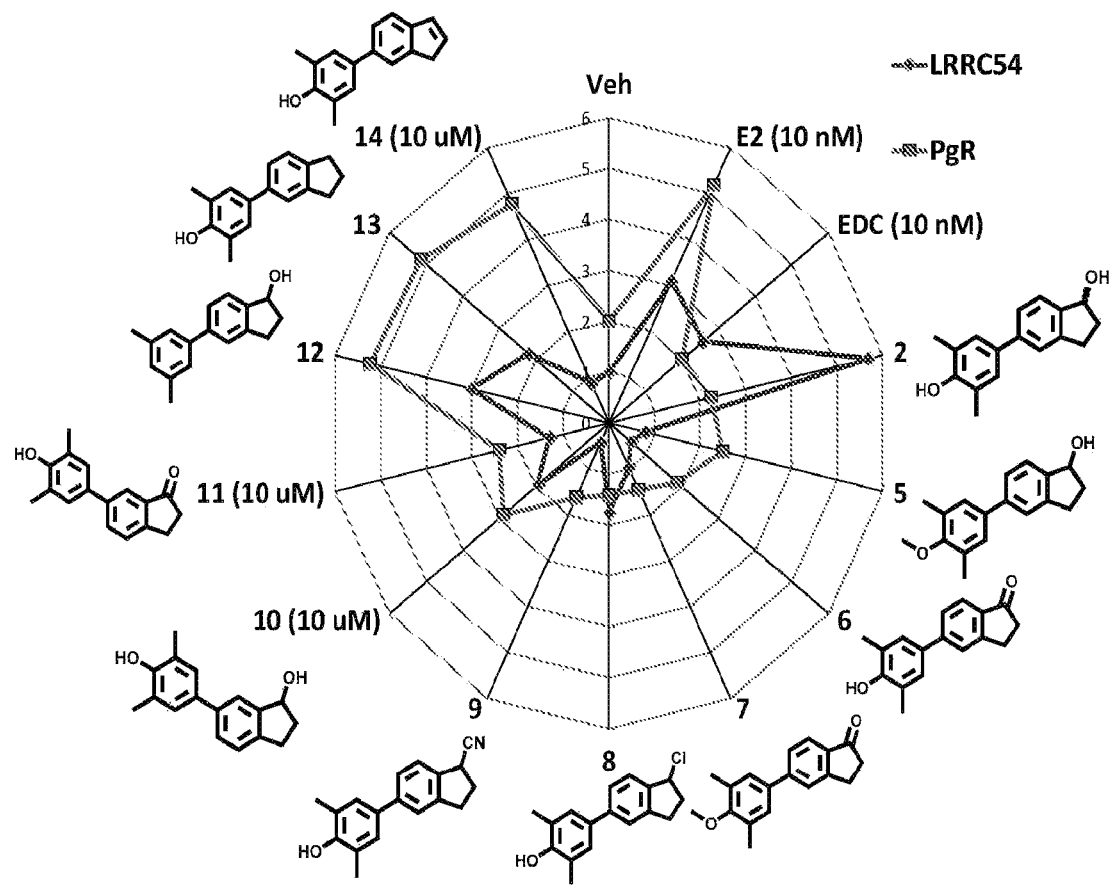
FIG. 15. The activities shown in FIG. 14 are shown here as a radar or star plot, with the red curve representing genomic activity (stimulation of the PgR gene) and the blue curve representing the non-genomic activity (stimulation of the LRRC54 gene). Selective non-genomic activity is evident when the points on the blue curve extend beyond the points on the red curve. From this it is clear that of the compounds in this figure, compound 2 (PaPE-1) has the greatest non-genomic activity together with very low genomic activity.
Figure 16:
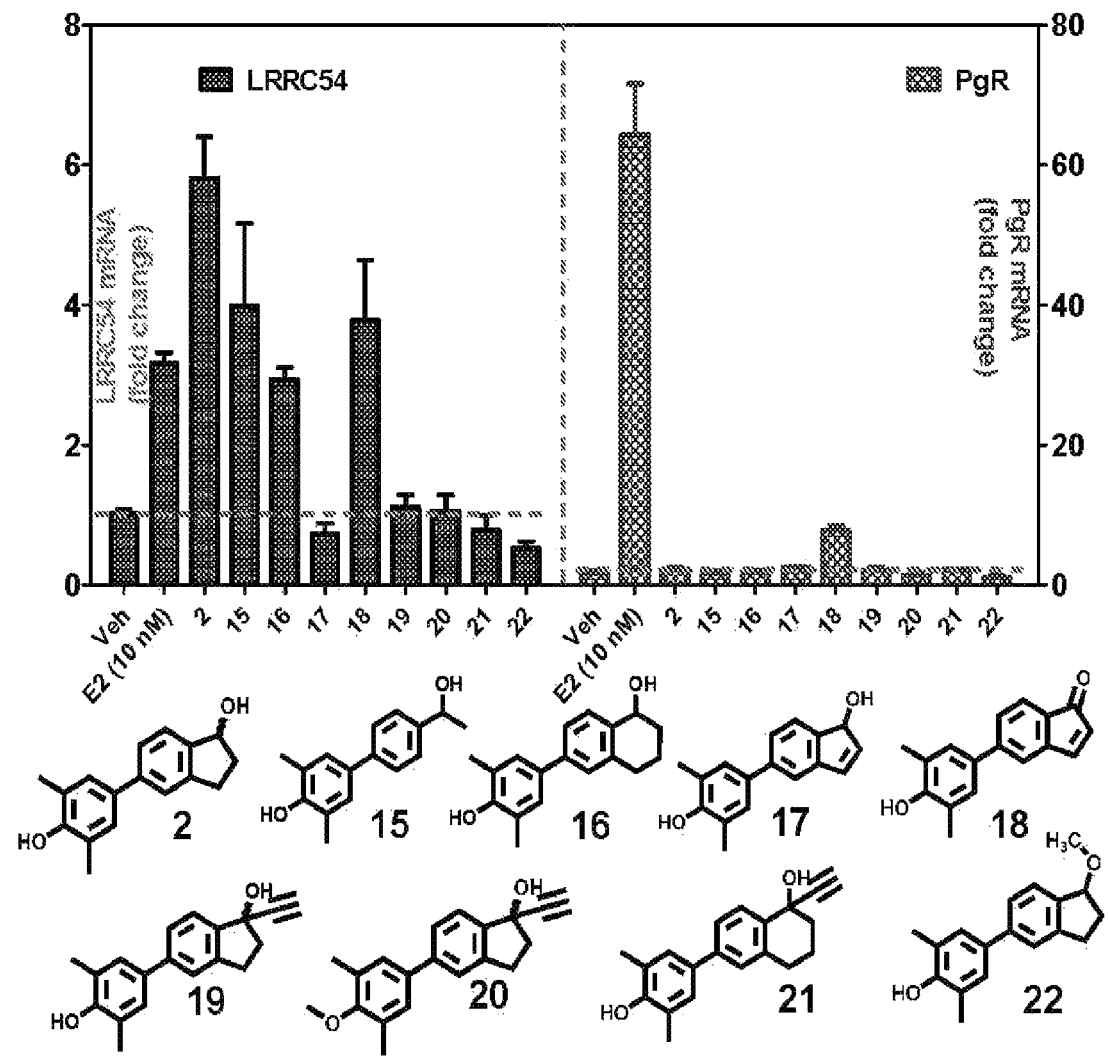
FIG. 16. Fold change in LRRC54 mRNA (the non-genomic gene) and PgR mRNA (the genomic gene) with PaPE-1 (compound 2) and various compounds.
Figure 17:
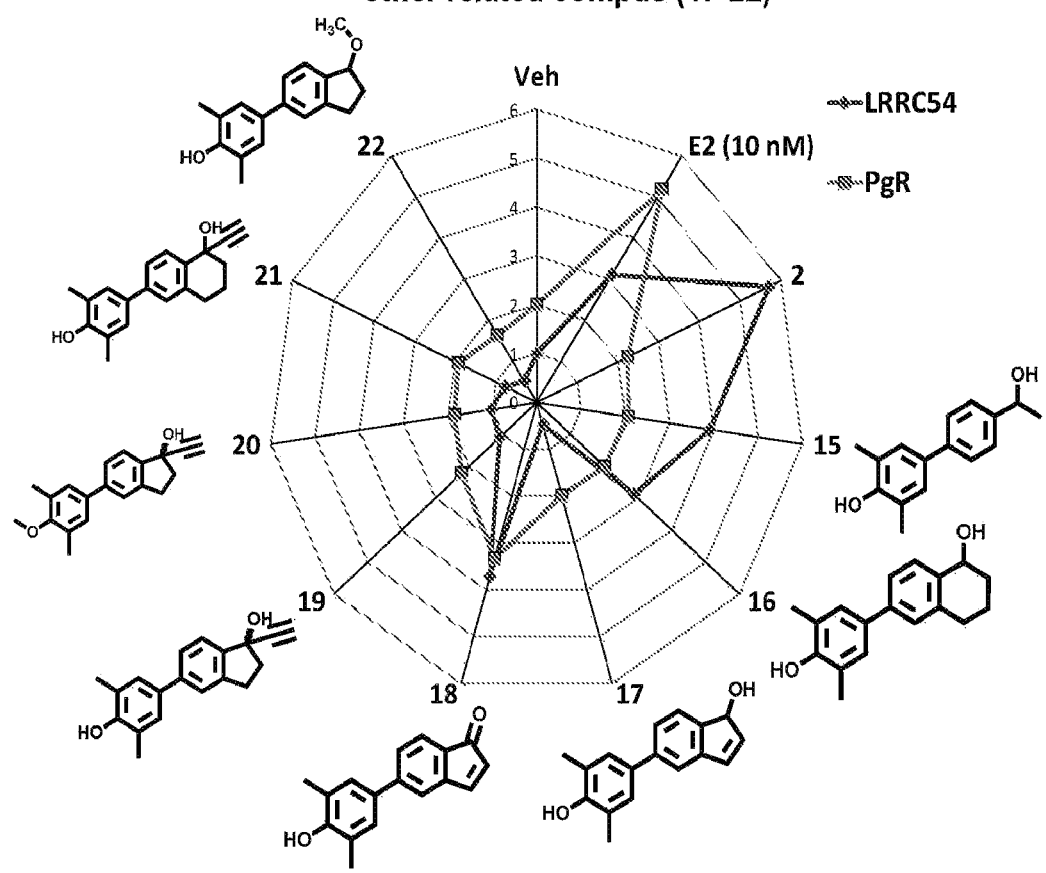
FIG. 17. The effect of PaPE-1 (compound 2) and various close analogs on the expression of LRRC54 mRNA (non-genomic) and PgR mRNA (genomic) genes demonstrated in a radar graph. As shown here, tetralone (compound 16, also termed PaPE-3) and its open ring system (compound 15, also termed PaPE-2) have some selectivity for the non-genomic gene but less than that of compound 2. Indene-1-ol system (compound 17) loses both LRRC54 and PgR activity. Indene-1-one system (compound 18) increases expression of both the non-genomic and genomic genes. 17-Ethynyl estradiol mimic compounds (compounds 19-21) do not have activity on either gene. When the alcoholic OH is blocked by a methyl group (compound 22), stimulation of both genomic and nongenomic gene expression is lost.
Figure 18:
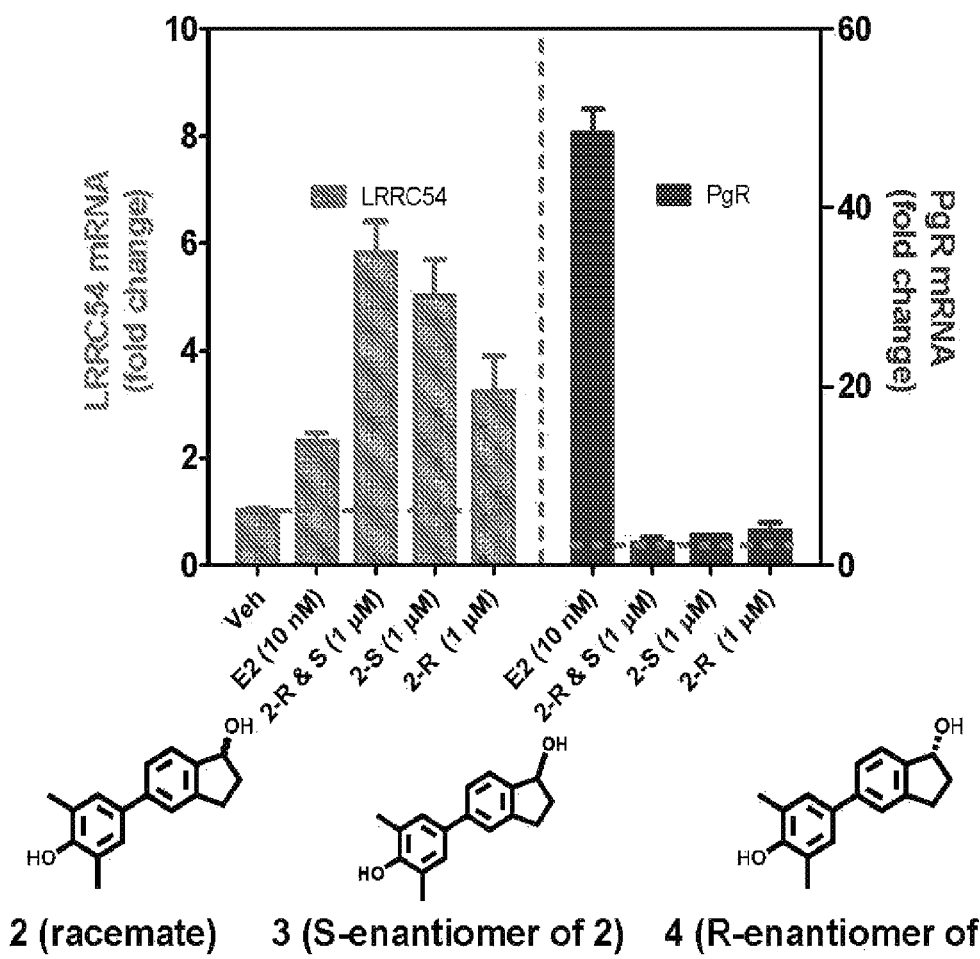
FIG. 18. Fold change of LRRC54 mRNA (the non-genomic gene) and PgR mRNA (the genomic gene) with PaPE-1, a racemate, (compound 2) and with the S-enantiomer (compound 3) and R-enantiomer (compound 4) of compound 2 (PaPE-1). The racemate and S-enantiomer have equivalent activities; the R-enantiomer has less non-genomic gene activity.
Figure 19:
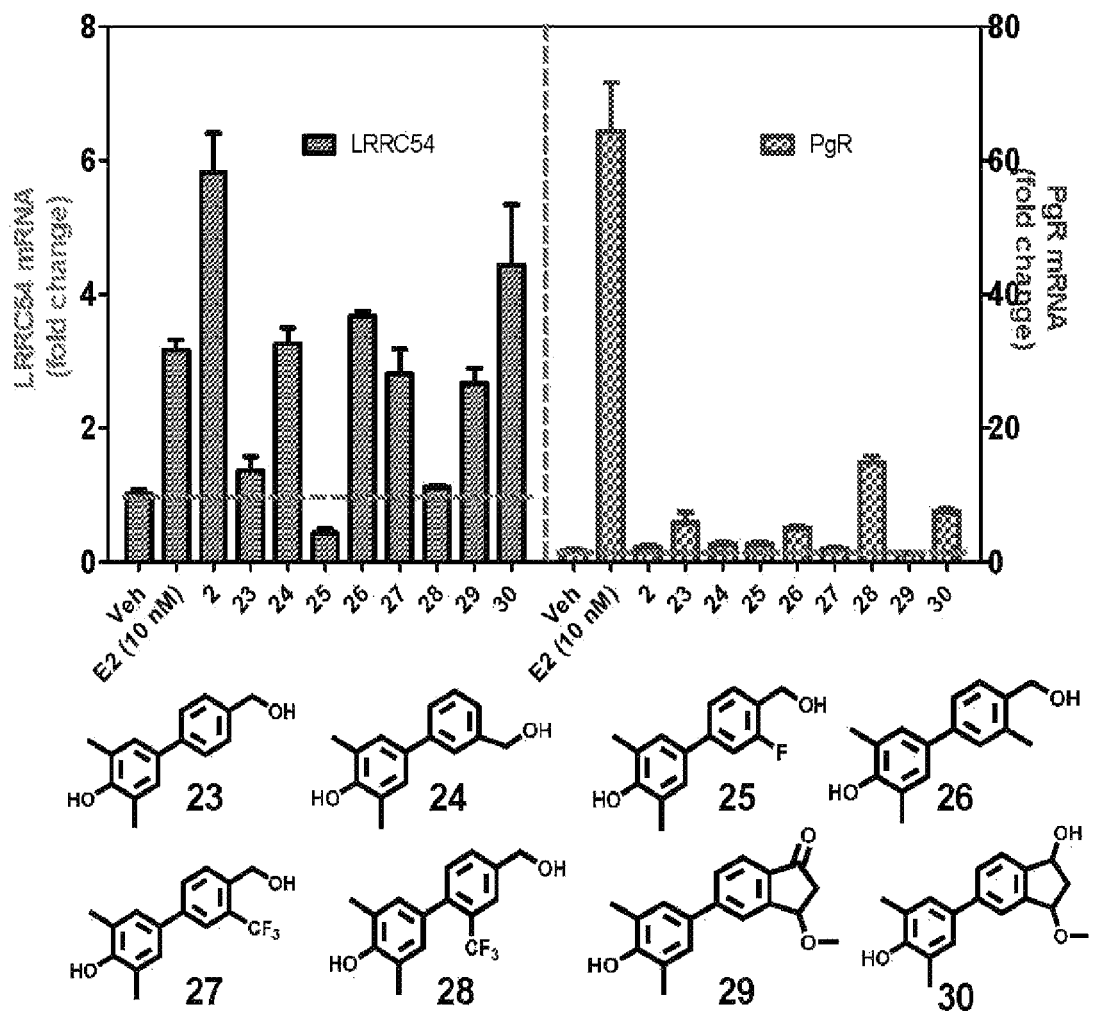
FIG. 19. Fold change of LRRC54 mRNA (the non-genomic gene) and PgR mRNA (the genomic gene) with various additional benzylic compounds and structurally modified PaPE derivatives.
Figure 20:
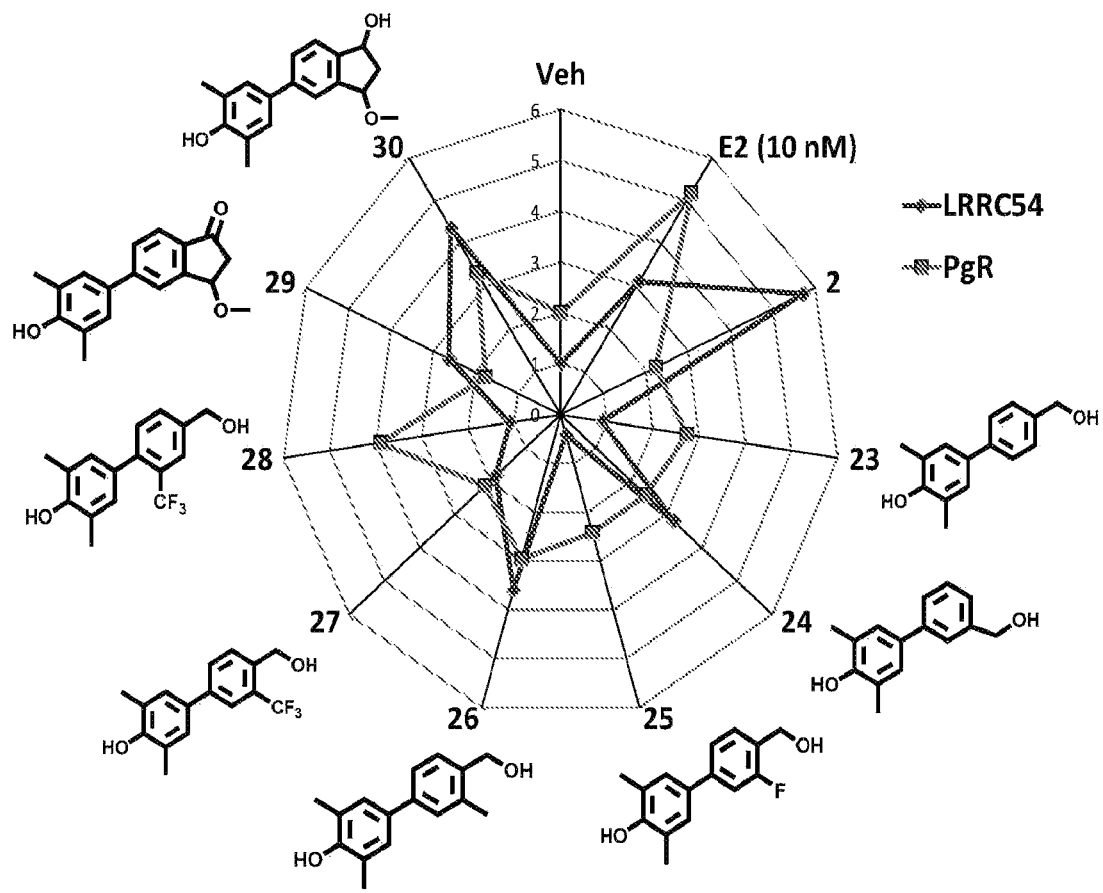
FIG. 20. Star plot of the data from FIG. 19. Among benzyl alcohol-type compounds (compounds 23-28), compounds 24, 26, and 27 showed similar levels of nongenomic gene expression as did estradiol (E2), but the genomic gene (PgR) expression was slight higher than the vehicle level. Compound 2 (PaPE-1) showed the greatest preferential nongenomic gene stimulation. Interestingly, compound 29 expressed LRRC54 similar level to E2, but it did not activate PgR above that of vehicle (veh.). Compound 30, derived by reduction of the ketone (compound 29), elevated both genomic and nongenomic gene expression to a higher level than does its parent compound 29.
Figure 21:
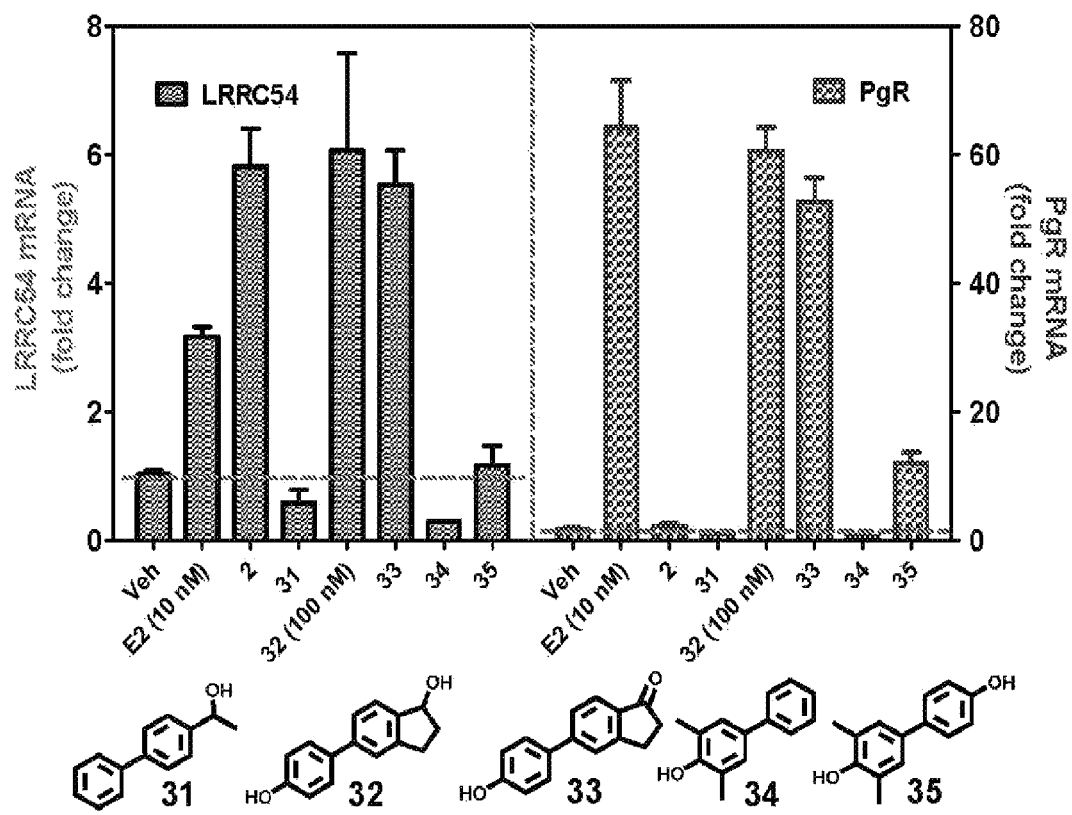
FIG. 21. Fold change of LRRC54 and PgR mRNA levels induced by various biphenyl type analogs lacking portions of the structure of PaPE-1 (compound 2).
Figure 22:
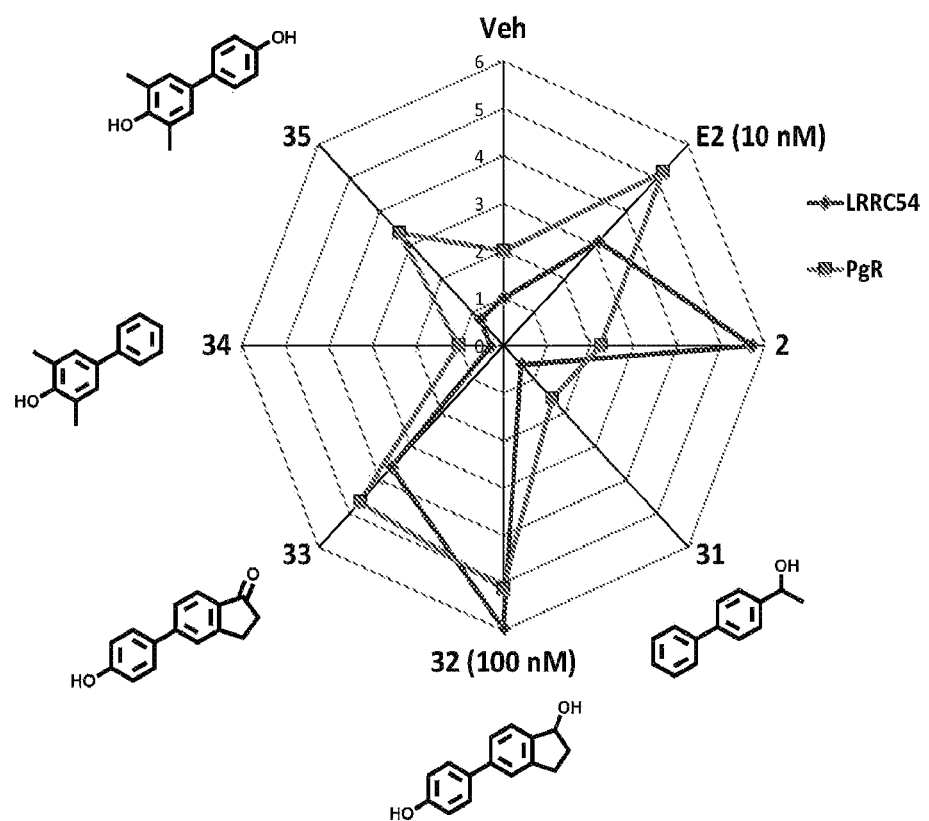
FIG. 22. Star plot of the data from FIG. 21. From this series, it can be seen that both the benzylic OH and two methyl groups flanking the phenolic OH in compound 2 (see FIGS. 14 and 15) are important to suppress genomic gene expression and stimulate LRRC54 gene activity. If the methyl groups and OH are eliminated (compound 31), both activities are lost. If only the methyl groups are removed from compounds 2 and 6, these derivatives (compounds 32-33) stimulate PgR gene expression at a level close to that of E2 while retaining LRRC54 gene induction similar to (compound 32) or somewhat less than (compound 33) that of compound 2 (PaPE-1). In addition to the important roles of the two methyl groups and the phenolic OH, elimination of the alkyl group bearing the aliphatic alcohol or its replacement with a phenol (compounds 34-35) causes loss of activity in stimulating the expression of both LRRC54 and PgR genes (compound 34) or principally loss of LRRC54 gene expression (compound 35).
Figure 23:
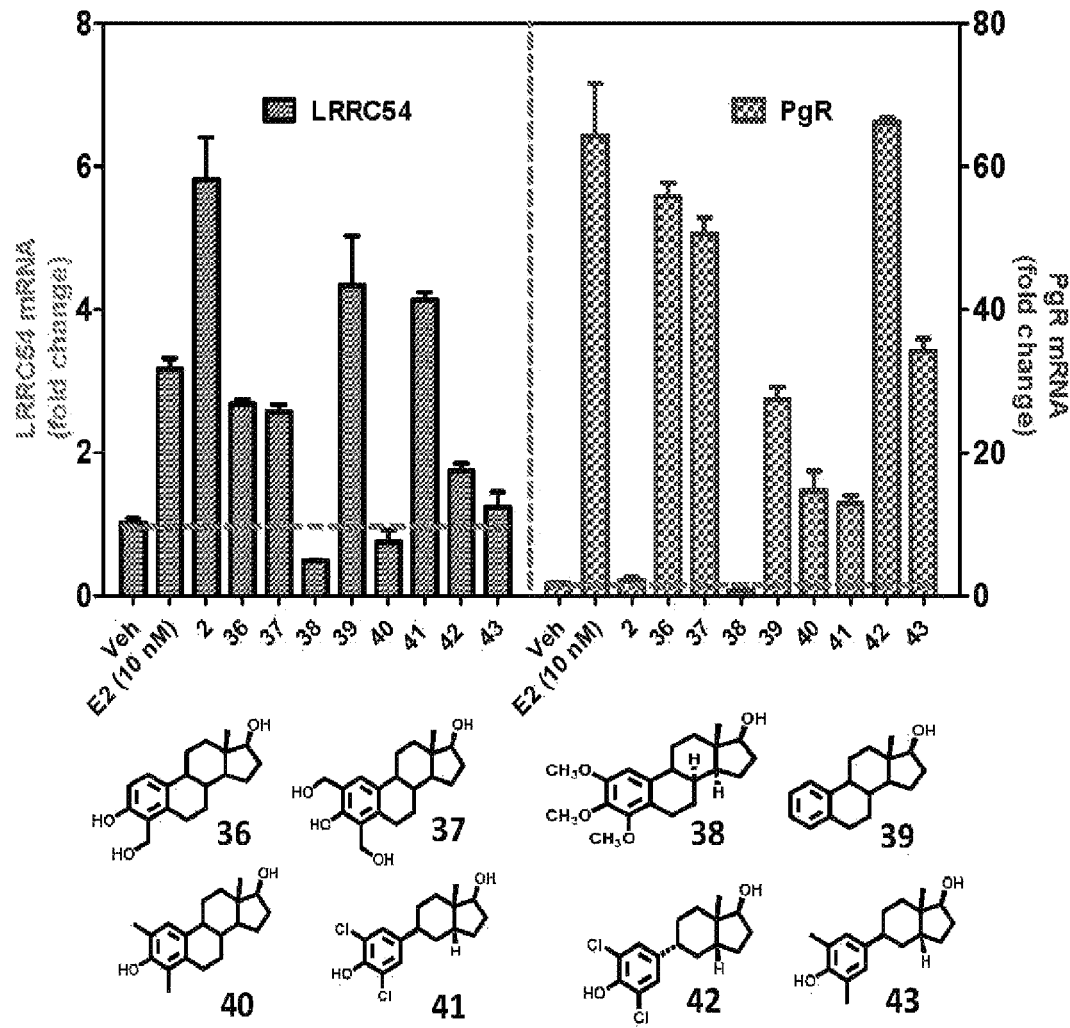
FIG. 23. Fold change of LRRC54 and PgR mRNA gene expression induced by various modified versions of estradiol (E2), compounds 36-43.
Figure 24:
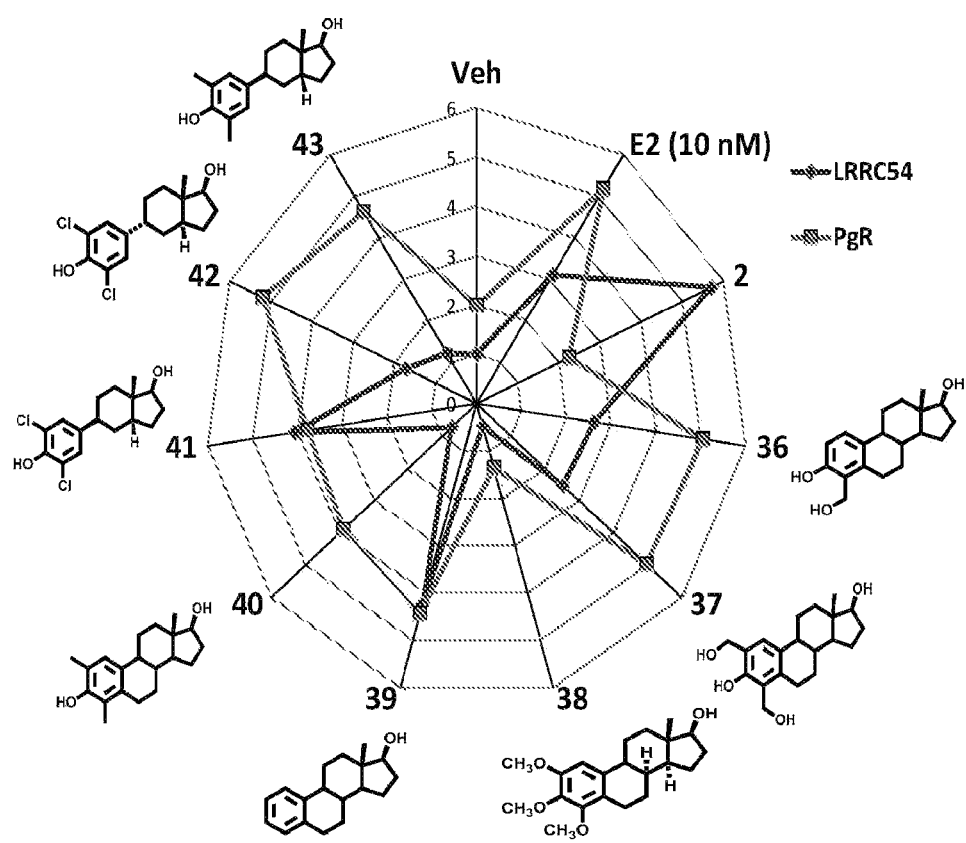
FIG. 24. Star plot of the data from FIG. 23. All of the modifications except that of compound 38 have strong activity on the genomic gene PgR. Non-genomic gene (LRRC54) activity similar to that of compound 2 (PaPR-1) is retained with compounds 39 and 41, and to a less extent with 36 and 37.

PaPE-1 activity is lost in ERα-knockout mice. A select number of effects of E2 and PaPE-1 on physiologic processes and gene expression were compared in wild type and ERα-knockout mice (ERKO) (FIG. 13). OVX mice were treated with E2 or PaPE-1 for 3 weeks, and as shown in FIG. 13A, the ability of E2 or PaPE-1 to diminish the body weight gain after ovariectomy was lost in the ERKO mice. E2 stimulation of uterine growth was, as expected, not observed in ERKO mice (FIG. 13B), nor was there a decrease in blood triglycerides after E2 or PaPE-1 (FIG. 13C). FIG. 13D shows that ERα is a mediator of the suppressive effect of PaPE-1 or E2 on FASN and SREBP1c genes seen in the liver of wild type mice that was not observed in ERKO mice.

Figure 8:
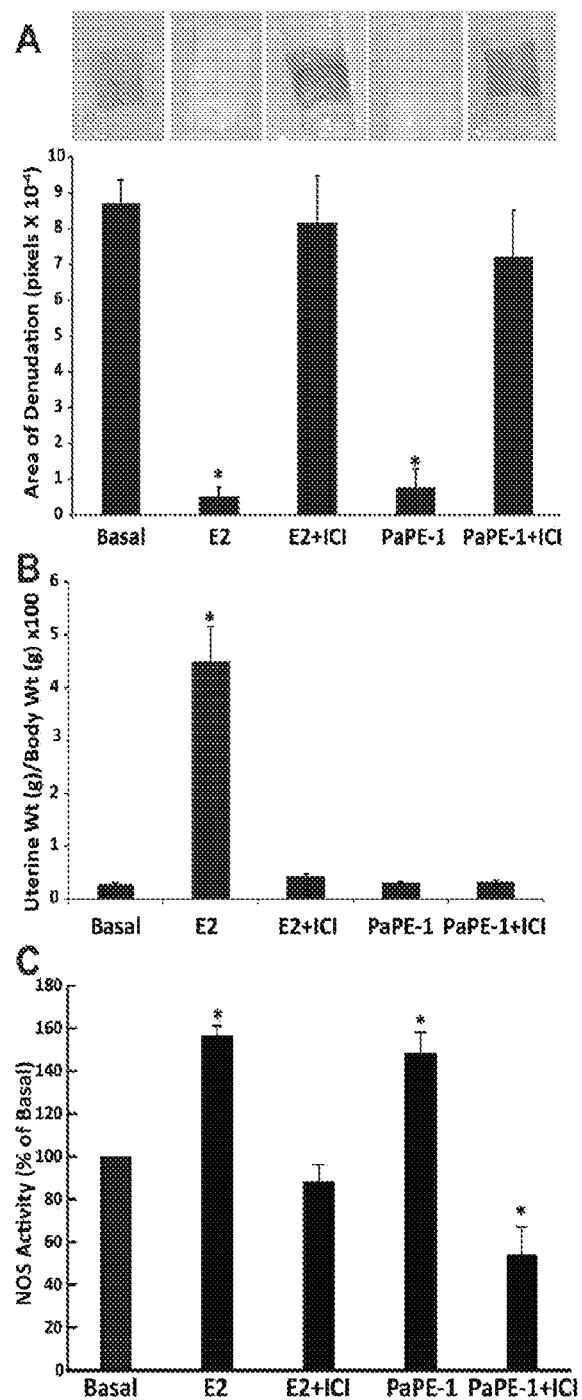
FIG. 8. PaPE-1, like E2, elicits repair of the vascular endothelium after injury and this is prevented by the antiestrogen ICI. (A) Carotid artery reendothelialization after an injury that denudes the endothelial layer in OVX mice treated with PaPE-1 or E2 in the absence or presence of the antiestrogen ICI 182,780 (ICI). *, p<0.05 vs. basal control. (B) PaPE-1 does not affect uterine weight in these experiments, whereas E2 increases uterine weight and this is blocked by ICI. (C) eNOS stimulation by E2 and PaPE-1 in the presence and absence of the antiestrogen ICI 182,780. BAEC were treated with ligands for 15 min and eNOS activity was monitored. *, p<0.05 vs. control.

The vascular effects of E2 and PaPE-1 were studied. Estrogens have potential beneficial actions on vascular cells, as exemplified by in vivo studies of carotid artery reendothelialization following perivascular electric injury in female mice. Following ovariectomy, mice were treated with vehicle, E2 or PaPE-1 for 18 days, at which time E2 and PaPE-1-treated mice were also administered a single dose of vehicle or the antiestrogen ICI 182,780. Three days later, carotid artery denudation was performed, and the mice received a second dose of vehicle or ICI while E2 or PaPE-1 was continued, and 72 h after denudation Evans blue dye was administered systemically to assess the remaining area of denudation. FIG. 8A, upper panel, shows Evans blue dye uptake by the intimal surface of the carotid artery. E2 and PaPE-1 caused similar marked endothelial repair, as indicated by the minimal area of remaining denudation, and the responses elicited by E2 and PaPE-1 were fully prevented by the antiestrogen ICI 182,780 (ICI, Fulvestrant). Summary data for the different treatment groups are shown in FIG. 8A, lower panel. In the same animals, uterine weight, which was greatly elevated by E2, was unaffected by PaPE-1, and as expected, the antiestrogen ICI blocked uterine stimulation by E2 (FIG. 8B).

To evaluate direct effects on endothelium, endothelial NO synthase (eNOS) activation was assessed by measuring the conversion of $^{14}C$-L-arginine to $^{14}C$-L-citrulline by intact primary bovine endothelial cells in culture. eNOS was activated by E2, as previously observed (Chambliss, J Clin Invest 120, 2319-2330, 2010), and there was a comparable response to PaPE-1; the effects of both E2 and PaPE-1 were fully attenuated by ICI (FIG. 8C).

Example 35: Characterization of Additional PaPEs

To further exemplify compounds that preferentially activate ER non-genomic signaling, results from PaPE-2 and PaPE-3 are presented, two ligands that are structurally related to PaPE-1 by being altered forms of the steroidal ligand, estradiol, but having variations in the structure of what was originally the estradiol D-ring, namely ring cleavage in PaPE-2 and ring enlargement in PaPE-3 (FIG. 1). To further diversify the structures of PaPEs, an additional ligand, PaPE-4 was also studied; this PaPE is derived from a non-steroidal estrogen, bisphenol A (BPA), and it retains the core bisphenol structure of BPA but has been modified to have reduced ER binding affinity by replacing one of the methyl groups with a polar bis-amide substituent. The ER binding and physical properties of PaPE-2, -3, and -4 are given in FIG. 1.

Figure 9:
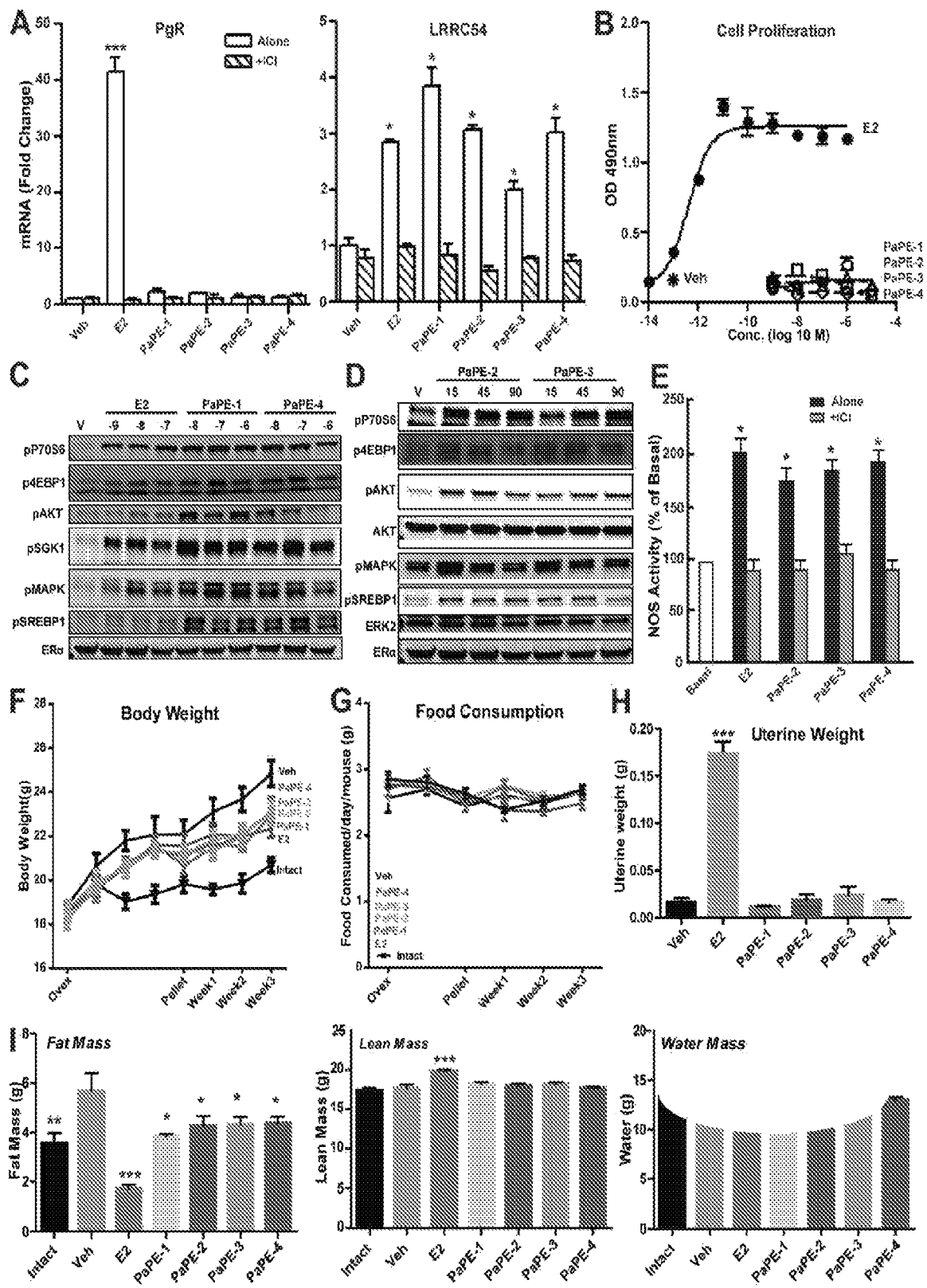
FIG. 9. Assessment of the activities of PaPE-2, PaPE-3, and PaPE-4 in MCF-7 cells, in bovine aortic endothelial cells (BAEC) cells, and in mice. (A) Preferential stimulation of extranuclear-initiated LRRC54 gene expression vs. direct nuclear PgR gene expression. MCF-7 cell treatment was with control vehicle (Veh), 10 nM E2, or 1 μM of the indicated PaPE for 4 h prior to RNA harvest and qPCR analysis. (B) Proliferation of MCF-7 cells after treatment with different concentrations of E2 or the PaPE for 6 days. (C) Stimulation of various cell signaling pathway activations by different concentrations of E2, PaPE-1, or PaPE-4 after 15 min treatment of MCF-7 cells. Level of ERα is also shown. (D) Time course of cell signaling pathway activations by PaPE-2 or PaPE-3, monitored at 15, 45, and 90 min. Level of ERα is shown, and total ERK2 is used as a loading control. (E) Stimulation of NOS activity during 15 min treatment of BAEC with 10 nM ligand alone or with cotreatment with 1 μM ICI 182,780. (F) The PaPEs and E2 reduce weight gain after ovariectomy in C57BL/6 mice. Animals were ovariectomized, and after 3 weeks, animals received pellets of E2 (5 μg/day), the PAPE (300 μg/day), or vehicle, and body weight was monitored over the next 3 weeks. A group of intact non-ovariectomized mice were included for comparison. Two-way ANOVA, Bonferroni posttest, * p<0.05,  p<0.01, * p<0.001, **** p<00.0001, comparing all treatments to vehicle (Veh.) (G) Food consumption was monitored over time. (H) Assessment of uterine weight gain in ovariectomized C57BL/6 mice after 3 weeks of pellets of E2 (5 μg/day) or PaPE-1, -2, -3 and -4 (300 μg/day). One-way ANOVA, Newman-Keuls post-test, * p<0.05,  p<0.01, * p<0.001, **** p<0.0001. (I) Fat mass, lean mass, and water mass were measured by EchoMRI at the end of the 3-week treatment period in mice shown in Panel F. One-way ANOVA, Newman-Keuls post-test, comparing intact and all treatments to vehicle (Veh.) * p<0.05,  p<0.01, * p<0.001, **** p<00.0001.

All of the PaPEs showed similar biological activities in vitro and in vivo. They all caused preferential non-genomic vs. genomic gene stimulation (LRRC54>PgR) compared to E2, which stimulated expression of both genes very well (FIG. 9A). In contrast to E2, none of the PaPEs stimulated proliferation of MCF-7 cells over a broad concentration range tested (FIG. 9B). All of the PaPEs increased activation of MAPK, mTOR and AKT signaling pathways, as monitored by pMAPK, pP70S6 and pSREBP1, and pAKT in these cells (FIGS. 9C and 9D). In endothelial cells, PaPE-2, -3, and -4, like E2, also increased NOS activity (FIG. 9E), as was seen with PaPE-1 (FIG. 8C), and the NOS stimulation was fully blocked with the antiestrogen, ICI. In vivo, the four PaPEs and E2 reduced body weight gain after ovariectomy (FIG. 9F), with no change in food consumption (FIG. 9G). The four PaPEs also did not elicit any increase in uterine weight, which, in contrast, was markedly increased by E2 (FIG. 9H). The reduction in body weight with the four PaPEs was largely due to a change in body fat mass, with little or no change in lean mass or water mass, as monitored by EchoMRI. E2 reduced fat mass more markedly, and did increase lean mass and water mass (FIG. 9I). These differential effects may account for the fact that the body weight of E2-treated animals matched that of the PaPE-treated animals.

Example 36: Investigation of ER Ligand Binding Dynamics Couple with Signal Transduction Pathways A computational model showing structural details of the accommodation of PaPE-1 in the ligand-binding pocket of ERα in comparison to E2 is presented in FIG. 2. Helices 3 and 6 constrict the A-ring end of the binding pocket, and E2 (silver/gray) forms hydrogen bonds to both GLU353 and ARG394, further stabilized by a crystallographic water (red dot) bridging GLU and ARG. By contrast, the ortho-methyl groups of PaPE-1 (in yellow) introduce steric clashes with H3 and H6, inducing a significant shift in ligand positioning. While the A-ring OH of PaPE1 maintains a hydrogen bond to GLU353 and the crystallographic water still bridges between GLU and ARG, direct ligand contact to ARG394 is broken (ER structure in yellow). At the D-ring end of the pocket, there is also a subtle shift in the positioning of HIS524. Overall, it appears that the reduced volume of the PaPE-1 ligand and the increased planarity due to the aromatic C-ring mimetic result in fewer van der Waals contacts throughout the central region of the pocket. All of these changes with respect to the ER-E2 complex are consistent with the greatly lower binding affinity of PaPE-1. Nevertheless, the overall shape of the ligand-binding pocket is not altered in a major way by the binding of PaPE-1, suggesting that PaPE-1 can still form a structurally competent, though short-lived complex with ER.

The dissociation rates of PaPE-1 and E2 were measured for ERα (FIGS. 10E and F), and they differ by nearly 2000 fold; the half-life of the ER-E2 complex is nearly 30 hours, whereas that of the PaPE-1 complex is less than 1 minute.

Example 37. Activation of Non-Genomic Genes by PaPEs

Compounds that have cause preferential activation of the LRRC54 gene to a higher level than the PgR gene are considered to have a preference for activation of the extra-nuclear-initiated or non-genomic pathway. In each case, this preference is apparent from the histograms showing the fold change in stimulation of the two genes as well as from the star or radar plots, where the activation of LRRC54 is plotted as points on a blue curve and the activation of PgR is plotted as points on a red curve. (FIGS. 14-33).

In the histograms, a compound shows pathway preference for activation of non-genomic genes when the fold activation of the non-genomic gene (LRRC54) is higher relative to the activation by estradiol (E2) compared to the activation of the genomic gene (PgR) relative to the activation by estradiol (E2). On the star or radar plots, preferential activation of the non-genomic gene is evident when the point on the blue curve extends further from the center of the plot than the point on the red curve.

Figure 25:
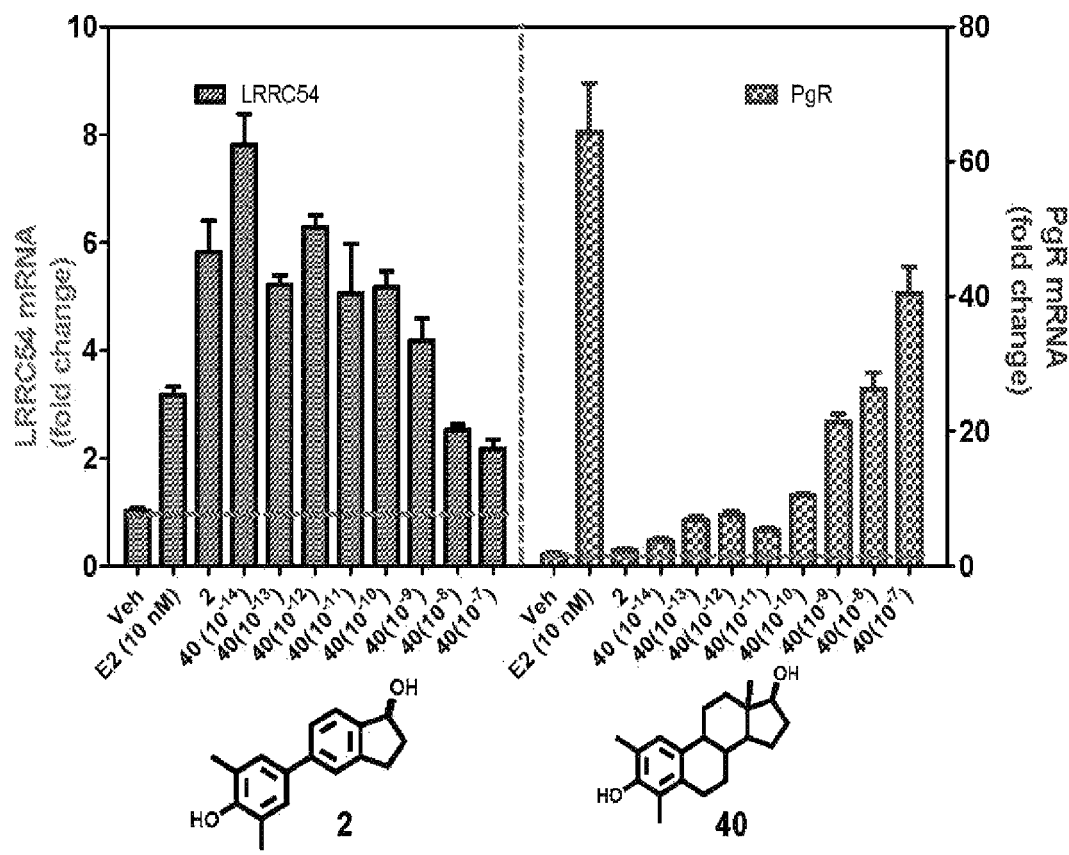
FIG. 25. Compound 40 selectively stimulates LRRC54 gene expression at femtomolar concentrations, with reduced expression at nanomolar to micromolar concentrations; genomic gene expression (PgR) increases only at higher concentrations, demonstrating a potency separation between non-genomic (highly sensitive) and genomic (less sensitive) signaling controlling target gene expression.
Figure 26:
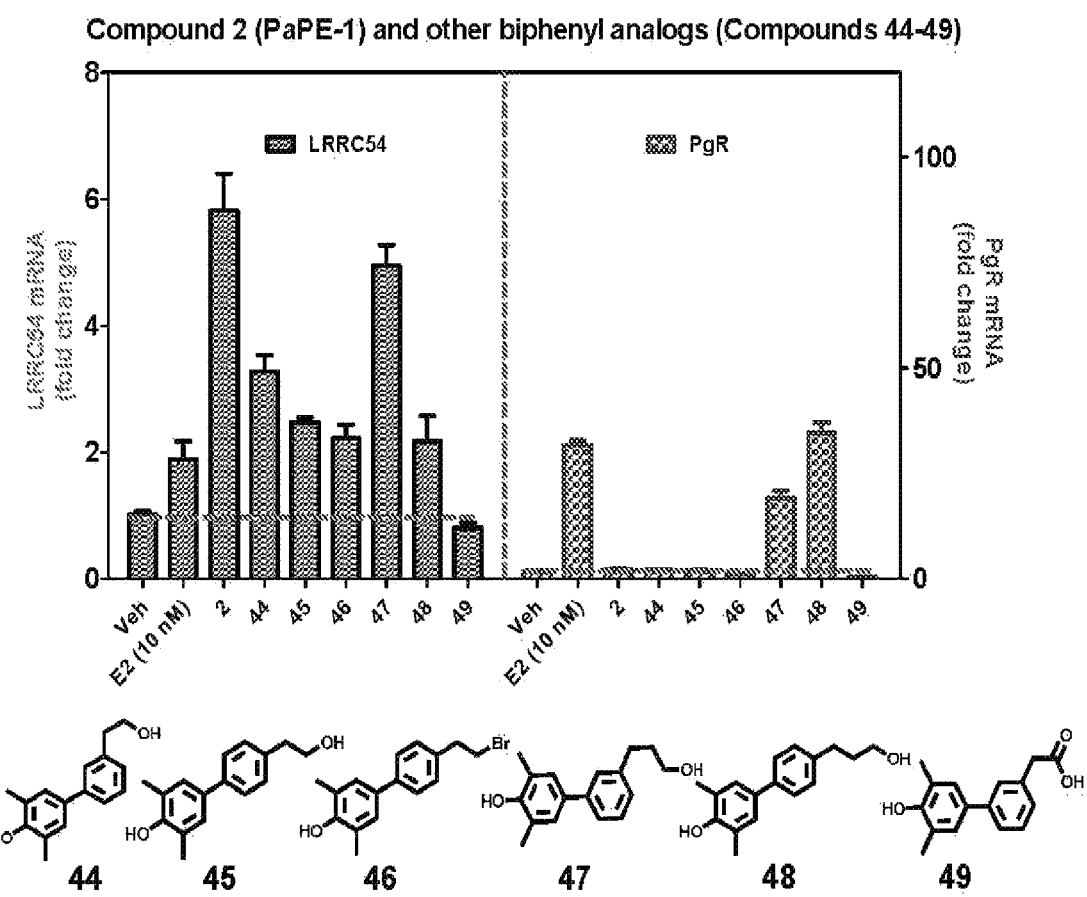
FIG. 26. Fold change of LRRC54 and PgR mRNA gene expression induced by various additional biphenyl compounds (44-49) to examine the effect of alkyl chain modifications while retaining the dimethyl phenol function.
Figure 27:
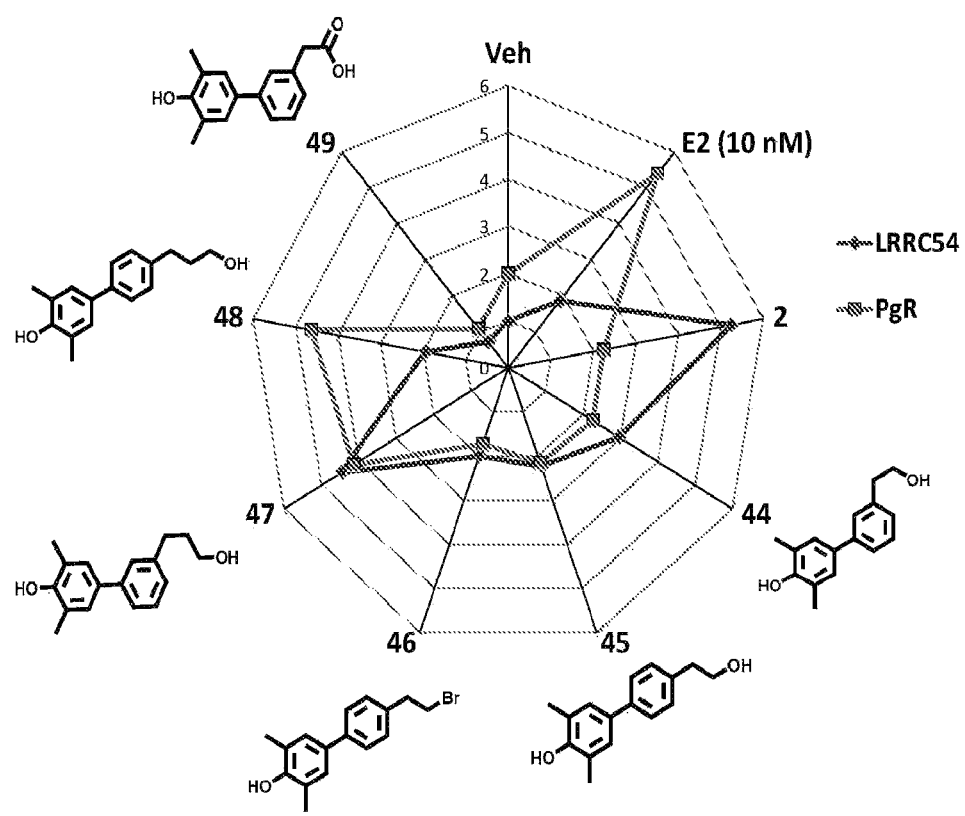
FIG. 27. Star plot of the data from FIG. 26. From this series, p- and m-phenethyl alcohol (compounds 44-45) as well as p-phenethyl bromide (compound 46) compounds preferentially stimulate LRRC54 better than E2. m- and p-Phenylpropyl alcohol group (compounds 47-48) stimulate expression of genomic PgR genes well with compound 47 also having good stimulation of the non-genomic LRRC54. The m-phenylacetic acid analog (compound 49) behaves like vehicle.
Figure 28:
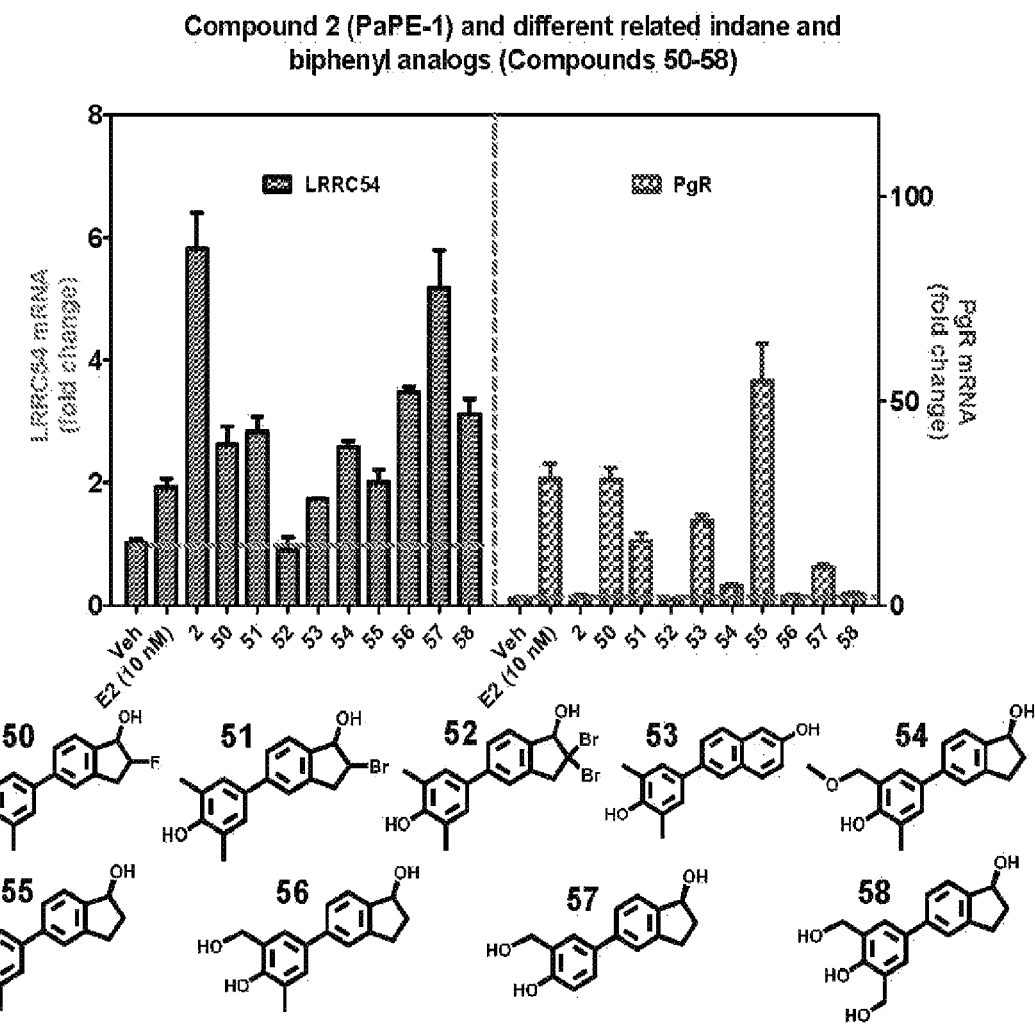
FIG. 28. Fold change of LRRC54 and PgR mRNA gene expression induced by additional indane derivatives (compounds 50-58).
Figure 29:
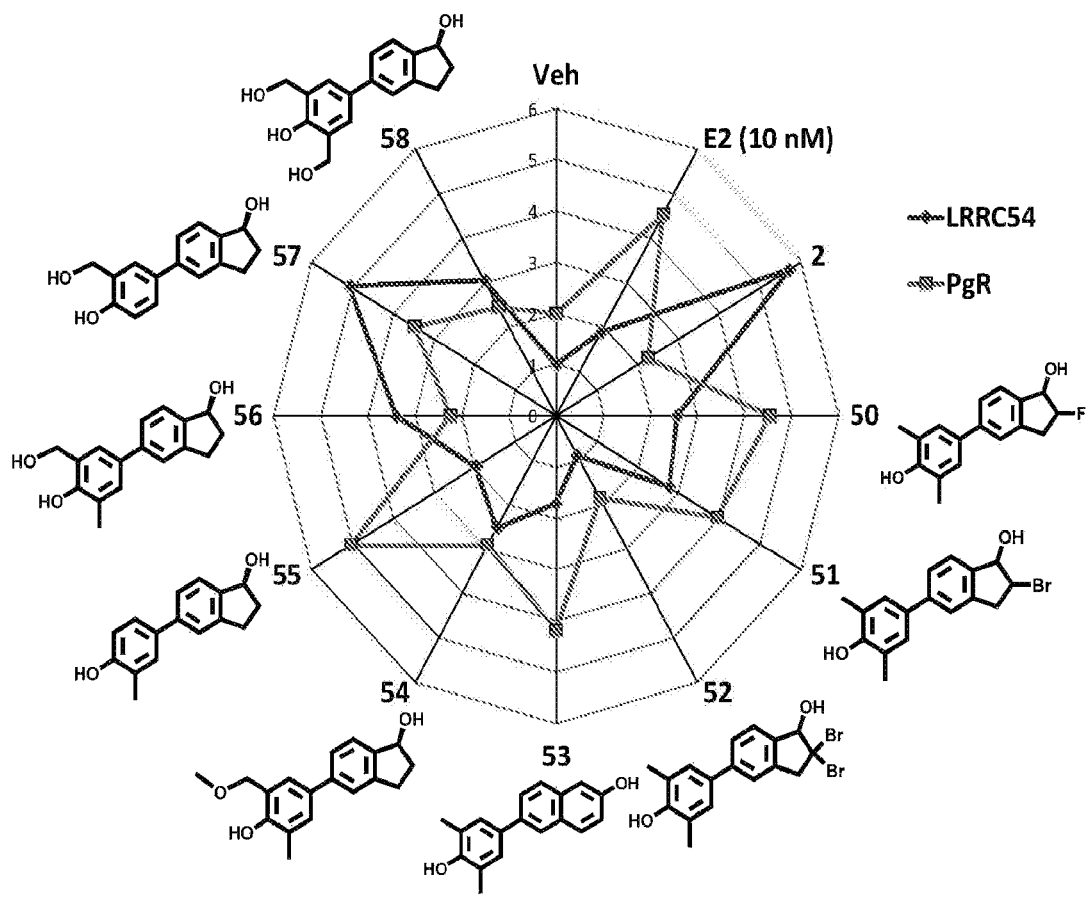
FIG. 29. Star plot of the data from FIG. 28. a-Fluoro (compound 50) and a-bromo (compound 51) substituted at 2 position of compound 2 (PaPE-1) stimulate both non-genomic LRRC54 and genomic PgR gene expression close to the level that of E2. Dibromo substituted compound (compound 52) and to some extent also the methoxy-substituted compound 54 show little expression of both genes. 2-Naphthol compound (compound 53) has a gene expression pattern equivalent to that of estradiol (E2). When one methyl group is deleted (compound 55), the PgR gene is stimulated two fold greater than that with E2. Addition of polar OH groups onto the aryl methyl(s) (compounds 56-58) increases the expression of the non-genomic LRRC54 gene, with compounds 56 and 57 showing considerable non-genomic gene selectivity.
Figure 30:
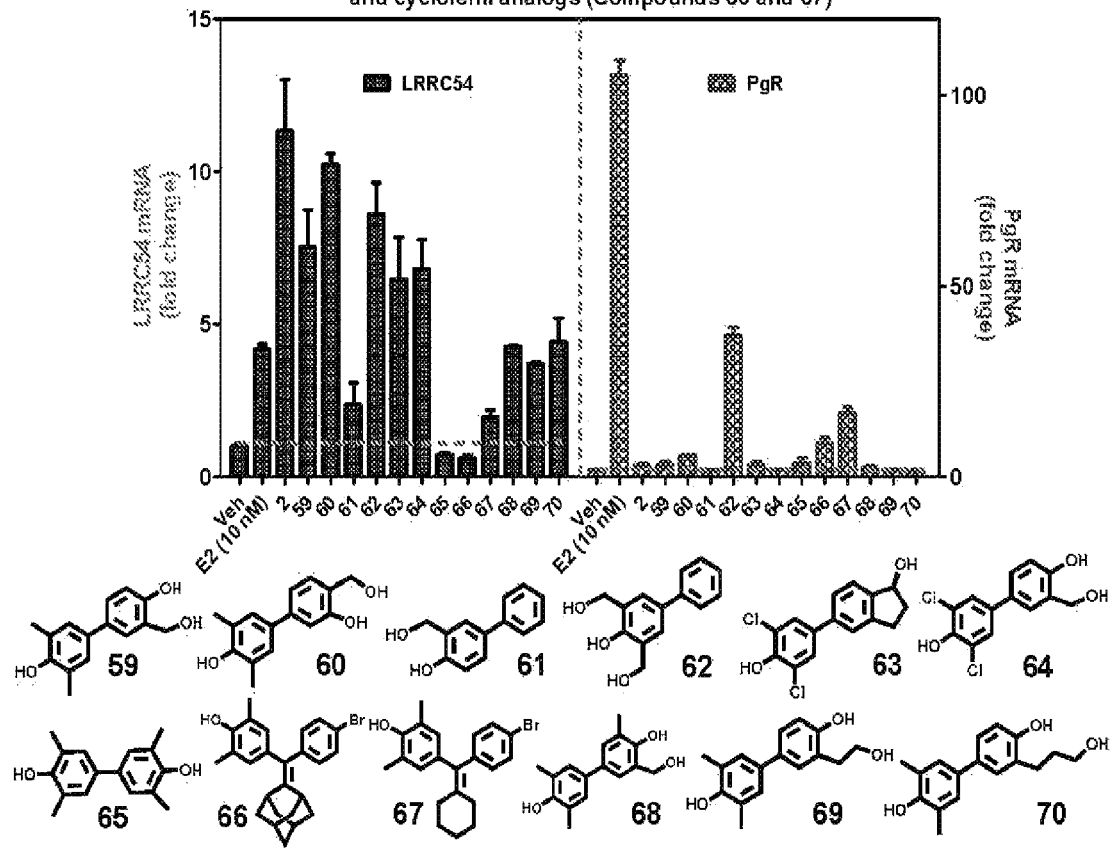
FIG. 30. Fold change of LRRC54 and PgR mRNA gene expression induced by additional biphenyl and cyclofenil mimic compounds (59-70).
Figure 31:
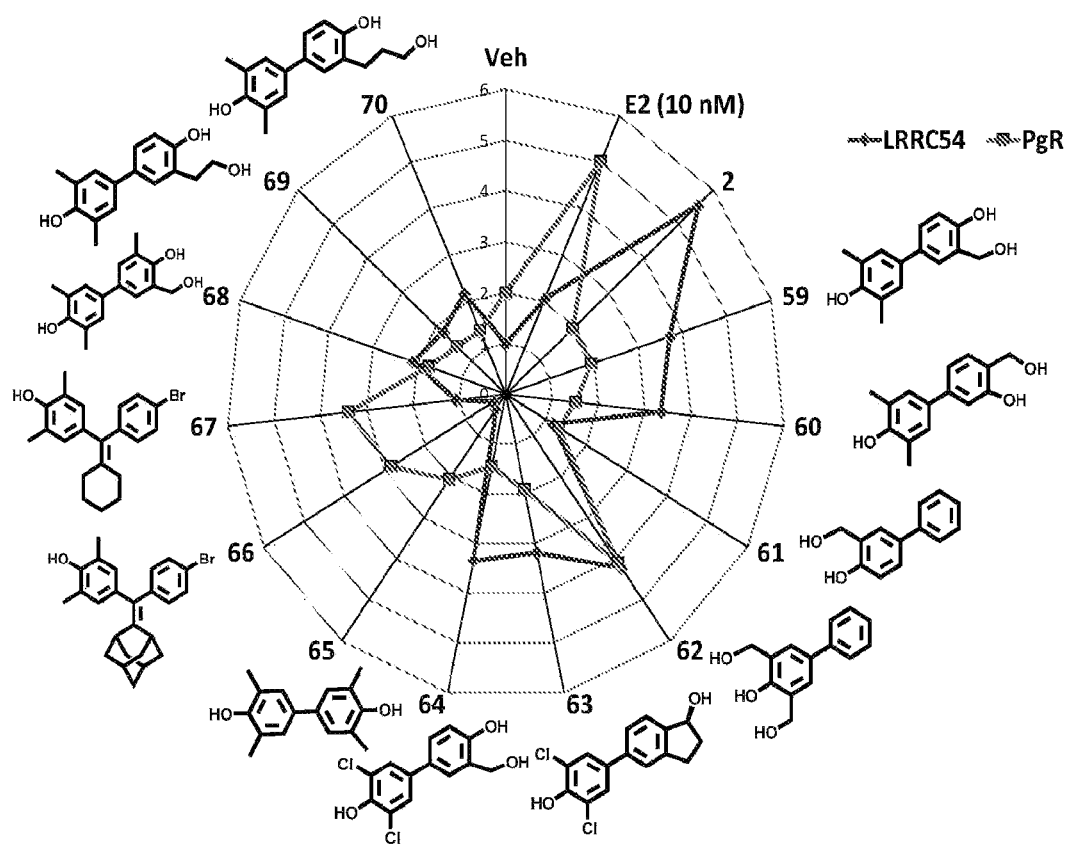
FIG. 31. Star plot of the data from FIG. 30. Phenolic benzyl alcohols which have an o,o'-dimethyl phenol (compounds 59 and 60) or an o,o'-dichloro phenol (compound 64) have selective expression of the non-genomic LRRC54 gene compared to E2, but the expression level is less than for compound 2. The dichloro analog of PaPE-1 (compound 63) stimulates the non-genomic gene LRRC54 selectively, but the activity is two-fold less than that of compound 2. 4-Hydroxy-3-hydroxymethyl-biphenyl (compound 61) stimulates LRRC54 a little better than vehicle (Veh.) and PgR not at all 4,4'-Dihydroxy-3,3',5,5'-tetramethylbiphenyl (compound 65) greatly suppresses LRRC54 gene expression, with PgR gene expression equivalent to that of vehicle (Veh.) The two cyclofenil type compounds (compounds 66-67) stimulate PgR gene selectively. An additional methyl group at the position ortho to the phenol in compound 59 (as in Compound 68) suppresses LRRC54 gene expression compared to that of the parent compound 59. An additional phenolic group above those in compounds 44 and 47 (as in compounds 69 and 70) does not improve the non-genomic LRRC54 gene response compared to those of compounds 44 and 47.
Figure 32:
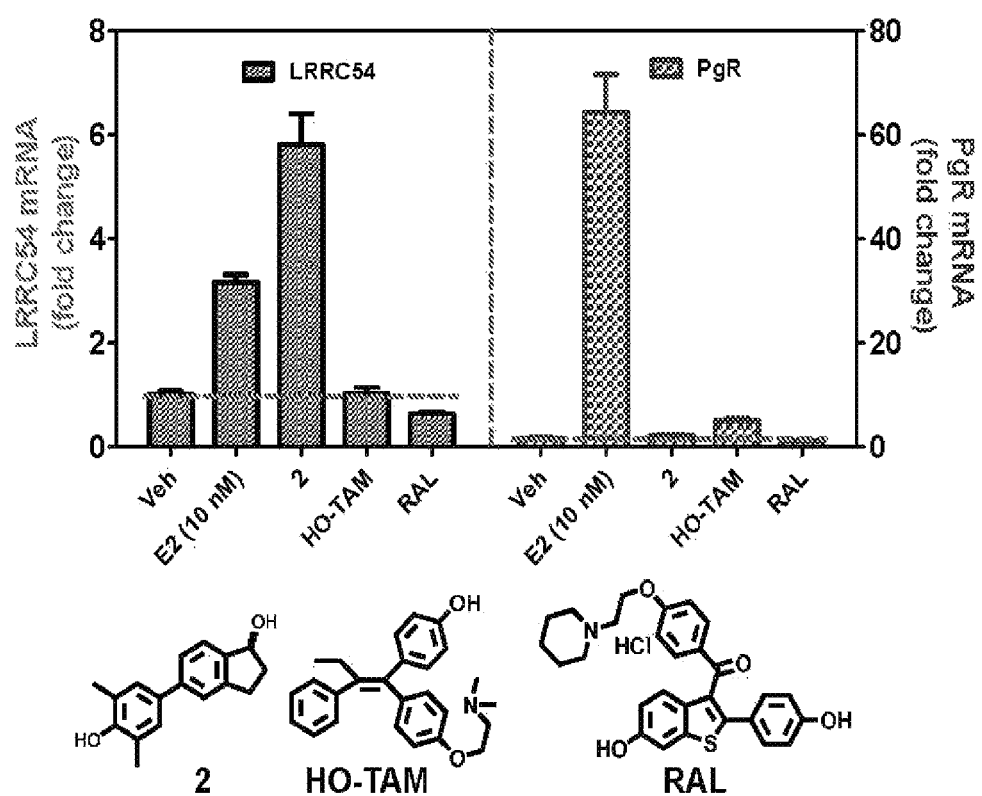
FIG. 32. Comparison of compound 2, hydroxytamoxifen (HO-TAM), and Raloxifene (RAL) compounds. Raloxifene blocks expression of both the non-genomic LRRC54 and genomic PgR genes. HO-TAM shows slight stimulation of the PgR gene but not the non-genomic LRRC54 gene.
Figure 33:
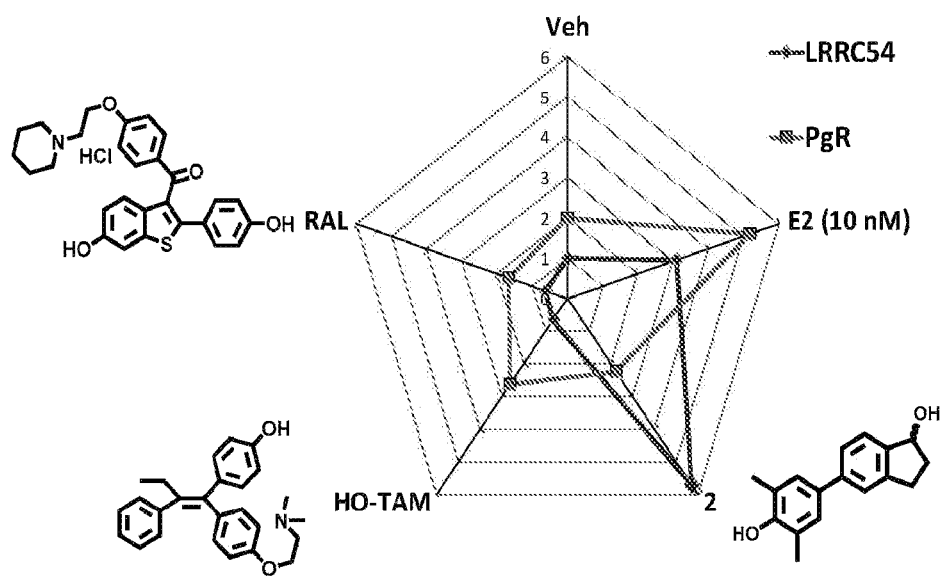
FIG. 33. Star plot of the data from FIG. 32. Neither Raloxifene (RAL) nor hydroxytamoxifen (TOT) show selective activation of the non-genomic gene LRRC54.

Examples of compounds showing clear evidence of preference for activation of the non-genomic pathway are: Compounds 2, 3, 4; 15, 16, 18; 24, 26, 29-30; 32; 41; 44-47; 56-58; 59-60; 63-64. At the appropriate concentration (picomolar), compound 40 also shows preference for the non-genomic pathway (FIG. 25).

Examples of compounds showing little or no preference for activation of the non-genomic pathway are: Compounds 5-14; 17, 19-22; 23, 25, 27-28; 31-35; 36-40, 42-43; 48-49; 50-55; 61, 62, 65-67.

The list of ERα and ERβ RBA value for selected compounds. RBA (relative binding affinity) values are a measure of binding affinity relative to that of estradiol, which has an RBA values of 100.

| Compound | ERα | ERβ |
| --- | --- | --- |
| 2 | 0.001 ± 0.001 | 0.002 ± 0.001 |
| 8 | 0.001 ± 0 | 0.006 ± 0.001 |
| 9 | 0.003 ± 0.001 | 0.002 ± 0.001 |
| 10 | 0.008 ± 0.002 | <0.001 |
| 12 | 0.001 ± 0 | 0.002 ± 0.001 |
| 15 | 0.002 ± 0.001 | 0.005 ± 0.003 |
| 16 | 0.002 ± 0.001 | 0.004 ± 0.003 |
| 17 | 0.003 ± 0.001 | 0.002 ± 0.001 |
| 19 | 0.004 ± 0.001 | <0.001 |
| 20 | <0.001 | <0.001 |
| 21 | 0.019 ± 0.004 | 0.012 ± 0.002 |
| 23 | 0.002 ± 0.001 | 0.002 ± 0.001 |
| 24 | 0.005 ± 0.001 | 0.004 ± 0 |
| 25 | 0.003 ± 0 | 0.009 ± 0 |
| 26 | <0.001 | 0.002 ± 0.001 |
| 27 | 0.003 ± 0.001 | 0.003 ± 0 |
| 28 | 0.008 ± 0.002 | 0.013 ± 0.002 |
| 30 | 0.002 ± 0.001 | 0.002 ± 0.001 |
| 32 | 0.005 ± 0.001 | 0.190 ± 0.04 |
| 35 | 0.011 ± 0.003 | 0.755 ± 0.20 |
| 40 | 0.302 ± 0.04 | 0.058 ± 0.01 |
| 41 | 0.004 ± 0.001 | 0.002 ± 0 |
| 42 | 0.004 ± 0 | 0.002 ± 0.001 |
| 43 | <0.001 | 0.001 |
| 44 | 0.001 | 0.001 |
| 45 | 0.001 | 0.002 |
| 55 | 0.002 | 0.004 |
| 56 | <0.001 | <0.001 |
| 60 | <0.001 | ~0.001 |
| 63 | 0.005 | 0.006 |

Example 38. Effect of PaPe-1 on Breast Cancer Cells

Figure 34:
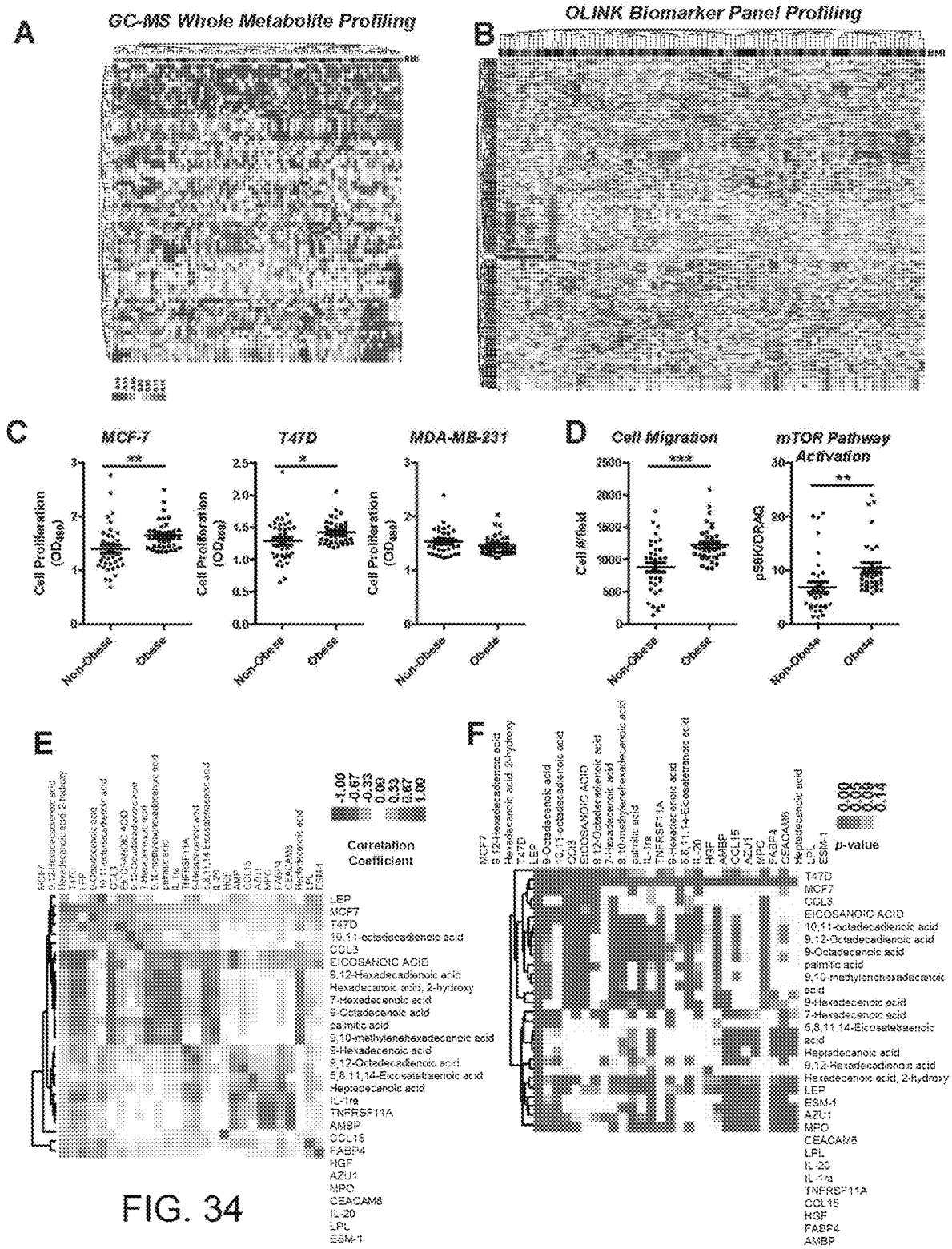
FIG. 34. Characterization of risk factors associated with tumors and aggressiveness in obese postmenopausal women. (A) Heatmap of the whole metabolite profiling of 100 serum samples from 63 obese or overweight vs. 37 non-obese postmenopausal women from Midlife Health Study that fits the criteria (BMI>25 obese or overweight, 2-3 years into menopause), as measured using GC-MS. For BMI red indicates higher values, whereas green indicates lower values. (B) OLINK Biomarker profiling of the same samples as in A. For BMI red indicates higher values, whereas green indicates lower values. (C) Cell proliferation assays were performed in both ERα-(+) and ERα-(−) breast cancer cell lines. The serum from 35 obese and 35 non-obese individuals was used to treat the cells for 7 days before analysis by the WST1 assay. Three technical replicates were used. Unpaired t-test was used to assess if serum from obese vs. non-obese individuals resulted in statistically significant difference in breast cancer cell line proliferation. *, $p<0.05$. Mean±SEM is plotted. (D) Cell migration was tested in BT474 cells treated with the serum samples of 35 obese and 35 non-obese individuals for 24 hours before measurement of cell number per field. The mTOR Pathway was found to be activated as indicated by increased pS6K activity by serum from 35 obese individuals but not by serum from 35 non-obese individuals in MCF-7 cells. All the assays were performed in triplicate in 96 well plates. Unpaired t-test was used to assess if serum from obese vs. non-obese individuals resulted in statistically significant difference in breast cancer cell line motility and mTOR pathway activation.  $p<0.01$, * $p<0.001$. Mean±SEM is plotted. (E) Correlation analysis (Pearson correlation coefficient) of biomarkers with the cell phenotype indexes. Those biomarkers that correlate with MCF-7 proliferation atp-val <0.05 are selected. Paired t-test with Bonferroni correction was used to identify the statistically significant difference. * $p<0.05$,  $p<0.01$, * $p<0.001$. F) Correlation analysis (p-val) of biomarkers from E.
Figure 35:
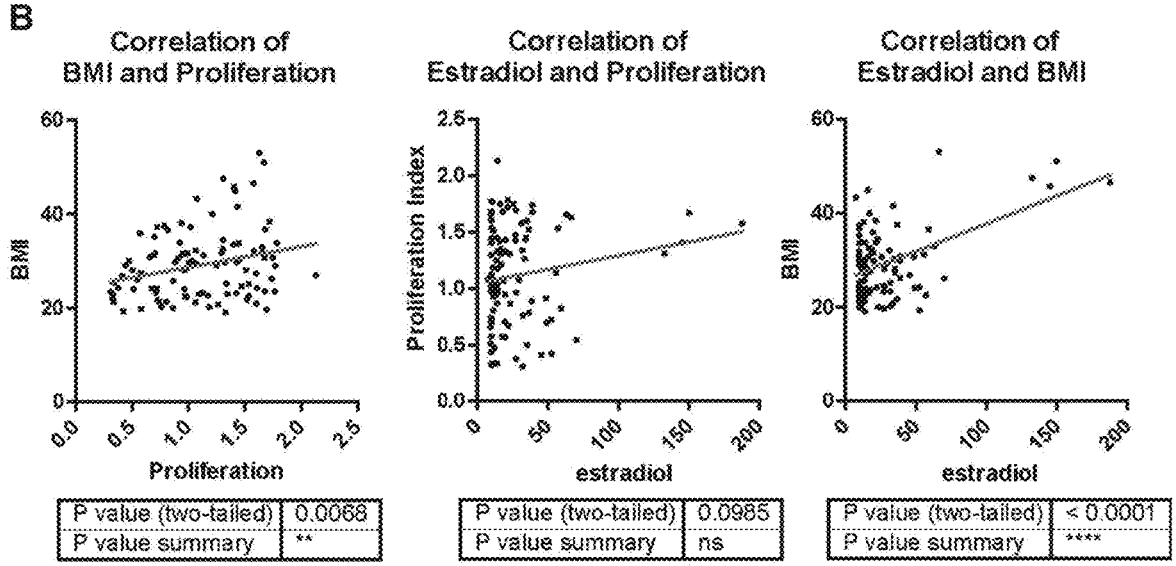
FIG. 35. Identification of factors associated with cell proliferation in obese postmenopausal women. (A) Association analysis of cell proliferation and BMI, estradiol, testosterone and progesterone. Pearson correlation coefficient (Upper panel) and p-value (Lower panel) were shown for each comparison. (B) Detailed association analysis was shown between proliferation and BMI, estradiol and proliferation, and BMI and estradiol. (C) The relative concentration of metabolites was measured and shown from serum samples grouped by proliferation index. Paired t-test with Bonferroni correction was used to identify the statistically significant difference. * p<0.05,  p<0.01, * p<0.001.
Figure 35:
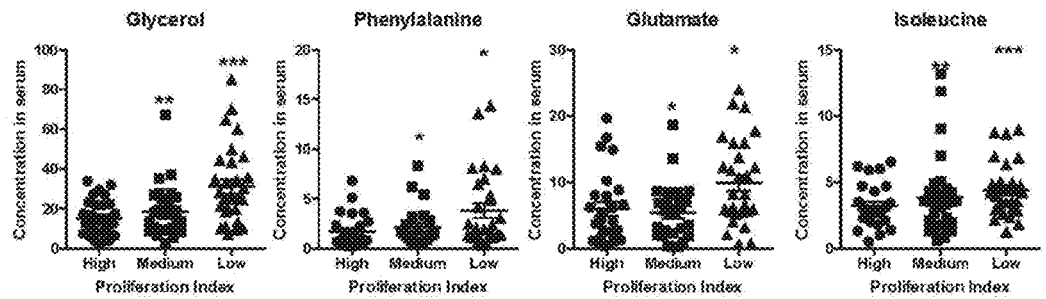

Identification of Factors from Obese Postmenopausal Women that Drive Breast Cancer Cell Proliferation and Aggressiveness To identify factors from serum that are associated with obesity, a total of 100 samples (37 non-obese, 63 obese-subjects) was used from the original study named "Midlife Health Study". Serum was collected from women who are residents of the Baltimore metropolitan region, which includes Baltimore City and several of its surrounding counties. BMI >25 was used as the cut-off to categorize an individual as overweight and obese. All the subjects were 2-3 years postmenopausal women. Whole metabolite profiling and OLINK biomarker profiling was performed for inflammation, CVD and oncology panels of these 100 samples (FIGS. 34A and B). These analysis showed that serum metabolite composition and protein composition to some extent stratified the samples based on the BMI of the subjects. Since breast cancer incidence follow-up for this study was not available, the serum from each individual was used to derive a proliferation index in ERα(+) MCF-7 and T47D cells and ERα(−) MDA-MB-231 cells (FIG. 34C). Cell proliferation was increased when ERα(+) but not ERα(−) cells were treated with serum from obese individuals. There was a statistically significant linear correlation between in vitro cell proliferation index and serum donor's BMI but not with estradiol, testosterone or progesterone levels (FIGS. 35A and B). A motility index was used for BT474 cells and mTOR pathway activation in MCF-7 cells as surrogates for measuring breast cancer aggressiveness (FIG. 34D). Since the original sample set is from cancer-free women, the levels of several well-known cancer serum biomarkers were measured to verify the ability of any biomarker identified of predicting the breast cancer outcome. For example, lower glycerol, phenylalanine, glutamate and isoleucine levels were found in the blood from breast cancer patients compared to healthy counterparts. Those serum samples associated with a higher proliferation index had a lower level of these metabolites compared with those samples associated with a lower proliferation index (FIG. 35C). Thus, the evaluation of cell proliferation, motility, and mTOR pathway activation was informative regarding breast cancer outcomes and was used to identify biomarkers that are associated with increased breast cancer aggressiveness.

Next, a correlation analysis was performed between the serum metabolite and biomarker levels and the cell proliferation index from ERα(+) cells. A heatmap was used to visualize correlation coefficients of metabolites and protein biomarkers that correlated with MCF-7 proliferation with a p-val<0.05. This analysis showed that several free fatty acids (FFAs), including oleic acid/9-octadecenoic acid (OA) and palmitic acid (hexadecanoic acid), leptin (LEP), cytokines CCL3 and IL-20, were positively correlated with MCF-7 and T47D cell proliferation (FIGS. 34E and F).

Figure 36:
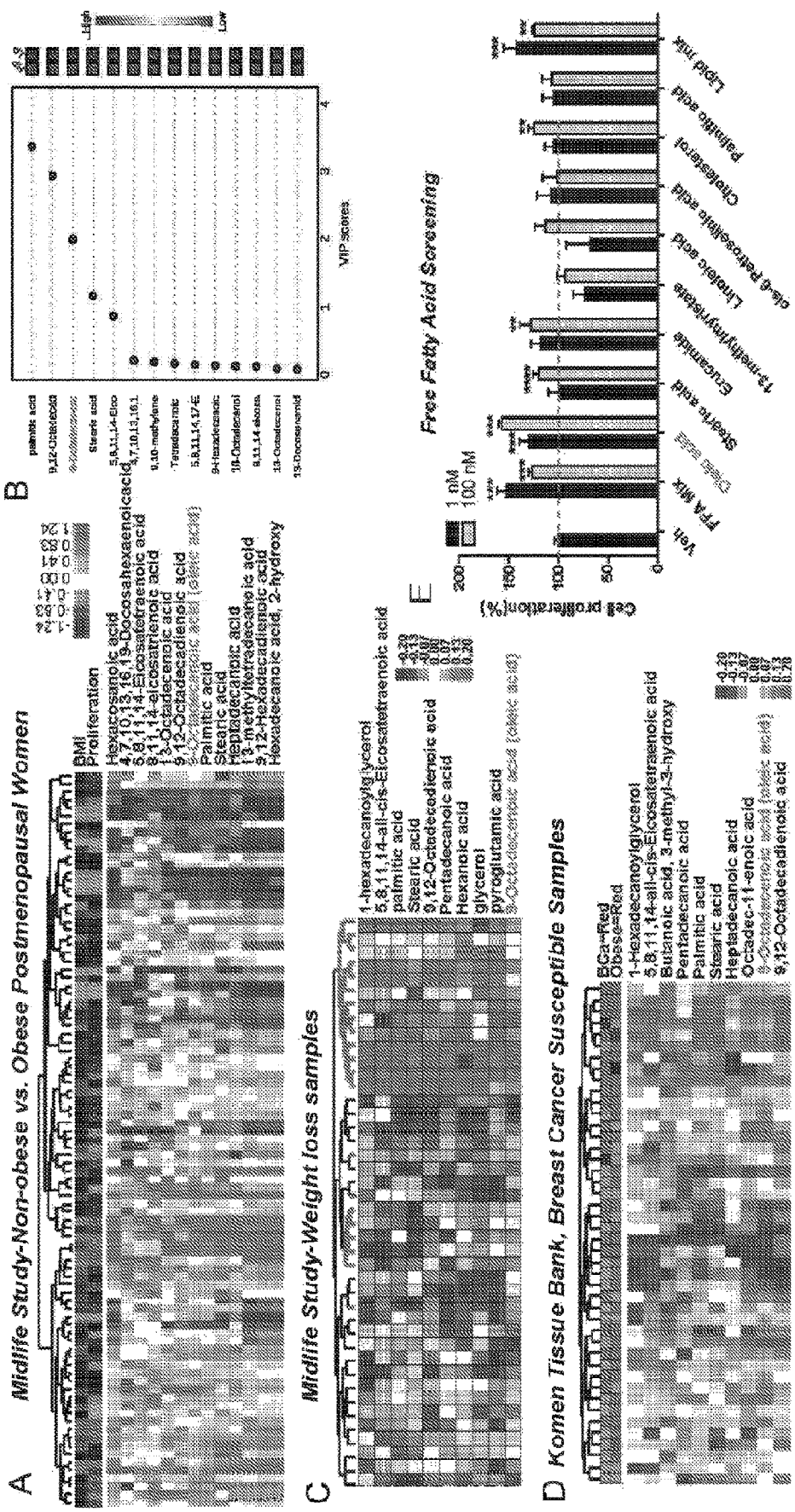
FIG. 36. Screening of FFAs for stimulating effects on cell proliferation. (A) Heatmap of the free fatty acid profiling of the same samples from FIG. 34A, measured using GC-MS. For BMI and proliferation red indicates higher values, whereas green indicates lower values. (B) Important features associated with high and low proliferation index using Partial Least Squares-Discriminant Analysis (PLS-DA) in Metaboanalyst. (C) Metabolomics analysis of Midlife health study-weight loss samples. Initial and final visit serum samples from 21 postmenopausal women from Midlife Health Study who met the following criteria was analyzed: BMI>25 at the initial visit and BMI<25 at the last visit. First visit samples (when individuals were obese or overweight) are indicated with red-thick lines. (D) Metabolomics analysis of Komen Tissue Bank Susceptible Samples. Serum samples are from 23 susceptible postmenopausal women who were cancer-free at the time of blood donation who later had breast cancer diagnosis and from 23 women who are cancer-free as has not reported breast cancer diagnosis (age, BMI, race matched controls). (E) Cell proliferation of MCF-7 cells in the presence of individual FFAs identified from FIGS. 36A and B. Cell proliferation was examined after treatment of cells with free fatty acids at two concentrations (1 and 100 nM). FFA mix contains all the single free fatty acids tested in this experiment. Lipid mix (mixture of cholesterol and fatty acids) was purchased from Sigma. Six replicates were used in each assay, and the experiment was repeated twice. An unpaired t-test was used to assess if various free fatty acid (FFA) treatments resulted in statistically significant stimulation of MCF-7 cell proliferation.  p<0.01, * p<0.001, **** p<0.0001. Mean±SEM is plotted.

Serum-Induced Proliferation of ERα(+) Breast Cancer Cells is Associated with FFAs To identify particular FFAs that might increase ERα (+) cell proliferation, the same serum samples were profiled for free fatty acids (FIGS. 36A and 2B), and verified that those samples that caused higher proliferation in breast cancer cells had higher levels of all FFAs analyzed. In addition, metabolite profiling was performed in a subset of samples from the Midlife health study, which included samples from 21 postmenopausal women who were obese at the beginning of the study that later lost weight and were non-obese by the end of the study. Initial samples (labeled with thick, red lines in the hierarchical tree) and final serum samples (labeled with black in the hierarchical tree) were profiled from these individuals and observed a reduction in FFAs levels after weight loss (FIG. 36C). Finally, A sample set obtained from Komen Tissue Bank, which included samples from postmenopausal women who donated blood when they were cancer-free and later had a diagnosis of breast cancer was used. Serum samples from age, BMI and race matched control samples were also used. This analysis showed that obese postmenopausal women who developed breast cancer had higher levels of FFAs in their serum as compared to the healthy controls (FIG. 36D). A follow-up screen was performed by testing the ability of each FFA to affect the proliferation of the ER (+) MCF-7 cell line. (FIG. 36E). It was found that unsaturated fatty acids and particularly OA was very efficient in increasing cell proliferation in MCF-7 cells. By contrast, the other FFAs were not as effective as OA in inducing cell proliferation (FIG. 36E).

Figure 37:
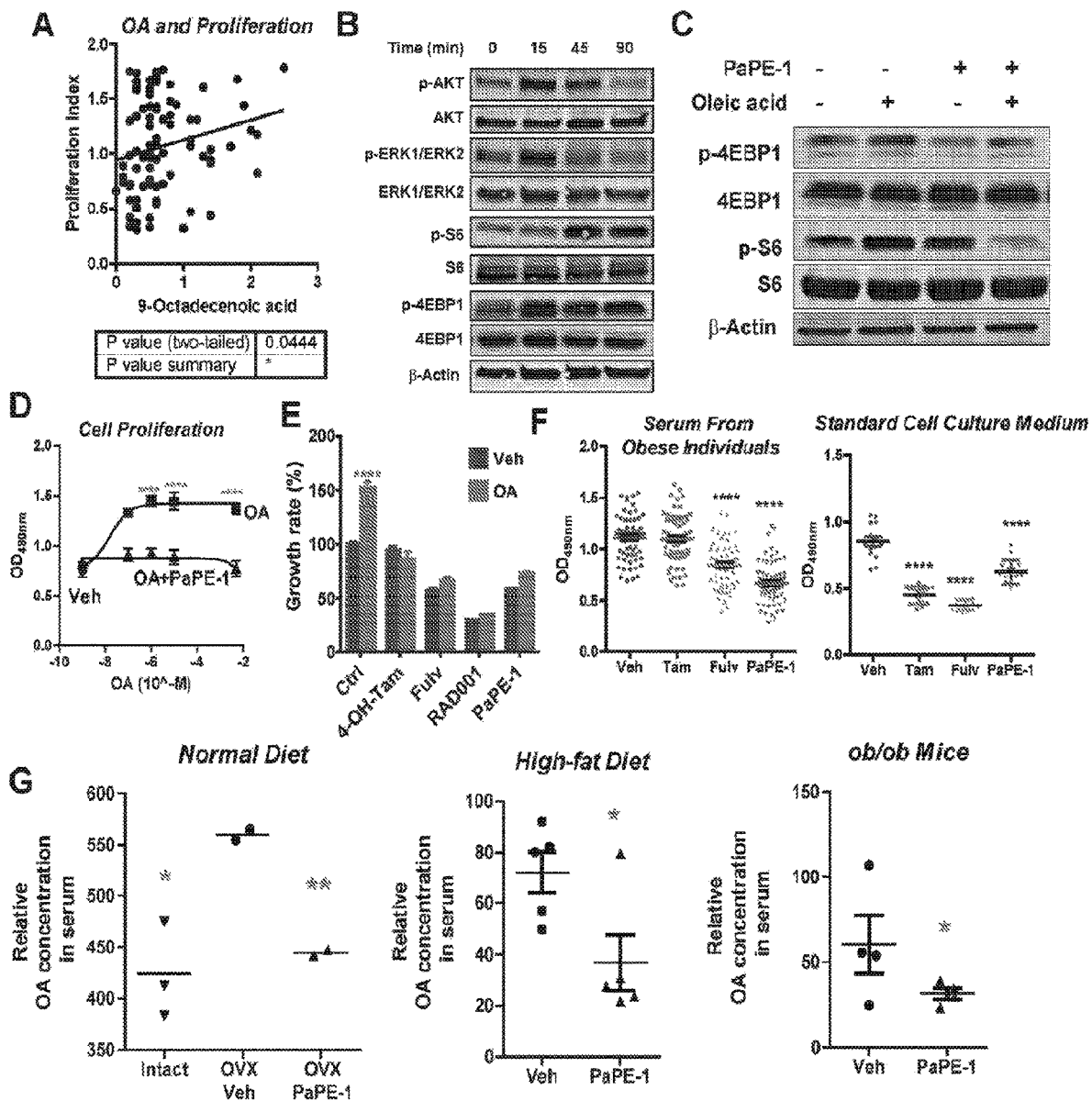
FIG. 37. PaPE-1 suppresses proliferation and pathway activation in MCF-7 cells and normalizes the oleic acid (OA) level increased by ovariectomy in mice. (A) Correlation of OA levels in serum from Midlife health study with MCF-7 cell proliferation. (B) mTOR pathway activation induced by OA in MCF-7 cells. Cells were treated with 100 nM oleic acid for 0, 15, 45, and 90 mins. Phosphorylation and total protein levels of AKT, ERK1/ERK2, S6, and 4EBP1 were examined by western blot analysis. The experiment was repeated two times and representative blots are shown. (C) Inhibition of OA-induced mTOR pathway activation by PaPE-1. Oleic acid stimulates the mTORC1 pathway, and PaPE-1 suppressed the activation in MCF-7 cells. MCF-7 cells were treated with control vehicle, and 100 nM Oleic acid, with or without PaPE-1 for 45 mins. Phosphorylated and total proteins levels of 4EBP1, P70S6K, and S6 were examined by western blot analysis. The experiment was repeated two times and representative blots are shown. (D) OA effect on MCF-7 cell proliferation with and without PaPE-1. Dose-response of OA on cell proliferation was tested alone or in combination with and without PaPE-1 (1 µM) for 6 days before WST1 assay. The experiment has six technical replicates and was repeated twice. A two-way analysis of variance (ANOVA) model was fitted to assess the contribution of OA dose and inhibitor (Ctrl, and PaPE-1) treatment on MCF-7 cell proliferation. When the main effects were statistically significant at α=0.05, pairwise t-tests with a Bonferroni correction were employed to identify if treatment were statistically different from each other. ** p<0.0001. Mean±SEM is plotted. (E) Inhibition of OA-induced MCF-7 cell proliferation by ERα and mTOR targeting agents. Cell proliferation was stimulated by 100 nM oleic acid and was suppressed by adding 1 µM 4-OH-Tamoxifen (4-OH-Tam), 1 µM Fulvestrant (Fulv), mTOR inhibitor 1 µM RAD001, and 1 µM PaPE-1. In the above cell proliferation experiments, MCF-7 cells were treated in whole growth medium adding the designated compounds. The treatment went for 6 days and OD at 450 was measured by WST1 assay. The data is represented from average of 6 replicates with standard error of mean. The experiment is repeated twice. A two-way analysis of variance (ANOVA) model was fitted to assess the contribution of ligand (Veh or OA) and inhibitor (Ctrl, 4-OH-Tam, Fulv, RAD001 and PaPE-1) treatment on MCF-7 cell proliferation. When the main effects were statistically significant at α=0.05, pairwise t-tests with a Bonferroni correction were employed to identify if treatment were statistically different from each other.  p<0.0001. Mean±SEM is plotted. (F) Inhibition of serum-induced MCF-7 cell proliferation by 4-OH-tam, Fulv and PaPE-1. The MCF-7 cells were treated with Veh, 1 µM 4-OH-tam, 1 µM Fulv, and 1 µM PaPE-1 for six days before WST-1 assay in serum from 63 obese individuals (Left) and in standard cell culture (Right). There are 3 technical replicates for each serum sample and 14 replicates for each treatment in standard cell culture media. A one-way analysis of variance (ANOVA) model was fitted to assess the contribution of ligands on serum- or standard cell culture medium-induced MCF-7 cell proliferation. When the main effects were statistically significant at α=0.05, pairwise t-tests with a Bonferroni correction were employed to identify if treatment were statistically different from each other. ** p<0.0001. Mean±SEM is plotted. (G) Restoration of OA levels with PaPE-1 after ovariectomy mice. Three different mice models were tested: wildtype C57BL mice under normal diet (N=2 mice per treatment group, experiment was repeated twice), wild-type C57BL mice under high-fat diet (N=5 animals per treatment group) and ob/ob mice (N=4 animals per treatment group) under normal diet. Mice were ovariectomized at six week old and Alzet slow release minipumps with Veh or PaPE-1 were implanted subcutaneously for six weeks. The OA concentration was measured in the serum using GC-MS. An unpaired t-test was used to assess if PaPE-iwas able to decrease the relative OA concentration in the serum compared to Veh treated animals. * p<0.05, ** p<0.01. Mean±SEM is plotted.

OA Increases Breast Cancer Cell Proliferation by Activating ERα and mTOR Signaling In order to verify OA as active component of FFA mixture in the serum abe to induce cell proliferation, an in vitro proliferation assay was performed and the assay validated that the high level of OA is significantly associated with higher proliferation index in breast cancer cells (FIG. 37A). Since it was found that sera from obese individuals also increases mTOR pathway activation (FIG. 34C), a time course experiment was performed using OA, and it was found that OA treatment caused a robust activation of mTOR pathway downstream targets Akt, S6 and 4EBP1 (FIG. 37B). ERK1/ERK2 was also activated but this activation was earlier and transient (FIG. 37B). Next, PaPE-1 was used and showed that PaPE-1 modulated ERα-mTOR signaling crosstalk, to see if OA worked through ERα-mTOR signaling. Treatment of the cells with PaPE-1 decreased OA-induced mTOR pathway activation (FIG. 37C) and OA-induced cell proliferation (FIG. 37D). To further confirm that OA-induced cell proliferation was through ERα and mTOR pathways, OA treatments were performed in the presence of 4-OH-Tamoxifen (R—OH-Tam), Fulvestrant (Fulv), an ERα antagonist, and RAD001, an mTOR pathway inhibitor. All of the tested agents blocked OA-induced cell proliferation (FIG. 37E). To ensure that serum from obese individuals also induced MCF-7 cells proliferation through ERα and mTOR pathways, cell proliferation assays were performed in the presence of 4-OH-Tam, Fulv and PaPE-1. Notably, PaPE-1 was the most effective agent in inhibiting serum-induced proliferation of MCF-7 cells (FIG. 37F left panel). However, in normal cell culture conditions, 4-OH-Tam and Fulv were better agents (FIG. 37F right panel), suggesting that treatment with the serum from obese individuals makes MCF-7 cells more susceptible to growth inhibitory effects of PaPE-1. Finally, to ensure that the high level of OA was independent from the diet but associated only with obesity status, both wild-type mice, that were either on normal or high-fat diet, and leptin-deficient (ob/ob) mice on normal diet were ovariectomized, and subcutaneously implanted with Alzet minipumps that delivered Veh or PaPE-1 over 6 weeks. PaPE-1 treatment reduced ovariectomy-induced weight gain without changing food intake. Ovariectomy-associated decrease in estrogen level causes an increase in OA level in serum in the ovariectomized animals compared to the intact animals (FIG. 37G, left panel). In all three models, treatment with PaPE-1 decreased serum levels of OA, suggesting that in addition to direct effects through ERα-mTOR signaling in breast cancers cells, PaPE-1 might prevent obesity-associated breast cancer by reducing serum level of OA systemically (FIG. 37G).

OA Induces Gene Expression Changes in Breast Cancer Cells that are Blocked by PaPE-1

Figure 38:
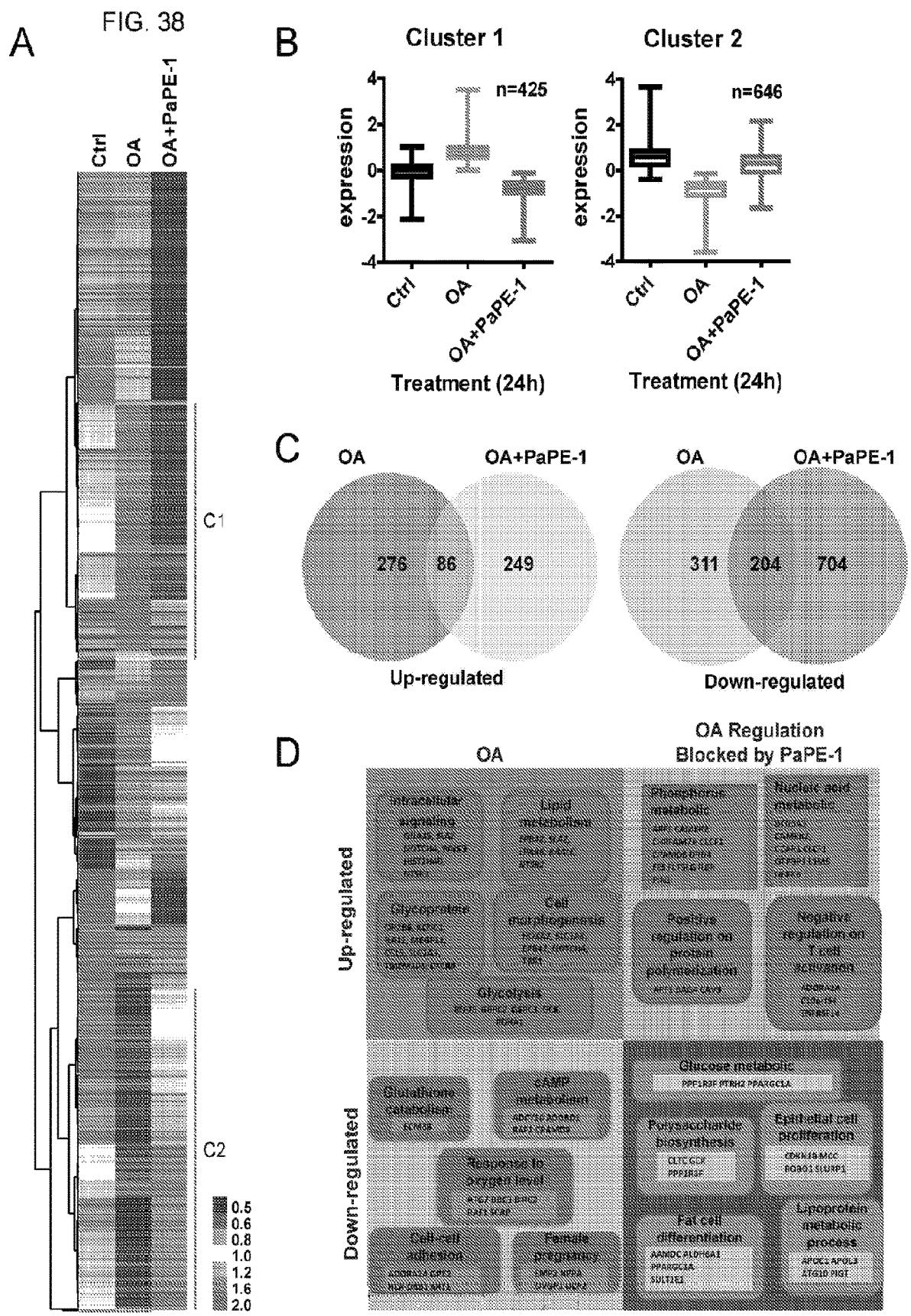
FIG. 38. Identification of genes induced by OA and PaPE-1's effect on the gene regulation. (A) RNA-Seq analysis of gene expression changes induced by OA and OA+PaPE1. Heat map of the genes with significant changed expression. MCF-7 cells were treated with Veh or 100 nM OA with and without 1 µM PaPE-1 for 24 h. RNA was isolated and RNA-Seq was performed using 2 samples from each treatment group. Differentially regulated genes were determined with p<0.05 and expression fold change >2. (B) Clusters from A. regulated by OA and reversed by PaPE-1. The average gene expression level of the cluster1 (C1) and 2 (C2) identified as PaPE-1 regulated high-fat genes. In C1, there are 425 genes whose expression were found stimulated in OA but not in the OA+PaPE-1 treatment. In C2, there are 646 genes whose expression were found suppressed in the OA but restored by OA+PaPE-1 treatment. (C) Venn diagram analysis. Venn diagram of the up- and down-regulated genes by OA alone or in combination with PaPE-1. (D) Examples of OA-regulated genes. Some of the top functions of the involved genes are presented.

To identify gene expression changes associated with OA-induced ERα and mTOR pathway modulation, MCF-7 cells were treated with vehicle (Ctrl), 100 nM OA or 100 nM OA in the presence of 1 μM PaPE-1 (FIG. 38A). OA upregulated about 350 genes, and activation of 80% of these upregulated genes was blocked by PaPE-1. On the other hand, about 500 genes were downregulated by OA, and PaPE-1 was able to restore expression of about 60% of these genes (FIGS. 38B and C). GO term analysis showed that OA upregulated those genes that were involved in cell proliferation, energy reserve metabolic process, epithelial cell migration and angiogenesis. On the other hand, OA treatment downregulated those genes that were involved in glucose and fatty acid metabolism and inhibitors of epithelial cell proliferation. (FIG. 38 4D)

FFA Treatment Induces Recruitment of ERα to Chromatin

Figure 39:
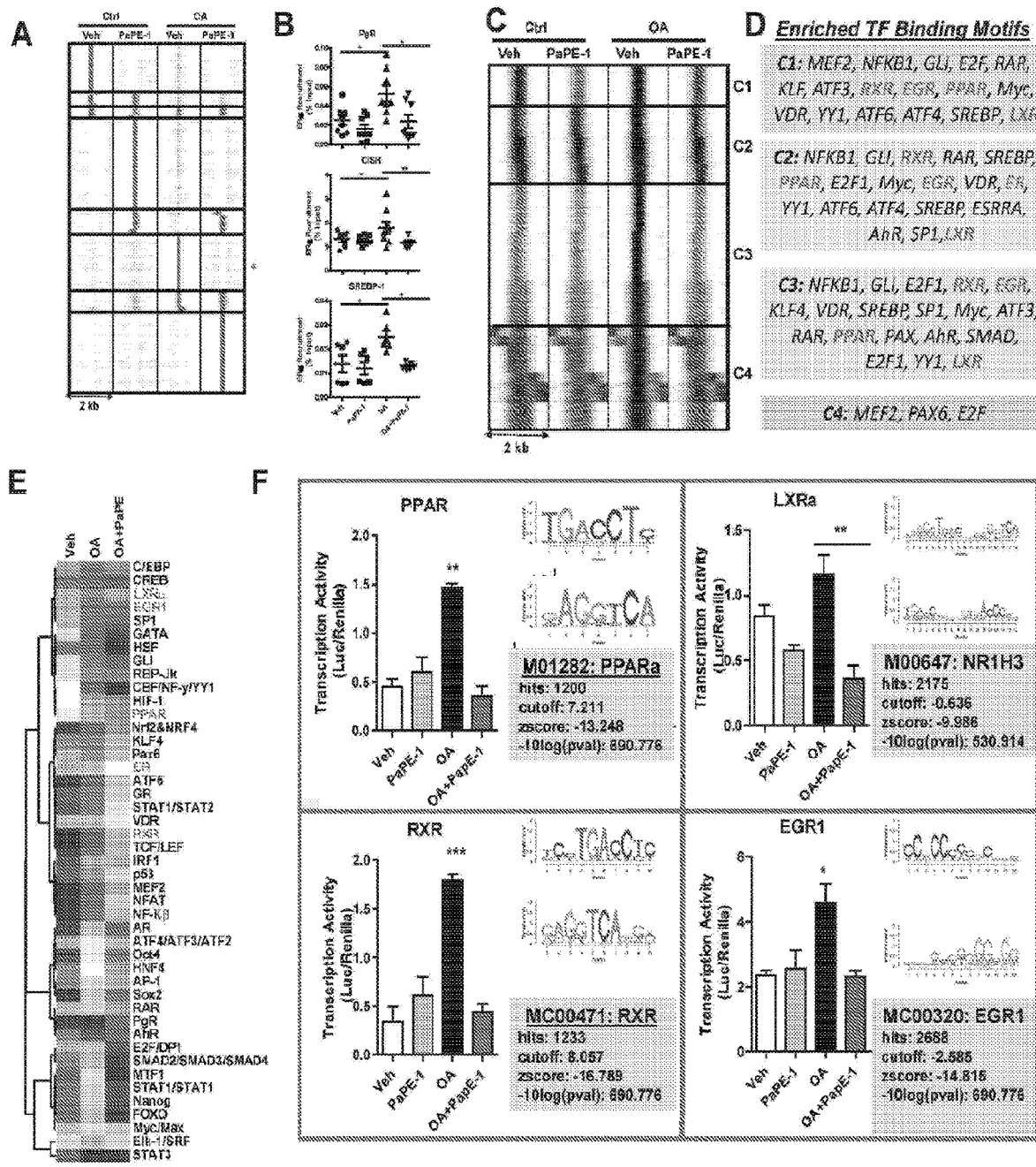
FIG. 39. ERα chromatin binding sites induced by OA and the effect of PaPE-1 in reversing these changes in the ERα cistrome. (A) Recruitment of ERα to chromatin in the presence of PaPE-1, OA and OA+PaPE-1. MCF-7 cells were treated with Veh and 100 nM OA with or without 1 µM PaPE-1 for 45 minutes. ERα-DNA complexes were pulled down using ERα antibodies. Three biological replicates were pooled and sequenced. Clustering of ERα binding sites in treatments of Veh (0.1% EtOH), PaPE-1 (1 µM), OA (100 nM), and OA (100 nM)+PaPE-1 (1 t.M) was done using seqMINER software. (B) Validation of effect of OA and PaPE-1 on the ERα binding at regulatory region of PgR, CISH and SREBP1C using ChIP-qPCR. MCF-7 cells were treated with Veh and 100 nM OA with or without 1 µM PaPE-1 for 45 minutes. ERα-DNA complexes were pulled down using ERα antibodies. Recruitment of ERα to PgR (chr11:100,904,522-100,905,458), CISH (chr3:50,642,336-50,643,191) and SREBP1 (chr17:17,743,329-17,743,912) sites were quantified by Q-PCR. The experiment was repeated 3 times with at least duplicates each time. Mean±SEM is plotted. A one-way analysis of variance (ANOVA) model was fitted to assess the contribution of ligand (Veh or OA) and inhibitor (Ctrl, PaPE-1) treatment on MCF-7 cell proliferation. When the main effects were statistically significant at $\alpha=0.05$, pairwise t-tests with a Bonferroni correction were employed to identify if treatment were statistically different from each other. * $p<0.05$, ** $p<0.01$. Mean±SEM is plotted. (C) Binding sites whose ERα occupation increased upon OA treatment (cluster marked by * in B). The ERα binding sites were separated into four clusters of characteristic patterns: C1, C2, C3 and C4. (D) Transcription Factor (TF) binding site enrichment was identified using Seqpos tool from Cistrome/Galaxy for clusters of C1, C2, C3 and C4. (E) Transcriptional activities of various TFs. 45 pathway CignalFinder Assay was used to transfect MCF-7 cells with indicated luciferase construct for 24 h. Cells were treated with Veh and 100 nM OA with or without 1 µM PaPE-1 for 24 hours before measurement by luciferase assay. The experiment was replicated two times with technical duplicates. Heatmap of transcriptional activity from a representative experiment is plotted using Treeview Java. (F) The example of transcriptional activity of selected factors from FIGS. 39D and E. The TF activity, TF motif and statistic are shown in detail for PPAR, LXRα, RXR and EGR1. Cignal PPAR, LXRa, RXR and EGR1 Reporter Assays were used to transfect MCF-7 cells in duplicate with indicated luciferase construct for 24 h. The experiment was repeated three times. Cells were treated with Veh, 1 µM PaPE-1, and 100n M OA with or without PaPE-1 for 24 hours before measurement by luciferase assay. An unpaired t-test was used to assess the impact of treatment (OA) and inhibitor (PaPE-1) on transcription factor activity in MCF-7 cells. * $p<0.05$,  $p<0.01$, * $p<0.001$. Mean±SEM is plotted.

To test if any of the gene expression changes induced by OA treatment occurred through direct ERα recruitment to chromatin, a ChIP-Seq experiment was performed which showed that ERα was recruited to novel chromatin sites upon OA treatment and most of this recruitment was blocked by PaPE-1 treatment (FIG. 39A). the pattern of ERα recruitment to various sites including a classic ERα binding site of PgR was verified (FIG. 39B). To understand the nature of ERα recruitment to chromatin in the presence of OA, binding sites that were occupied by ERα upon OA treatment were studied (FIGS. 39A and C). There were four main clusters that were named C1, C2, C3 and C4 (FIG. 39C). The majority of these binding events were associated with genes whose expression was increased upon OA treatment. Then transcription factor binding motif enrichment analysis was performed using Seqpos tool from Cistrome/Galaxy. Interestingly, none of the clusters, except C2, had any enrichment of EREs, which suggested a potential tethering mode of recruitment for ERα to these sites (FIG. 39D). Next, the transcriptional activity of some of these factors was analyzed using a luciferase-based system called Cignal finder assay (FIG. 39E). Exposure to OA increased transcriptional activities of PPAR, LXR and RXR (FIGS. 39E and F), suggesting that ERα might be recruiting and partnering with these nuclear receptors to regulate gene expression, resulting in changes that are essential for metabolic processes and survival of breast cancer cells.

OA Treatment Causes Metabolic Reprogramming in Breast Cancer Cells

Figure 40:
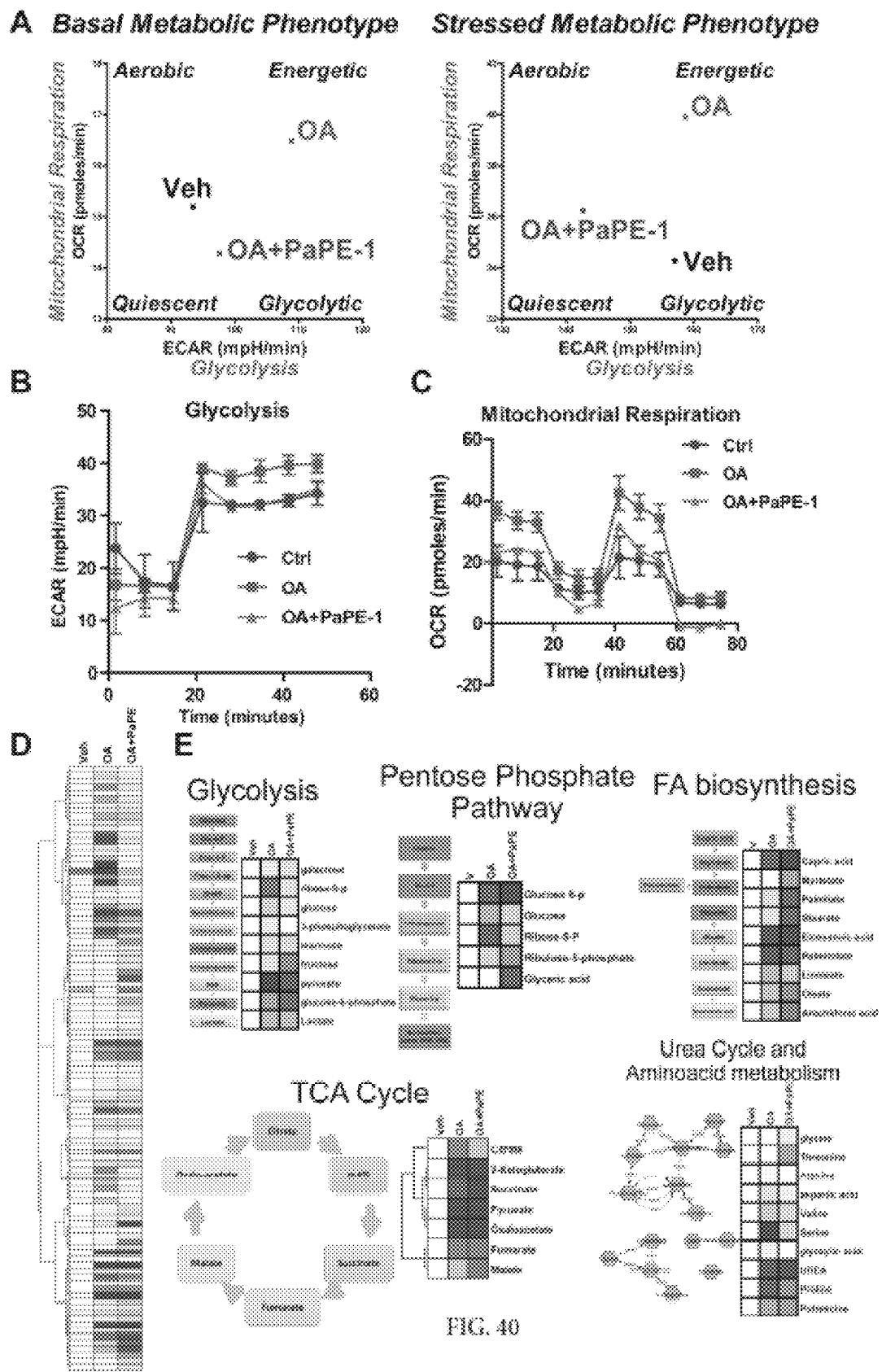
FIG. 40. PaPE-1 normalizes the metabolic pathways affected by OA. (A) Cell metabolic phenotype assay using the Seahorse energy phenotype kit. Cells treated with Veh, OA, and OA+PaPE-1 for 24 hours were tested for the energy phenotype at basal level (Left) and under metabolic stress upon inhibition of glycolysis or mitochondrial activity (Right). Each experiment was replicated twice with three technical replicates. Results from a representative experiment are shown. (B) Glycolysis was stimulated in OA-treated cells but normalized by adding PaPE-1. Cells of the same treatment as in FIG. 40C were measured using the Glycolysis stress assay, and ECAR levels were shown at different time points. Each experiment was replicated twice with three technical replicates. Results from a representative experiment are shown. (C) Mitochondrial energy production was measured separately using the Mitostress kit. Cells were treated in the same way as described above. Each experiment was replicated twice with three technical replicates. Results from a representative experiment are shown. (D) Metabolomics analysis of MCF-7 cells. MCF-7 cells were treated in triplicate using Veh, 100 nM OA with/without 1 µM PaPE-1 for 24 hours before harvest in cold methanol. Each replicate were pooled and submitted for whole metabolite analysis. The experiment was repeated twice. Representative results of metabolites from one of the experiments were clustered using Cluster3 and visualized using Treeview Java. (E) Specific metabolic pathways identified by Metscape plugin of Cytoscape. For glycolysis, pentose phosphate pathway, fatty acid biosynthesis, TCA cycle, urea cycle and amino acid metabolism, the levels of affected substrates and their position in the pathway are shown.

The gene expression, ERα ChIP-Seq and transcription factor activity assays pointed out a potential change in metabolic pathways in MCF-7 cells upon OA exposure. Therefore cell metabolic phenotyping assays were performed, which revealed that in the presence of OA, the cells adopted an energetic phenotype and coped with the metabolic stress better by increasing their aerobic and glycolytic metabolic potential (FIG. 40A). The cells were more glycolytic (FIG. 40B), and their mitochondrial metabolism was increased (FIG. 40C), and OA-induced glycolytic and aerobic respiration was reversed by PaPE-1 treatment. Next, parallel metabolomics experiments were performed in MCF-7 cells that were consistent with findings from cell phenotype experiments (FIG. 40D), had increased metabolites for the pentose pathway (FIG. 40E) and certain amino-acids including proline (FIG. 40E). OA downregulated many of the TCA cycle metabolites except malate and fumarate, suggesting an increase in malate shunt from the cytosol, which is consistent with the increase in certain amino acid levels as well as increased mitochondrial activity (FIG. 40E). Finally, fatty acid biosynthetic pathways were overall downregulated up until linoleate synthesis, suggesting a negative feed back loop due to high levels of extracellular OA (FIG. 40E). Overall, these analyses suggest that OA treatment causes significant metabolic reprogramming of breast cancer cells which can be reversed by PaPE-1 treatment.

Example 39. Effect of PaPE-1 on Severity of Stroke Injury and Outcome in Mice

Figure 41:
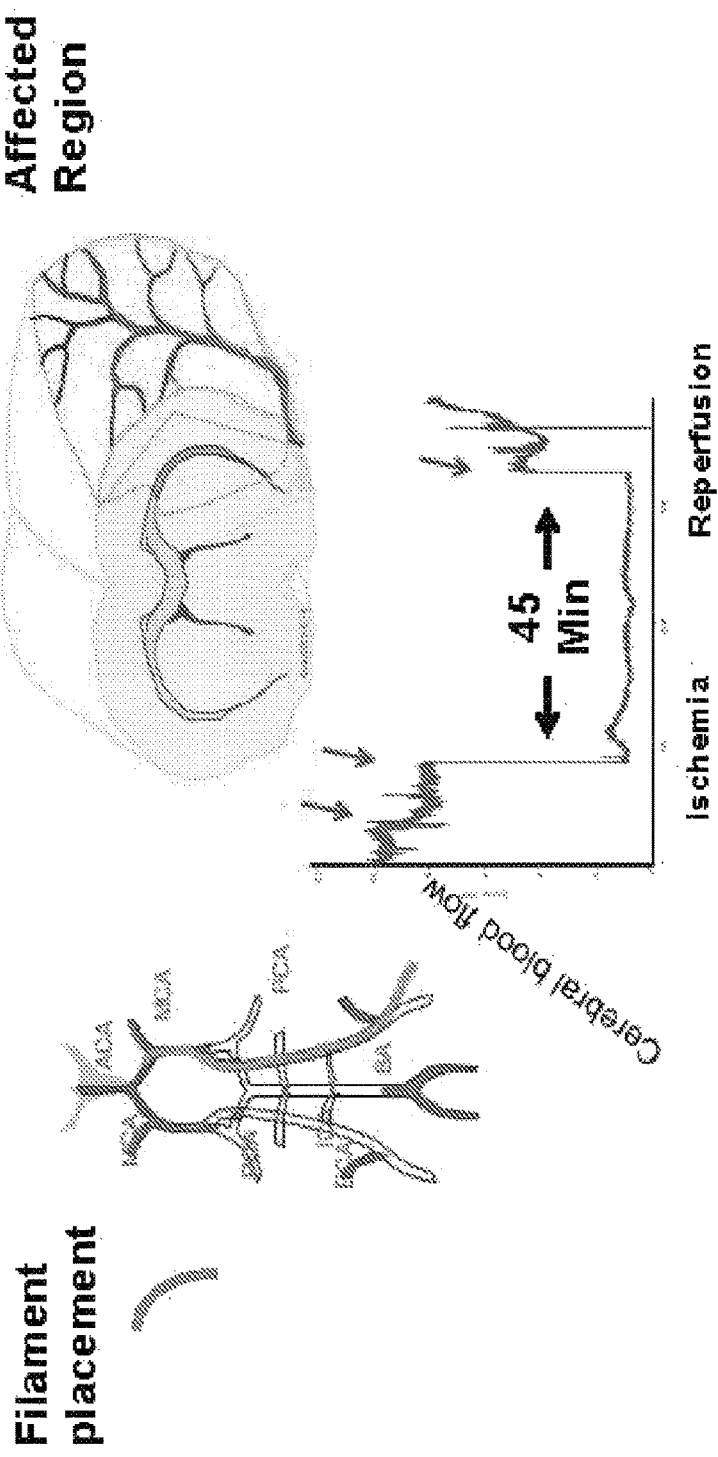
FIG. 41. Stroke Model in Mice

Female 8 week-old C57BL/6 mice were ovariectomized. Then, following a 2 week washout period subcutaneous pellet implants were implanted containing vehicle, estradiol, or PaPE-1 (randomized, n=9-10/group). One week later the mice underwent cerebral ischemia-reperfusion injury invoked by middle cerebral artery occlusion for 30 min followed by a 90 min reperfusion period. One cohort received rotorod training prior to 45-min transient middle cerebral artery occlusion (tMCAo), with MRI and rotorod assessed through 2 weeks post-tMCAo. Splenic leukocyte subpopulations and uterine weights were quantified. Another cohort was subjected to 45-min tMCAo to quantify leukocytes subpopulations in the brain, spleen, and blood 3d post-stroke. MRI were performed 3 and 7 days post-stroke, and rotorod testing was performed throughout a 13 day post-stroke period. (FIG. 41).

Mice experienced a 53% decline in rotorod performance from baseline at 2d post-tMCAo. PaPE-1 improved functional recovery to 85% (p=0.005) and 82% (p=0.001) of baseline and at 6d and 13d post-tMCAo, respectively, while estradiol treatment improved function only at d13 (p=0.005) post-stroke. Compared with vehicle, both PaPE-1 and estradiol significantly reduced infarct volumes at 3d and 7d post-tMCAo. Further, PaPE-1 and estradiol treatment also reduced the numbers of leukocytes infiltrated in the brain 3 days post-stroke by 93% (p=0.002) and 63% (p=0.019), respectively. Compared with vehicle, however, estradiol caused an increase in uterine wet weight whereas PaPE-1 had no effect.

Figure 42:
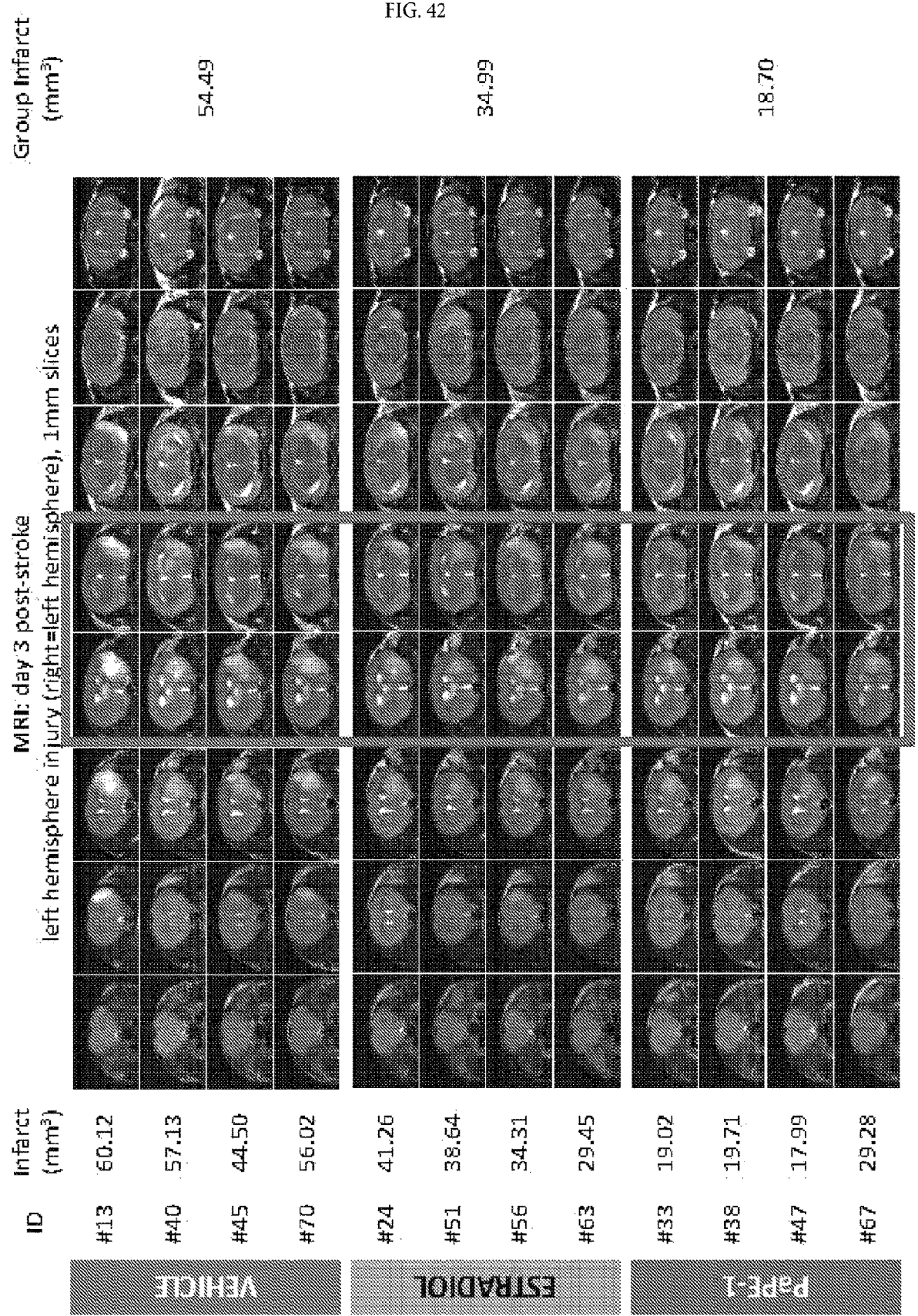
FIG. 42. Severity of CNS injury on MRI at 3 and 7 days was decreased as compared to control.
Figure 43:
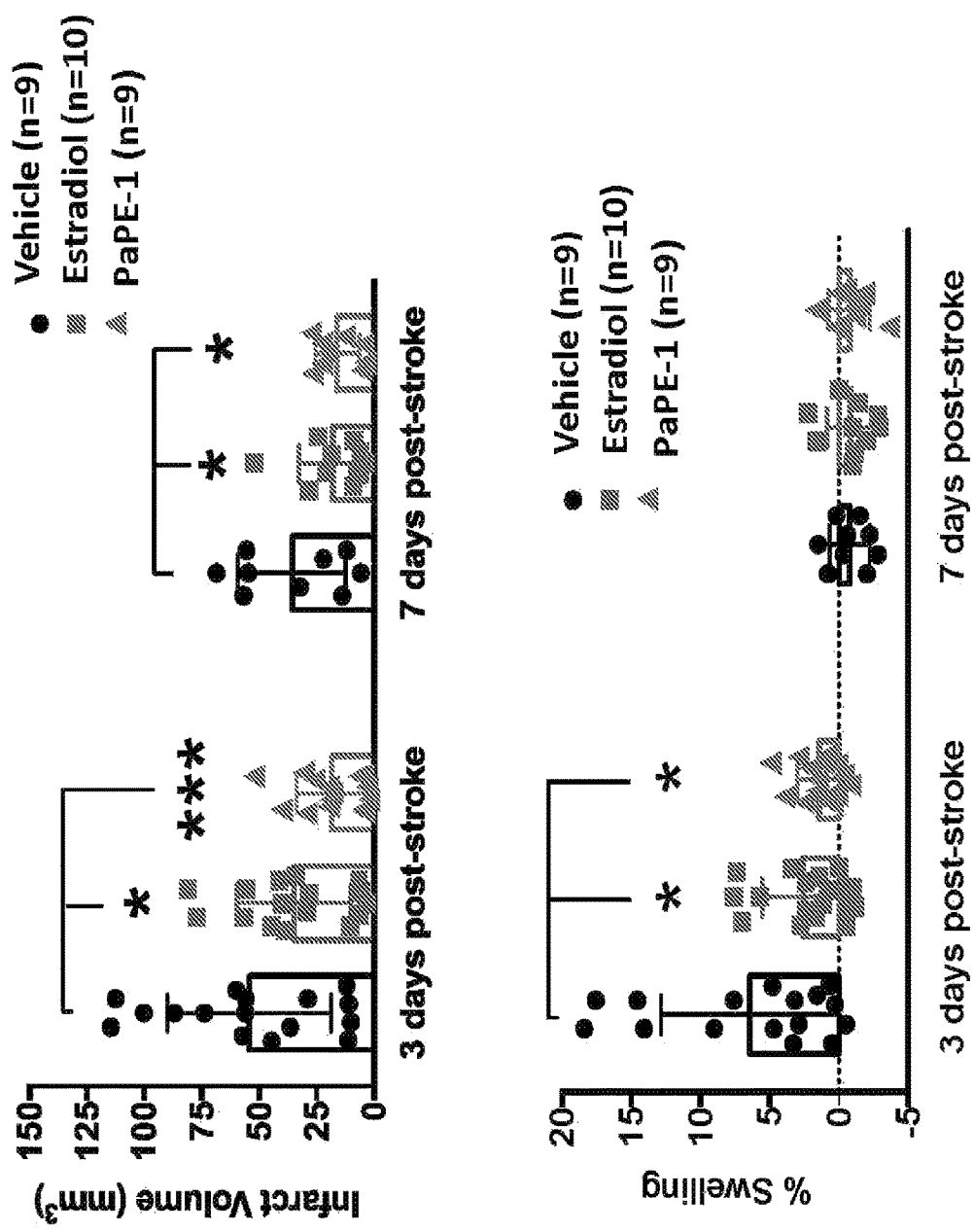
FIG. 43. Severity of CNS injury on MRI at 3 and 7 days was decreased by estradiol and particularly by PaPE-1, as compared to control.
Figure 44:
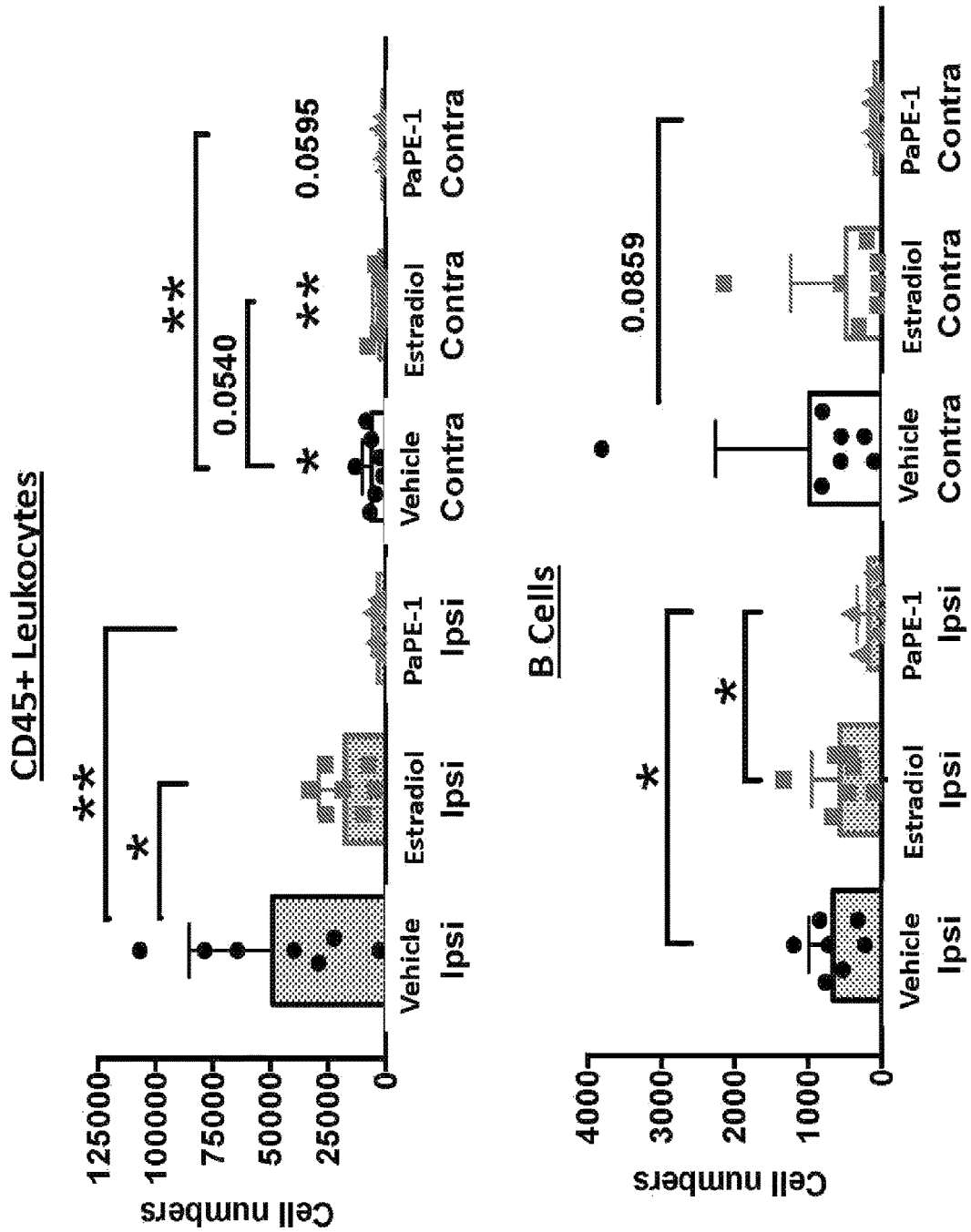
FIG. 44. Attenuation in CNS injury by estradiol and particularly by PaPE-1 is associated with decrease in leukocyte recruitment to the CNS ipsilateral to the injury.
Figure 45:
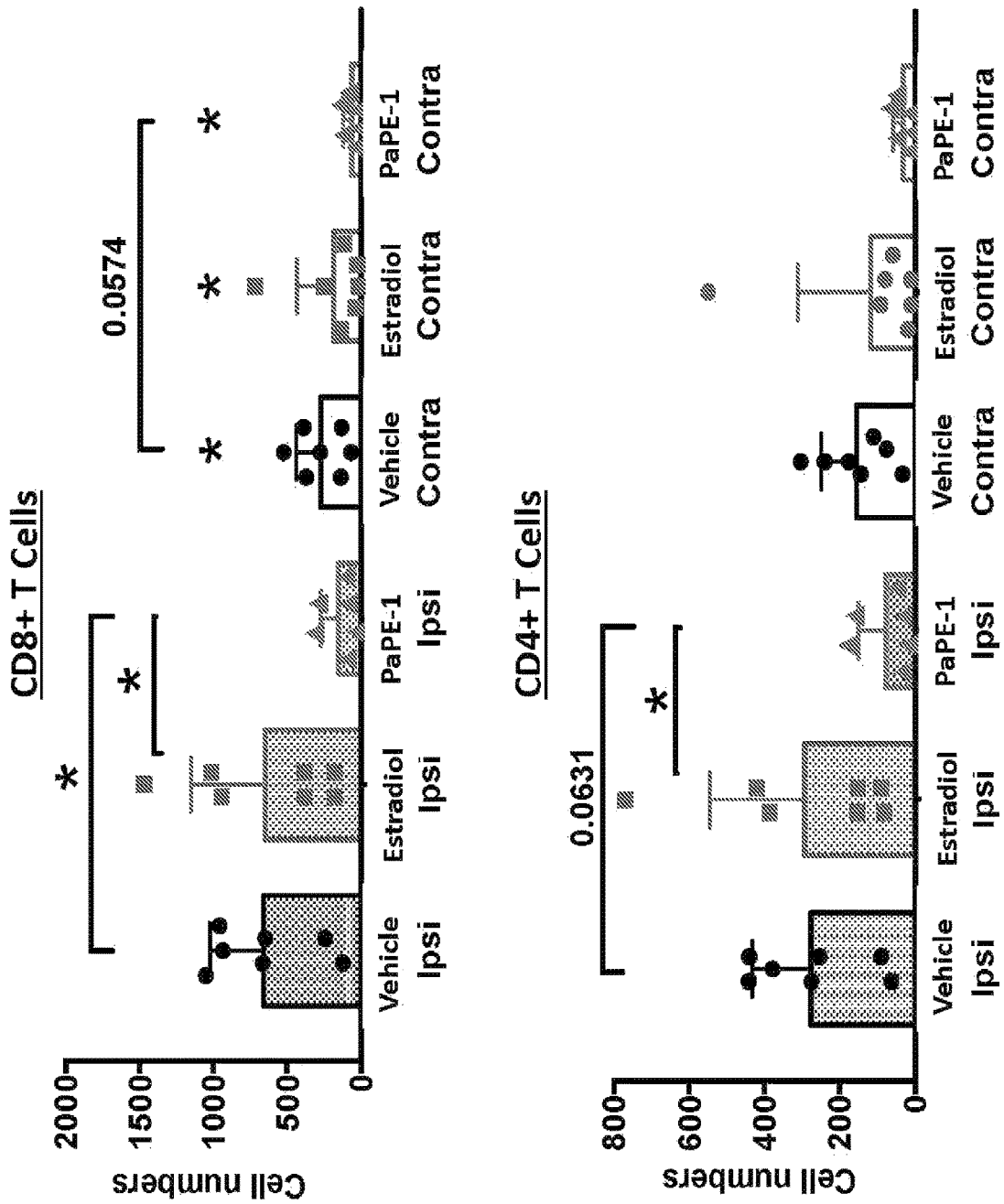
FIG. 45. Attenuation in CNS injury by estradiol and particularly by PaPE-1 is associated with decrease in leukocyte recruitment to the CNS ipsilateral to the injury.
Figure 46:
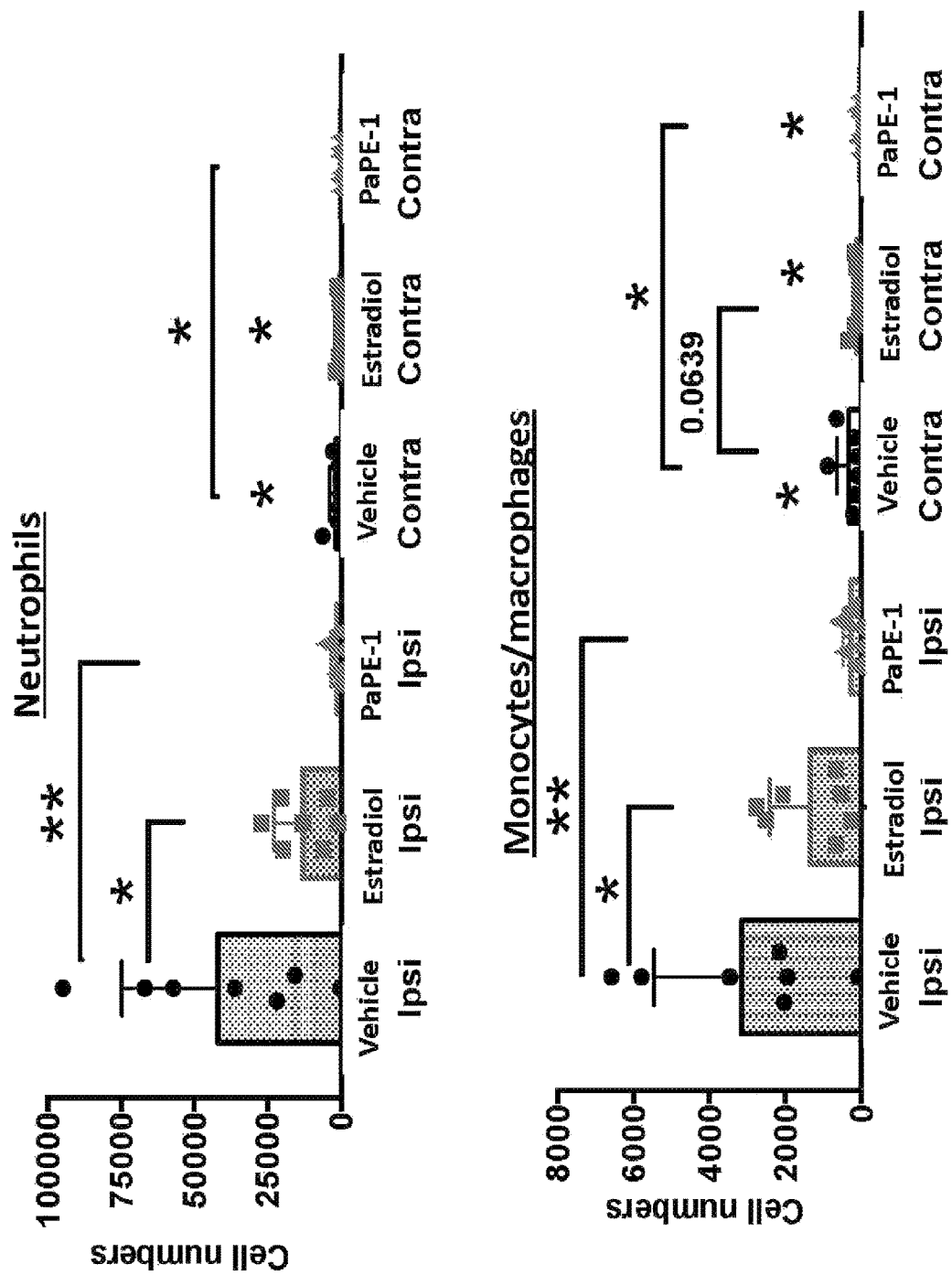
FIG. 46. Attenuation in CNS injury by estradiol and particularly by PaPE-1 is associated with decrease in leukocyte recruitment to the CNS ipsilateral to the injury.
Figure 47:
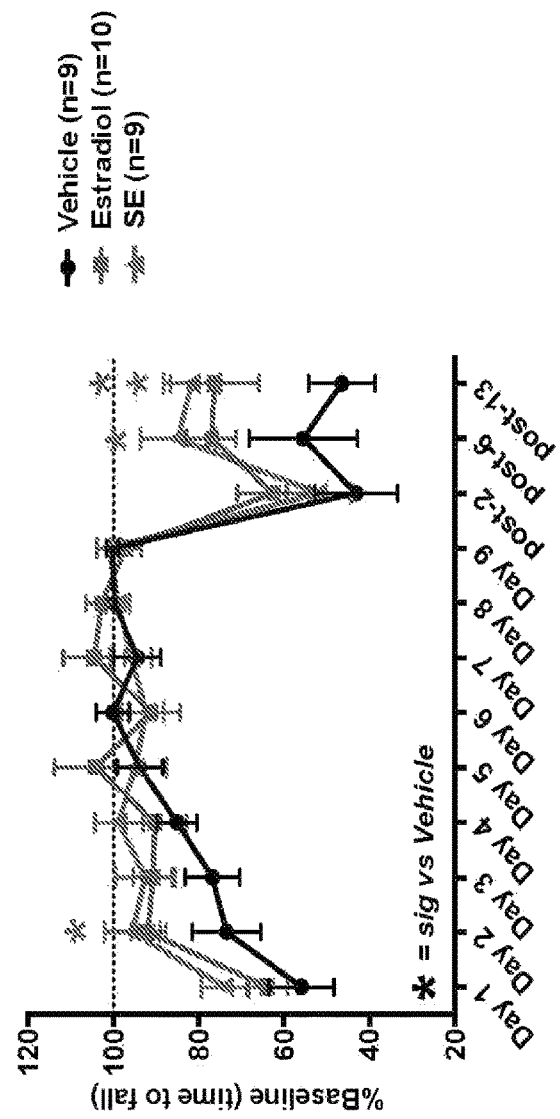
FIG. 47. Estradiol and PaPE-1 resulted in improved function post-stroke as assessed with rotorod testing.

With E2 and PaPE-1 treatment, the severity of CNS injury on MRI at 3 and 7 days was decreased compared with control treatment (FIGS. 42 and 43). The degree of swelling associated with the injury was also attenuated by E2 and PaPE-1 3 days post-stroke (FIGS. 42 and 43). The attenuation in CNS injury with E2 and PaPE-1 was associated with a decrease in leukocyte recruitment to the CNS ipsilateral to the injury (FIGS. 44-46). E2 and PaPE-1 additionally resulted in improved function post-stroke assessed with rotorod testing (FIG. 47).

ThePaPE-1 cumulative findings indicate that non-nuclear estrogen receptor activation with PaPE-1 affords protection from stroke injury and its adverPaPE-1 sequelae in mice.

All patents, publications and references cited herein are hereby fully incorporated by reference. In case of conflict between the present disclosure and incorporated patents, publications, and references, the present disclosure should control.

The invention claimed is:

1. A compound of formula (i):

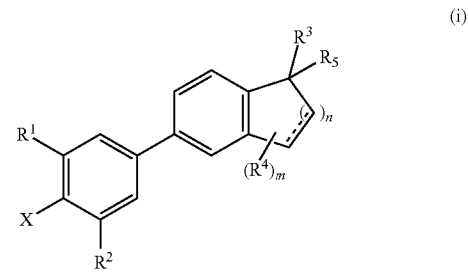

or stereoisomers, or pharmaceutically acceptable salts thereof;

wherein n is an integer from 0 to 4;

m is an integer from 0 to 4;

X is hydroxy or $C_{1-4}$ alkoxy;

$R_1$ and $R_2$ are independently H, hydroxy, $C_{1-4}$ alkyl, $C_{1-4}$ alkoxy, —S—$C_{1-4}$ alkyl, or halo;

$R_3$ is H, hydroxy, cyano, halo, $C_{1-4}$ alkyl, or $C_{1-4}$ alkoxy;

each $R_4$ is independently hydrogen, hydroxy, oxo, halo, $C_{1-4}$ alkyl, or $C_{1-4}$ alkoxy;

$R_5$ is H or $C_{1-4}$ alkynyl; and

--- is an optional double bond;

wherein a $C_{1-4}$ alkyl or $C_{1-4}$ alkoxy is optionally substituted with one or more of halo, cyano, amino, hydroxy, and $C_{1-4}$ alkoxy.

2. A compound according to claim 1, or a pharmaceutically acceptable salt thereof, wherein at least one of $R_1$ and $R_2$ is $C_{1-4}$ alkyl.

3. A compound according to claim 1, or a pharmaceutically acceptable salt thereof, wherein $R_1$ and $R_2$ are independently selected from H, methyl, ethyl, chloro, —CH$_2$OH, and CH$_2$OMe.

4. A compound according to claim 1, or a pharmaceutically acceptable salt thereof, wherein $R_3$ is selected from H, OH, chloro, cyano, or methoxy.

5. A compound according to claim 1, or a pharmaceutically acceptable salt thereof, wherein the compound is selected from the group consisting of:

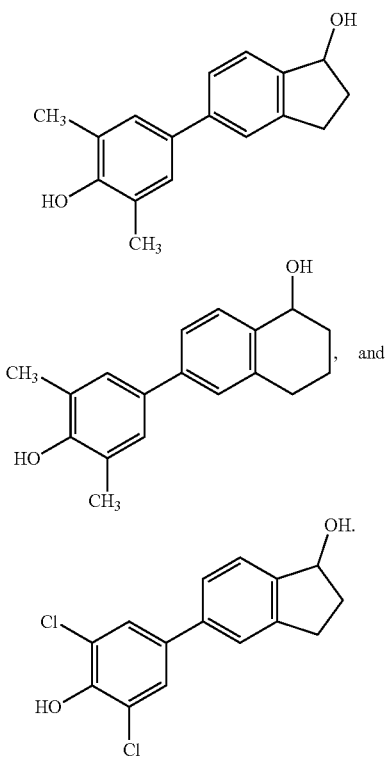

6. A compound according to claim 1 of formula (ii):

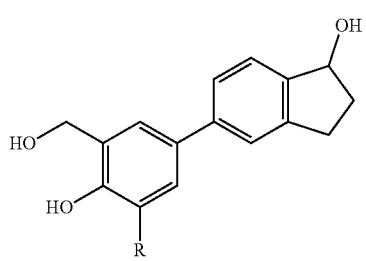

and stereoisomers and salts thereof
wherein
R is H or methyl.

7. A pharmaceutical composition comprising a compound of claim 1, or a pharmaceutically acceptable salt thereof, and a pharmaceutically acceptable excipient.

8. A method of treating a disease or condition in a subject, the method comprising administering a therapeutically effective amount of a compound according to claim 1, or a pharmaceutically acceptable salt thereof, wherein the disease or condition is selected from postmenopausal symptoms, cardiovascular disease, stroke, vascular disease, bone disease, metabolic disease, arthritis, osteoporosis, obesity, vasomotor/hot flush, cognitive decline, and cancer.

9. A kit comprising a compound of claim 1, or a pharmaceutically acceptable salt thereof, and instructions for use.

10. A compound according to claim 1, or a pharmaceutically acceptable salt thereof, wherein $R_3$ is hydroxy.

11. A compound according to claim 10, or a pharmaceutically acceptable salt thereof, wherein both $R_1$ and $R_2$ are $C_{1-4}$ alkyl.

12. A compound according to claim 10, or a pharmaceutically acceptable salt thereof, wherein at least one of $R_1$ and $R_2$ is methyl.

13. A compound according to claim 10, or a pharmaceutically acceptable salt thereof, wherein $R_1$ and $R_2$ are independently selected from H, methyl, ethyl, chloro, —CH$_2$OH, and —CH$_2$OMe.

14. A compound according to claim 10, or a pharmaceutically acceptable salt thereof, wherein $R_4$ is selected from fluoro, chloro, bromo, methoxy, hydroxy, and oxo.

15. A compound according to claim 10, or a pharmaceutically acceptable salt thereof, wherein $R_5$ is H.

16. A compound according to claim 10, or a pharmaceutically acceptable salt thereof, wherein $R_5$ is —C≡CH.

17. A compound according to claim 10, or a pharmaceutically acceptable salt thereof, wherein m is 0.

18. A compound according to claim 10, or a pharmaceutically acceptable salt thereof, wherein n is 1.

19. A compound according to claim 10, or a pharmaceutically acceptable salt thereof, wherein n is 2.

20. A compound selected from the group consisting of:

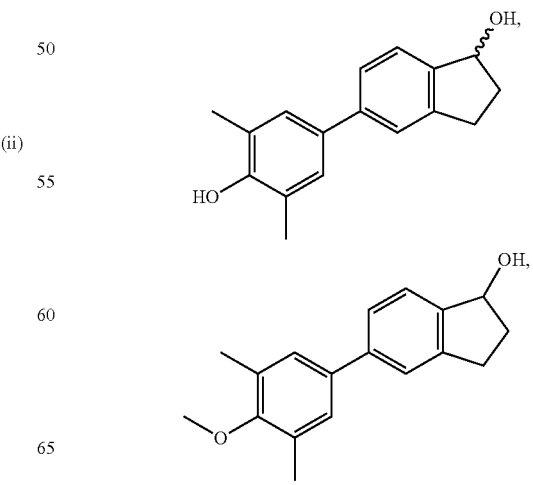

89
-continued
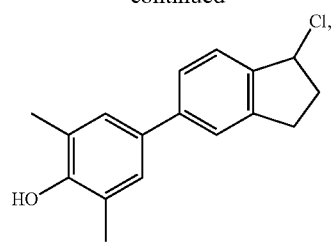
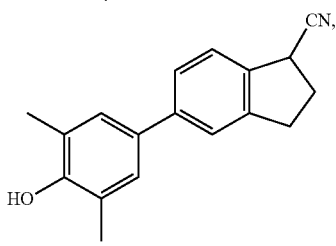
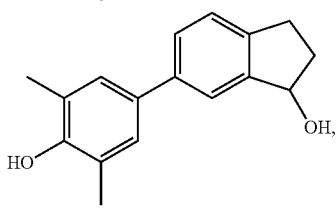
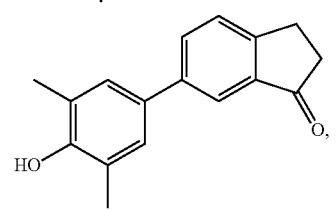
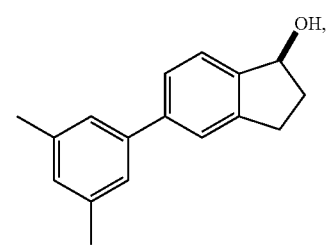
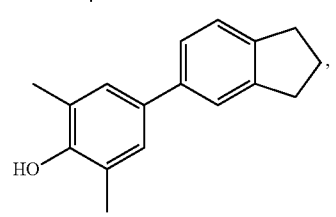
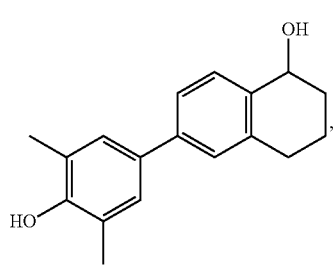
90
-continued
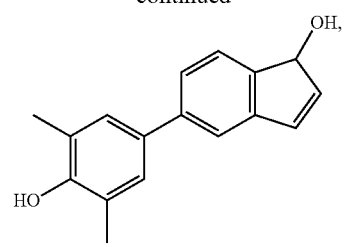
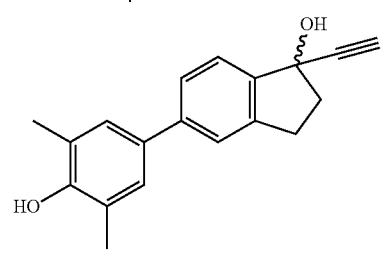
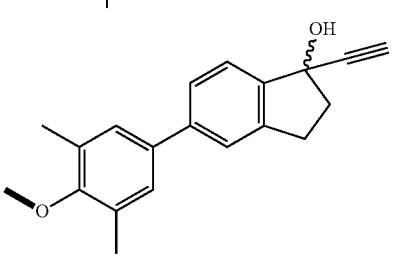
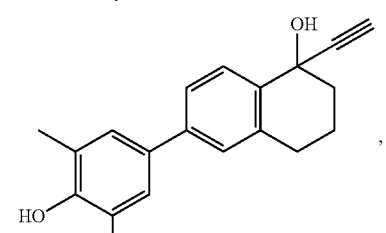
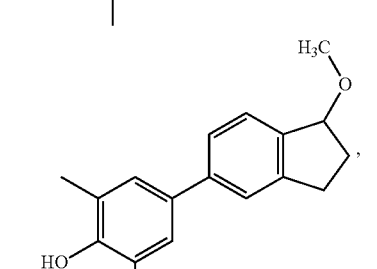
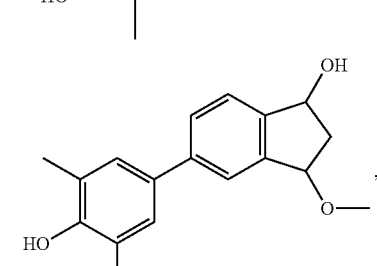
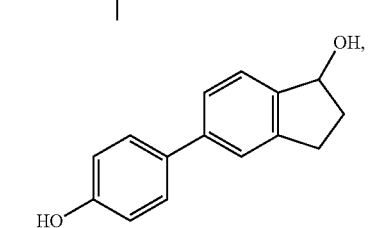

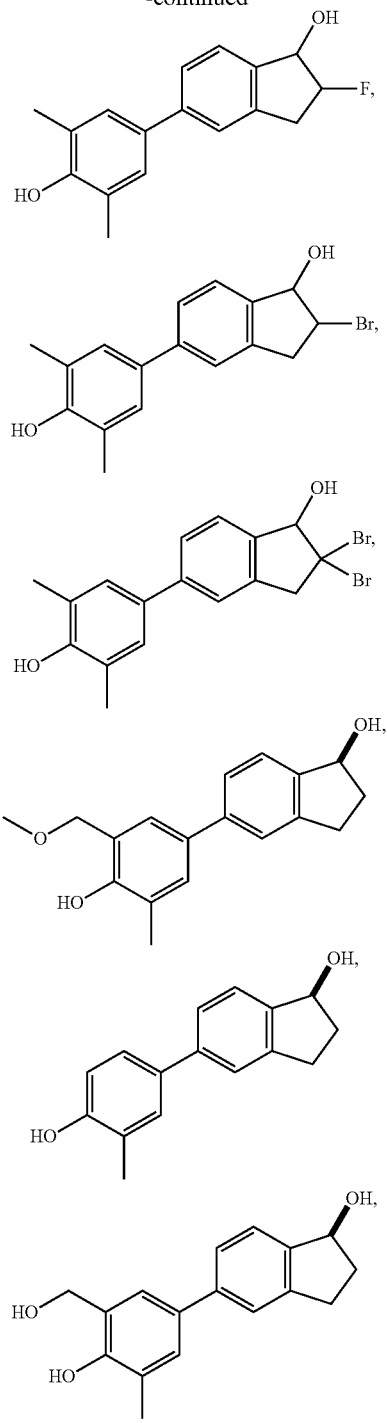
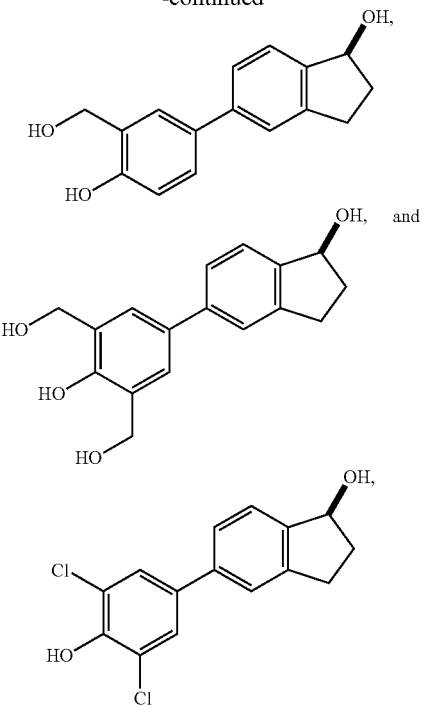
or a pharmaceutically acceptable salt thereof.
21. A compound according to claim 1, selected from the group consisting of:
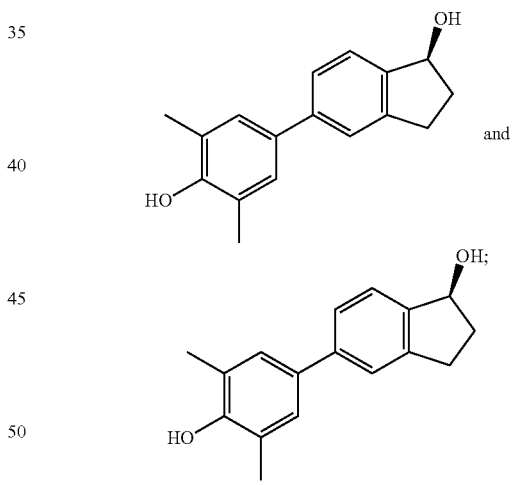
or a pharmaceutically acceptable salt thereof.
* * * * *